US010174104B2

(12) United States Patent
Sahin et al.

(10) Patent No.: US 10,174,104 B2
(45) **Date of Patent: *Jan. 8, 2019**

(54) MONOCLONAL ANTIBODIES AGAINST CLAUDIN-18 FOR TREATMENT OF CANCER

(71) Applicant: Ganymed Pharmaceuticals AG, Mainz (DE)

(72) Inventors: Ugur Sahin, Mainz (DE); Özlem Türeci, Mainz (DE); Dirk Usener, Wiesbaden (DE); Stefan Fritz, Flonheim (DE); Christoph Uherek, Ginsheim (DE); Gunda Brandenburg, Mainz (DE); Harald-Gerhard Geppert, Hannover (DE); Anja Kristina Schröder, Mainz (DE); Phillippe Thiel, Planegg (DE)

(73) Assignee: GANYMED PHARMACEUTICALS GMBH, Mainz (DE)

( * ) Notice: Subject to any disclaimer, the term of this patent is extended or adjusted under 35 U.S.C. 154(b) by 121 days.

This patent is subject to a terminal disclaimer.

(21) Appl. No.: 14/661,846

(22) Filed: Mar. 18, 2015

(65) Prior Publication Data

US 2015/0252103 A1 Sep. 10, 2015

Related U.S. Application Data

(60) Continuation of application No. 13/306,545, filed on Nov. 29, 2011, now Pat. No. 9,499,609, which is a division of application No. 12/094,530, filed as application No. PCT/EP2006/011302 on Nov. 24, 2006, now Pat. No. 8,168,427.

(30) Foreign Application Priority Data

Nov. 24, 2005 (EP) .................................... 05025657

(51) Int. Cl.

| | |
|---|---|
| ***C07K 16/00*** | (2006.01) |
| ***A61K 39/395*** | (2006.01) |
| ***C07K 16/18*** | (2006.01) |
| ***A61K 47/68*** | (2017.01) |
| ***A61K 51/10*** | (2006.01) |
| ***C07K 16/30*** | (2006.01) |
| ***A61K 45/06*** | (2006.01) |
| ***C07K 16/28*** | (2006.01) |
| *A61K 39/00* | (2006.01) |

(52) U.S. Cl.

CPC .......... *C07K 16/18* (2013.01); *A61K 39/3955* (2013.01); *A61K 45/06* (2013.01); *A61K 47/6803* (2017.08); *A61K 47/6807* (2017.08); *A61K 47/6809* (2017.08); *A61K 47/6813* (2017.08); *A61K 47/6821* (2017.08); *A61K 47/6823* (2017.08); *A61K 47/6829* (2017.08); *A61K 47/6851* (2017.08); *A61K 47/6859* (2017.08); *A61K 47/6863* (2017.08); *A61K 47/6869* (2017.08); *A61K 51/1063* (2013.01); *C07K 16/28* (2013.01); *C07K 16/3046* (2013.01); *A61K 2039/505* (2013.01); *C07K 2317/14* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/73* (2013.01); *C07K 2317/732* (2013.01); *C07K 2317/734* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 4,439,196 | A | 3/1984 | Higuchi |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,522,811 | A | 6/1985 | Eppstein et al. |
| 4,596,556 | A | 6/1986 | Morrow et al. |
| 4,790,824 | A | 12/1988 | Morrow et al. |
| 4,881,175 | A | 11/1989 | Ladner |
| 4,941,880 | A | 7/1990 | Burns |
| 4,946,778 | A | 8/1990 | Ladner et al. |
| 4,954,617 | A | 9/1990 | Fanger et al. |
| 5,013,653 | A | 5/1991 | Huston et al. |

(Continued)

FOREIGN PATENT DOCUMENTS

| | | | |
|---|---|---|---|
| AU | 2003282101 | A1 | 6/2004 |
| CA | 2379661 | A1 | 9/2003 |

(Continued)

OTHER PUBLICATIONS

Heiskala, et al., "The Roles of Claudin Superfamily Proteins in Paracellular Transport," Traffic, vol. 2, No. 2, pp. 92-98 (2001).

(Continued)

*Primary Examiner* — Mark Halvorson

(74) *Attorney, Agent, or Firm* — Neal, Gerber & Eisenberg LLP; Kevin A. O'Connor

(57) ABSTRACT

The present invention provides antibodies useful as therapeutics for treating and/or preventing diseases associated with cells expressing CLD18, including tumor-related diseases such as gastric cancer, esophageal cancer, pancreatic cancer, lung cancer, ovarian cancer, colon cancer, hepatic cancer, head-neck cancer, and cancer of the gallbladder.

24 Claims, 51 Drawing Sheets

Specification includes a Sequence Listing.

(56) References Cited

U.S. PATENT DOCUMENTS

| | | | |
|---|---|---|---|
| 5,064,413 | A | 11/1991 | McKinnon et al. |
| 5,091,513 | A | 2/1992 | Huston et al. |
| 5,132,405 | A | 7/1992 | Huston et al. |
| 5,258,498 | A | 11/1993 | Huston et al. |
| 5,260,203 | A | 11/1993 | Ladner et al. |
| 5,312,335 | A | 5/1994 | McKinnon et al. |
| 5,374,548 | A | 12/1994 | Caras |
| 5,383,851 | A | 1/1995 | McKinnon, Jr. et al. |
| 5,399,163 | A | 3/1995 | Peterson et al. |
| 5,399,331 | A | 3/1995 | Loughrey et al. |
| 5,416,016 | A | 5/1995 | Low et al. |
| 5,455,030 | A | 10/1995 | Ladner et al. |
| 5,476,786 | A | 12/1995 | Huston |
| 5,482,858 | A | 1/1996 | Huston et al. |
| 5,624,821 | A | 4/1997 | Winter et al. |
| 5,648,260 | A | 7/1997 | Winter et al. |
| 5,869,045 | A | 2/1999 | Hellstrom et al. |
| 6,121,022 | A | 9/2000 | Presta et al. |
| 6,194,551 | B1 | 2/2001 | Idusogie et al. |
| 6,235,481 | B1 | 5/2001 | Horikawa et al. |
| 6,277,375 | B1 | 8/2001 | Ward |
| 6,380,362 | B1 | 4/2002 | Watson et al. |
| 6,946,263 | B2 | 9/2005 | Ferrara et al. |
| 6,951,920 | B2 | 10/2005 | Gao et al. |
| 7,060,800 | B2 | 6/2006 | Gorman |
| 7,071,304 | B2 | 7/2006 | Eaton et al. |
| 7,074,912 | B2 | 7/2006 | Eaton et al. |
| 7,098,312 | B2 | 8/2006 | Baker et al. |
| 7,109,292 | B2 | 9/2006 | Goddard et al. |
| 7,125,962 | B2 | 10/2006 | Baker et al. |
| 7,153,939 | B2 | 12/2006 | Goddard et al. |
| 7,189,563 | B2 | 3/2007 | Eaton et al. |
| 7,189,821 | B2 | 3/2007 | Goddard et al. |
| 7,193,059 | B2 | 3/2007 | Goddard et al. |
| 7,193,074 | B2 | 3/2007 | Goddard et al. |
| 7,196,166 | B2 | 3/2007 | Goddard et al. |
| 7,196,167 | B2 | 3/2007 | Goddard et al. |
| 7,202,335 | B2 | 4/2007 | Goddard et al. |
| 7,211,645 | B2 | 5/2007 | Goddard et al. |
| 7,223,841 | B2 | 5/2007 | Goddard et al. |
| 7,232,889 | B2 | 6/2007 | Goddard et al. |
| 7,241,872 | B2 | 7/2007 | Goddard et al. |
| 7,253,256 | B2 | 8/2007 | Goddard et al. |
| 7,271,247 | B2 | 9/2007 | Goddard et al. |
| 7,309,769 | B2 | 12/2007 | Goddard et al. |
| 7,317,093 | B2 | 1/2008 | Goddard et al. |
| 7,319,008 | B2 | 1/2008 | Goddard et al. |
| 7,339,024 | B2 | 3/2008 | Goddard et al. |
| 7,339,034 | B2 | 3/2008 | Goddard et al. |
| 7,351,543 | B2 | 4/2008 | Goddard et al. |
| 7,351,804 | B2 | 4/2008 | Goddard et al. |
| 7,368,531 | B2 | 5/2008 | Rosen et al. |
| 7,375,184 | B2 | 5/2008 | Goddard et al. |
| 7,399,834 | B2 | 7/2008 | Botstein et al. |
| 7,405,268 | B2 | 7/2008 | Goddard et al. |
| 7,411,051 | B2 | 8/2008 | Rosen et al. |
| 7,423,120 | B2 | 9/2008 | Goddard et al. |
| 7,425,605 | B2 | 9/2008 | Goddard et al. |
| 7,427,668 | B2 | 9/2008 | Gorman |
| 7,488,796 | B2 | 2/2009 | Goddard et al. |
| 7,495,083 | B2 | 2/2009 | Goddard et al. |
| 7,507,404 | B2 | 3/2009 | Goddard et al. |
| 7,527,933 | B2 | 5/2009 | Sahin et al. |
| 7,538,086 | B2 | 5/2009 | Goddard et al. |
| 7,696,317 | B2 | 4/2010 | Gorman |
| 7,696,319 | B2 | 4/2010 | Baker et al. |
| 7,893,211 | B2 | 2/2011 | Gorman |
| 8,088,588 | B2 | 1/2012 | Sahin et al. |
| 8,148,507 | B2 | 4/2012 | Parham et al. |
| 8,168,427 | B2 | 5/2012 | Sahin et al. |
| 8,425,902 | B2 | 4/2013 | Sahin et al. |
| 8,426,573 | B2 | 4/2013 | Parham et al. |
| 8,586,047 | B2 | 11/2013 | Sahin et al. |
| 8,637,012 | B2 | 1/2014 | Sahin et al. |
| 8,945,847 | B2 | 2/2015 | Benvenisty et al. |
| 9,044,382 | B2 | 6/2015 | Tureci et al. |
| 2002/0119130 | A1 | 8/2002 | Eaton et al. |
| 2003/0008352 | A1 | 1/2003 | Baker et al. |
| 2003/0008353 | A1 | 1/2003 | Baker et al. |
| 2003/0017468 | A1 | 1/2003 | Chen et al. |
| 2003/0017534 | A1 | 1/2003 | Buelow et al. |
| 2003/0018172 | A1 | 1/2003 | Eaton et al. |
| 2003/0022296 | A1 | 1/2003 | Baker et al. |
| 2003/0022298 | A1 | 1/2003 | Baker et al. |
| 2003/0022835 | A1 | 1/2003 | Watson et al. |
| 2003/0027268 | A1 | 2/2003 | Baker et al. |
| 2003/0027272 | A1 | 2/2003 | Baker et al. |
| 2003/0027279 | A1 | 2/2003 | Baker et al. |
| 2003/0027281 | A1 | 2/2003 | Baker et al. |
| 2003/0032113 | A1 | 2/2003 | Baker et al. |
| 2003/0032119 | A1 | 2/2003 | Baker et al. |
| 2003/0036119 | A1 | 2/2003 | Baker et al. |
| 2003/0036146 | A1 | 2/2003 | Baker et al. |
| 2003/0038827 | A1 | 2/2003 | Baker et al. |
| 2003/0040053 | A1 | 2/2003 | Baker et al. |
| 2003/0040057 | A1 | 2/2003 | Baker et al. |
| 2003/0040061 | A1 | 2/2003 | Baker et al. |
| 2003/0040078 | A1 | 2/2003 | Baker et al. |
| 2003/0040471 | A1 | 2/2003 | Watson et al. |
| 2003/0044925 | A1 | 3/2003 | Baker et al. |
| 2003/0049756 | A1 | 3/2003 | Baker et al. |
| 2003/0054406 | A1 | 3/2003 | Baker et al. |
| 2003/0054468 | A1 | 3/2003 | Baker et al. |
| 2003/0060602 | A1 | 3/2003 | Eaton et al. |
| 2003/0068682 | A1 | 4/2003 | Baker et al. |
| 2003/0068684 | A1 | 4/2003 | Baker et al. |
| 2003/0068726 | A1 | 4/2003 | Baker et al. |
| 2003/0073129 | A1 | 4/2003 | Baker et al. |
| 2003/0073821 | A1 | 4/2003 | Eaton et al. |
| 2003/0082626 | A1 | 5/2003 | Baker et al. |
| 2003/0083462 | A1 | 5/2003 | Baker et al. |
| 2003/0096954 | A1 | 5/2003 | Baker et al. |
| 2003/0100061 | A1 | 5/2003 | Baker et al. |
| 2003/0109672 | A1 | 6/2003 | Baker et al. |
| 2003/0113795 | A1 | 6/2003 | Baker et al. |
| 2003/0118592 | A1 | 6/2003 | Ledbetter et al. |
| 2003/0119097 | A1 | 6/2003 | Baker et al. |
| 2003/0120053 | A1 | 6/2003 | Baker et al. |
| 2003/0125535 | A1 | 7/2003 | Baker et al. |
| 2003/0130483 | A1 | 7/2003 | Eaton et al. |
| 2003/0133939 | A1 | 7/2003 | Ledbetter et al. |
| 2003/0135034 | A1 | 7/2003 | Baker et al. |
| 2003/0138882 | A1 | 7/2003 | Eaton et al. |
| 2003/0152939 | A1 | 8/2003 | Smithson et al. |
| 2003/0166104 | A1 | 9/2003 | Baker et al. |
| 2003/0166114 | A1 | 9/2003 | Baker et al. |
| 2003/0171550 | A1 | 9/2003 | Eaton et al. |
| 2003/0180839 | A1 | 9/2003 | Eaton et al. |
| 2003/0180840 | A1 | 9/2003 | Eaton et al. |
| 2003/0180841 | A1 | 9/2003 | Eaton et al. |
| 2003/0180842 | A1 | 9/2003 | Eaton et al. |
| 2003/0180843 | A1 | 9/2003 | Eaton et al. |
| 2003/0180844 | A1 | 9/2003 | Eaton et al. |
| 2003/0180846 | A1 | 9/2003 | Eaton et al. |
| 2003/0180848 | A1 | 9/2003 | Eaton et al. |
| 2003/0180850 | A1 | 9/2003 | Eaton et al. |
| 2003/0180853 | A1 | 9/2003 | Eaton et al. |
| 2003/0180855 | A1 | 9/2003 | Eaton et al. |
| 2003/0180856 | A1 | 9/2003 | Eaton et al. |
| 2003/0180857 | A1 | 9/2003 | Eaton et al. |
| 2003/0180858 | A1 | 9/2003 | Eaton et al. |
| 2003/0180859 | A1 | 9/2003 | Eaton et al. |
| 2003/0180862 | A1 | 9/2003 | Eaton et al. |
| 2003/0180863 | A1 | 9/2003 | Eaton et al. |
| 2003/0180904 | A1 | 9/2003 | Eaton et al. |
| 2003/0180908 | A1 | 9/2003 | Eaton et al. |
| 2003/0180909 | A1 | 9/2003 | Eaton et al. |
| 2003/0180910 | A1 | 9/2003 | Eaton et al. |
| 2003/0180912 | A1 | 9/2003 | Eaton et al. |
| 2003/0180913 | A1 | 9/2003 | Eaton et al. |
| 2003/0180914 | A1 | 9/2003 | Eaton et al. |
| 2003/0180915 | A1 | 9/2003 | Eaton et al. |
| 2003/0180916 | A1 | 9/2003 | Eaton et al. |
| 2003/0180917 | A1 | 9/2003 | Eaton et al. |

(56) References Cited

U.S. PATENT DOCUMENTS

| | | | |
|---|---|---|---|
| 2003/0180918 | A1 | 9/2003 | Eaton et al. |
| 2003/0180920 | A1 | 9/2003 | Eaton et al. |
| 2003/0180921 | A1 | 9/2003 | Eaton et al. |
| 2003/0180922 | A1 | 9/2003 | Eaton et al. |
| 2003/0181637 | A1 | 9/2003 | Eaton et al. |
| 2003/0181638 | A1 | 9/2003 | Eaton et al. |
| 2003/0181641 | A1 | 9/2003 | Eaton et al. |
| 2003/0181650 | A1 | 9/2003 | Eaton et al. |
| 2003/0181652 | A1 | 9/2003 | Eaton et al. |
| 2003/0181666 | A1 | 9/2003 | Eaton et al. |
| 2003/0181675 | A1 | 9/2003 | Eaton et al. |
| 2003/0181680 | A1 | 9/2003 | Eaton et al. |
| 2003/0181697 | A1 | 9/2003 | Eaton et al. |
| 2003/0181700 | A1 | 9/2003 | Eaton et al. |
| 2003/0181701 | A1 | 9/2003 | Eaton et al. |
| 2003/0181702 | A1 | 9/2003 | Eaton et al. |
| 2003/0181703 | A1 | 9/2003 | Eaton et al. |
| 2003/0186318 | A1 | 10/2003 | Baker et al. |
| 2003/0186407 | A1 | 10/2003 | Eaton et al. |
| 2003/0187189 | A1 | 10/2003 | Baker et al. |
| 2003/0187195 | A1 | 10/2003 | Baker et al. |
| 2003/0187196 | A1 | 10/2003 | Eaton et al. |
| 2003/0187239 | A1 | 10/2003 | Baker et al. |
| 2003/0187242 | A1 | 10/2003 | Eaton et al. |
| 2003/0190669 | A1 | 10/2003 | Eaton et al. |
| 2003/0190698 | A1 | 10/2003 | Eaton et al. |
| 2003/0191290 | A1 | 10/2003 | Eaton et al. |
| 2003/0195347 | A1 | 10/2003 | Baker et al. |
| 2003/0206188 | A1 | 11/2003 | Baker et al. |
| 2003/0211574 | A1 | 11/2003 | Baker et al. |
| 2004/0010134 | A1 | 1/2004 | Rosen et al. |
| 2004/0018969 | A1 | 1/2004 | Rosen et al. |
| 2004/0058411 | A1 | 3/2004 | Eaton et al. |
| 2005/0026211 | A1 | 2/2005 | Chen et al. |
| 2005/0181375 | A1 | 8/2005 | Aziz et al. |
| 2005/0196832 | A1 | 9/2005 | Goddard et al. |
| 2005/0202526 | A1 | 9/2005 | Baker et al. |
| 2006/0035852 | A1 | 2/2006 | Sahin et al. |
| 2006/0073544 | A1 | 4/2006 | Baker et al. |
| 2006/0073545 | A1 | 4/2006 | Baker et al. |
| 2006/0084794 | A1 | 4/2006 | Rosen et al. |
| 2007/0065859 | A1 | 3/2007 | Wang et al. |
| 2007/0072175 | A1 | 3/2007 | Cooper et al. |
| 2007/0099251 | A1 | 5/2007 | Zhang et al. |
| 2007/0099833 | A1 | 5/2007 | Rosen et al. |
| 2007/0224663 | A1 | 9/2007 | Rosen et al. |
| 2008/0050726 | A1 | 2/2008 | Wang et al. |
| 2008/0166350 | A1 | 7/2008 | Tureci et al. |
| 2008/0286821 | A1 | 11/2008 | Eaton et al. |
| 2009/0018031 | A1 | 1/2009 | Trinklein et al. |
| 2009/0197301 | A1 | 8/2009 | Baker et al. |
| 2010/0021886 | A1 | 1/2010 | Wang et al. |
| 2010/0286048 | A1 | 11/2010 | Rosen et al. |
| 2011/0190380 | A1 | 8/2011 | Feinstein et al. |
| 2012/0164160 | A1 | 6/2012 | Sahin et al. |
| 2012/0195830 | A1 | 8/2012 | Sahin et al. |
| 2014/0073524 | A1 | 3/2014 | Hood et al. |
| 2015/0252104 | A1 | 9/2015 | Sahin et al. |
| 2016/0185860 | A1 | 6/2016 | Sahin et al. |

FOREIGN PATENT DOCUMENTS

| | | | |
|---|---|---|---|
| CN | 101584860 | A | 11/2009 |
| DE | 10254601 | A1 | 6/2004 |
| DE | 10354601 | B3 | 6/2005 |
| DE | 112005002742 | A5 | 8/2007 |
| EP | 0338841 | A1 | 10/1989 |
| EP | 1430902 | A1 | 6/2004 |
| EP | 1790664 | A1 | 5/2007 |
| EP | 1948693 | A1 | 7/2008 |
| EP | 1983002 | A2 | 10/2008 |
| EP | 1997832 | A1 | 12/2008 |
| EP | 2036987 | A1 | 3/2009 |
| EP | 2145902 | A2 | 1/2010 |
| EP | 2295469 | A2 | 3/2011 |
| EP | 2311877 | A2 | 4/2011 |
| EP | 2311878 | A2 | 4/2011 |
| EP | 2311879 | A2 | 4/2011 |
| EP | 2325210 | A1 | 5/2011 |
| EP | 2366709 | A1 | 9/2011 |
| EP | 2371848 | A1 | 10/2011 |
| EP | 2371849 | A1 | 10/2011 |
| EP | 2380903 | A1 | 10/2011 |
| EP | 2383288 | A2 | 11/2011 |
| EP | 2392593 | A2 | 12/2011 |
| EP | 2402758 | A2 | 1/2012 |
| EP | 2481814 | A2 | 8/2012 |
| EP | 2664676 | A1 | 11/2013 |
| FR | 2876705 | A1 | 4/2006 |
| JP | 2000032984 | A | 2/2000 |
| JP | 2002524103 | A | 8/2002 |
| JP | 2003000249 | A | 1/2003 |
| JP | 2004520814 | A | 7/2004 |
| KR | 1020050083962 | A | 8/2005 |
| WO | WO8704462 | A1 | 7/1987 |
| WO | WO8800052 | A1 | 1/1988 |
| WO | WO8901036 | A1 | 2/1989 |
| WO | WO9109974 | A1 | 7/1991 |
| WO | WO9204381 | A1 | 3/1992 |
| WO | WO9410332 | A1 | 5/1994 |
| WO | WO9602552 | A1 | 2/1996 |
| WO | WO9633265 | A1 | 10/1996 |
| WO | WO9633739 | A1 | 10/1996 |
| WO | WO9725426 | A2 | 7/1997 |
| WO | WO9945962 | A1 | 9/1999 |
| WO | WO9964452 | A1 | 12/1999 |
| WO | WO0008206 | A1 | 2/2000 |
| WO | WO0012708 | A2 | 3/2000 |
| WO | WO0015659 | A2 | 3/2000 |
| WO | WO0015796 | A2 | 3/2000 |
| WO | WO0020447 | A2 | 4/2000 |
| WO | WO0023603 | A2 | 4/2000 |
| WO | WO0053756 | A2 | 9/2000 |
| WO | WO0053757 | A2 | 9/2000 |
| WO | WO0056889 | A2 | 9/2000 |
| WO | WO0058473 | A2 | 10/2000 |
| WO | WO0073348 | A2 | 12/2000 |
| WO | WO0073454 | A1 | 12/2000 |
| WO | WO0075316 | A1 | 12/2000 |
| WO | WO0075327 | A1 | 12/2000 |
| WO | WO0077037 | A2 | 12/2000 |
| WO | WO0078961 | A1 | 12/2000 |
| WO | WO0104311 | A1 | 1/2001 |
| WO | WO0116318 | A2 | 3/2001 |
| WO | WO0127257 | A1 | 4/2001 |
| WO | WO0140466 | A2 | 6/2001 |
| WO | WO0148192 | A1 | 7/2001 |
| WO | WO0149715 | A2 | 7/2001 |
| WO | WO0154708 | A1 | 8/2001 |
| WO | WO0155314 | A2 | 8/2001 |
| WO | WO0155318 | A2 | 8/2001 |
| WO | WO0155326 | A2 | 8/2001 |
| WO | WO0155367 | A1 | 8/2001 |
| WO | WO0162920 | A2 | 8/2001 |
| WO | WO0168848 | A2 | 9/2001 |
| WO | WO0170979 | A2 | 9/2001 |
| WO | WO0175067 | A2 | 10/2001 |
| WO | WO0177137 | A1 | 10/2001 |
| WO | WO0190357 | A1 | 11/2001 |
| WO | WO0202621 | A2 | 1/2002 |
| WO | WO0214500 | A2 | 2/2002 |
| WO | WO2002014499 | A2 | 2/2002 |
| WO | WO0218576 | A2 | 3/2002 |
| WO | WO0220569 | A2 | 3/2002 |
| WO | WO0222885 | A1 | 3/2002 |
| WO | WO0243478 | A2 | 6/2002 |
| WO | WO02061087 | A2 | 8/2002 |
| WO | WO02066682 | A2 | 8/2002 |
| WO | WO02068579 | A2 | 9/2002 |
| WO | WO02068600 | A2 | 9/2002 |
| WO | WO02103028 | A2 | 12/2002 |
| WO | WO03004604 | A2 | 1/2003 |
| WO | WO03014303 | A2 | 2/2003 |
| WO | WO03101283 | A2 | 12/2003 |

(56) References Cited

FOREIGN PATENT DOCUMENTS

| | | | |
|---|---|---|---|
| WO | WO2004029207 | A2 | 4/2004 |
| WO | WO2004035607 | A2 | 4/2004 |
| WO | WO2004045535 | A2 | 6/2004 |
| WO | WO2004047863 | A2 | 6/2004 |
| WO | WO2004063351 | A2 | 7/2004 |
| WO | WO2004063355 | A2 | 7/2004 |
| WO | WO2004074455 | A2 | 9/2004 |
| WO | WO2005005601 | A2 | 1/2005 |
| WO | WO2005032495 | A2 | 4/2005 |
| WO | WO2005052182 | A2 | 6/2005 |
| WO | WO2005061548 | A1 | 7/2005 |
| WO | WO2005076939 | A2 | 8/2005 |
| WO | WO2005082398 | A2 | 9/2005 |
| WO | WO2005111198 | A1 | 11/2005 |
| WO | WO2005113587 | A2 | 12/2005 |
| WO | WO2005114221 | A2 | 12/2005 |
| WO | WO2006023121 | A1 | 3/2006 |
| WO | WO2006024283 | A2 | 3/2006 |
| WO | WO2006042995 | A1 | 4/2006 |
| WO | WO2007018843 | A2 | 2/2007 |
| WO | WO2007021423 | A2 | 2/2007 |
| WO | WO2007027867 | A2 | 3/2007 |
| WO | WO2007035676 | A2 | 3/2007 |
| WO | WO2007035690 | A2 | 3/2007 |
| WO | WO2007047796 | A2 | 4/2007 |
| WO | WO2007059997 | A1 | 5/2007 |
| WO | WO2007115045 | A2 | 10/2007 |
| WO | WO2008013948 | A2 | 1/2008 |
| WO | WO2008013954 | A2 | 1/2008 |
| WO | WO2008021115 | A2 | 2/2008 |
| WO | WO2008021290 | A2 | 2/2008 |
| WO | WO2008043561 | A2 | 4/2008 |
| WO | WO2008073919 | A2 | 6/2008 |
| WO | WO2008082730 | A2 | 7/2008 |
| WO | WO2008095152 | A2 | 8/2008 |
| WO | WO2008145338 | A2 | 12/2008 |
| WO | WO2008152822 | A1 | 12/2008 |
| WO | WO2008154333 | A2 | 12/2008 |
| WO | WO2009015050 | A2 | 1/2009 |
| WO | WO2009035497 | A2 | 3/2009 |
| WO | WO2009037090 | A1 | 3/2009 |
| WO | WO2009038090 | A1 | 3/2009 |
| WO | WO2009047362 | A2 | 4/2009 |
| WO | WO2009102367 | A2 | 8/2009 |
| WO | WO2009148593 | A1 | 12/2009 |
| WO | WO2010045889 | A1 | 4/2010 |
| WO | WO2010108638 | A1 | 9/2010 |
| WO | WO2010120526 | A2 | 10/2010 |
| WO | WO2010141093 | A2 | 12/2010 |
| WO | WO2011038461 | A1 | 4/2011 |
| WO | WO2011068839 | A1 | 6/2011 |
| WO | WO2011113546 | A1 | 9/2011 |
| WO | WO2011154139 | A2 | 12/2011 |
| WO | WO2011163267 | A2 | 12/2011 |
| WO | WO2012070014 | A2 | 5/2012 |
| WO | WO2012096272 | A1 | 7/2012 |
| WO | WO2012120026 | A1 | 9/2012 |
| WO | WO2013151672 | A2 | 10/2013 |
| WO | WO2013167153 | A1 | 11/2013 |
| WO | WO2013167259 | A1 | 11/2013 |
| WO | WO2013174403 | A1 | 11/2013 |
| WO | WO2013174404 | A1 | 11/2013 |
| WO | WO2013174509 | A1 | 11/2013 |
| WO | WO2013174510 | A1 | 11/2013 |
| WO | WO2014025198 | A2 | 2/2014 |
| WO | WO2014025199 | A2 | 2/2014 |
| WO | WO2014031859 | A2 | 2/2014 |
| WO | WO2014039893 | A1 | 3/2014 |

OTHER PUBLICATIONS

Nacht, et al., "Combining Serial Analysis of Gene Expression and Array Technologies to Identify Genes Differentially Expressed in Breast Cancer," Cancer Research, vol. 59, No. 21, pp. 5464-5470 (1999).

Ross, et al., "Systematic Variation in Gene Expression Patterns in Human Cancer Cell Lines," Nature Genetics, vol. 24, No. 3, pp. 227-235 (2000).

Tanaka, "Pathologic Studies on the Lesion of Gastric Cancer and the Distribution of its Metastases The Comparative Study Between Gastrectomied and Non-Gastrectomied Cases," Journal of the Showa Medical Association, vol. 23, No. 8, pp. 40-65 (1963).

Yagi, et al., "A Case of Krukenberg's Tumor, Advances in Obstetrics and Gynecology," vol. 11, No. 4, pp. 324-326 (1959).

Vang, R. et al., "Signet-ring Stromal Tumor of the Ovary: Clinicopathologic Analysis and Comparison With Krukenberg Tumor", Int J Gynecol Pathol, (Jan. 2004); 23(1): 45-51.

Teeling, Jessica L. et al., "The Biological Activity of Human CD20 Monoclonal Antibodies Is Linked to Unique Epitopes on CD20", The Journal of Immunology, (2006), 177:362-371.

Cragg, Mark S. et al., "Complement-mediated Lysis by Anti-CD20 mAb Correlates With Segregation Into Lipid Rafts", Blood, (Feb. 1, 2003), vol. 101, No. 3.

Guan-zhen, Yu, et al., Reduced Protein Expression of Metastasis-related Genes (nm23, KISS1, KAI1 and p53) in Lymph Node and Liver Metastases of Gastric Cancer, Int. J. Exp. Path. (2007), 88, pp. 175-183.

Bindon, Carol I. et al., "Importance of Antigen Specificity for Complement-mediated Lysis by Monoclonal Antibodies", Eur. J. Immunol., (1988), 18:1507-1514.

Ragupathi, Govind, et al., "Antibodies Against Tumor Cell Glycolipids and Proteins, But Not Mucins, Mediate Complement-Dependent Cytotoxicity", The Journal of Immunology, (2005), 174:5706-5712.

Riemer A B et al: "Matching of trastuzumab (Herceptin (R)) epitope mimics onto the surface of Her-2/neu—a new method of epitope definition", Molecular Immunology, Pergamon, GB, Bd. 42, Nr. 9, May 1, 2015 (May 1, 2005), Seiten 1121-1124.

P. Büchler et al: "Therapy for pancreatic cancer with a recombinant humanized anti-HER2 antibody (herceptin)", Journal of Gastrointestinal Surgery, Bd. 5, Nr. 2, Apr. 1, 2001 (Apr. 1, 2001), Seiten 139-146.

Azorsa et al., J. Immunol. Methods (1999) 229: 35-48.

Final Office Action dated Jan. 18, 2012 in U.S. Appl. No. 12/423,153.

Fischer, R., et al. (1999) Biol. Chem. 380: 825-836.

Fu et al., EMBO J. (1996) 15:4392-4401.

Gajewski et al., J. Immunol. (1995) 154:5637-5648.

Gardsvoll, J. Immunol. Methods (2000) 234:107-116.

Glennie et al. J. Immunol. (1987) 139: 2367-2375.

Goodman and Gilman, "The Pharmacological Basis of Therapeutics", 8th Edition, 1990, McGraw-Hill, Inc., in particular Chapter 52 (Antineoplastic Agents (Paul Calabrese and Bruce A. Chabner).

Graziano, R. F. et al. (1995) J. Immunol. 155 (10): 4996-5002.

Greenbaum et al., Genome Biology (2003) vol. 4, Issue 9, pp. 117.1-117.8.

Greenberg, J. Immunol. (1986) 136(5):1917.

Gruber et al., Genomics (1998) 54:200-14.

Guo et al., How is mRNA expression predictive for protein expression? A correlation study on human circulating monocytes, Acta Biochim Biophhys Sin (2008) 40:426-436.

Gura (Science, 1997, 278:1041-1042).

Haga, et al., G Protein-Coupled Receptors (1999) ISBN: 0849333849.

Hakomori, S., Cancer Research (1996) 56:5309-5318.

Hall, Stephen S., "IL-12 at the Crossroads",Science (1995) 268:1432-1434.

Harlow & Lane, Antibodies, A Laboratory Manual, 1988, p. 140-240.

Harlow et al., Using Antibodies: A Laboratory Manual: Portable Protocol NO (1999) ISBN 0879695447.

Haupt et al., 2002, Exp. Biol. Med. 227:227-237.

Hayat, M.A., Microscopy, Immunohistochemistry and Antigen Retrieval Methods: For Light and Electron Microscopy (2002) ISBN: 0306467704.

Hell et al., Laboratory Investigation (1995) 73:492-496.

Hellstrom et al., "Antibodies for Drug Delivery", in Controlled Drug Delivery (2nd Ed.).

(56) References Cited

OTHER PUBLICATIONS

Herbert et al., The Dictionary of Immunology, Academic Press, 3rd Edition, London (1985) p. 58-59.
Hewitt et al., BMC Cancer, 6:1471-2407 (2006).
Hillier et al., Genome Research (1996) 6:807-828.
Hoetelmans, Rob W.M.,et al., Applied Immuno. & Molecular Morphology 9(4): 346-351, 2001.
Holliger, P., et al. (1993) Proc. Natl. Acad. Sci. USA 90: 6444-6448.
Horikawa, Y., et al., Bell GI Nat. Genet. (Oct. 2000) 26(2):163-75.
Hsu, in Tissue Culture Methods and Applications, Kruse and Patterson, Eds (1973) Academic Press, NY, see abstract, p. 764.
Huston et al. (1988) Proc. Natl. Acad. Sci. USA 85:5879-5883.
Intellectual Property Office of New Zealand, Examination Report re Patent Application No. 595896, dated Oct. 21, 2011 (3 pages).
International Search Report, PCT/EP2005/005410, dated Aug. 30, 2005, 4 pgs.
Int'l Prelim. Report on Patentability for PCT/EP2008/004197, dated Dec. 1, 2009.
Int'l Search Report for PCT/EP2008/004197, dated Nov. 21, 2008.
Int'l Preliminary Report on Patentability for PCT/EP2013/001331 dated Nov. 11, 2014.
Int'l Search Report for PCT/EP2012/001991 dated Sep. 13, 2012.
Int'l Search Report for PCT/EP2013/001331 dated Oct. 7, 2013.
J. Golay, M. Introna, Arch. Biochem. Biophys (2012), doi: 10.1016/j.abb 2012.02.011.
Jang et al., Clinical Exp. Metastasis (1997) 15:469-483.
Jiang et al (J. Biol. Chern, 2003, 278(7) 4763-4769).
Jones, P. et al. (1986) Nature 321:522-525.
Jung et al., Mol. Cells (2001) 12:41-49.
Kaiser (Science, 2006, 313; 1370).
Karpovsky et al. (1984) J. Exp. Med. 160: 1686.
Kasinrerk et al., Hybrid Hybridomics (2002) 21:287-293.
Kast et al., Cell (1989) 59:603-614.
Kayyem et al., Eur. J. Biochem. (1992) 208:1-8.
Keogh et al., J. Immunol. (2001) 167:787-96.
Kessels et al., Nat. Immunol. (2001) 2:957-61.
Klamp Thorsten et al: Cancer Research. vo 1. 71. No. 2. Jan. 15, 2011 (Jan. 15, 2011). pp. 516-527. XP002678744.
Kohler and Milstein, Nature 256: 495 (1975).
Koslowski et al., Multiple Splice Variants of Lactate Dehydrogenase C Selectively Expressed in Human Cancer, Cancer Research (2002) 62:6750-6755.
Kozak, 1991, J. Biol. Chem. 266: 19867-19870.
Kraus et al., in Methods in Molecular Biology series, Recombinant antibodies for cancer therapy ISBN-0-89603-918-8.
Kreig et al., Nature (1995) 374:546-9.
Krontiris and Capizzi, Internal Medicine, 4th Edition, Editor-in-chief Jay Stein, Elsevier Science (1994) Chapters 71-72, pp. 699-715.
Kuby, Janis Immunology, W. H. Freeman and Company New York, N Y (1992).
Landor M. (1995) Maternal-fetal transfer of immunoglobulines, Ann. Allergy Asthma Immunol. 74: 279-283.
Lee et al., Genomics (2000) 70:354-63.
Lemoine et al., Methods Mol. Biol. (1997) 75:441-7.
Lemon, W.J., et al., Identification of candidate lung cancer susceptibility genes in mouse using oligonucleotide arrays, Journal of Medical Genetics (2002) 39:644-655.
Leuenberger, et al. "A multilingual glossary of biotechnological terms: (IUPAC Recommendations)", Helvetica Chimica Acta, CH-4010 Basel, Switzerland, (1995).
Liu, Ma et al. (1985) Proc. Natl. Acad. Sci. USA 82: 8648.
Lohi et al., J. Biol. Chem. (2002) 277:14246-54.
Lynch (1998) Identification and Expression of G-Protein Coupled Receptors, Receptor Biochemistry and Methodology, ASIN: 0471183105.
Lynch et al., Eur. J. Immunol. (1991) 21:1403-1410.
Maloy et al., Proc. Natl. Acad. Sci. USA (2001) 98:3299-303.
Mar. 25, 2004, "Human gene of the invention NOV20a SEQ ID No. 489", XP002656866.
Matsushita et al (FEBS Letters, 1999, vol. 443, pp. 348-352).
Matz et al. Nucleic Acids Research, 1999, vol. 27, No. 6, 1558.
Merrifield (1964).
Monteiro, R. C. et al. (1992) J. Immunol. 148: 1764.
Morris, Glenn E., Epitope Mapping Protocols (Methods in Molecular Biology) ISBN-089603-375-9.
Morrison, S. (1985) Science 229: 1202.
Morton, H. C. et al. (1996) Critical Reviews in Immunology 16: 423-440.
NCBI, "claudin-18A2.1 [*Homo sapiens*]." Retrieved from the Internet Sep. 15, 2009, http://www.ncbi.nim.nih.gov/protein/16224169.
NCBI, "*Homo sapiens* claudin-18A2.1 mRNA, complete cds, alternatively spliced." Retrieved from the Internet Sep. 15, 2009, http://www.ncbi.nim.nih.gov.nuccore/16224168?report=genbank&log$=seqview.
Neddleman and Wunsch, 1970, J. Mol. Biol. 48, 443.
Niimi et al., Am. J. Hum. Genet. (2002) 70:718-25.
Niimi et al., Claudine-18, A Novel Downstream Target Gene for the T/EBP/NKX2. Homeodomain Trnascription Factor, Encodes Lung-and Stomach-Specific Isoforms Through Alternative Splicing, Molecular and Cellular Biology, vol. 21, No. 21, 2001, pp. 7380-7390, XP002375751.
Non-Final Office Action dated Oct. 19, 2010 in U.S. Appl. No. 12/326,997.
Notice of Allowance dated Jul. 3, 2013 in U.S. Appl. No. 12/423,153.
O'Dowd et al., Discovery of Three Novel G-Protein-Coupled Receptor Genes, Genomics (1998) 47-310-313.
Office Action dated Dec. 11, 2012 in U.S. Appl. No. 12/423,153.
Office Action dated Mar. 22, 2012 in U.S. Appl. No. 12/423,153.
Office Action dated Jul. 19, 2012 in U.S. Appl. No. 12/423,153.
Office Action dated Sep. 9, 2011 in U.S. Appl. No. 12/423,153.
Office Action for U.S. Appl. No. 12/601,488, dated Apr. 19, 2012.
Office Action with English translation for Japanese patent application No. JP2004-554414.
Okazaki, Y., et al., Analysis of the mouse transcriptome based on functional annotation of 60,770 full-length cDNAs, Nature (2002) 420(6915):563-573.
Orntoft et al., Genome-wide Study of Gene Copy Numbers, Transcripts, and Protein Levels in Pairs of Non-invasive and Invasive Human Transitional Cell Carcinomas, Molecular & Cellular Proteomics (2002) 1:37-45.
Ossendorp et al., Immunol. Lett. (2000) 74:75-9.
Ossendorp et al., J. Exp. Med. (1998) 187:693-702.
Pardoll, D., Nature Medicine Vaccine Supplement (1998) 4:525-531.
Park et al., Cancer Epidemiol Biomarkers Prev. (2002) 11:739-44.
Paulus Behring Ins. Mitt. (1985) No. 78, 118-132.
PCT Int'l Bureau, IPRP for Appln No. PCT/EP2006/011302.
PCT Int'l Bureau, ISR for Appln No. PCT/EP2006/011302.
PCT Int'l Bureau, Written Opinion of the Int'l Searching Authority for Appln No. PCT/Ep2006/011302.
Pearlman et al., Dig. Dis. Sci. (2000) 45:298-05.
Abaza et al (Journal of Protein Chemistry, vol. 11, No. 5, 1992, pp. 433-444).
Adams et al., Science (1991) 252:1651 (http://www.ncbi.nlm.nih.gov/BLAST).
Advisory Action for U.S. Appl. No. 12/601,488, dated Jun. 26, 2012.
Al-Agha et al., Arch. Pathol. Lab. Med. 130:1725-1730 (2006).
Altman et al., Science (1996) 274:94-96.
Anderson et al., J. Immunol. (1989) 143:1899-1904.
Appella et al., Biomed Pept Proteins Nucleic Acids (1995) 1:177-84.
Arnon et al., "Monoclonal Antibodies for Immunotargeting of Drugs in Cancer Therapy", in Monoclonal Antibodies and Cancer Therapy.
Baldwin et al. (eds) pp. 303-316 (Academic Press 1985).
Baranova et al., In Silico Screening for Tumour-Specific Expressed Sequences in Human Genome, FEBS Letters (2001) 508:143-148.
Basic Local Alignment Search Tool (BLAST), NCBI Blast:Nucleoride Sequence (180 letters). http://blast/ncbi/nlm.nih.gov/Blast.cgi, dated Mar. 6, 2010 (4 pages).

(56) References Cited

OTHER PUBLICATIONS

Basic Local Alignment Search Tool (BLAST), NCBI Blast:Nucleoride Sequence (786 letters). http://blast/ncbi/nlm.nih.gov/Blast.cgi, dated Mar. 6, 2010 (4 pages).
Benedict et al (J. Exp. Medicine, 2001, 193(1) 89-99).
Bennett et al., Nature (1998) 393:478.
Benny K.C. Lo Antibody Engineering ISBN 1-58829-092-1.
Berge, S. M., et al. (1977) J. Pharm. Sci. 66:1-19.
Berzofsky et al., "Antibody-Antigen Interactions" In Fundamental Immunology, Paul, W. E., Ed., Raven Press New York, N Y (1984).
Bingle et al., Biochem. Biophys. Acta. (2000) 1493:363-7.
Bird et al. (1988) Science 242: 423-426.
Bloeman, P.G. et al. (1995) FEBS Lett. 357: 140.
Brennan et al. (Science (1985) 229: 81-83.
Brennan et al., J. Autoimmunity (1989) 2 (suppl.): 177-186.
Briscoe et al. (1995) Am. J. Physiol. 1233: 134.
Burgess et al (J of Cell Bio. 111 :2129-2138, 1990).
Buskens, C. et al., Digestive Disease Week Abstracts and Itinerary Planner (2003) abstract No. 850.
Chomczynski & Sacchi, Anal. Biochem. (1987) 162:156-9.
Clark, W.R., The Experimental Foundations of Modern Immunology (1986) Wiley & Sons, Inc., New York.
Coleman et al (Research in Immunology, 1994; 145(1): 33-36).
Cunningham-Rundles et al. (1992) Biological activities of polyethylene-glycoll. Immunoglobulin conjugates. Resistance to enzymatic degradation J. Immunol. Methods, 152: 177-190.
Current Protocols in Protein Chemistry, John Wiley & Sons Ltd., Wiley InterScience.
Dabbs, David J., MD, "Microscopy, Immunohistochemistry, and Antigen Retrieval Methods: For Light and Electron Microscopy" ISBN: 0306467704.
Dabbs, J., MD, Diagnostic Immunohistochemistry (2001) ISBN: 0443065667.
Database Genbank, Sequence having accession No. AF221069, Oct. 10, 2001.
De Wildt et al., J. Immunol. Methods (1997) 207: 61-67.
Dillman, Monoclonal Antibodies for Treating Cancer, Annals of Internal Medicine, 1989 111:592-603.
Drexler et al., Leukemia and Lymphoma (1993) 9:1-25.
Dunbar et al., Curr. Biol. (1998) 8:413-416.
Durand et al., Clinical Chemistry (2000) 46:795-805.
EMBL:AK025111, http://ibis/exam/dbfetch.jsp?id=EMBL%3AAK02511 (2 pages).
Embleton et al., Immunol. Ser. (1984) 23:181-207.
Engberg, J., et al., Recombinant antibodies with the antigen-specific, MHC restricted specificity of T cells: novel reagents for basic and clinical investigations and immunotherapy, Immunotechnology (1999) 4:273-278.
European Search Report for patent application No. 11 00 7306, dated Feb. 28, 2012.
European Search Report for patent application No. 11 00 7308.7, dated Nov. 7, 2012.
European Search Report for patent application No. 11 00 7310.3, dated Jun. 27, 2012.
European Search Report for patent application No. 11 00 7311.1, dated Jun. 27, 2012.
European Search Report for patent application No. 11 00 7313.7, dated Jun. 29, 2012.
European Search Report for patent application No. 11 00 7317.8, dated Jun. 25, 2012.
European Search Report for patent application No. 11 00 7326.9, dated Mar. 19, 2012.
Examiner's report No. 2 on Australian patent application No. 20003282101 of Sep. 4, 2009.
Hellstrom et al. "Antibodies for Drug Delivery," in Controlled Drug Delivery (2nd Ed.) (1987).
Westwood, O et al. Epitope Mapping: A Practical Approach Approach Series, 248 (Mar. 2001).
Kraus et al. in Methods in Molecular biology series, Recombinant antibodies for cancer therapy ISBN-0-89603-918-8 (2003).
Merrifield, R.B. Solid-Phase Peptide Synthesis. III. An Improved Synthesis of Bradykinin, Biochemistry, 3:1385-90, 1964 (1964).
Morris, Glenn E., Epitope Mapping Protocols (Methods in Molecular Biology) ISBN 089603-375-9, (1996).
Office Action with English translation for Japanese patent application No. JP2004-554414, dated Mar. 2, 2010.
PCT Int'l Bureau, IPRP for Appln No. PCT/EP2006/011302, dated May 27, 2008.
PCT Int'l Bureau, ISR for Appln No. PCT/EP2006/011302, dated May 31, 2007.
PCT Int'l Bureau, Written Opinion of the Int'l Searching Authority for Appln No. PCT/EP2006/011302, dated May 24, 2008.
Amon et al., "Monoclonal Antibodies for Immunotargeting of Drugs in Cancer Therapy", in Monoclonal Antibodies and Cancer Therapy, (1985).
Hayat, M.A., "Microscopy, Immunohistochemistry, and Antigen Retrieval Methods: For Light and Electron Microscopy" ISBN: 0306467704, (2007).
EMBL:AK025111, http://ibis/exam/dbfetch.jsp?id=EMBL%3AAK02511, (Oct. 7, 2008). 2 pages.
Examiner's report No. 2 on Australian patent application No. 20003282101, dated Sep. 4, 2009.
De Pascalis, et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, vol. 169, pp. 3076-3084, 2002.
MacCallum, et al., "Antibody-antigen Interactions: Contact Analysis and Binding Site Topography," Journal of Molecular Biology, vol. 262, pp. 732-745, 1996.
Paul, "Fundamental Immunology," Third Edition, Laboratory of Immunology, National Institute of Allergy and Infectious Diseases, pp. 292-295, 1993.
Vajdos, et al., "Comprehensive Functional Maps of the Antigen-binding Site of an Anti-ErbB2 Antibody Obtained with Shotgun Scanning Mutagenesis," Journal of Molecular Biology, vol. 320, pp. 415-428, 2002.
Wu, et al., "Humanization of a Murine Monoclonal Antibody by Simultaneous Optimization of Framework and CDR Residues," Journal of Molecular Biology, vol. 294, pp. 151-162, 1999.
Strejan et al. (1984) J. Neuroimmunol. 7: 27.
Taber's Cyclopedic Medical Dictionary (1985) F.A. Davis Company, Philadelphia, p. 274.
Tachihara-Yoshikawa et al, Expression of Secretoglobin3A2 (SCGB3A2) in Primary Pulmonary Carcinomas, Fukushima J. Med. Sci., vol. 54, No. 2 (2008).
Tatsuya Haga, "G Protein-Coupled Receptors" ISBN: 0849333849 (1999).
Terminal Disclaimer filed Mar. 7, 2013 in U.S. Appl. No. 12/423,153.
Terminal Disclaimer filed Jun. 17, 2013 in U.S. Appl. No. 12/423,153.
Thorpe et al., "The Preparation and Cytotoxic Properties of Antibody-Toxin Conjugates" Immunol. Rev., 62: 119-58 (1982).
Thorpe, Antibody Carriers of Cytotoxic Agents in Cancer Therapy: A Review, in Monoclonal Antibodies '84: Biological and Clinical Applications (1985).
Tian et al., Integrated Genomic and Proteomic Analyses of Gene Expression in Mammalian Cells, Molecular & Cellular Proteomics (2004) 3:960-969.
Tremblay et al., Mol. Cell Biochem, (2002) 230-31.
Umezawa et al., (1988) Biochem. Biophys. Res. Commun. 153: 1038.
Vallejo et al., Biochimie (2000) 82:1129-1133.
Van Der Bruggen et al., Science (1991) 254:1643-1647.
Vasmatzis et al., Proc. Natl. Acad. Sci. USA (1998) 95:300-304.
Velders MP et al., British Journal of Cancer (1998), 78(4), 478-483.
Verma, R., et alo. (1998) J. Immunol. Meth. 216: 165-181.
Ward et al., Nature 341: 544-546 (1989).
Weiner L. M. et al, 2009, Lancet 373: 1033-1040.
Weiner, L. M., 1999, Seminars in Oncology 26: 41-50.
Wentworth et al., Mol. Immunol. (1995) 32:603-12.
Westwood, O. et al. Epitope Mapping: A Practical Approach Practical Approach Series, 248 (Mar. 2001).
Wheeler et al., Nucleic Acids Research (2000) 28:10-14.

(56) References Cited

OTHER PUBLICATIONS

Zellner et al., Clin. Can. Res. (1998) 4:1797-1802.
Zheng, P. et al., Proc. Natl. Acad. Sci. USA (1998) 95(11):6284-6289.
Zimmer, Cell Motility and the Cytoskeleton (1991) 20:325-337.
Benny K.C. Lo Antibody Engineering ISBN 1-58829-092-1 (2004).
Current Protocols in Protein Chemistry, John Wiley & Sons Ltd., Wiley InterScience (1994).
Dabbs, David J., MD, "Microscopy, Immunohistochemistry, and Antigen Retrieval Methods: For Light and Electron Microscopy" ISBN: 0306467704 (2002).
Pearson and Lipman, 1988, Proc. Natl Acad. Sci. USA 85, 2444.
Pennisi, Science (1997) 276:1023-1024.
Pinchera et al. (eds) pp. 475-506 (1985) Analysis Results, and Future Prospective of the Therapeutic Use of Radiolabeled Antibodi in Cancer therapy, in Monoclonal Antibodies for Cancer Detection and Therapy.
Poljak, R. J., et al. (1994) Structure 2: 1121-1123.
Pollock, et al. (1999) J. Immunol. Meth. 231: 147-157.
Queen, C. et al. (1989 Proc. Natl. Acad. Sci. U.S.A. 86: 10029-10033.
Rader, C., et al., J. Biol. Chem. (May 2000) 275(18):13668-76.
Ranade, V.V. (1989) J. Clin. Pharmacol. 29: 685.
Reiko Kurotani, et al., Secretoglobin3A2/uterglobin-related protein 1 is a novel marker for pulmonary carcinoma in mice and humans, Lung Cancer 71, pp. 42-48 (2011).
Reisfeld et al. (eds.) pp. 243-256 (Alan R. Liss, Inc. 1985).
Reiter et al., Peptide-specific killing of antigen-presenting cells by a recombinant antibody-toxin fusion protein targeted to Major Histocompatibility Complex/Peptide Class I Complexes with T Cell Receptor-like Specificity, Proc. Natl. Acad. Sci. USA (1997) 94:4631-4636.
Remington: The Science and Practice of Pharmacy, 19th Edition, Gennaro, Ed., Mack Publishing Co., Easton, PA, 1995.
Restriction Requirement dated Mar. 24, 2011 in U.S. Appl. No. 12/423,153.
Riddel, et al., Science (1992) 257:238.
Ridge et al., Nature (1998) 393:474.
Riechmann, L. et al. (1998) Nature 332: 323-327.
Robinson et al. (eds.), pp. 623-653 (Marcel Dekker, Inc. 1987).
Robinson Handbook of Flow Cytometry Methods. Wiley-Liss, New York, 1993.
Roguska et al., 2004, Curr. Prot. Pharmacy., Unit 9.7 (Abstract).
Roitt, I., Essential Immunology (1991) 7th Ed., Blackwell Scientific Publications, Oxford.
Rossi et al., Am. J. Clin. Pathol. 124:295 (2005).
Rudikoff et al (PNAS, USA, 1982,79: 1979-1983).
Rudolph, M. & Wilson, I.A., The specificity of TCR/pMHC interaction, Current Opinion in Immunology (2002) 14:52-65.
Sahin et al., Clinical Cancer Res. (Dec. 2008) 14:7624-7634.
Sahin et al., Current Opinion in Immunology (1997) 9:709-716.
Sambrook et al., Molecular Cloning: A Laboratory Manual, 2nd Edition (1989) Cold Spring Harbor Laboratory Press, Cold Spring Harbor, N.Y. Ausubel et al., F.M. Current Protocols in Molecular Biology, Wiley & Sons, Inc., New York.
Sanada et al, 2006, Journal of Pathology, vol. 208, 633-642.
Scallon et al., 2006, J. Immunother. 29:351-364.
Scheurle et al., Cancer Gene Discovery Using Digital Differential Display, Cancer Res., 60:4037-4043 (2000).
Schmitt et al., Nucleic Acids Research (1999) 27:4251-4260.
Schonberger et al., Nature (1998) 393:480.
Schroff, Robert W., et al., T65 Antigen Modulation in a Phase I Monoclonal Antibody Trial with Chronic164 Lymphocytic Leukemia Patients, The Journal of Immunology, vol. 133, No. 3, 1641-1648, Sep. 1984.
Secretoglobin Family 3A member 2 Precursor—*Homo sapiens* (Human), http//www.uniprot.org/uniprot/Q96P, dated Nov. 1, 2012 (4 pages).
Sep. 29, 2000, "*Homo sapiens* cDNA: FLJ21458 fis, clone COL04713", XP002656867.
Shankavaram et al., Transcript and protein expression profiles of the NCI-60 cancer cell panel: an integromic microarray study, Mol. Cancer Ther. (2007) 6(3):820-32.
Shepherd et al., Monoclonal Antibodies: A Practical Approach (2000) ISBN 0-19-63722-9.
Shi et al., J. Histochem. Cytochem. (1991) 39:741-748.
Shields et al. (2002) JBC, 277: 26733.
Shin et al., Lab. Invest (1991) 64:693-702.
Shinakawa T et al, The Journal of Biological Chemistry, Jan. 31, 2003, vol. 278, No. 5, p. 3466-3473.
Shin-iciro Kitajiri et al., Expression patterns of claudins, tight junction adhesion molecules, in the inner ear, Hearing Research, vol. 187, Jan. 31, 2004, pp. 25-34.
Shiomi et al. (Tumori, 2001, 87(3): Abstract).
Okumura Shun-ichiro et al., "Cloning of a G-Protein-Coupled Receptor That Shows an Activity to Transform NIH3T3 Cells and is Expressed in Gastric Cancer Cells", Cancer Sci., 95(2):131-135 (2004).
Smith and Waterman, 1981 Ads App. Math. 2, 482.
So et al., Mol. Cells (1997) 7:178-186.
Spieker-Polet et al., Proc. Natl. Acad. Sci. U.S.A. 92:9348 (1995).
Spiller et al., J. Immunol. Methods (1999) 224:51-60.
Spiro, Robert G., Protein Glycosylation: nature, distribution, enzymatic formation, and disease implications of glycopeptide bonds, Glycobioloby vol. 12, No. 4, pp. 43R-56R (2002).
Stanislawski et al., Nat Immunol. (2001) 2:962-70.
Stockwin and Holmes, 2003, Biochem. Soc. Trans. 31:433-436.

85A3 (182-D756-002)

24H5 (182-D758-034)

Stomach carcinomas

Lung carcinomas

MONOCLONAL ANTIBODIES AGAINST CLAUDIN-18 FOR TREATMENT OF CANCER

CROSS-REFERENCE TO RELATED APPLICATIONS

This application is a continuation of U.S. application Ser. No. 13/306,545, filed Nov. 29, 2011, which is a division of U.S. application Ser. No. 12/094,530, filed Dec. 3, 2008 and issued as U.S. Pat. No. 8,168,427 on May 1, 2012, which claims priority to Patent Cooperation Treaty Application assigned International No. PCT/EP2006/011302, filed Nov. 24, 2006, which claims priority to European Patent Application No. 05025657.7, filed Nov. 24, 2005, the entire contents of which are incorporated herein by reference.

BACKGROUND

Antibody-based therapies for cancer have the potential of higher specificity and lower side effect profile as compared to conventional drugs. The reason is a precise distinction between normal and neoplastic cells by antibodies and the fact, that their mode of action relies on less toxic immunological anti-tumor mechanisms, such as complement activation and recruitment of cytotoxic immune cells.

Targets for antibody-based therapies need to have particular qualities, which form the basis for proper discrimination between normal and neoplastic cells. Obviously, a target with either exclusive restriction to tumor cells and entirely undetectable on normal tissues is ideal for the development of efficient and safe antibody therapeutics. In another aspect, a high-level overexpression may be the basis for the therapeutic window and low side effects exemplified by the human epidermal growth factor receptor type 2 (HER-2), which as a result of gene amplification is a good target for the antibody trastuzumab (Herceptin).

Other targets for antibodies which are either already approved or in clinical development for tumor therapy have distinct qualities, which are not based on a numeric overexpression of target molecules on tumor cells. In the case of antibodies to the proteoglycan MUC-1, a peptide repeat epitope in the backbone of the target is underglycosylated in tumor cells and thus altered to its normal counterpart. In the case of antibodies to CD20 (rituximab), CD52 (Campath-1H) and CD22 (epratuzumab), antibody targets have comparable expression levels on tumor cells and normal lymphocytes. Here, the ablation of normal cells by the antibody is tolerable since target-negative stem cells restore the normal lymphocyte repertoire. Other examples of differential accessibility of antibody targets are carcinoembryonal antigen (CEA) and carboanhydrase IX (CA9). Both antigens are expressed on normal epithelia of colon and kidney, respectively. However, radioactively labeled imaging antibodies do distinguish well between tumor and normal tissue, and cytotoxic antibodies are well tolerated. This is most likely due to a restricted expression of CA9 and CEA on the luminal side of normal epithelial tissue where IgG antibodies do not have access. Also antigen epithelial cell adhesion molecule (Ep-CAM) belongs to this category. As a homotypic cell adhesion molecule for epithelial cells it is localized in the intercellular space. Intriguingly, whereas high-affinity anti-Ep-CAM antibodies are very toxic, intermediate-affinity antibodies are well tolerated. This suggests accessibility of the Ep-CAM target on normal cells but also indicates that kinetics of antibody binding may open a therapeutic window.

One possibility is that other epithelial cell-specific proteins involved in cell/cell adhesion may be also attractive for antibody approaches, since they may be barely accessible in well-structured epithelia to antibodies but become exposed on tumor cells. We therefore analyzed proteins involved in organizing epithelial tissue architecture for their suitability as targets for therapeutic antibodies. A protein, which particularly attracted our attention is claudin 18.

The claudin 18 (CLD18) molecule (Genbank accession number: splice variant 1 (CLD18A1): NP_057453, NM_016369, and splice variant 2 (CLD18A2): NM_001002026, NP_001002026) is an integral transmembrane protein with a molecular weight of approximately 27.9/27.72 kD. Claudins are integral membrane proteins located within the tight junctions of epithelia and endothelia. Tight junctions organize a network of interconnected strands of intramembranous particles between adjacent cells. In tight junctions, occludin and claudins are the most prominent transmembrane protein components. Due to their strong intercellular adhesion properties they create a primary barrier to prevent and control the paracellular transport of solutes and restrict the lateral diffusion of membrane lipids and proteins to maintain cellular polarity. Tight junction forming proteins are critically involved in organizing epithelial tissue architecture. We assumed that such proteins may be barely accessible to antibodies in well-structured epithelia but become exposed on tumor cells.

CLD18 is a tetraspanin and has as such 4 hydrophobic regions. We have generated data indicating that CLD18 displays several different conformations, which may be selectively addressed by antibodies. One conformation (CLD18-Conformation-1) implies, that all four hydrophobic regions serve as regular transmembrane domains (TM) and two extracellular loops (loop1 embraced by hydrophobic region 1 and hydrophobic region 2; loop2 embraced by hydrophobic regions 3 and 4) are formed, as described for the vast majority of claudin family members. A second conformation (CLD18-Conformation-2) implies that, as described for PMP22, another member of the tetraspanin family (Taylor et al., J. Neurosc. Res. 62:15-27, 2000), that the second and third hydrophobic domains do not fully cross the plasma membrane so that portion (loopD3) in between the first and fourth transmembrane domain is extracellular. A third conformation (CLD18-Conformation-3) implies, a large extracellular domain with two internal hydrophobic regions embraced by the first and fourth hydrophobic region, which serve as regular transmembrane domains. Due to the presence of classical N-glycosylation site in loopD3 the Claudin-18 topology variants CLD18 topology-2- and CLD18 topology-3 harbour an additional extracellular N-glycosylation site.

Another level of complexity is added to CLD18 molecule by the presence of two different splice variants, which are described in mouse and in human (Niimi, Mol. Cell. Biol. 21:7380-90, 2001). The splice variants CLD18A1 and CLD18A2 differ in the first 21 N-terminal amino acids, which comprise the first TM and loop1, whereas the primary protein sequence of the C-terminus is identical.

CLD18A1 is selectively expressed on normal lung and stomach epithelia, whereas CLD18A2 is expressed only on gastric cells (Niimi, Mol. Cell. Biol. 21:7380-90, 2001). Most importantly, CLD18A2 is restricted to the differentiated short-lived cells of stomach epithelium but is devoid from the gastric stem cell region. Using sensitive RT-PCR, we have shown that both variants are not detectable at all in any other normal human organ, but are robustly expressed in several cancer types including stomach, esophageal, pancreatic and lung tumors as well as human cancer cell lines. Expression is most prominent in the adenocarcinoma subtypes of these indications.

The molecular weight of the protein differs in some cancers and adjacent normal tissue. The higher molecular weight protein observed in healthy tissue can be transferred into the same molecular weight as observed in cancer by treating tissue lysates with the deglycosylating compound PNGase F. This suggests, that CLD18 is less N-glycosylated in cancer as compared to its normal tissue counterpart. This structural difference is likely to give rise to an altered epitope. A classical N-glycosylation motif is in position aa 116 within the loopD3 domain of the molecule.

The terms "CLD18" and "CLD18-variant" according to the invention shall encompass (i) CLD18-splice variants, (ii) CLD18-N-glycosylation variants, (iii) CLD18-conformation variants, (iv) CLD18-free and homotypically/heterotypically associated variants localized at intercellular tight junctions and (v) CLD18-cancer related and CLD18-non-cancer cell related variants.

The molecular and functional characteristics of CLD18 make this molecule a highly interesting target for antibody based cancer therapy. These are in particular (i) the absence of CLD18 from the vast majority of toxicity relevant normal tissues, (ii) the restriction of CLD18A2 variant expression to a dispensible cell population as differentiated gastric cells, which can be replenished by target-negative stem cells of the stomach, (iii) hints to potential differential glycosylation between normal and neoplastic cells, and (iv) the presence of different conformational topologies. Moreover, the role of CLD18 as tight junction protein may further contribute to a good therapeutic window. Because tumor cells express claudins but often do not form classical tight junctions by homotypic and heterotypic association of claudins as found in normal epithelial tissue, tumor cells may have a considerable pool of free claudin that is amenable to extracellular antibody binding and immunotherapy. It is possible that binding epitopes of claudins in healthy epithelium are shielded within tight junctions from the access by such antibodies.

The object of the invention is to provide antibodies useful for therapy of diseases wherein CLD18 is expressed, such as tumor diseases. The antibodies described herein have also utility in diagnosing such diseases.

SUMMARY OF THE INVENTION

The present invention generally provides antibodies useful as therapeutics for treating and/or preventing diseases associated with cells expressing CLD18, including tumor-related diseases such as gastric cancer, esophageal cancer, pancreatic cancer, lung cancer, ovarian cancer, colon cancer, hepatic cancer, head-neck cancer, and cancer of the gallbladder.

In one aspect the invention relates to an antibody having the ability of binding to CLD18 and mediating killing of cells expressing CLD18. Preferably, the antibody binds to CLD18A and CLD18A2 and more preferably binds to CLD18A2 but not to CLD18A1. Preferably, antibodies of the invention bind to and are specific for loop1 or loop2 of CLD-conformation-1. In further preferred embodiments, the antibody of the invention binds to and is specific for loopD3 of CLD-conformation-2 and, in particular, binds at or around a potential N-glycosylation site at position 116 within loopD3. In further embodiments, the antibody of the invention is specific for the unglycosylated form of the potential N-glycosylation site at position 116 within loopD3.

Killing of cells by the antibody of the invention is preferably induced by binding of the antibody to CLD18 expressed by said cells, more preferably by binding of the antibody to CLD18A2 expressed by said cells. In one embodiment, binding of the antibody of the invention to CLD18A1 expressed by said cells does not induce killing of said cells.

The cells expressing CLD18 are preferably cancer cells and are, in particular, selected from the group consisting of tumorigenic gastric, esophageal, pancreatic, lung, ovarian, colon, hepatic, head-neck, and gallbladder cancer cells.

Preferably the antibody of the invention mediates killing of cells by inducing complement dependent cytotoxicity (CDC) mediated lysis, antibody dependent cellular cytotoxicity (ADCC) mediated lysis, apoptosis, homotypic adhesion, and/or phagocytosis, preferably by inducing CDC mediated lysis and/or ADCC mediated lysis.

In one embodiment the antibody of the invention does not induce CDC mediated lysis of cells.

Preferably, ADCC mediated lysis of cells takes place in the presence of effector cells, which in particular embodiments are selected from the group consisting of monocytes, mononuclear cells, NK cells and PMNs, and phagocytosis is by macrophages.

The antibody of the invention may be a monoclonal, chimeric, human, or humanized antibody, or a fragment of an antibody and may be selected from the group consisting of an IgG1, an IgG2, preferably IgG2a and IgG2b, an IgG3, an IgG4, an IgM, an IgA1, an IgA2, a secretory IgA, an IgD, and an IgE antibody.

According to all aspects of the invention, CLD18 is preferably human CLD18, preferably human CLD18A2, and CLD18A2 preferably has the amino acid sequence according to SEQ ID NO:2 and CLD18A1 preferably has the amino acid sequence according to SEQ ID NO:8.

In particular preferred embodiments, the antibody of the invention binds to native epitopes of CLD18 present on the surface of living cells. In further preferred embodiments, the antibody of the invention is specific for cancer cells, preferably stomach cancer cells.

In certain embodiments of the invention CLD18 is expressed on the surface of cells.

Antibodies of the invention may be obtained by a method comprising the step of immunizing an animal with a protein or peptide having an amino acid sequence selected from the group consisting of SEQ ID NO:2, 4, 6, 16, 18, 20, 21-23, and 26-31, or an immunogenic fragment thereof, or a nucleic acid or host cell expressing said protein or peptide, or immunogenic fragment thereof. Preferably, an antibody of the invention is specific for the afore mentioned proteins, peptides or immunogenic fragments thereof.

In a particularly preferred embodiment, the antibody of the invention is produced by a clone having the accession no. DSM ACC2737 (182-D1106-055), DSM ACC2738 (182-D1106-056), DSM ACC2739 (182-D1106-057), DSM ACC2740 (182-D1106-058), DSM ACC2741 (182-D1106-059), DSM ACC2742 (182-D1106-062), DSM ACC2743 (182-D1106-067), DSM ACC2745 (182-D758-035), DSM ACC2746 (182-D758-036), DSM ACC2747 (182-D758-040), DSM ACC2748 (182-D1106-061), DSM ACC2808 (182-D1106-279), DSM ACC2809 (182-D1106-294), or DSM ACC2810 (182-D1106-362).

In one embodiment the antibody of the invention is coupled to a therapeutic agent such as a toxin, a radioisotope, a drug or a cytotoxic agent.

In a further aspect the invention relates to a hybridoma capable of producing the antibody of the invention. Preferred hybridomas are those having the accession no. DSM ACC2737 (182-D1106-055), DSM ACC2738 (182-D1106-056), DSM ACC2739 (182-D1106-057), DSM ACC2740 (182-D1106-058), DSM ACC2741 (182-D1106-059), DSM ACC2742 (182-D1106-062), DSM ACC2743 (182-D1106-067), DSM ACC2745 (182-D758-035), DSM ACC2746 (182-D758-036), DSM ACC2747 (182-D758-040), DSM ACC2748 (182-D1106-061), DSM ACC2808 (182-D1106-279), DSM ACC2809 (182-D1106-294), or DSM ACC2810 (182-D1106-362).

Antibodies of the invention are designated herein by referring to the designation of the antibody, e.g. 182-D758-035, and/or by referring to the clone producing the antibody, e.g. 26D12.

The invention also relates to a pharmaceutical composition comprising an antibody of the invention and/or a conjugate thereof with a therapeutic agent, and a pharmaceutically acceptable carrier.

In a further aspect the invention relates to a method of inhibiting growth and/or killing of a cell expressing CLD18, preferably CLD18A2, comprising contacting the cell with an effective amount of an antibody of the invention and/or a conjugate thereof with a therapeutic agent. CLD18 is preferably expressed on the surface of said cell.

In a further aspect the invention relates to a method of treating or preventing a disease or disorder involving cells expressing CLD18, preferably CLD18A2, comprising administering to a subject an antibody of the invention, a conjugate thereof with a therapeutic agent, or a pharmaceutical composition comprising the antibody of the invention or the conjugate thereof with a therapeutic agent. Preferably the disease or disorder is a tumor-related disease and in particular embodiments is selected from the group consisting of gastric cancer, esophageal cancer, pancreatic cancer, lung cancer, ovarian cancer, colon cancer, hepatic cancer, head-neck cancer, and cancer of the gallbladder. CLD18 is preferably expressed on the surface of said cells.

Preferably, the antibodies of the invention have the ability to discriminate CLD18-variants expressed by different cell types including cancer cells and non-malignant cells. In a particularly preferred embodiment, the antibodies of the invention have the ability to bind to CLD18A2 while they do not bind to CLD18A1, or bind to CLD18A1 with a lower specificity compared to the binding specificity to CLD18A2.

The term "binding" according to the invention preferably relates to a specific binding. "Specific binding" means that an agent such as an antibody binds stronger to a target such as an epitope for which it is specific compared to the binding to another target. An agent binds stronger to a first target compared to a second target if it binds to the first target with a dissociation constant (KD) which is lower than the dissociation constant for the second target. Preferably the dissociation constant ($K_D$) for the target to which the agent binds specifically is more than 10-fold, preferably more than 20-fold, more preferably more than 50-fold, even more preferably more than 100-fold, 200-fold, 500-fold or 1000-fold lower than the dissociation constant ($K_D$) for the target to which the agent does not bind specifically.

The antibodies of the invention mediate killing of cells expressing CLD18, preferably CLD18A2, by binding to CLD18, preferably expressed on the surface of said cells. In one embodiment, antibodies of the invention induce complement dependent cytotoxicity (CDC), e.g. at least about 20-40% CDC mediated lysis, preferably about 40-50% CDC mediated lysis, and more preferably more than 50% CDC mediated lysis of cells expressing CLD18. Such antibodies are exemplified herein by the following antibodies: 37H8, 38G5, 38H3, 39F11, 61C2, 26B5, 26D12, 28D10, 163E12, 175D10, 45C1, 125E1, ch-163E12, and ch-175D10. Alternatively or in addition to inducing CDC, antibodies of the invention may induce antibody dependent cellular cytotoxicity (ADCC) of cells expressing CLD18 in the presence of effector cells (e.g., monocytes, mononuclear cells, NK cells and PMNs). Such antibodies are exemplified herein by the following antibodies: 37G11, 37H8, 38G5, 38H3, 39F11, 43A11, 61C2, 26B5, 26D12, 28D10, 42E12, 163E12, 175D10, 45C1, and 125E1. Antibodies of the invention may have the ability to induce apoptosis of cells expressing CLD18, induce homotypic adhesion of cells expressing CLD18 and/or induce phagocytosis of cells expressing CLD18 in the presence of macrophages. The antibodies of the invention may have one or more of the above described functional properties. Preferably, antibodies of the invention induce CDC mediated lysis and ADCC mediated lysis of cells expressing CLD18 and more preferably induce ADCC mediated lysis of cells expressing CLD18 while they do not induce CDC mediated lysis of said cells. Exemplary target cells for antibodies of the present invention include, but are not limited to, cancer cells expressing CLD18, preferably CLD18A2, such as tumorigenic gastric, pancreatic, esophageal and lung cancer cells. In a particular preferred embodiment, killing of cells mediated by antibodies of the invention is CLD18A2 specific, i.e. antibodies of the invention mediate killing of cells, preferably CDC and/or ADCC mediated lysis of cells, expressing CLD18A2 but do not mediate killing of cells expressing CLD18A1 but not expressing CLD18A2. The antibodies described above may be used to mediate killing of tumor cells in the treatment or prevention of cancer such as gastric cancer, esophageal cancer, pancreatic cancer, lung cancer, ovarian cancer, colon cancer, hepatic cancer, head-neck cancer, and cancer of the gallbladder.

Antibodies of the invention may be categorized into distinct classes according to their binding properties and their ability to mediate effector function on cells expressing CLD18. The antibodies of the invention may be categorized according to their binding properties to and/or effector functions mediated on cells expressing either CLD18A1 or CLD18A2 (discrimination of CLD18 splice variants), binding properties to and/or effector functions mediated on cells expressing either glycosylated or non-glycosylated CLD18 variants (discrimination between CLD18-variants with and without N-glycosylation), binding properties to and/or effector functions mediated on either cancer cells or normal cell types (discrimination between CLD18-variants expressed by tumor cells or normal nonmalignant cells).

binding properties to CLD18-epitopes masked by the formation of tight junctions, abilities to induce aggregate formation of CLD18 on living cells, and abilities to bind a non-human CLD18 variant, particularly CLD18 variants from mice, rats, rabbits and primates.

Antibodies of the invention may have one or more of the following properties whereby reference is given to specific examples of antibodies of the invention described herein (24H5, 26B5, 26D12, 28D10, 37G11, 37H8, 38G5, 38H3, 39F11, 41C6, 42E12, 43A11, 44E10, 47D12, 61C2, 75B8, 85A3, 9E8, 19B9, 45C1, 125E1, 163E12, 166E2, 175D10, ch-43A11, ch-45C1, ch-125E1, ch-163E12, ch-166E2, ch-175D10):

a) binding to CLD18A2 as well as to CLD18A (e.g. 26D12, 28D10, 37H8, 38H3, 39F11, 61C2, and 41C6)

b) binding to CLD18A2 but not to CLD18A1 (e.g. 26B5, 37G11, 38G5, 42E12, and 43A11, 45C1, 125E1, 163E12, 166E2, 175D10, ch-43A11, ch-45C1, ch-125E1, ch-163E12, ch-166E2, ch-175D10)
c) binding to CLD18 naturally expressed by tumor cells but not to CLD18 naturally expressed by non-cancer cells or tissues such as cells of stomach and lung (e.g 26B5, 75B8, 24H5, 39F11, 45C1, 125E1, 163E12, 166E2, 175D10).
d) mediating CDC induced killing of cells, which express CLD18A2 but not of cells which express CLD18A (e.g. 26D12, 28D10, 37H8, and 39F11, 163E12, ch-125E1, ch-163E12, ch-175D10)
e) mediating ADCC induced killing of cells expressing CLD18 (e.g. 26B5, 37G11, 37H8, 38G5, 38H3, 39F1, 43A11, 47D12, and 61C2, ch-163E12, ch-175D10)
f) mediating ADCC induced killing but not CDC mediated killing of cells expressing CLD18 (e.g. 37G11, 42E12, and 43A11)
g) mediating ADCC induced killing and CDC induced killing of cells expressing CLD18A2 (e.g. 37H8, 38H3, 39F11, ch-163E12, ch-175D10).

As exemplified herein, antibodies of the invention further encompasses molecules, which
a) bind to differentiated cells of normal stomach, but not to stem cells of stomach (e.g. 39F11)
b) do not bind to normal gastric tissue as well as other normal organs but exclusively to cancer cells (e.g. 26B5)
c) bind to an epitope encompassing a non-glycosylated Asn at position 116 of CLD18
d) which bind to human as well as to mouse CLD18 allowing to thoroughly perform preclinical toxicity studies in mice.

Antibodies of the invention may be derived from different species, including but not limited to mouse, rat, rabbit, guinea pig and human. Antibodies of the invention also include chimeric molecules in which an antibody constant region derived from one species, preferably human, is combined with the antigen binding site derived from another species. Moreover antibodies of the invention include humanized molecules in which the antigen binding sites of an antibody derived from a non-human species are combined with constant and framework regions of human origin.

Antibodies of the invention include polyclonal and monoclonal antibodies and include IgG2a (e.g. IgG2a, κ, λ), IgG2b (e.g. IgG2b, κ, λ), IgG3 (e.g. IgG3, κ, λ) and IgM antibodies. However, other antibody isotypes are also encompassed by the invention, including IgG1, IgA1, IgA2, secretory IgA, IgD, and IgE antibodies. The antibodies can be whole antibodies or antigen-binding fragments thereof including, for example, Fab, $F(ab')_2$, Fv, single chain Fv fragments or bispecific antibodies. Furthermore, the antigen-binding fragments include binding-domain immunoglobulin fusion proteins comprising (i) a binding domain polypeptide (such as a heavy chain variable region or a light chain variable region) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. Such binding-domain immunoglobulin fusion proteins are further disclosed in US2003/0118592 and US 2003/0133939.

Antibodies of the present invention preferably dissociate from CLD18 with a dissociation equilibrium constant (KD) of approximately 1-100 nM or less. Preferably, antibodies of the invention do not cross-react with related cell-surface antigens and thus do not inhibit their function.

In preferred embodiments, antibodies of the present invention can be characterized by one or more of the following properties:
a) specificity for CLD18, in particular specificity for CLD18A2;
b) a binding affinity to CLD18, in particular CLD18A2, of about 100 nM or less, preferably, about 5-10 nM or less and, more preferably, about 1-3 nM or less,
c) the ability to mediate a high level of CDC on either CD55/59 negative or CD55/59 positive cells;
d) the ability to inhibit the growth of cells which express CLD18;
e) the ability to induce apoptosis of cells which express CLD18;
f) the ability to induce homotypic adhesion of cells which express CLD18;
g) the ability to induce ADCC of cells which express CLD18 in the presence of effector cells;
h) the ability to prolong survival of a subject having tumor cells which express CLD18;
i) the ability to deplete cells which express CLD18;
j) the ability to deplete cells which express low levels of CLD18 and/or
k) the ability to aggregate CLD18 on the surface of living cells The anti-CLD18 antibodies of the present invention can be derivatized, linked to or co-expressed to other binding specificities. In a particular embodiment, the invention provides a bispecific or multispecific molecule comprising at least one first binding specificity for CLD18 (e.g., an anti-CLD18 antibody or mimetic thereof), and a second binding specificity for a effector cell, such as a binding specificity for an Fc receptor (e.g., a Fc-gamma receptor, such as Fc-gamma RI, or any other Fc receptor) or a T cell receptor, e.g., CD3.

Accordingly, the present invention includes bispecific and multispecific molecules that bind to both CLD18 and to an Fc receptor or a T cell receptor, e.g. CD3. Examples of Fc receptors are IgG receptor, Fc-gamma receptor (FcγR), such as FcγRI (CD64), FcγRII (CD32), and FcγRIII (CD16). Other Fc receptors, such as IgA receptors (e.g., FcαRI), also can be targeted. The Fc receptor is preferably located on the surface of an effector cell, e.g., a monocyte, macrophage or an activated mononuclear cell. In a preferred embodiment, the bispecific and multispecific molecules bind to an Fc receptor at a site which is distinct from the immunoglobulin Fc (e.g., IgG or IgA) binding site of the receptor. Therefore, the binding of the bispecific and multispecific molecules is not blocked by physiological levels of immunoglobulins.

In yet another aspect, anti-CLD18 antibodies of the invention are derivatized, linked to or co-expressed with another functional molecule, e.g., another peptide or protein (e.g., a Fab' fragment). For example, an antibody of the invention can be functionally linked (e.g., by chemical coupling, genetic fusion, noncovalent association or otherwise) to one or more other molecular entities, such as another antibody (e.g. to produce a bispecific or a multispecific antibody), a cytotoxin, cellular ligand or antigen (e.g. to produce an immunoconjugate, such as an immunotoxin). An antibody of the present invention can be linked to other therapeutic moieties, e.g., a radioisotope, a small molecule anti-cancer drug, a recombinant cytokine or chemokine. Accordingly, the present invention encompasses a large variety of antibody conjugates, bispecific and multispecific molecules, and fusion proteins, all of which bind to CLD18 expressing cells and which can be used to target other molecules to such cells.

In still another aspect, the invention provides compositions, e.g., pharmaceutical and diagnostic compositions/kits, comprising a pharmaceutically acceptable carrier formulated along with one or a combination of antibodies of the invention. In a particular embodiment, the composition includes a combination of antibodies which bind to distinct epitopes or which possess distinct functional characteristics, such as inducing CDC and/or ADCC and inducing apoptosis. In this embodiment of the invention, antibodies may be used in combination, e. g., as a pharmaceutical composition comprising two or more anti-CLD18 monoclonal antibodies. For example, anti-CLD18 antibodies having different but complementary activities can be combined in a single therapy to achieve a desired therapeutic effect. In a preferred embodiment, the composition includes an anti-CLD18 antibody that mediates CDC combined with another anti-CLD18 antibody that induces apoptosis. In another embodiment, the composition includes an anti-CLD18 antibody that mediates highly effective killing of target cells in the presence of effector cells, combined with another anti-CLD18 antibody that inhibits the growth of cells expressing CLD18.

The present invention also includes the simultaneous or sequential administration of two or more anti-CLD18 antibodies of the invention, wherein at least one of said antibodies is a chimeric anti-CLD18 antibody and at least one further antibody is a human anti-CLD18 antibody, the antibodies binding to the same or different epitopes of CLD18. Preferably, a chimeric CLD18 antibody of the invention is administered first followed by the administration of a human anti-CLD18 antibody of the invention, wherein the human anti-CLD18 antibody is preferably administered for an extended period of time, i.e. as maintenance therapy.

Antibodies, immunoconjugates, bispecific and multispecific molecules and compositions of the present invention can be used in a variety of methods for inhibiting growth of cells expressing CLD18, in particular CLD18A2 and/or selectively killing cells expressing CLD18, in particular CLD18A2 by contacting the cells with an effective amount of the antibody, immunoconjugate, bispecific/multispecific molecule or composition, such that the growth of the cell is inhibited and/or the cell is killed. In one embodiment, the method includes killing of the cell expressing CLD18, optionally in the presence of effector cells, for example, by CDC, apoptosis, ADCC, phagocytosis, or by a combination of two or more of these mechanisms. Cells expressing CLD18 which can be inhibited or killed using the antibodies of the invention include cancer cells such as tumorigenic stomach, pancreatic, esophageal, lung, ovarian, colon, hepatic, head-neck, and gallbladder cells.

Accordingly, antibodies of the present invention can be used to treat and/or prevent a variety of diseases involving cells expressing CLD18 by administering the antibodies to patients suffering from such diseases. Exemplary diseases that can be treated (e.g., ameliorated) or prevented include, but are not limited to, tumorigenic diseases. Examples of tumorigenic diseases, which can be treated and/or prevented include gastric cancer, pancreatic cancer, esophageal cancer, lung cancer, ovarian cancer, colorectal cancer, hepatic cancer, head-neck cancer, and cancer of the gallbladder.

In a particular embodiment of the invention, the subject being administered the antibody is additionally treated with a chemotherapeutic agent, radiation, or an agent that modulates, e.g., enhances or inhibits, the expression or activity of an Fc receptor, e.g. an Fc-gamma receptor, such as a cytokine. Typical cytokines for administration during treatment include granulocyte colony-stimulating factor (G-CSF), granulocyte-macrophage colony-stimulating factor (GM-CSF), interferon-γ (IFN-γ), and tumor necrosis factor (TNF). Typical therapeutic agents include, among others, anti-neoplastic agents such as doxorubicin, cisplatin, taxotere, 5-fluoruracil, methotrexat, gemzitabin and cyclophosphamide.

In yet another aspect, the invention relates to an immunization strategy to immunize non-human animals such as mice with human CLD18 or a peptide fragment thereof, preferably CLD18A2 or a peptide fragment thereof to obtain antibodies. Preferred peptides for immunization are those selected from the group consisting of SEQ ID NO:2, 4, 6, 16, 18, 20-23, and 26-31. Accordingly, in preferred embodiments, the antibodies of the invention are those obtained by immunization using peptides selected from the group consisting of SEQ ID NO:2, 4, 6, 16, 18, 20-23, and 26-31. Analogously, antibodies to CLD18 can be generated in a transgenic non-human animal, such as a transgenic mouse. The transgenic non-human animal may be a transgenic mouse having a genome comprising a heavy chain transgene and a light chain transgene encoding all or a portion of an antibody.

Wildtype as well as transgenic non-human animals can be immunized with a purified or enriched preparation of CLD18 antigen and/or nucleic acids and/or cells expressing CLD18 or a peptide fragment thereof. Preferably, the non-human animal, is capable of producing multiple isotypes of human monoclonal antibodies to CLD18 (e.g., IgG, IgA and/or IgM) by undergoing V-D-J recombination and isotype switching. Isotype switching may occur by e.g., classical or non-classical isotype switching.

Accordingly, in yet another aspect, the invention provides isolated B cells from a non-human animal as described above. The isolated B cells can then be immortalized by fusion to an immortalized cell to provide a source (e.g., a hybridoma) of antibodies of the invention. Such hybridomas (i.e., which produce antibodies of the invention) are also included within the scope of the invention.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as *E. coli*, and fungi, such as yeast. Alternatively, they can be produced recombinantly in a transgenic non-human animal or plant.

Preferred hybridoma cells for producing antibodies of the invention are those sequenced or deposited at the DSMZ (Mascheroder Weg 1b, 31824 Braunschweig, Germany; new address: Inhoffenstr. 7B, 31824 Braunschweig, Germany) having the following designations and accession numbers:

a. 182-D1106-055, accession no. DSM ACC2737, deposited on Oct. 19, 2005
b. 182-D1106-056, accession no. DSM ACC2738, deposited on Oct. 19, 2005
c. 182-D1106-057, accession no. DSM ACC2739, deposited on Oct. 19, 2005
d. 182-D1106-058, accession no. DSM ACC2740, deposited on Oct. 19, 2005
e. 182-D1106-059, accession no. DSM ACC2741, deposited on Oct. 19, 2005
f. 182-D1106-062, accession no. DSM ACC2742, deposited on Oct. 19, 2005,
g. 182-D1106-067, accession no. DSM ACC2743, deposited on Oct. 19, 2005
h. 182-D758-035, accession no. DSM ACC2745, deposited on Nov. 17, 2005
i. 182-D758-036, accession no. DSM ACC2746, deposited on Nov. 17, 2005 j. 182-D758-040, accession no. DSM ACC2747, deposited on Nov. 17, 2005
k. 182-D1106-061, accession no. DSM ACC2748, deposited on Nov. 17, 2005
l. 182-D1106-279, accession no. DSM ACC2808, deposited on Oct. 26, 2006
m. 182-D1106-294, accession no. DSM ACC2809, deposited on Oct. 26, 2006,
n. 182-D1106-362, accession no. DSM ACC2810, deposited on Oct. 26, 2006.

Preferred antibodies of the invention are those produced by and obtainable from the above-described hybridomas; i.e. 37G11 in the case of 182-D1106-055, 37H8 in the case of 182-D1106-056, 38G5 in the case of 182-D1106-057, 38H3 in the case of 182-D1106-058, 39F11 in the case of 182-D1106-059, 43A11 in the case of 182-D1106-062, 61C2 in the case of 182-D1106-067, 26B5 in the case of 182-D758-035, 26D12 in the case of 182-D758-036, 28D10 in the case of 182-D758-040, 42E12 in the case of 182-D1106-061, 125E1 in the case of 182-D1106-279, 163E12 in the case of 182-D1106-294, and 175D10 in the case of 182-D1106-362; and the chimerized and humanized forms thereof.

In preferred embodiments, antibodies, in particular chimerised forms of antibodies according to the invention include antibodies comprising a heavy chain constant region (CH) comprising an amino acid sequence derived from a human heavy chain constant region such as the amino acid sequence represented by SEQ ID NO: 46 or 150 or a fragment thereof. In further preferred embodiments, antibodies, in particular chimerised forms of antibodies according to the invention include antibodies comprising a light chain constant region (CL) comprising an amino acid sequence derived from a human light chain constant region such as the amino acid sequence represented by SEQ ID NO: 41 or 148 or a fragment thereof. In a particular preferred embodiment, antibodies, in particular chimerised forms of antibodies according to the invention include antibodies which comprise a CH comprising an amino acid sequence derived from a human CH such as the amino acid sequence represented by SEQ ID NO: 46 or 150 or a fragment thereof and which comprise a CL comprising an amino acid sequence derived from a human CL such as the amino acid sequence represented by SEQ ID NO: 41 or 148 or a fragment thereof.

A CH comprising the amino acid sequence represented by SEQ ID NO: 46 may be encoded by a nucleic acid comprising the nucleic acid sequence represented by SEQ ID NO: 45. A CH comprising the amino acid sequence represented by SEQ ID NO: 150 may be encoded by a nucleic acid comprising the nucleic acid sequence represented by SEQ ID NO: 149. A CL comprising the amino acid sequence represented by SEQ ID NO: 41 may be encoded by a nucleic acid comprising the nucleic acid sequence represented by SEQ ID NO: 40. A CL comprising the amino acid sequence represented by SEQ ID NO: 148 may be encoded by a nucleic acid comprising the nucleic acid sequence represented by SEQ ID NO: 147.

In certain preferred embodiments, chimerised forms of antibodies include antibodies comprising a heavy chain comprising an amino acid sequence selected from the group consisting of SEQ ID NO: 115, 116, 117, 118, 119, 120, and a fragment thereof and/or comprising a light chain comprising an amino acid sequence selected from the group consisting of SEQ ID NO: 121, 122, 123, 124, 125, 126, 127, 128, 129, and a fragment thereof.

In certain preferred embodiments, chimerised forms of antibodies include antibodies comprising a combination of heavy chains and light chains selected from the following possibilities (i) to (ix):

(i) the heavy chain comprises an amino acid sequence represented by SEQ ID NO: 115 or a fragment thereof and the light chain comprises an amino acid sequence represented by SEQ ID NO: 122 or a fragment thereof,
(ii) the heavy chain comprises an amino acid sequence represented by SEQ ID NO: 116 or a fragment thereof and the light chain comprises an amino acid sequence represented by SEQ ID NO: 121 or a fragment thereof,
(iii) the heavy chain comprises an amino acid sequence represented by SEQ ID NO: 117 or a fragment thereof and the light chain comprises an amino acid sequence represented by SEQ ID NO: 123 or a fragment thereof,
(iv) the heavy chain comprises an amino acid sequence represented by SEQ ID NO: 119 or a fragment thereof and the light chain comprises an amino acid sequence represented by SEQ ID NO: 126 or a fragment thereof,
(v) the heavy chain comprises an amino acid sequence represented by SEQ ID NO: 118 or a fragment thereof and the light chain comprises an amino acid sequence represented by SEQ ID NO: 125 or a fragment thereof,
(vi) the heavy chain comprises an amino acid sequence represented by SEQ ID NO: 120 or a fragment thereof and the light chain comprises an amino acid sequence represented by SEQ ID NO: 124 or a fragment thereof,
(vii) the heavy chain comprises an amino acid sequence represented by SEQ ID NO: 120 or a fragment thereof and the light chain comprises an amino acid sequence represented by SEQ ID NO: 127 or a fragment thereof,
(viii) the heavy chain comprises an amino acid sequence represented by SEQ ID NO: 120 or a fragment thereof and the light chain comprises an amino acid sequence represented by SEQ ID NO: 128 or a fragment thereof, and
(ix) the heavy chain comprises an amino acid sequence represented by SEQ ID NO: 120 or a fragment thereof and the light chain comprises an amino acid sequence represented by SEQ ID NO: 129 or a fragment thereof.

"Fragment" or "fragment of an amino acid sequence" as used above relates to a part of an antibody sequence, i.e. a sequence which represents the antibody sequence shortened at the N- and/or C-terminus, which when it replaces said antibody sequence in an antibody retains binding of said antibody to CLD18 and preferably functions of said antibody as described herein, e.g. CDC mediated lysis or ADCC mediated lysis. Preferably, a fragment of an amino acid sequence comprises at least 80%, preferably at least 90%, 95%, 96%, 97%, 98%, or 99% of the amino acid residues from said amino acid sequence. A fragment of an amino acid sequence selected from the group consisting of SEQ ID NO: 115, 116, 117, 118, 119, 120, 121, 122, 123, 124, 125, 126, 127, 128, and 129 preferably relates to said sequence wherein 17, 18, 19, 20, 21, 22 or 23 amino acids at the N-terminus are removed. Fragments of amino acid sequences described herein may be encoded by respective fragments of nucleic acid sequences encoding said amino acid sequences.

A heavy chain comprising an amino acid sequence represented by SEQ ID NO: 115 may be encoded by a nucleic acid comprising the nucleic acid sequence represented by SEQ ID NO: 100. A heavy chain comprising an amino acid sequence represented by SEQ ID NO: 116 may be encoded by a nucleic acid comprising the nucleic acid sequence represented by SEQ ID NO: 101. A heavy chain comprising an amino acid sequence represented by SEQ ID NO: 117 may be encoded by a nucleic acid comprising the nucleic acid sequence represented by SEQ ID NO: 102. A heavy chain comprising an amino acid sequence represented by SEQ ID NO: 119 may be encoded by a nucleic acid comprising the nucleic acid sequence represented by SEQ ID NO: 104. A heavy chain comprising an amino acid sequence represented by SEQ ID NO: 118 may be encoded by a nucleic acid comprising the nucleic acid sequence represented by SEQ ID NO: 103. A heavy chain comprising an amino acid sequence represented by SEQ ID NO: 120 may be encoded by a nucleic acid comprising the nucleic acid sequence represented by SEQ ID NO: 105.

A light chain comprising an amino acid sequence represented by SEQ ID NO: 122 may be encoded by a nucleic acid comprising the nucleic acid sequence represented by SEQ ID NO: 107. A light chain comprising an amino acid sequence represented by SEQ ID NO: 121 may be encoded by a nucleic acid comprising the nucleic acid sequence represented by SEQ ID NO: 106. A light chain comprising an amino acid sequence represented by SEQ ID NO: 123 may be encoded by a nucleic acid comprising the nucleic acid sequence represented by SEQ ID NO: 108. A light chain comprising an amino acid sequence represented by SEQ ID NO: 126 may be encoded by a nucleic acid comprising the nucleic acid sequence represented by SEQ ID NO: 111. A light chain comprising an amino acid sequence represented by SEQ ID NO: 125 may be encoded by a nucleic acid comprising the nucleic acid sequence represented by SEQ ID NO: 110. A light chain comprising an amino acid sequence represented by SEQ ID NO: 124 may be encoded by a nucleic acid comprising the nucleic acid sequence represented by SEQ ID NO: 109. A light chain comprising an amino acid sequence represented by SEQ ID NO: 127 may be encoded by a nucleic acid comprising the nucleic acid sequence represented by SEQ ID NO: 112. A light chain comprising an amino acid sequence represented by SEQ ID NO: 128 may be encoded by a nucleic acid comprising the nucleic acid sequence represented by SEQ ID NO: 113. A light chain comprising an amino acid sequence represented by SEQ ID NO: 129 may be encoded by a nucleic acid comprising the nucleic acid sequence represented by SEQ ID NO: 114.

In a preferred embodiment, an antibody of the invention comprises a heavy chain variable region (VH) comprising an amino acid sequence selected from the group consisting of SEQ ID NO: 132, 133, 134, 135, 136, 137, and a fragment thereof.

In a preferred embodiment, an antibody of the invention comprises a light chain variable region (VL) comprising an amino acid sequence selected from the group consisting of SEQ ID NO: 138, 139, 140, 141, 142, 143, 144, 145, 146, and a fragment thereof.

In certain preferred embodiments, an antibody of the invention comprises a combination of heavy chain variable region (VH) and light chain variable region (VL) selected from the following possibilities (i) to (ix):

(i) the VH comprises an amino acid sequence represented by SEQ ID NO: 132 or a fragment thereof and the VL comprises an amino acid sequence represented by SEQ ID NO: 139 or a fragment thereof, (ii) the VH comprises an amino acid sequence represented by SEQ ID NO: 133 or a fragment thereof and the VL comprises an amino acid sequence represented by SEQ ID NO: 138 or a fragment thereof, (iii) the VH comprises an amino acid sequence represented by SEQ ID NO: 134 or a fragment thereof and the VL comprises an amino acid sequence represented by SEQ ID NO: 140 or a fragment thereof, (iv) the VH comprises an amino acid sequence represented by SEQ ID NO: 136 or a fragment thereof and the VL comprises an amino acid sequence represented by SEQ ID NO: 143 or a fragment thereof, (v) the VH comprises an amino acid sequence represented by SEQ ID NO: 135 or a fragment thereof and the VL comprises an amino acid sequence represented by SEQ ID NO: 142 or a fragment thereof, (vi) the VH comprises an amino acid sequence represented by SEQ ID NO: 137 or a fragment thereof and the VL comprises an amino acid sequence represented by SEQ ID NO: 141 or a fragment thereof, (vii) the VH comprises an amino acid sequence represented by SEQ ID NO: 137 or a fragment thereof and the VL comprises an amino acid sequence represented by SEQ ID NO: 144 or a fragment thereof, (viii) the VH comprises an amino acid sequence represented by SEQ ID NO: 137 or a fragment thereof and the VL comprises an amino acid sequence represented by SEQ ID NO: 145 or a fragment thereof, (ix) the VH comprises an amino acid sequence represented by SEQ ID NO: 137 or a fragment thereof and the VL comprises an amino acid sequence represented by SEQ ID NO: 146 or a fragment thereof.

A VH comprising an amino acid sequence represented by SEQ ID NO: 132 may be encoded by a nucleic acid comprising the nucleic acid sequence represented by SEQ ID NO: 55. A VH comprising an amino acid sequence represented by SEQ ID NO: 133 may be encoded by a nucleic acid comprising the nucleic acid sequence represented by SEQ ID NO: 56. A VH comprising an amino acid sequence represented by SEQ ID NO: 134 may be encoded by a nucleic acid comprising the nucleic acid sequence represented by SEQ ID NO: 57. A VH comprising an amino acid sequence represented by SEQ ID NO: 136 may be encoded by a nucleic acid comprising the nucleic acid sequence represented by SEQ ID NO: 59. A VH comprising an amino acid sequence represented by SEQ ID NO: 135 may be encoded by a nucleic acid comprising the nucleic acid sequence represented by SEQ ID NO: 58. A VH comprising an amino acid sequence represented by SEQ ID NO: 137 may be encoded by a nucleic acid comprising the nucleic acid sequence represented by SEQ ID NO: 60.

A VL comprising an amino acid sequence represented by SEQ ID NO: 139 may be encoded by a nucleic acid comprising the nucleic acid sequence represented by SEQ ID NO: 62. A VL comprising an amino acid sequence represented by SEQ ID NO: 138 may be encoded by a nucleic acid comprising the nucleic acid sequence represented by SEQ ID NO: 61. A VL comprising an amino acid sequence represented by SEQ ID NO: 140 may be encoded by a nucleic acid comprising the nucleic acid sequence represented by SEQ ID NO: 63. A VL comprising an amino acid sequence represented by SEQ ID NO: 143 may be encoded by a nucleic acid comprising the nucleic acid sequence represented by SEQ ID NO: 66. A VL comprising an amino acid sequence represented by SEQ ID NO: 142 may be encoded by a nucleic acid comprising the nucleic acid sequence represented by SEQ ID NO: 65. A VL comprising an amino acid sequence represented by SEQ ID NO: 141 may be encoded by a nucleic acid comprising the nucleic acid sequence represented by SEQ ID NO: 64. A VL comprising an amino acid sequence represented by SEQ ID NO: 144 may be encoded by a nucleic acid comprising the nucleic acid sequence represented by SEQ ID NO: 67. A VL comprising an amino acid sequence represented by SEQ ID NO: 145 may be encoded by a nucleic acid comprising the nucleic acid sequence represented by SEQ ID NO: 68. A VL comprising an amino acid sequence represented by SEQ ID NO: 146 may be encoded by a nucleic acid comprising the nucleic acid sequence represented by SEQ ID NO: 69.

In a preferred embodiment, an antibody of the invention comprises a VH comprising a set of complementarity-determining regions CDR1, CDR2 and CDR3 selected from the following embodiments (i) to (vi):

(i) CDR: positions 45-52 of SEQ ID NO: 115, CDR2: positions 70-77 of SEQ ID NO: 115, CDR3: positions 116-125 of SEQ ID NO: 115, (ii) CDR1: positions 45-52 of SEQ ID NO: 116, CDR2: positions 70-77 of SEQ ID NO: 116, CDR3: positions 116-126 of SEQ ID NO: 116, (iii) CDR1: positions 45-52 of SEQ ID NO: 117, CDR2: positions 70-77 of SEQ ID NO: 117, CDR3: positions 116-124 of SEQ ID NO: 117, (iv) CDR1: positions 45-52 of SEQ ID NO: 118, CDR2: positions 70-77 of SEQ ID NO: 118, CDR3: positions 116-126 of SEQ ID NO: 118, (v) CDR1: positions 44-51 of SEQ ID NO: 119, CDR2: positions 69-76 of SEQ ID NO: 119, CDR3: positions 115-125 of SEQ ID NO: 119, and (vi) CDR1: positions 45-53 of SEQ ID NO: 120, CDR2: positions 71-78 of SEQ ID NO: 120, CDR3: positions 117-128 of SEQ ID NO: 120.

In a preferred embodiment, an antibody of the invention comprises a VL comprising a set of complementarity-determining regions CDR1, CDR2 and CDR3 selected from the following embodiments (i) to (ix):

(i) CDR1: positions 47-58 of SEQ ID NO: 121, CDR2: positions 76-78 of SEQ ID NO: 121, CDR3: positions 115-123 of SEQ ID NO: 121, (ii) CDR1: positions 49-53 of SEQ ID NO: 122, CDR2: positions 71-73 of SEQ ID NO: 122, CDR3: positions 110-118 of SEQ ID NO: 122, (iii) CDR1: positions 47-52 of SEQ ID NO: 123, CDR2: positions 70-72 of SEQ ID NO: 123, CDR3: positions 109-117 of SEQ ID NO: 123, (iv) CDR1: positions 47-58 of SEQ ID NO: 124, CDR2: positions 76-78 of SEQ ID NO: 124, CDR3: positions 115-123 of SEQ ID NO: 124, (v) CDR1: positions 47-58 of SEQ ID NO: 125, CDR2: positions 76-78 of SEQ ID NO: 125, CDR3: positions 115-123 of SEQ ID NO: 125, (vi) CDR1: positions 47-58 of SEQ ID NO: 126, CDR2: positions 76-78 of SEQ ID NO: 126, CDR3: positions 115-122 of SEQ ID NO: 126, (vii) CDR1: positions 47-58 of SEQ ID NO: 127, CDR2: positions 76-78 of SEQ ID NO: 127, CDR3: positions 115-123 of SEQ ID NO: 127, (viii) CDR1: positions 47-58 of SEQ ID NO: 128, CDR2: positions 76-78 of SEQ ID NO: 128, CDR3: positions 115-123 of SEQ ID NO: 128, and (ix) CDR1: positions 47-52 of SEQ ID NO: 129, CDR2: positions 70-72 of SEQ ID NO: 129, CDR3: positions 109-117 of SEQ ID NO: 129.

In a preferred embodiment, an antibody of the invention comprises a combination of VH and VL each comprising a set of complementarity-determining regions CDR1, CDR2 and CDR3 selected from the following embodiments (i) to (ix):

(i) VH: CDR1: positions 45-52 of SEQ ID NO: 115, CDR2: positions 70-77 of SEQ ID NO: 115, CDR3: positions 116-125 of SEQ ID NO: 115, VL: CDR1: positions 49-53 of SEQ ID NO: 122, CDR2: positions 71-73 of SEQ ID NO: 122, CDR3: positions 110-118 of SEQ ID NO: 122, (ii) VH: CDR1: positions 45-52 of SEQ ID NO: 116, CDR2: positions 70-77 of SEQ ID NO: 116, CDR3: positions 116-126 of SEQ ID NO: 116, VL: CDR1: positions 47-58 of SEQ ID NO: 121, CDR2: positions 76-78 of SEQ ID NO: 121, CDR3: positions 115-123 of SEQ ID NO: 121, (iii) VH: CDR1: positions 45-52 of SEQ ID NO: 117, CDR2: positions 70-77 of SEQ ID NO: 117, CDR3: positions 116-124 of SEQ ID NO: 117, VL: CDR1: positions 47-52 of SEQ ID NO: 123, CDR2: positions 70-72 of SEQ ID NO: 123, CDR3: positions 109-117 of SEQ ID NO: 123, (iv) VH: CDR1: positions 44-51 of SEQ ID NO: 119, CDR2: positions 69-76 of SEQ ID NO: 119, CDR3: positions 115-125 of SEQ ID NO: 119, VL: CDR1: positions 47-58 of SEQ ID NO: 126, CDR2: positions 76-78 of SEQ ID NO: 126, CDR3: positions 115-122 of SEQ ID NO: 126, (v) VH: CDR1: positions 45-52 of SEQ ID NO: 118, CDR2: positions 70-77 of SEQ ID NO: 118, CDR3: positions 116-126 of SEQ ID NO: 118. VL: CDR1: positions 47-58 of SEQ ID NO: 125, CDR2: positions 76-78 of SEQ ID NO: 125, CDR3: positions 115-123 of SEQ ID NO: 125, (vi) VH: CDR1: positions 45-53 of SEQ ID NO: 120, CDR2: positions 71-78 of SEQ ID NO: 120, CDR3: positions 117-128 of SEQ ID NO: 120, VL: CDR1: positions 47-58 of SEQ ID NO: 124, CDR2: positions 76-78 of SEQ ID NO: 124, CDR3: positions 115-123 of SEQ ID NO: 124, (vii) VH: CDR1: positions 45-53 of SEQ ID NO: 120, CDR2: positions 71-78 of SEQ ID NO: 120, CDR3: positions 117-128 of SEQ ID NO: 120, VL: CDR1: positions 47-58 of SEQ ID NO: 127, CDR2: positions 76-78 of SEQ ID NO: 127, CDR3: positions 115-123 of SEQ ID NO: 127, (viii) VH: CDR1: positions 45-53 of SEQ ID NO: 120, CDR2: positions 71-78 of SEQ ID NO: 120, CDR3: positions 117-128 of SEQ ID NO: 120, VL: CDR1: positions 47-58 of SEQ ID NO: 128, CDR2: positions 76-78 of SEQ ID NO: 128, CDR3: positions 115-123 of SEQ ID NO: 128, and (ix) VH: CDR1: positions 45-53 of SEQ ID NO: 120, CDR2: positions 71-78 of SEQ ID NO: 120, CDR3: positions 117-128 of SEQ ID NO: 120, VL: CDR1: positions 47-52 of SEQ ID NO: 129, CDR2: positions 70-72 of SEQ ID NO: 129, CDR3: positions 109-117 of SEQ ID NO: 129.

In further preferred embodiments, an antibody of the invention preferably comprises one or more of the complementarity-determining regions (CDRs), preferably at least the CDR3 variable region, of the heavy chain variable region (VH) and/or of the light chain variable region (VL) of a monoclonal antibody against CLD18, preferably of a monoclonal antibody against CLD18 described herein, and preferably comprises one or more of the complementarity-determining regions (CDRs), preferably at least the CDR3 variable region, of the heavy chain variable regions (VH) and/or light chain variable regions (VL) described herein. In one embodiment said one or more of the complementarity-determining regions (CDRs) are selected from a set of complementarity-determining regions CDR1, CDR2 and CDR3 described herein. In a particularly preferred embodiment, an antibody of the invention preferably comprises the complementarity-determining regions CDR1, CDR2 and CDR3 of the heavy chain variable region (VH) and/or of the light chain variable region (VL) of a monoclonal antibody against CLD18, preferably of a monoclonal antibody against CLD18 described herein, and preferably comprises the complementarity-determining regions CDR1, CDR2 and CDR3 of the heavy chain variable regions (VH) and/or light chain variable regions (VL) described herein.

In one embodiment an antibody of the invention comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of antibodies of the present invention made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment an antibody of the invention comprising one or more CDRs, a set of CDRs or a combination of sets of CDRs as described herein comprises said CDRs in a human antibody framework.

Reference herein to an antibody comprising with respect to the heavy chain thereof a particular chain, or a particular region or sequence preferably relates to the situation wherein all heavy chains of said antibody comprise said particular chain, region or sequence. This applies correspondingly to the light chain of an antibody.

The present invention also relates to nucleic acids comprising genes or nucleic acid sequences encoding antibodies or parts thereof, e.g. an antibody chain, as described herein. The nucleic acids may be comprised in a vector, e.g., a plasmid, cosmid, virus, bacteriophage or another vector used e.g. conventionally in genetic engineering. The vector may comprise further genes such as marker genes which allow for the selection of the vector in a suitable host cell and under suitable conditions. Furthermore, the vector may comprise expression control elements allowing proper expression of the coding regions in suitable hosts. Such control elements are known to the artisan and may include a promoter, a splice cassette, and a translation initiation codon.

Preferably, the nucleic acid of the invention is operatively attached to the above expression control sequences allowing expression in eukaryotic or prokaryotic cells. Control elements ensuring expression in eukaryotic or prokaryotic cells are well known to those skilled in the art.

Methods for construction of nucleic acid molecules according to the present invention, for construction of vectors comprising the above nucleic acid molecules, for introduction of the vectors into appropriately chosen host cells, for causing or achieving the expression are well-known in the art.

A further aspect of the present invention relates to a host cell comprising a nucleic acid or vector as disclosed herein.

Other features and advantages of the instant invention will be apparent from the following detailed description and claims.

BRIEF DESCRIPTION OF THE DRAWINGS

As shown in FIG. 17A, specific protein expression was detected in normal stomach mucosa, whereas all other tested normal tissue were negative. As shown in FIG. 17B, strong CLD18A2 expression was found in stomach and lung carcinomas.

DETAILED DESCRIPTION OF THE INVENTION

Figure 1:
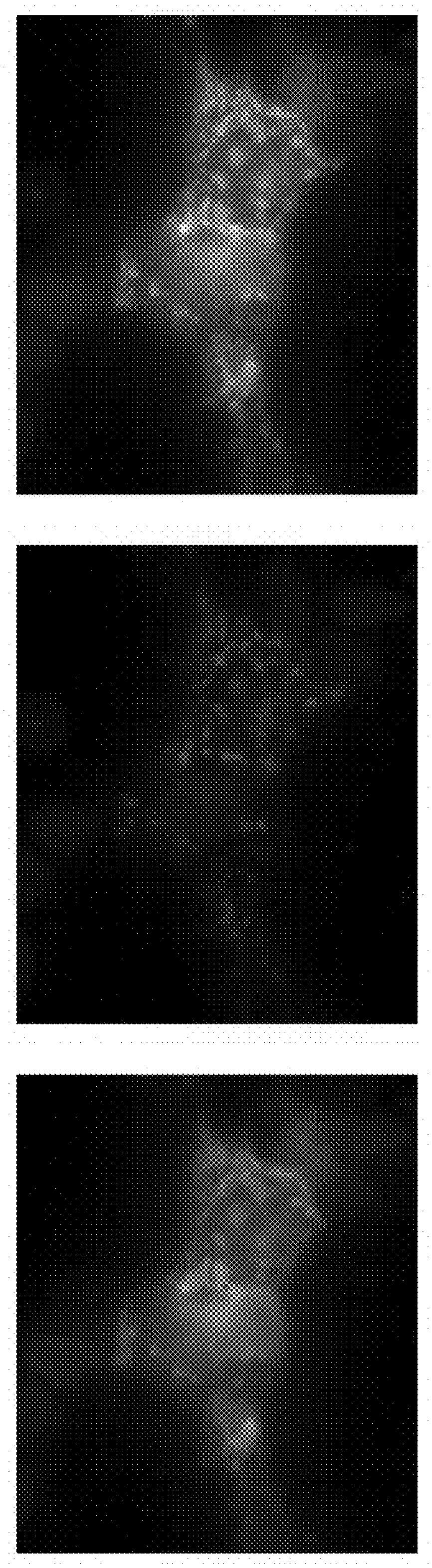
FIG. 1 shows an immunofluorescence analysis of HEK293 cells transfected with CLD18A2 coupled to a green fluorochrome and reacted with mouse serum after DNA immunisation with SEQ ID NO: 15 fused to a helper epitope.

The antibodies described herein may be isolated monoclonal antibodies which specifically bind to an epitope present on CLD18. Isolated monoclonal antibodies encompassed by the present invention include IgA, IgG1-4, IgE, IgM, and IgD antibodies. In one embodiment the antibody is an IgG1 antibody, more particularly an IgG1, kappa or IgG1, lambda isotype. In another embodiment the antibody is an IgG3 antibody, more particularly an IgG3, kappa or IgG3, lambda isotype. In yet another embodiment the antibody is an IgG4 antibody, more particularly an IgG4, kappa or IgG4, lambda isotype. In still another embodiment the antibody is an IgA1 or IgA2 antibody. In still another embodiment the antibody is an IgM antibody.

In one embodiment the invention relates to antibodies which specifically bind to cells expressing CLD18, and preferably (i) bind to cells expressing CLD18A2, and (ii) do not bind to cells not expressing CLD18A2 but expressing CLD18A1. The antibodies of the invention preferably (i) mediate killing of cells expressing CLD18A2, and (ii) do not mediate killing of cells not expressing CLD18A2 but expressing CLD18A1.

In another embodiment, the invention relates to antibodies which (i) bind to tumor cells expressing CLD18, (ii) do not bind to CLD18 expressing cells of normal stomach mucosa, and/or (iii) do not bind to CLD18 expressing cells of non-cancer lung tissue.

The invention also includes antibodies which (i) mediate killing of tumor cells expressing CLD18, (ii) do not mediate killing of CLD18 expressing cells of normal stomach mucosa, and/or (iii) do not mediate killing of CLD18 expressing cells of non-cancer lung tissue.

In particular embodiments, the antibodies of the invention (i) bind to an epitope on CLD18A2 which is not present on CLD18A1, preferably SEQ ID NO: 21, 22, and 23, (ii) bind to an epitope localized on the CLD18A2-loop1, preferably SEQ ID NO: 28, (iii) bind to an epitope localized on the CLD18A2-loop2, preferably SEQ ID NO: 30, (iv) bind to an epitope localized on the CLD18A2-loopD3, preferably SEQ ID NO: 31, (v) bind to an epitope, which encompass CLD18A2-loop1 and CLD18A2-loopD3, (vi) bind to a non-glycosylated epitope localized on the CLD18A2-loopD3, preferably SEQ ID NO: 29, or (vii) bind to an epitope present in human and mouse CLD18 (SEQ ID NO: 2, SEQ ID NO: 8 and SEQ ID NO: 35, SEQ ID NO: 37, respectively).

In particularly preferred embodiments, the antibodies of the invention bind to an epitope on CLD18A2 which is not present on CLD18A1.

Antibodies of the invention include fully human antibodies. Such antibodies may be produced in a non-human transgenic animal, e.g., a transgenic mouse, capable of producing multiple isotypes of human monoclonal antibodies to CLD18 by undergoing V-D-J recombination and isotype switching. Such transgenic animal can also be a transgenic rabbit for producing polyclonal antibodies such as disclosed in US 2003/0017534.

Binding of an antibody of the invention to the CLD18 antigen may mediate the killing of cells expressing CLD18 (e.g. a tumor cell), e.g. by activation of the complement system. The killing of cells expressing CLD18 may occur by one or more of the following mechanisms: complement dependent cytotoxity (CDC) of cells expressing CLD18; apoptosis of cells expressing CLD18; effector cell phagocytosis of cells expressing CLD18; or effector cell antibody dependent cellular cytotoxicity (ADCC) of cells expressing CLD18.

In order that the present invention may be more readily understood, certain terms are first defined. Additional definitions are set forth throughout the detailed description.

DEFINITION OF TERMS

The term "CLD18" relates to claudin-18 and includes any variants, including CLD18A1 and CLD18A2, conformations, isoforms and species homologs of CLD18 which are naturally expressed by cells or are expressed by cells transfected with the CLD18 gene. Preferably, "CLD18" relates to human CLD18, in particular CLD18A2 (SEQ ID NOs: 1, 2) and/or CLD18A1 (SEQ ID NOs: 7, 8), more preferably CLD18A2.

The term "CLD18A1" includes posttranslationally modified variants, isoforms and species homologs of human CLD18A1 which are naturally expressed by cells or are expressed on cells transfected with the CLD18A1 gene.

The term "CLD18A2" includes posttranslationally modified variants, isoforms and species homologs of human CLD18A2 which are naturally expressed by cells or are expressed on cells transfected with the CLD18A2 gene.

The term "CLD18 variant" shall encompass (i) CLD18 splice variants, (ii) CLD18-posttranslationally modified variants, particularly including variants with different N-glycosylation status, (iii) CLD18 conformation variants, particularly including CLD18-conformation-1, CLD18-conformation-2 and CLD18-conformation-3, (iv) CLD18 free and homotypically/heterotypically associated variants localized at intercellular tight junctions, (v) CLD18 cancer related and CLD18 non-cancer related variants.

The term "raft" refers to the sphingolipid- and cholesterol-rich membrane microdomains located in the outer leaflet area of the plasma membrane of a cell. The ability of certain proteins to associate within such domains and their ability of forming "aggregates" or "focal aggregates" can effect the protein's function. For example, the translocation of CLD18 molecules into such structures, after being bound by antibodies of the present invention, creates a high density of CLD18 antigen-antibody complexes in the plasma membranes. Such a high density of CLD18 antigen-antibody complexes can enable efficient activation of the complement system during CDC.

The terms "conformation" and "topology" describe how an integral membrane molecule is positioned in the cell surface membrane, and, in particular, which of its regions are extracellular and thus eligible for antibodies. CLD18 for example can exist in three different conformations, which most likely depend on whether it is prevalent as homomers or heteromers and whether it is integrated in supramolecular tight junction structures or "free". These different states result in different epitopes eligible to antibodies.

According to the invention, the term "disease" refers to any pathological state, including cancer, in particular those forms of cancer described herein.

By "tumor" is meant an abnormal group of cells or tissue that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The term "treatment of a disease" includes curing, shortening the duration, ameliorating, preventing, slowing down or inhibiting progression or worsening, or preventing or delaying the onset of a disease or the symptoms thereof.

According to the invention, a sample may be any sample useful according to the present invention, in particular a biological sample such a tissue sample, including bodily fluids, and/or a cellular sample and may be obtained in the conventional manner such as by tissue biopsy, including punch biopsy, and by taking blood, bronchial aspirate, sputum, urine, feces or other body fluids. According to the invention, the term "biological sample" also includes fractions of biological samples.

The term "antibody" refers to a glycoprotein comprising at least two heavy (H) chains and two light (L) chains inter-connected by disulfide bonds, or an antigen binding portion thereof. The term "antibody" also includes all recombinant forms of antibodies, in particular of the antibodies described herein, e.g., antibodies expressed in prokaryotes, unglycosylated antibodies, and any antigen-binding antibody fragments and derivatives as described below. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

The constant regions of the antibodies may mediate the binding of the immunoglobulin to host tissues or factors, including various cells of the immune system (e.g., effector cells) and the first component (C1q) of the classical complement system.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

The term "antigen-binding portion" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) $F(ab')_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding portion" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "epitope" means a protein determinant capable of binding to an antibody, wherein the term "binding" herein preferably relates to a specific binding. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "discontinuous epitope" as used herein, means a conformational epitope on a protein antigen which is formed from at least two separate regions in the primary sequence of the protein.

The term "bispecific molecule" is intended to include any agent, e.g., a protein, peptide, or protein or peptide complex, which has two different binding specificities. For example, the molecule may bind to, or interact with (a) a cell surface antigen, and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to CLD18, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

The invention also includes derivatives of the antibodies described herein. The term "antibody derivatives" refers to any modified form of an antibody, e.g., a conjugate of the antibody and another agent or antibody. As used herein, an antibody is "derived from" a particular germline sequence if the antibody is obtained from a system by immunizing an animal or by screening an immunoglobulin gene library, and wherein the selected antibody is at least 90%, more preferably at least 95%, even more preferably at least 96%, 97%, 98%, or 99% identical in amino acid sequence to the amino acid sequence encoded by the germline immunoglobulin gene. Typically, an antibody derived from a particular germline sequence will display no more than 10 amino acid differences, more preferably, no more than 5, or even more preferably, no more than 4, 3, 2, or 1 amino acid difference from the amino acid sequence encoded by the germline immunoglobulin gene.

As used herein, the term "heteroantibodies" refers to two or more antibodies, derivatives thereof, or antigen binding regions linked together, at least two of which have different specificities. These different specificities include a binding specificity for an Fc receptor on an effector cell, and a binding specificity for an antigen or epitope on a target cell, e.g., a tumor cell.

The antibodies described herein may be human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The antibodies described herein are preferably isolated. An "isolated antibody" as used herein, is intended to refer to an antibody which is substantially free of other antibodies having different antigenic specificities (e.g., an isolated antibody that specifically binds to CLD18 is substantially free of antibodies that specifically bind antigens other than CLD18). An isolated antibody that specifically binds to an epitope, isoform or variant of human CLD18 may, however, have cross-reactivity to other related antigens, e.g., from other species (e.g., CLD18 species homologs). Moreover, an isolated antibody may be substantially free of other cellular material and/or chemicals. In one embodiment of the invention, a combination of "isolated" monoclonal antibodies relates to antibodies having different specificities and being combined in a well defined composition.

According to the invention, the term "binding" preferably relates to "specific binding". As used herein, "specific binding" refers to antibody binding to a predetermined antigen. Typically, the antibody binds with an affinity corresponding to a KD of about $1\times10^{-7}$ M or less, and binds to the predetermined antigen with an affinity corresponding to a KD that is at least two orders of magnitude lower than its affinity for binding to a non-specific antigen (e.g., BSA, casein) other than the predetermined antigen or a closely-related antigen.

The term "KD" (M), as used herein, is intended to refer to the dissociation equilibrium constant of a particular antibody-antigen interaction.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that a nucleic acid is also functionally linked to the expression control sequence naturally and the term "heterologous" means that a nucleic acid is not functionally linked to the expression control sequence naturally.

A nucleic acid, such as a nucleic acid expressing RNA and/or protein or peptide, and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

According to the invention the term "promoter" or "promoter region" relates to a nucleic acid sequence which is located upstream (5') to the nucleic acid sequence being expressed and controls expression of the sequence by providing a recognition and binding site for RNA-polymerase. The "promoter region" may include further recognition and binding sites for further factors which are involved in the regulation of transcription of a gene. A promoter may control the transcription of a prokaryotic or eukaryotic gene. Furthermore, a promoter may be "inducible" and may initiate transcription in response to an inducing agent or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

According to the invention, the term "expression" is used in its most general meaning and comprises the production of RNA or of RNA and protein/peptide. It also comprises partial expression of nucleic acids. Furthermore, expression may be carried out transiently or stably.

In a preferred embodiment, a nucleic acid molecule is according to the invention present in a vector, where appropriate with a promoter, which controls expression of the nucleic acid. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

As the vector for expression of an antibody, either of a vector type in which the antibody heavy chain and light chain are present in different vectors or a vector type in which the heavy chain and light chain are present in the same vector can be used.

The teaching given herein with respect to specific nucleic acid and amino acid sequences, e.g. those shown in the sequence listing, is to be construed so as to also relate to modifications of said specific sequences resulting in sequences which are functionally equivalent to said specific sequences, e.g. amino acid sequences exhibiting properties identical or similar to those of the specific amino acid sequences and nucleic acid sequences encoding amino acid sequences exhibiting properties identical or similar to those of the amino acid sequences encoded by the specific nucleic acid sequences. One important property is to retain binding of an antibody to its target or to sustain effector functions of an antibody. Preferably, a sequence modified with respect to a specific sequence, when it replaces the specific sequence in an antibody retains binding of said antibody to CLD18 and preferably functions of said antibody as described herein, e.g. CDC mediated lysis or ADCC mediated lysis.

It will be appreciated by those skilled in the art that in particular the sequences of the CDR, hypervariable and variable regions can be modified without losing the ability to bind CLD18. For example, CDR regions will be either identical or highly homologous to the regions specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions specifically disclosed herein.

It is to be understood that the specific nucleic acids described herein also include nucleic acids modified for the sake of optimizing the codon usage in a particular host cell or organism. Differences in codon usage among organisms can lead to a variety of problems concerning heterologous gene expression. Codon optimization by changing one or more nucleotides of the original sequence can result in an optimization of the expression of a nucleic acid, in particular in optimization of translation efficacy, in a homologous or heterologous host in which said nucleic acid is to be expressed. For example if nucleic acids derived from human and encoding constant regions and/or framework regions of antibodies are to be used according to the present invention, e.g. for preparing chimeric or humanised antibodies, it may be preferred to modify said nucleic acids for the sake of optimization of codon usage, in particular if said nucleic acids, optionally fused to heterologous nucleic acids such as nucleic acids derived from other organisms as described herein, are to be expressed in cells from an organism different from human such as mouse or hamster. For example, the nucleic acid sequences encoding human light and heavy chain constant regions such as those according to SEQ ID NOs: 40 and 45, respectively, can be modified to include one or more, preferably, at least 1, 2, 3, 4, 5, 10, 15, 20 and preferably up to 10, 15, 20, 25, 30, 50, 70 or 100 or more nucleotide replacements resulting in an optimized codon usage but not resulting in a change of the amino acid sequence. Such nucleotide replacements preferably relate to replacements of nucleotides in SEQ ID Nos: 40 and 45, respectively, selected from the replacements shown in the following alignment of SEQ ID Nos: 40 and 45, respectively, with their modified counterparts and not resulting in a change in the encoded amino acid sequence or relate to corresponding replacements at corresponding positions in other nucleic acid sequences encoding human light and heavy chain constant regions, respectively. Preferably, all of the replacements shown in the following alignments of SEQ ID Nos: 40 and 45, respectively, with their modified counterparts not resulting in a change in the encoded amino acid sequence are effected in nucleic acid sequences encoding human light and heavy chain constant regions, respectively.

```
Alignment of SEQ ID NO: 40 and SEQ ID NO: 147:
CGTACGGTGGCTGCACCATCTGTCTTCATCTTCCCGCCATCTGATGAGCAGTTGAAATCT     60
||||||||||| || ||    || ||||||||||| ||    || |||||| |||| ||
CGTACGGTGGCCGCTCCCAGCGTGTTCATCTTCCCCCCCAGCGACGAGCAGCTGAAGTCC     60

GGAACTGCCTCTGTTGTGTGCCTGCTGAATAACTTCTATCCCAGAGAGGCCAAAGTACAG    120
|| || |||   || |||||||||||||| |||||||| ||| | |||||||| || |||
GGCACCGCCAGCGTGGTGTGCCTGCTGAACAACTTCTACCCCCGGGAGGCCAAGGTGCAG    120

TGGAAGGTGGATAACGCCCTCCAATCGGGTAACTCCCAGGAGAGTGTCACAGAGCAGGAC    180
||||||||||| |||||||| ||    || |||  ||||||||| ||||| |||||||||
TGGAAGGTGGACAACGCCCTGCAGAGCGGCAACAGCCAGGAGAGCGTCACCGAGCAGGAC    180

AGCAAGGACAGCACCTACAGCCTCAGCAGCACCCTGACGCTGAGCAAAGCAGACTACGAG    240
|||||||||  |||||||||||| |||||||||||||| |||||||| || |||||||||
AGCAAGGACTCCACCTACAGCCTGAGCAGCACCCTGACCCTGAGCAAGGCCGACTACGAG    240

AAACACAAAGTCTACGCCTGCGAAGTCACCCATCAGGGCCTGAGCTCGCCCGTCACAAAG    300
|| ||||| || ||||||||||| || ||||| |||||||||  |   ||||| || |||
AAGCACAAGGTGTACGCCTGCGAGGTGACCCACCAGGGCCTGTCCAGCCCCGTGACCAAG    300

AGCTTCAACAGGGGAGAGTGTTAG                                        324
|||||||||||||| ||||| |||
AGCTTCAACAGGGGCGAGTGCTAG                                        324

Alignment of SEQ ID NO: 45 and SEQ ID NO: 149:
GGCCCATCGGTCTTCCCCCTGGCACCCTCCTCCAAGAGCACCTCTGGGGGCACAGCGGCC     60
||||||   || ||||||||||| |||  |  ||||||||||   || |||||||| |||
GGCCCAAGCGTGTTCCCCCTGGCCCCCAGCAGCAAGAGCACCAGCGGCGGCACAGCCGCC     60

CTGGGCTGCCTGGTCAAGGACTACTTCCCCGAACCGGTGACGGTGTCGTGGAACTCAGGC    120
|||||||||||||| ||||||||||||||||| || ||||| |||   ||||||   ||
CTGGGCTGCCTGGTGAAGGACTACTTCCCCGAGCCCGTGACCGTGAGCTGGAACAGCGGA    120

GCCCTGACCAGCGGCGTGCACACCTTCCCGGCTGTCCTACAGTCCTCAGGACTCTACTCC    180
|||||||||  |||||||||||||||||| || || || |||  |   || || |||  |
GCCCTGACCTCCGGCGTGCACACCTTCCCCGCCGTGCTGCAGAGCAGCGGCCTGTACAGC    180

CTCAGCAGCGTGGTGACCGTGCCCTCCAGCAGCTTGGGCACCCAGACCTACATCTGCAAC    240
|| |||||||||||||||||||||  ||||||| ||||||||||||||||||||||||||
CTGAGCAGCGTGGTGACCGTGCCCAGCAGCAGCCTGGGCACCCAGACCTACATCTGCAAC    240

GTGAATCACAAGCCCAGCAACACCAAGGTGGACAAGAAAGTTGAGCCCAAATCTTGTGAC    300
||||| ||||||||||||||||||||||||||||||| ||| ||||||||    || |||
GTGAACCACAAGCCCAGCAACACCAAGGTGGACAAGAGAGTGGAGCCCAAGAGCTGCGAC    300

AAAACTCACACATGCCCACCGTGCCCAGCACCTGAACTCCTGGGGGGACCGTCAGTCTTC    360
|| || ||||| ||||| || |||||||| || || || ||||| |||||    || |||
AAGACCCACACCTGCCCCCCCTGCCCAGCCCCAGAGCTGCTGGGCGGACCCAGCGTGTTC    360

CTCTTCCCCCCAAAACCCAAGGACACCCTCATGATCTCCCGGACCCCTGAGGTCACATGC    420
|| |||||||| || |||||||||||||| ||||||  | ||||||| ||||| || |||
CTGTTCCCCCCCAAGCCCAAGGACACCCTGATGATCAGCAGGACCCCCGAGGTGACCTGC    420

GTGGTGGTGGACGTGAGCCACGAAGACCCTGAGGTCAAGTTCAACTGGTACGTGGACGGC    480
||||||||||||||||||||||| ||||| ||||| ||||||||||||||||||||||||
GTGGTGGTGGACGTGAGCCACGAGGACCCAGAGGTGAAGTTCAACTGGTACGTGGACGGC    480

GTGGAGGTGCATAATGCCAAGACAAAGCCGCGGGAGGAGCAGTACAACAGCACGTACCGT    540
||||||||||| || |||||||| |||||  | |||||||||||||||||||| ||| |
GTGGAGGTGCACAACGCCAAGACCAAGCCCAGAGAGGAGCAGTACAACAGCACCTACAGG    540

GTGGTCAGCGTCCTCACCGTCCTGCACCAGGACTGGCTGAATGGCAAGGAGTACAAGTGC    600
|||||   ||| || ||||| |||||||||||||||||||| |||||||| |||||||||
GTGGTGTCCGTGCTGACCGTGCTGCACCAGGACTGGCTGAACGGCAAGGAATACAAGTGC    600

AAGGTCTCCAACAAAGCCCTCCCAGCCCCCATCGAGAAAACCATCTCCAAAGCCAAAGGG    660
|||||||||||||| ||||| |||||||||||||| || ||||||  ||| ||||| ||
AAGGTCTCCAACAAGGCCCTGCCAGCCCCCATCGAAAAGACCATCAGCAAGGCCAAGGGC    660
```

-continued

```
CAGCCCCGAGAACCACAGGTGTACACCCTGCCCCCATCCCGGGATGAGCTGACCAAGAAC      720
||||| || || || ||||||||||||||||||||   |||||| ||| |||||||||||
CAGCCACGGGAGCCCCAGGTGTACACCCTGCCCCCCAGCCGGGAGGAGATGACCAAGAAC      720

CAGGTCAGCCTGACCTGCCTGGTCAAAGGCTTCTATCCCAGCGACATCGCCGTGGAGTGG      780
|||||   ||||||||| ||||| || |||||||| ||||||||||||||||||||||||
CAGGTGTCCCTGACCTGTCTGGTGAAGGGCTTCTACCCCAGCGACATCGCCGTGGAGTGG      780

GAGAGCAATGGGCAGCCGGAGAACAACTACAAGACCACGCCTCCCGTGCTGGACTCCGAC      840
|||||||| || ||||| |||||||||||||||||||| || || |||||||||  ||||
GAGAGCAACGGCCAGCCCGAGAACAACTACAAGACCACCCCCCCAGTGCTGGACAGCGAC      840

GGCTCCTTCTTCCTCTATAGCAAGCTCACCGTGGACAAGAGCAGGTGGCAGCAGGGGAAC      900
|||  ||||||||| || |||||||| ||||||||||||  ||||||||||||||| |||
GGCAGCTTCTTCCTGTACAGCAAGCTGACCGTGGACAAGTCCAGGTGGCAGCAGGGCAAC      900

GTCTTCTCATGCTCCGTGATGCATGAGGCTCTGCACAACCACTACACGCAGAAGAGCCTC      960
|| |||   |||  ||||||||| ||||| ||||||||||||||||| ||||||  |||
GTGTTCAGCTGCAGCGTGATGCACGAGGCCCTGCACAACCACTACACCCAGAAGTCCCTG      960

TCCCTGTCTCCGGGTAAATGA                                             981
  ||||   || || || |
AGCCTGAGCCCCGGCAAGTAG                                             981
```

Furthermore, it may be desired according to the present invention to modify the amino acid sequences described herein, in particular those of human heavy chain constant regions to adapt the sequence to a desired allotype, e.g. an allotype found in the Caucasian population. Such modifications are preferably selected from the group consisting of the following amino acid replacements within SEQ ID NO: 46 or at corresponding positions within other human heavy chain constant regions: K93R, D235E, and L237M. Preferably, all of these modifications are included in amino acid sequences of human heavy chain constant regions.

According the invention, the term "corresponding positions" relates to nucleotides or amino acid residues which in a sequence alignment of two nucleic acid or protein sequences are aligned to each other.

Preferably the degree of identity between a specific nucleic acid sequence described herein and a nucleic acid sequence which is modified with respect to said specific nucleic acid sequence will be at least 70%, preferably at least 75%, more preferably at least 80%, even more preferably at least 90% or most preferably at least 95%, 96%, 97%, 98% or 99%. Preferably, the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

Preferably the degree of similarity, preferably identity between a specific amino acid sequence described herein and an amino acid sequence which is modified with respect to said specific amino acid sequence such as between amino acid sequences showing substantial homology will be at least 70%, preferably at least 80%, even more preferably at least 90% or most preferably at least 95%, 96%, 97%, 98% or 99%.

All of the above described modified sequences are within the scope of the present invention.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The "percentage identity" is obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

"Conservative substitutions," may be made, for instance, on the basis of similarity in polarity, charge, solubility, hydrophobicity, hydrophilicity, and/or the amphipathic nature of the residues involved. For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine: (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt [alpha]-helices. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

The present invention comprises antibodies in which alterations have been made in the Fc region in order to change the functional or pharmacokinetic properties of the antibodies. Such alterations may result in a decrease or increase of C1q binding and CDC or of FcγR binding and ADCC. Substitutions can, for example, be made in one or more of the amino acid residues of the heavy chain constant region, thereby causing an alteration in an effector function while retaining the ability to bind to the antigen as compared with the modified antibody, cf. U.S. Pat. Nos. 5,624,821 and 5,648,260.

The in vivo half-life of antibodies can be improved by modifying the salvage receptor epitope of the Ig constant domain or an Ig-like constant domain such that the molecule does not comprise an intact CH2 domain or an intact Ig Fc region, cf. U.S. Pat. Nos. 6,121,022 and 6,194,551. The in vivo half-life can furthermore be increased by making mutations in the Fc region, e.g., by substituting threonine for leucine at position 252, by substituting threonine for serine at position 254, or by substituting threonine for phenylalanine at position 256, cf. U.S. Pat. No. 6,277,375.

Furthermore, the glycosylation pattern of antibodies can be modified in order to change the effector function of the antibodies. For example, the antibodies can be expressed in a transfectoma which does not add the fucose unit normally attached to Asn at position 297 of the Fc region in order to enhance the affinity of the Fc region for Fc-Receptors which, in turn, will result in an increased ADCC of the antibodies in the presence of NK cells, cf. Shield et al. (2002) JBC, 277: 26733. Furthermore, modification of galactosylation can be made in order to modify CDC.

Alternatively, in another embodiment, mutations can be introduced randomly along all or part of a anti-CLD18 antibody coding sequence, such as by saturation mutagenesis, and the resulting modified anti-CLD18 antibodies can be screened for binding activity.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells. NS/0 cells, and lymphocytic cells.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

The terms "transgenic animal" refers to an animal having a genome comprising one or more transgenes, preferably heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-CLD18 antibodies when immunized with CLD18 antigen and/or cells expressing CLD18. The human heavy chain transgene can be integrated into the chromosomal DNA of the mouse, as is the case for transgenic mice, e.g., HuMAb mice, such as HCo7 or HCol2 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to CLD18 (e.g., IgG, IgA and/or IgE) by undergoing V-D-J recombination and isotype switching.

Mechanisms of mAb Action

Although the following provides considerations regarding the mechanism underlying the therapeutic efficacy of antibodies of the invention it is not to be considered as limiting to the invention in any way.

The antibodies described herein preferably interact with components of the immune system, preferably through ADCC or CDC. Antibodies of the invention can also be used to target payloads (e.g., radioisotopes, drugs or toxins) to directly kill tumor cells or can be used synergistically with traditional chemotherapeutic agents, attacking tumors through complementary mechanisms of action that may include anti-tumor immune responses that may have been compromised owing to a chemotherapeutic's cytotoxic side effects on T lymphocytes.

Antibody-dependent Cell-mediated Cytotoxicity. ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-dependent Cytotoxicity. CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1 q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

Production of Antibodies

Antibodies of the invention can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies directed against CLD18 can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607.

Yet another strategy for generating monoclonal antibodies is to directly isolate genes encoding antibodies from lymphocytes producing antibodies of defined strategy e.g. see Babcock et al., 1996; A novel strategy for generating monoclonal antibodies from single, isolated lymphocytes producing antibodies of defined strategy. For details of recombinant antibody engineering see also Welschof and Kraus, Recombinant antibodies for cancer therapy ISBN-0-89603-918-8 and Benny K. C. Lo Antibody Engineering ISBN 1-58829-092-1.

Immunizations

To generate antibodies to CLD18, mice can be immunized with carrier-conjugated peptides derived from the CLD18 sequence, an enriched preparation of recombinantly expressed CLD18 antigen or fragments thereof and/or cells expressing CLD18, as described. Alternatively, mice can be immunized with DNA encoding full length human CLD18 (e.g. SEQ ID NO: 1) or fragments thereof, in particular those of SEQ ID Nos:15, 17, and 19. In the event that immunizations using a purified or enriched preparation of the CLD18 antigen do not result in antibodies, mice can also be immunized with cells expressing CLD18, e.g., a cell line, to promote immune responses.

The immune response can be monitored over the course of the immunization protocol with plasma and serum samples being obtained by tail vein or retroorbital bleeds. Mice with sufficient titers of anti-CLD18 immunoglobulin can be used for fusions. Mice can be boosted intraperitonealy or intravenously with CLD18 expressing cells 3 days before sacrifice and removal of the spleen to increase the rate of specific antibody secreting hybridomas.

Generation of Hybridomas Producing Monoclonal Antibodies

To generate hybridomas producing monoclonal antibodies to CLD18, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using CLD18 expressing cells, antibodies with specificity for CLD18 can be identified. The antibody secreting hybridomas can be replated, screened again, and if still positive for anti-CLD18 monoclonal antibodies can be subcloned by limiting dilution. The stable subclones can then be cultured in vitro to generate antibody in tissue culture medium for characterization.

Generation of Transfectomas Producing Monoclonal Antibodies

Antibodies of the invention also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells. NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. *E. coli*. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Use of Partial Antibody Sequences to Express Intact Antibodies (i.e. Humanization and Chimerisation).

a) Chimerization

Murine monoclonal antibodies can be used as therapeutic antibodies in humans when labeled with toxins or radioactive isotopes. Nonlabeled murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

b) Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann. L. et al. (1998) Nature 332: 323-327; Jones, P. et al. (1986) Nature 321: 522-525; and Queen, C. et al. (1989) Proc. Natl. Acad. Sci. U.S.A. 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962). Partial heavy and light chain sequences spanning the CDR regions are typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266: 19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed chimerized or humanized heavy and light chain variable regions are then combined with cloned promoter, leader, translation initiation, constant region, 3' untranslated, polyadenylation, and transcription termination sequences to form expression vector constructs.

The heavy and light chain expression constructs can be combined into a single vector, co-transfected, serially transfected, or separately transfected into host cells which are then fused to form a host cell expressing both chains. Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric IgG1, Kappa or IgG4, Kappa antibodies. Similar plasmids can be constructed for expression of other heavy chain isotypes, or for expression of antibodies comprising lambda light chains.

Thus, in another aspect of the invention, the structural features of the anti-CLD18 antibodies of the invention, are used to create structurally related humanized anti-CLD18 antibodies that retain at least one functional property of the antibodies of the invention, such as binding to CLD18. More specifically, one or more CDR regions of mouse monoclonal antibodies can be combined recombinantly with known human framework regions and CDRs to create additional, recombinantly-engineered, humanized anti-CLD18 antibodies of the invention.

Binding to Antigen Expressing Cells

The ability of the antibody to bind CLD18 can be determined using standard binding assays, such as those set forth in the examples (e.g., ELISA, Western Blot, Immunofluorescence and flow cytometric analysis)

Characterization of Binding of Antibodies

To purify anti-CLD18 antibodies, selected hybridomas can be grown in two-liter spinner-flasks for monoclonal antibody purification. Alternatively, anti-CLD18 antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-CLD18 monoclonal antibodies bind to unique epitopes, site-directed or multi-site directed mutagenesis can be used.

Isotype Determination

To determine the isotype of purified antibodies, isotype ELISAs with various commercial kits (e.g. Zymed, Roche Diagnostics) can be performed. Wells of microtiter plates can be coated with anti-mouse Ig. After blocking, the plates are reacted with monoclonal antibodies or purified isotype controls, at ambient temperature for two hours. The wells can then be reacted with either mouse IgG1, IgG2a, IgG2b or IgG3, IgA or mouse IgM-specific peroxidase-conjugated probes. After washing, the plates can be developed with ABTS substrate (1 mg/ml) and analyzed at OD of 405-650. Alternatively, the IsoStrip Mouse Monoclonal Antibody Isotyping Kit (Roche, Cat. No. 1493027) may be used as described by the manufacturer.

Flow Cytometric Analysis

In order to demonstrate presence of anti-CLD18 antibodies in sera of immunized mice or binding of monoclonal antibodies to living cells expressing CLD18, flow cytometry can be used. Cell lines expressing naturally or after transfection CLD18 and negative controls lacking CLD18 expression (grown under standard growth conditions) can be mixed with various concentrations of monoclonal antibodies in hybridoma supernatants or in PBS containing 1% FBS, and can be incubated at 4° C. for 30 min. After washing, the APC- or Alexa647-labeled anti IgG antibody can bind to CLD18-bound monoclonal antibody under the same conditions as the primary antibody staining. The samples can be analyzed by flow cytometry with a FACS instrument using light and side scatter properties to gate on single, living cells. In order to distinguish CLD18-specific monoclonal antibodies from non-specific binders in a single measurement, the method of co-transfection can be employed. Cells transiently transfected with plasmids encoding CLD18 and a fluorescent marker can be stained as described above. Transfected cells can be detected in a different fluorescence channel than antibody-stained cells. As the majority of transfected cells express both transgenes, CLD18-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

Tight junction proteins tend to be internalized, if cell contact to neighbouring cells of particularly adherent cells is lost by e.g. detachment of cells. Cell surface expression of CLD18 can be optimized by a) adjusting culture conditions, e.g. culturing in higher cell density in a standardized manner, using mild detachment (e.g. 2 mM EDTA/PBS or accutase), processing at room temperature, and adding inhibitors of endocytosis (e.g. sodium azide) or activators of CLD18 transcription or translation, and by b) selecting and cloning of cells maintaining CLD18 in high levels at the cell surface, e.g. by selection with antibiotics in terms of transfected cells, by immunomagnetic or FACS cell sorting, and by limited dilution cloning.

Immunofluorescence Microscopy

In order to demonstrate presence of anti-CLD18 antibodies in sera of immunized mice or binding of monoclonal antibodies to living cells expressing CLD18, immunofluorescence microscopy analysis can be used. For example, cell lines expressing either spontaneously or after transfection CLD18 and negative controls lacking CLD18 expression are grown in chamber slides under standard growth conditions in DMEM/F12 medium, supplemented with 10% fetal calf serum (FCS), 2 mM L-glutamine, 100 IU/ml penicillin and 100 μg/ml streptomycin. Cells can then be fixed with methanol or paraformaldehyde or left untreated. Cells can then be reacted with monoclonal antibodies against CLD18 for 30 min. at 25° C. After washing, cells can be reacted with an Alexa555-labelled anti-mouse IgG secondary antibody (Molecular Probes) under the same conditions. Cells can then be examined by fluorescence microscopy.

Total CLD18 levels in cells can be observed when cells are methanol fixed or paraformaldehyde fixed and permeabilized with Triton X-100. In living cells and non-permeabilized, paraformaldehyde fixed cells surface localization of CLD18 can be examined. Additionally targeting of CLD18 to tight junctions can be analyzed by co-staining with tight junction markers such as ZO-1. Furthermore, effects of antibody binding and CLD18 localization within the cell membrane can be examined.

Western Blot

Anti-CLD18 IgG can be further tested for reactivity with CLD18 antigen by Western Blotting. Briefly, cell extracts from cells expressing CLD18 and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Immunohistochemistry

Anti-CLD18 mouse IgGs can be further tested for reactivity with CLD18 antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously (e.g. DAN-G, SNU-16, or KATO-III) or after transfection (e.g. HEK293) CLD18. For immunostaining antibodies reactive to CLD18 can be incubated followed by horseradish-peroxidase conjugated goat anti-mouse or goat anti-rabbit antibodies (DAKO) according to the vendors instructions.

Phagocytic and Cell Killing Activities of Antibodies In Vitro

In addition to binding specifically to CLD18, anti-CLD18 antibodies can be tested for their ability to mediate phagocytosis and killing of cells expressing CLD18. The testing of monoclonal antibody activity in vitro will provide an initial screening prior to testing in vivo models.

Antibody Dependent Cell-mediated Cytotoxicity (ADCC):

Briefly, polymorphonuclear cells (PMNs), NK cells, monocytes, mononuclear cells or other effector cells, from healthy donors can be purified by Ficoll Hypaque density centrifugation, followed by lysis of contaminating erythrocytes. Washed effector cells can be suspended in RPMI supplemented with 10% heat-inactivated fetal calf serum or, alternatively with 5% heat-inactivated human serum and mixed with $^{51}Cr$ labeled target cells expressing CLD18, at various ratios of effector cells to target cells. Alternatively, the target cells may be labeled with a fluorescence enhancing ligand (BATDA). A highly fluorescent chelate of Europium with the enhancing ligand which is released from dead cells can be measured by a fluorometer. Another alternative technique may utilize the transfection of target cells with luciferase. Added lucifer yellow may then be oxidated by viable cells only. Purified anti-CLD18 IgGs can then be added at various concentrations. Irrelevant human IgG can be used as negative control. Assays can be carried out for 4 to 20 hours at 37° C. depending on the effector cell type used. Samples can be assayed for cytolysis by measuring $^{51}$Cr release or the presence of the EuTDA chelate in the culture supernatant. Alternatively, luminescence resulting from the oxidation of lucifer yellow can be a measure of viable cells.

Anti-CLD18 monoclonal antibodies can also be tested in various combinations to determine whether cytolysis is enhanced with multiple monoclonal antibodies.

Complement Dependent Cytotoxicity (CDC):

Monoclonal anti-CLD18 antibodies can be tested for their ability to mediate CDC using a variety of known techniques. For example, serum for complement can be obtained from blood in a manner known to the skilled person. To determine the CDC activity of mAbs, different methods can be used. $^{51}$Cr release can for example be measured or elevated membrane permeability can be assessed using a propidium iodide (PI) exclusion assay. Briefly, target cells can be washed and $5\times10^5$/ml can be incubated with various concentrations of mAb for 10-30 min. at room temperature or at 37° C. Serum or plasma can then be added to a final concentration of 20% (v/v) and the cells incubated at 37° C. for 20-30 min. All cells from each sample can be added to the PI solution in a FACS tube. The mixture can then be analyzed immediately by flow cytometry analysis using FACSArray.

In an alternative assay, induction of CDC can be determined on adherent cells. In one embodiment of this assay, cells are seeded 24 h before the assay with a density of $3\times10^4$/well in tissue-culture flat-bottom microtiter plates. The next day growth medium is removed and the cells are incubated in triplicates with antibodies. Control cells are incubated with growth medium or growth medium containing 0.2% saponin for the determination of background lysis and maximal lysis, respectively. After incubation for 20 min. at room temperature supernatant is removed and 20% (v/v) human plasma or serum in DMEM (prewarmed to 37° C.) is added to the cells and incubated for another 20 min. at 37° C. All cells from each sample are added to propidium iodide solution (10 μg/ml). Then, supernatants are replaced by PBS containing 2.5 μg/ml ethidium bromide and fluorescence emission upon excitation at 520 nm is measured at 600 nm using a Tecan Safire. The percentage specific lysis is calculated as follows: % specific lysis=(fluorescence sample−fluorescence background)/(fluorescence maximal lysis−fluorescence background)×100.

Inhibition of Cell Proliferation by Monoclonal Antibodies:

To test for the ability to initiate apoptosis, monoclonal anti-CLD18 antibodies can, for example, be incubated with CLD18 positive tumor cells, e.g., SNU-16, DAN-G, KATO-III or CLD18 transfected tumor cells at 37° C. for about 20 hours. The cells can be harvested, washed in Annexin-V binding buffer (BD biosciences), and incubated with Annexin V conjugated with FITC or APC (BD biosciences) for 15 min. in the dark. All cells from each sample can be added to PI solution (10 μg/ml in PBS) in a FACS tube and assessed immediately by flow cytometry (as above). Alternatively, a general inhibition of cell-proliferation by monoclonal antibodies can be detected with commercially available kits. The DELFIA Cell Proliferation Kit (Perkin-Elmer, Cat. No. AD0200) is a non-isotopic immunoassay based on the measurement of 5-bromo-2'-deoxyuridinc (BrdU) incorporation during DNA synthesis of proliferating cells in microplates. Incorporated BrdU is detected using europium labelled monoclonal antibody. To allow antibody detection, cells are fixed and DNA denatured using Fix solution. Unbound antibody is washed away and DELFIA inducer is added to dissociate europium ions from the labelled antibody into solution, where they form highly fluorescent chelates with components of the DELFIA Inducer. The fluorescence measured—utilizing time-resolved fluorometry in the detection—is proportional to the DNA synthesis in the cell of each well.

Preclinical Studies

Monoclonal antibodies which bind to CLD18 also can be tested in an in vivo model (e.g. in immune deficient mice carrying xenografted tumors inoculated with cell lines expressing CLD18, e.g. DAN-G, SNU-16, or KATO-III, or after transfection, e.g. HEK293) to determine their efficacy in controlling growth of CLD18-expressing tumor cells.

In vivo studies after xenografting CLD18 expressing tumor cells into immunocompromised mice or other animals can be performed using antibodies of the invention. Antibodies can be administered to tumor free mice followed by injection of tumor cells to measure the effects of the antibodies to prevent formation of tumors or tumor-related symptoms. Antibodies can be administered to tumor-bearing mice to determine the therapeutic efficacy of respective antibodies to reduce tumor growth, metastasis or tumor related symptoms. Antibody application can be combined with application of other substances as cystostatic drugs, growth factor inhibitors, cell cycle blockers, angiogenesis inhibitors or other antibodies to determine synergistic efficacy and potential toxicity of combinations. To analyze toxic side effects mediated by antibodies of the invention animals can be inoculated with antibodies or control reagents and thoroughly investigated for symptoms possibly related to CLD18-antibody therapy. Possible side effects of in vivo application of CLD18 antibodies particularly include toxicity at CLD18 expressing tissues including stomach and lung. Antibodies recognizing CLD18 in human and in other species, e.g. mice, are particularly useful to predict potential side effects mediated by application of monoclonal CLD18-antibodies in humans.

Epitope Mapping

Mapping of epitopes recognized by antibodies of invention can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

I. Bispecific/Multispecific Molecules which Bind to CLD18

In yet another embodiment of the invention, antibodies to CLD18 can be derivatized or linked to another functional molecule, e.g., another peptide or protein (e.g., an Fab' fragment) to generate a bispecific or multispecific molecule which binds to multiple binding sites or target epitopes. For example, an antibody of the invention can be functionally linked (e.g. by chemical coupling, genetic fusion, noncovalent association or otherwise) to one or more other binding molecules, such as another antibody, peptide or binding mimetic.

Accordingly, the present invention includes bispecific and multispecific molecules comprising at least one first binding specificity for CLD18 and a second binding specificity for a second target epitope. In a particular embodiment of the invention, the second target epitope is an Fc receptor, e.g. human Fc-gammaRI (CD64) or a human Fc-alpha receptor (CD89), or a T cell receptor, e.g. CD3. Therefore, the invention includes bispecific and multispecific molecules capable of binding both to Fc-gammaR, Fc-alphaR or Fc-epsilonR expressing effector cells (e.g. monocytes, macrophages or polymorphonuclear cells (PMNs)), and to target cells expressing CLD18. These bispecific and multispecific molecules may target CLD18 expressing cells to effector cell and may trigger Fc receptor-mediated effector cell activities, such as phagocytosis of CLD18 expressing cells, antibody dependent cellular cytotoxicity (ADCC), cytokine release, or generation of superoxide anion.

Bispecific and multispecific molecules of the invention can further include a third binding specificity, in addition to an anti-Fc binding specificity and an anti-CLD18 binding specificity. In one embodiment, the third binding specificity is an anti-enhancement factor (EF) portion, e.g. a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T cell (e.g., via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one antibody, including, e.g., an Fab, Fab', $F(ab')_2$, Fv, or a single chain Fv. The antibody may also be a light chain or heavy chain dimer, or any minimal fragment thereof such as a Fv or a single chain construct as described in Ladner et al., U.S. Pat. No. 4,946,778. The antibody may also be a binding-domain immunoglobulin fusion protein as disclosed in US2003/0118592 and US 2003/0133939.

In one embodiment bispecific and multispecific molecules of the invention comprise a binding specificity for an Fc-gammaR or an Fc-alphaR present on the surface of an effector cell, and a second binding specificity for a target cell antigen, e.g., CLD18.

In one embodiment, the binding specificity for an Fc receptor is provided by a monoclonal antibody, the binding of which is not blocked by human immunoglobulin G (IgG). As used herein, the term "IgG receptor" refers to any of the eight gamma-chain genes located on chromosome 1. These genes encode a total of twelve transmembrane or soluble receptor isoforms which are grouped into three Fc-gamma receptor classes: Fc-gammaRI (CD64), Fc-gammaRII (CD32), and Fc-gammaRIII (CD16). In one preferred embodiment, the Fc-gamma receptor is a human high affinity Fc-gammaRI.

The production and characterization of these preferred monoclonal antibodies are described by Fanger et al. in WO 88/00052 and in U.S. Pat. No. 4,954,617. These antibodies bind to an epitope of Fc-gammaRI, Fc-gammaRII or Fc-gammayRIII at a site which is distinct from the Fcγ binding site of the receptor and, thus, their binding is not blocked substantially by physiological levels of IgG. Specific anti-Fc-gammaRI antibodies useful in this invention are mAb 22, mAb 32, mAb 44, mAb 62 and mAb 197. In other embodiments, the anti-Fcγ receptor antibody is a humanized form of monoclonal antibody 22 (H22). The production and characterization of the H22 antibody is described in Graziano, R. F. et al. (1995) J. Immunol. 155 (10): 4996-5002 and WO 94/10332. The H22 antibody producing cell line was deposited at the American Type Culture Collection on Nov. 4, 1992 under the designation HA022CL1 and has the accession No. CRL 11177.

In still other preferred embodiments, the binding specificity for an Fc receptor is provided by an antibody that binds to a human IgA receptor, e.g., an Fc-alpha receptor (Fc-alphaRI (CD89)), the binding of which is preferably not blocked by human immunoglobulin A (IgA). The term "IgA receptor" is intended to include the gene product of one alpha-gene (Fc-alphaRI) located on chromosome 19. This gene is known to encode several alternatively spliced transmembrane isoforms of 55 to 110 kDa. Fc-alphaRI (CD89) is constitutively expressed on monocytes/macrophages, eosinophilic and neutrophilic granulocytes, but not on non-effector cell populations. Fc-alphaRI has medium affinity for both IgA1 and IgA2, which is increased upon exposure to cytokines such as G-CSF or GM-CSF (Morton. H. C. et al. (1996) Critical Reviews in Immunology 16: 423-440). Four Fc-alphaRI-specific monoclonal antibodies, identified as A3, A59, A62 and A77, which bind Fc-alphaRI outside the IgA ligand binding domain, have been described (Monteiro, R. C. et al. (1992) J. Immunol. 148: 1764).

Fc-alphaRI and Fc-gammaRI are preferred trigger receptors for use in the invention because they (1) are expressed primarily on immune effector cells, e.g., monocytes, PMNs, macrophages and dendritic cells: (2) are expressed at high levels (e.g., 5,000-100,000 per cell); (3) are mediators of cytotoxic activities (e.g., ADCC, phagocytosis); (4) mediate enhanced antigen presentation of antigens, including self-antigens, targeted to them.

In another embodiment the bispecific molecule is comprised of two monoclonal antibodies according to the invention which have complementary functional activities, such as one antibody predominately working by inducing CDC and the other antibody predominately working by inducing apoptosis.

An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include cells of myeloid or lymphoid origin, e.g, lymphocytes (e.g., B cells and T cells including cytolytic T cells (CTLs), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cellular cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of Fc-gammaRI has been found to be up-regulated by interferon gamma (IFN-γ). This enhanced expression increases the cytotoxic activity of Fc-gammaRI-bearing cells against targets. An effector cell can phagocytose or lyse a target antigen or a target cell.

"Target cell" shall mean any undesirable cell in a subject (e.g., a human or animal) that can be targeted by an antibody of the invention. In preferred embodiments, the target cell is a cell expressing or overexpressing CLD18. Cells expressing CLD18 typically include tumor cells.

Bispecific and multispecific molecules of the present invention can be made using chemical techniques (see e.g., D. M. Kranz et al. (1981) Proc. Natl. Acad. Sci. USA 78:5807), "polydoma" techniques (See U.S. Pat. No. 4,474,893, to Reading), or recombinant DNA techniques.

In particular, bispecific and multispecific molecules of the present invention can be prepared by conjugating the constituent binding specificities, e.g., the anti-FcR and anti-CLD18 binding specificities, using methods known in the art. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl-4-(N-maleimidomethyl)cyclohexane-1-carboxylate (sulfo-SMCC) (see e.g., Karpovsky et al. (1984) J. Exp. Med. 160: 1686; Liu, M A et al. (1985) Proc. Natl. Acad. Sci. USA 82: 8648). Other methods include those described by Paulus (Behring Ins. Mitt. (1985) No. 78, 118-132); Brennan et al. (Science (1985) 229: 81-83), and Glennie et al. (J. Immunol. (1987) 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a mAb×mAb, mAb×Fab, Fab×F(ab')$_2$ or ligand×Fab fusion protein. A bispecific and multispecific molecule of the invention, e.g., a bispecific molecule, can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a γ-counter or a scintillation counter or by autoradiography.

II. Immunoconjugates

In another aspect, the present invention features an anti-CLD18 antibody conjugated to a therapeutic moiety or agent, such as a cytotoxin, a drug (e.g., an immunosuppressant) or a radioisotope. Such conjugates are referred to herein as "immunoconjugates". Immunoconjugates which include one or more cytotoxins are referred to as "immunotoxins". A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Suitable therapeutic agents for forming immunoconjugates of the invention include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Antibodies of the present invention also can be conjugated to a radioisotope, e.g., iodine-131, yttrium-90 or indium-111, to generate cytotoxic radiopharmaceuticals for treating a CLD18-related disorder, such as a cancer. The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pincheract al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

In a further embodiment, the antibodies according to the invention are attached to a linker-chelator, e.g., tiuxetan, which allows for the antibody to be conjugated to a radioisotope.

III. Pharmaceutical Compositions

In another aspect, the present invention provides a composition, e.g., a pharmaceutical composition, containing one or a combination of antibodies of the present invention. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995. In one embodiment, the compositions include a combination of multiple (e.g., two or more) isolated antibodies of the invention which act by different mechanisms, e.g., one antibody which predominately acts by inducing CDC in combination with another antibody which predominately acts by inducing apoptosis.

Pharmaceutical compositions of the invention also can be administered in combination therapy, i.e., combined with other agents. For example, the combination therapy can include a composition of the present invention with at least one anti-inflammatory agent or at least one immunosuppressive agent. In one embodiment such therapeutic agents include one or more anti-inflammatory agents, such as a steroidal drug or a NSAID (nonsteroidal anti-inflammatory drug). Preferred agents include, for example, aspirin and other salicylates, Cox-2 inhibitors, such as rofecoxib (Vioxx) and celecoxib (Celebrex), NSAIDs such as ibuprofen (Motrin, Advil), fenoprofen (Nalfon), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), and indomethacin (Indocin).

In another embodiment, such therapeutic agents include agents leading to the depletion or functional inactivation of regulatory T cells like low dose cyclophosphamid, anti-CTLA4 antibodies, anti-IL2 or anti-IL2-receptor antibodies.

In yet another embodiment, such therapeutic agents include one or more chemotherapeutics, such as Taxol derivatives, taxotere, gemcitabin, 5-Fluoruracil, doxorubicin (Adriamycin), cisplatin (Platinol), cyclophosphamide (Cytoxan, Procytox, Neosar). In another embodiment, antibodies of the present invention may be administered in combination with chemotherapeutic agents, which preferably show therapeutic efficacy in patients suffering from stomach, esophageal, pancreatic and lung cancer.

In yet another embodiment, the antibodies of the invention may be administered in conjunction with radiotherapy and/or autologous peripheral stem cell or bone marrow transplantation.

In still another embodiment, the antibodies of the invention may be administered in combination with one or more antibodies selected from anti-CD25 antibodies, anti-EPCAM antibodies, anti-EGFR, anti-Her2/neu, and anti-CD40 antibodies.

In yet a further embodiment, the antibodies of the invention may be administered in combination with an anti-C3b(i) antibody in order to enhance complement activation.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge. S. M., et al. (1977) J. Pharm. Sci. 66: 1-19).

Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) J. Neuroimmunol. 7: 27).

Pharmaceutically acceptable carriers include sterile aqueous solutions or dispersions and sterile powders for the extemporaneous preparation of sterile injectable solutions or dispersions. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect.

Generally, out of one hundred percent, this amount will range from about 0.01 percent to about ninety-nine percent of active ingredient, preferably from about 0.1 percent to about 70 percent, most preferably from about 1 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In one embodiment the monoclonal antibodies of the invention are administered in crystalline form by subcutaneous injection, cf. Yang et al. (2003) PNAS, 100 (12): 6934-6939. When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

In one embodiment, the antibodies of the invention may be administered by infusion, preferably slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months. The dosage can be determined or adjusted by measuring the amount of circulating monoclonal anti-CLD18 antibodies upon administration in a biological sample by using anti-idiotypic antibodies which target the anti-CLD18 antibodies.

In yet another embodiment, the antibodies are administered by maintenance therapy, such as, e.g., once a week for a period of 6 months or more.

In still another embodiment, the antibodies according to the invention may be administered by a regimen including one infusion of an antibody against CLD18 followed by an infusion of an antibody against CLD18 conjugated to a radioisotope. The regimen may be repeated, e.g., 7 to 9 days later.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include those described in: U.S. Pat. No. 4,487,603, which discloses an implantable micro-infusion pump for dispensing medication at a controlled rate: U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments: and U.S. Pat. No. 4,475,196, which discloses an osmotic drug delivery system.

Many other such implants, delivery systems, and modules are known to those skilled in the art. In certain embodiments, the antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, and thus enhance targeted drug delivery (see, e.g., V. V. Ranade (1989) J. Clin. Pharmacol. 29: 685). Exemplary targeting moieties include folate or biotin (see, e.g., U.S. Pat. No. 5,416,016 to Low et al.); mannosides (Umezawa et al., (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); and surfactant protein A receptor (Briscoe et al. (1995) Am. J. Physiol. 1233: 134).

In one embodiment of the invention, the therapeutic compounds of the invention are formulated in liposomes. In a more preferred embodiment, the liposomes include a targeting moiety. In a most preferred embodiment, the therapeutic compounds in the liposomes are delivered by bolus injection to a site proximal to the desired area, e.g., the site of a tumor. The composition must be fluid to the extent that easy syringability exists. It must be stable under the conditions of manufacture and storage and must be preserved against the contaminating action of microorganisms such as bacteria and fungi.

In a further embodiment, antibodies of the invention can be formulated to prevent or reduce their transport across the placenta. This can be done by methods known in the art, e.g., by PEGylation of the antibodies or by use of F(ab)2' fragments. Further references can be made to "Cunningham-Rundles C, Zhuo Z, Griffith B, Keenan J. (1992) Biological activities of polyethylene-glycol immunoglobulin conjugates. Resistance to enzymatic degradation. J. Immunol. Methods, 152: 177-190; and to "Landor M. (1995) Maternal-fetal transfer of immunoglobulins, Ann. Allergy Asthma Immunol. 74: 279-283.

A "therapeutically effective dosage" for tumor therapy can be measured by objective tumor responses which can either be complete or partial. A complete response (CR) is defined as no clinical, radiological or other evidence of disease. A partial response (PR) results from a reduction in aggregate tumor size of greater than 50%. Median time to progression is a measure that characterizes the durability of the objective tumor response.

A "therapeutically effective dosage" for tumor therapy can also be measured by its ability to stabilize the progression of disease. The ability of a compound to inhibit cancer can be evaluated in an animal model system predictive of efficacy in human tumors. Alternatively, this property of a composition can be evaluated by examining the ability of the compound to inhibit cell growth or apoptosis by in vitro assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

IV. Uses and Methods of the Invention

The antibodies (including immunoconjugates, bispecifics/multispecifics, compositions and other derivatives described herein) of the present invention have numerous therapeutic utilities involving the treatment of disorders involving cells expressing CLD18. For example, the antibodies can be administered to cells in culture, e.g., in vitro or ex vivo, or to human subjects, e.g., in vivo, to treat or prevent a variety of disorders such as those described herein. As used herein, the term "subject" is intended to include human and non-human animals which respond to the antibodies against CLD18. Preferred subjects include human patients having disorders that can be corrected or ameliorated by killing diseased cells, in particular cells characterized by an altered expression pattern of CLD18 compared to normal cells.

A therapeutic effect in the treatments discussed herein is preferably achieved through the functional properties of the antibodies of the invention to mediate killing of cells e.g. by inducing complement dependent cytotoxicity (CDC) mediated lysis, antibody dependent cellular cytotoxicity (ADCC) mediated lysis, apoptosis, homotypic adhesion, and/or phagocytosis, preferably by inducing CDC mediated lysis and/or ADCC mediated lysis.

For example, in one embodiment, antibodies of the present invention can be used to treat a subject with a tumorigenic disorder, e.g., a disorder characterized by the presence of tumor cells expressing CLD18 including, for example, gastric cancer. Examples of tumorigenic diseases which can be treated and/or prevented encompass all CLD18 expressing cancers and tumor entities including stomach cancer, esophageal cancer, pancreatic cancer, lung cancer, ovarian cancer, breast cancer, colorectal cancer, hepatic cancer, cancer of the gallbladder and head-neck cancer. These cancers may be in early, intermediate or advanced stages, e.g. metastasis.

The pharmaceutical compositions and methods of treatment described according to the invention may also be used for immunization or vaccination to prevent a disease described herein.

In another embodiment, antibodies of the invention can be used to detect levels of CLD18 or particular forms of CLD18, or levels of cells which contain CLD18 on their membrane surface, which levels can then be linked to certain diseases or disease symptoms such as described above. Alternatively, the antibodies can be used to deplete or interact with the function of CLD18 expressing cells, thereby implicating these cells as important mediators of the disease. This can be achieved by contacting a sample and a control sample with the anti-CLD18 antibody under conditions that allow for the formation of a complex between the antibody and CLD18. Any complexes formed between the antibody and CLD18 are detected and compared in the sample and a control sample, i.e. a reference sample.

Antibodies of the invention can be initially tested for their binding activity associated with therapeutic or diagnostic uses in vitro. For example, the antibodies can be tested using flow cytometric assays as described herein.

Moreover, activity of the antibodies in triggering at least one effector-mediated effector cell activity, including inhibiting the growth of and/or killing of cells expressing CLD18, can be assayed. For example, the ability of the antibodies to trigger CDC and/or apoptosis can be assayed. Protocols for assaying for CDC, homotypic adhesion, molecular clustering or apoptosis are described herein.

The antibodies of the invention can be used to elicit in vivo or in vitro one or more of the following biological activities: to inhibit the growth of and/or differentiation of a cell expressing CLD18; to kill a cell expressing CLD18; to mediate phagocytosis or ADCC of a cell expressing CLD18 in the presence of effector cells; to mediate CDC of a cell expressing CLD18 in the presence of complement; to mediate apoptosis of a cell expressing CLD18, to induce homotypic adhesion; and/or to induce translocation into lipid rafts upon binding CLD18.

In a particular embodiment, the antibodies are used in vivo or in vitro to treat, prevent or diagnose a variety of CLD18-related diseases. Examples of CLD18-related diseases include, among others, cancers such as gastric cancer, pancreatic cancer, esophageal cancer, lung cancer and cancers as those listed above.

CLD18A2 is also expressed in differentiated normal stomach cells. Possible antibody induced clinical side effects by killing of these cells may be reduced or avoided by parallel administration of stomach protective drugs such as antacida, or inhibitors of the gastric proton pump such as omeprazol or related drugs.

Suitable routes of administering the antibody compositions of the invention in vivo and in vitro are well known in the art and can be selected by those of ordinary skill.

As described above, anti-CLD18 antibodies of the invention can be co-administered with one or other more therapeutic agents, e.g., a cytotoxic agent, a radiotoxic agent, antiangiogeneic agent or and immunosuppressive agent to reduce the induction of immune responses against the antibodies of invention. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as listed above. Co-administration of the anti-CLD18 antibodies of the present invention with chemotherapeutic agents provides two anti-cancer agents which operate via different mechanisms yielding a cytotoxic effect to tumor cells. Such co-administration can solve problems due to development of resistance to drugs or a change in the antigenicity of the tumor cells which would render them unreactive with the antibody.

In another particular embodiment of the invention, the subject being administered the antibody is additionally treated with an antiagionic agent including antibodies targeting VEGF or VEGFR and one or more chemical compounds inhibiting angiogenesis. Pretreatment with or parallel application of these drugs may improve the penetration of antibodies in bulk tumors.

In another particular embodiment of the invention, the subject being administered the antibody is additionally treated with a compound inhibiting growth factor receptor signaling including monoclonal antibodies binding to the EGFR receptor as well as chemical compounds inhibiting signaling initiated by the EGFR, Her1 or Her2/neu receptor.

Target-specific effector cells, e.g., effector cells linked to compositions (e.g. antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$ to $10^9$ but will vary depending on the therapeutic purpose. In general, the amount will be sufficient to obtain localization at the target cell, e.g., a tumor cell expressing CLD18, and to effect cell killing by, e.g., phagocytosis. Routes of administration can also vary.

Therapy with target-specific effector cells can be performed in conjunction with other techniques for removal of targeted cells. For example, anti-tumor therapy using the compositions of the invention and/or effector cells armed with these compositions can be used in conjunction with chemotherapy. Additionally, combination immunotherapy may be used to direct two distinct cytotoxic effector populations toward tumor cell rejection. For example, anti-CLD18 antibodies linked to anti-Fc-RI or anti-CD3 may be used in conjunction with IgG- or IgA-receptor specific binding agents.

Bispecific and multispecific molecules of the invention can also be used to modulate Fc-gammaR or Fc-alphaR levels on effector cells, such as by capping and eliminating receptors on the cell surface. Mixtures of anti-Fc receptors can also be used for this purpose.

The compositions (e.g., antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions of the invention can also be lysed by complement. In yet another embodiment, the compositions of the invention do not activate complement.

The compositions of the invention can also be administered together with complement. Accordingly, within the scope of the invention are compositions comprising antibodies, multispecific or bispecific molecules and serum or complement. These compositions are advantageous in that the complement is located in close proximity to the antibodies, multispecific or bispecific molecules.

Alternatively, the antibodies, multispecific or bispecific molecules of the invention and the complement or serum can be administered separately. Binding of the compositions of the present invention to target cells causes translocation of the CLD18 antigen-antibody complex into lipid rafts of the cell membrane. Such translocation creates a high density of antigen-antibody complexes which may efficiently activate and/or enhance CDC.

Also within the scope of the present invention are kits comprising the antibody compositions of the invention (e.g., antibodies and immunoconjugates) and instructions for use. The kit can further contain one or more additional reagents, such as an immunosuppressive reagent, a cytotoxic agent or a radiotoxic agent, or one or more additional antibodies of the invention (e.g., an antibody having a complementary activity).

Accordingly, patients treated with antibody compositions of the invention can be additionally administered (prior to, simultaneously with, or following administration of a antibody of the invention) with another therapeutic agent, such as a cytotoxic or radiotoxic agent, which enhances or augments the therapeutic effect of the antibodies of the invention.

In other embodiments, the subject can be additionally treated with an agent that modulates, e.g., enhances or inhibits, the expression or activity of Fc-gamma or Fc-alpha receptors by, for example, treating the subject with a cytokine. Preferred cytokines include granulocyte colony-stimulating factor (G-CSF), granulocyte-macrophage colony-stimulating factor (GM-CSF), interferon-γ (IFN-γ), and tumor necrosis factor (TNF). Other important agents for increasing the therapeutic efficacy of the antibodies and pharmaceutical compositions described herein are β-glucans which are homopolysaccharides of branched glucose residues and are produced by a variety of plants and microorganisms, for example, bacteria, algae, fungi, yeast and grains. Fragments of β-glucans produced by organisms may be also be used. Preferably, the β-glucan is a polymer of β(1,3) glucose wherein at least some of the backbone glucose units, e.g. 3-6% of the backbone glucose units, possess branches such as β(1,6) branches.

In a particular embodiment, the invention provides methods for detecting the presence of CLD18 antigen in a sample, or measuring the amount of CLD18 antigen, comprising contacting the sample, and a control sample, with a antibody which specifically binds to CLD18, under conditions that allow for formation of a complex between the antibody or portion thereof and CLD18. The formation of a complex is then detected, wherein a difference complex formation between the sample compared to the control sample is indicative for the presence of CLD18 antigen in the sample.

In still another embodiment, the invention provides a method for detecting the presence or quantifying the amount of CLD18-expressing cells in vivo or in vitro. The method comprises (i) administering to a subject a composition of the invention conjugated to a detectable marker; (ii) exposing the subject to a means for detecting said detectable marker to identify areas containing CLD18-expressing cells.

Methods as described above are useful, in particular, for diagnosing CLD18-related diseases and/or the localization of CLD18-related diseases such as cancer diseases. Preferably an amount of CLD18, preferably CLD18-A2 in a sample which is higher than the amount of CLD18, preferably CLD18-A2, in a control sample is indicative for the presence of a CLD18-related disease in a subject, in particular a human, from which the sample is derived.

In yet another embodiment immunoconjugates of the invention can be used to target compounds (e.g., therapeutic agents, labels, cytotoxins, radiotoxins immunosuppressants, etc.) to cells which have CLD18 expressed on their surface by linking such compounds to the antibody. Thus, the invention also provides methods for localizing ex vivo or in vitro cells expressing CLD18, such as circulating tumor cells.

The present invention is further illustrated by the following examples which are not be construed as limiting the scope of the invention.

EXAMPLES

1. Generation of Murine Antibodies Against CLD18 a. Immunizations:

Balb/c or C57/BL6 mice were immunized with eucaryotic expression vectors, encoding human CLD18 fragments (SEQ ID NO: 15, 16; 17, 18). 50 μg or 25 μg of plasmid DNA was injected into the quadriceps (intramuscular, i.m.) on days 1 and 10 for generation of monoclonal antibodies of Set1 or alternatively on days 1 and 9, 1 and 11, or 1, 16 and 36 for generation of monoclonal antibodies of Set2 in the presence of adjuvants, for example CpG (for details see Tab. 1b). CpG as well as cells transfected with CLD18A2 (SEQ ID NO: 1) alone or co-transfected additionally with murine soluble CD40L encoding RNA were injected intramuscularly, PEI-Man was injected intramuscularly or intraperitonally. The presence of antibodies directed against human CLD18 in sera of mice was monitored by immune fluorescence microscopy between day 16 and 43 depending on the specific immunization protocol used. The immune fluorescence was determined using HEK293 cells transiently transfected with a nucleic acid encoding a fusion construct comprising human CLD18A2 (SEQ ID NOs: 1, 2) and a fluorescent reporter protein. Mice with detectable immune responses (FIG. 1) were boosted three days prior to splenectomy for generation of monoclonal antibodies of Set1, or mice were boosted three days, three and two days, or mice were boosted four, three and two days prior to splenectomy for generation of monoclonal antibodies of Set2 by intraperitonal injection of $5\times10^7$ or alternatively $1\times10^8$ HEK293 cells transiently transfected with a nucleic acid encoding human CLD18A2 (SEQ ID NOs: 1, 2) (for details see Tab. 1b). In Tab. 1a the immunization protocols used are dedicated to the respective monoclonal antibodies.

TABLE 1a

Immunisation protocols used for generation of monoclonal antibodies

| mAB | Immunisation protocol* | mAB | Immunisation protocol* |
|---|---|---|---|
| Set1 | | | |
| 24H5 | 40 | 42E12 | 45 |
| 26B5 | 40 | 43A11 | 45 |
| 26D12 | 40 | 44E10 | 45 |
| 28D10 | 40 | 47D12 | 45 |
| 37G11 | 45 | 61C2 | 45 |
| 37H8 | 45 | 75B8 | 6 |
| 38G5 | 45 | 85A3 | 6 |
| 38H3 | 45 | 9E8 | 40 |
| 39F11 | 45 | 19B9 | 40 |
| 41C6 | 45 | | |
| Set2 | | | |
| 45C1 | 53 | 166E2 | 51 |
| 125E1 | 45 | 175D10 | 51 |
| 163E12 | 51 | | |

*For specific immunization protocols see Tab. 1b

TABLE 1b

Detailed immunisation protocols

| | Immunisation (prime and boosts with DNA) | | | | Boosts with transfected cells | | |
|---|---|---|---|---|---|---|---|
| Immunisation protocol | with DNA vectors encoding CLD18 fragments | with adjuvant | on day | Serum-monitoring on day | Cells transfected with CLD18A2 (SEQ ID NO: 1) alone | Cells co-transfected with CLD18A2 (SEQ ID NO: 1) and with murine soluble CD40L encoding RNA | days prior to splenectomy |
| 6 | SEQ ID NO: 15: 50 μg | 50 μg CpG | 1 and 10 | 18 | 5 × $10^7$ transfected MC3T3 cells | none | 3 |
| 40 | SEQ ID NO: 17: 50 μg | 50 μg CpG | 1 and 10 | 18 | | 5 × $10^7$ HEK293 cells; 100 μg CPG as adjuvant | 3 |
| 45 | SEQ ID NO: 15: 50 μg | 50 μg CpG | 1 and 9 | 16 | | 1 × $10^8$ HEK293 cells | 3 |

TABLE 1b-continued

Detailed immunisation protocols

| Immunisation protocol | Immunisation (prime and boosts with DNA): with DNA vectors encoding CLD18 fragments | with adjuvant | on day | Serum-monitoring on day | Boosts with transfected cells: Cells transfected with CLD18A2 (SEQ ID NO: 1) alone | Cells co-transfected with CLD18A2 (SEQ ID NO: 1) and with murine soluble CD40L encoding RNA | days prior to splenectomy |
|---|---|---|---|---|---|---|---|
| 51 | SEQ ID NO: 15: 25 μg | 2.5 μl PEI-Man* (150 mM) in $H_2O$ with 5% Glucose | 1, 16 and 36 | 22, 30 and 43 | 5 × $10^7$ transfected HEK293 cells | none | 3 and 2 |
| 53 | Priming: SEQ ID NO: 15: 25 μg, and SEQ ID NO: 17: 25 μg; Boosting: SEQ ID NO: 17: 50 μg | 50 μg CpG in $H_2O$ with 5% Glucose | 1 and 11 | 20 | 5 × $10^7$ transfected HEK293 cells | none | 4, 3 and 2 |

*in vivo-jetPEI ™-Man from PolyPlus Transfection b. Generation of Hybridomas Producing Human Monoclonal Antibodies to CLD18:

Mouse splenocytes were isolated and fused with PEG to a mouse myeloma cell line based on standard protocols. The resulting hybridomas were then screened for production of immunoglobulines with CLD18 specificity using HEK293 cells transfected with a nucleic acid encoding human CLD18 by FACS analysis.

Single cell suspensions of splenic lymphocytes from immunized mice were fused with P3X63Ag8U.1 nonsecreting mouse myeloma cells (ATCC, CRL 1597) in a 2:1 ratio using 50% PEG (Roche Diagnostics, CRL 738641). Cells were plated at approximately 3×$10^4$/well in flat bottom microtiter plates, followed by about two week incubation in selective medium containing 10% fetal bovine serum, 2% hybridoma fusion and cloning supplement (HFCS, Roche Diagnostics, CRL 1 363 735) plus 10 mM HEPES, 0.055 mM 2-mercaptoethanol, 50 μg/ml gentamycin and 1×HAT (Sigma, CRL H0262). After 10 to 14 days individual wells were screened by flow cytometry for anti-CLD18 monoclonal antibodies. The antibody secreting hybridomas were replated, screened again and, if still positive for anti-CLD18 monoclonal antibodies, were subcloned by limiting dilution. The stable subclones were then cultured in vitro to generate small amounts of antibody in tissue culture medium for characterization. At least one clone from each hybridoma, which retained the reactivity of parent cells (by FACS), was chosen. 9 vial cell banks were generated for each clone and stored in liquid nitrogen.

c. Selection of Monoclonal Antibodies Binding to CLD18:

To determine the isotype of antibodies, an isotype ELISA was performed. The mouse monoAB ID Kit (Zymed, CRL 90-6550) or alternatively the IsoStrip Mouse Monoclonal Antibody Isotyping Kit (Roche, Cat. No. 1493027) was used to determine Ig subclasses of the identified CLD18 reactive monoclonal antibodies.

Defined as Set1, nineteen hybridoma cell lines were generated, six from a fusion of cells from a C57/BL6 mouse immunized with CLD18A2-LoopD3 (SEQ ID NOs: 17, 18), thirteen from a fusion of cells from a Balb/c mouse immunized with CLD18A2-Loop1 (SEQ ID NOs: 15, 16), expressing the following antibodies:

24H5, 26B5, 26D12, 28D10, 37G11, 37H8, 38G5, 38H3, 39F11, 41C6, 42E12, 43A11, 44E10, 47D12, 61C2, 75B8, 85A3, 9E8, 19B9

24H5: mouse monoclonal IgG2b, κ antibody, 182-D758-034

26B5: mouse monoclonal IgG2a, κ antibody, 182-D758-035, DSM ACC2745

26D12: mouse monoclonal IgG3, κ antibody, 182-D758-036, DSM ACC2746

28D10: mouse monoclonal IgG3, κ antibody, 182-D758-040, DSM ACC2747

37G11: mouse monoclonal IgG2a, κ antibody, 182-D1106-055, DSM ACC2737

37H8: mouse monoclonal IgG3, κ antibody, 182-D1106-056, DSM ACC2738

38G5: mouse monoclonal IgG3, κ antibody, 182-D1106-057, DSM ACC2739

38H3: mouse monoclonal IgG3, κ antibody, 182-D1106-058, DSM ACC2740

39F11: mouse monoclonal IgG3, κ antibody, 182-D1106-059, DSM ACC2741

41C6: mouse monoclonal IgG2a, κ antibody, 182-D1106-060

42E12: mouse monoclonal IgG2a, κ antibody, 182-D1106-061, DSM ACC2748

43A11: mouse monoclonal IgG2a, κ antibody, 182-D1106-062, DSM ACC2742

44E10: mouse monoclonal IgG3, κ antibody, 182-D1106-063

47D12: mouse monoclonal IgG3, κ antibody, 182-D1106-064

61C2: mouse monoclonal IgG2b, κ antibody, 182-D1106-067, DSM ACC2743

75B8: mouse monoclonal IgM, κ antibody, 182-D756-001

85A3: mouse monoclonal IgM, κ antibody, 182-D756-002

9E8: mouse monoclonal IgM, κ antibody, 182-D758-011

19B9: mouse monoclonal IgM, κ antibody, 182-D758-024

Defined as Set2, five hybridoma cell lines were generated, one from a fusion of cells from a Balb/c mouse immunized with CLD18A2-LoopD3 (SEQ ID NOs: 17, 18) and CLD18A2-LoopD1 (SEQ ID NOs: 15, 16), four from a fusion of cells from a Balb/c mouse immunized with CLD18A2-LoopD1 (SEQ ID NOs: 15, 16), expressing the following antibodies:

45C1, 125E1, 163E12, 166E2, 175D10

45C1: mouse monoclonal IgG2a, κ antibody, 182-D758-187

125E1: mouse monoclonal IgG2a, κ antibody, 182-D1106-279, DSM ACC2808

163E12: mouse monoclonal IgG3, κ antibody, 182-D1106-294, DSM ACC2809

166E2: mouse monoclonal IgG3, κ antibody, 182-D1106-308

175D10: mouse monoclonal IgG1, κ antibody, 182-D1106-362, DSM ACC2810

2. Production of Monoclonal Antibodies

Production and Purification of Monoclonal Antibodies Reactive to CLD18:

To produce mg amounts of antibody for functional characterization, hybridoma cells were seeded in dialysis based bioreactors (CELLine CL1000, Integra, Chur, CH) at $2\times10^6$ cells/ml. Antibody containing supernatant was harvested once weekly. Mouse monoclonal antibody was purified using Melon Gel (Pierce, Rockford, USA) and concentrated by ammonium sulphate precipitation or alternatively purified by ProteinA using FPLC. Antibody concentration and purity was determined by BCA-Assay and purity checked by sodium dodecylsulphate gel electrophoresis and coomassie staining.

3. Binding Characteristics of Monoclonal Antibodies a. Quality Control of Transfectants in WB, IF:

To generate CLD18A2 expressing cells, HEK293 or CHO cells were transfected with nucleic acids encoding CLD18A2 (SEQ ID NOs: 1, 2) or CLD18A2-myc (SEQ ID NOs: 3, 4).

Figure 2:
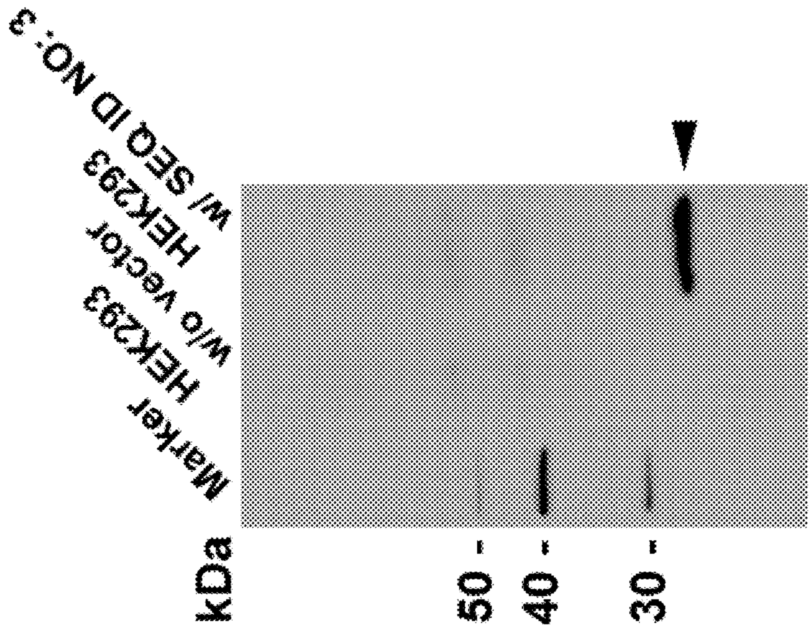
FIG. 2 shows a Western blot analysis of HEK293 cells transfected with CLD18A2-myc (SEQ ID NO: 3) and untransfected HEK293 cells with the monoclonal mouse-anti-c-myc antibody 9E11 (Serotec, CRL MCA2200).

HEK293 cells were transfected with CLDN18A2-myc (SEQ ID NOs: 3, 4) or left untransfected. 24 hours post transfection, cells were harvested, lysed and subjected to sodium dodecylsulphate gel electrophoresis. The gel was blotted and stained with a mouse anti-myc antibody. After incubation with a peroxidase labelled anti mouse antibody, the blot was developed with ECL reagent and visualized using a LAS-3000 imager (Fuji). Only in the transfected cells but not in the negative control, a band with the expected molecular weight of CLD18-myc was observed (FIG. 2).

Figure 3:
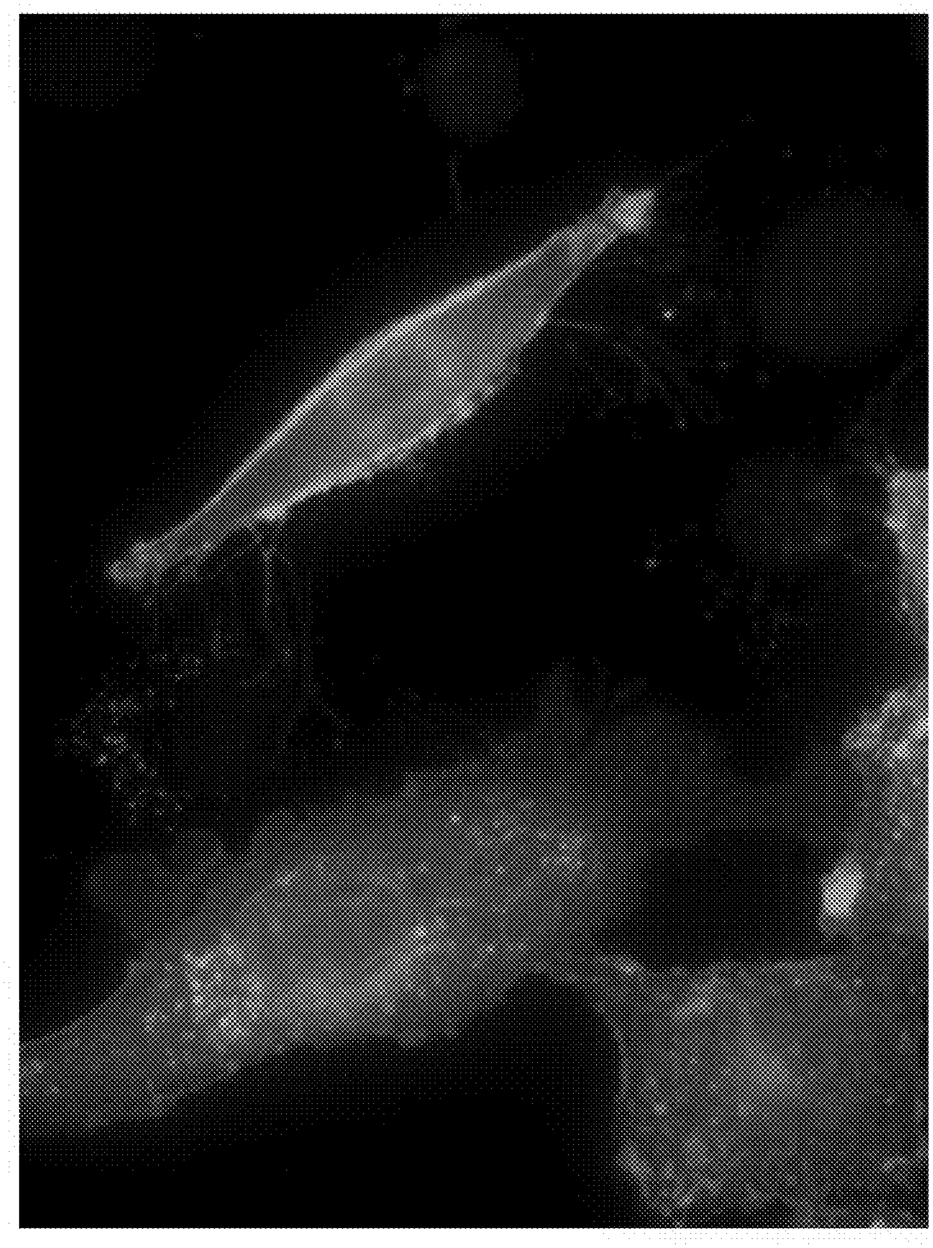
FIG. 3 shows an immunofluorescence analysis using CHO cells transfected with CLD18A2 and a polyclonal rabbit-anti-CLD18 antibody (Zymed, CRL 38-8000).

CHO cells were transfected with CLD18A2 (SEQ ID NOs: 1, 2) and grown on chamber slides for 24 h. Cells were fixed with methanol and stained with a rabbit polyclonal antibody against CLD18 at 1 μg/ml for 60 min. at 25° C. After washing, cells were stained with an Alexa488 labelled goat anti-rabbit IgG (Molecular Probes) and evaluated by fluorescence microscopy. FIG. 3 shows transfected CHO cells, expressing CLD18 on the cell membrane as well as untransfected cells.

Figure 4B:
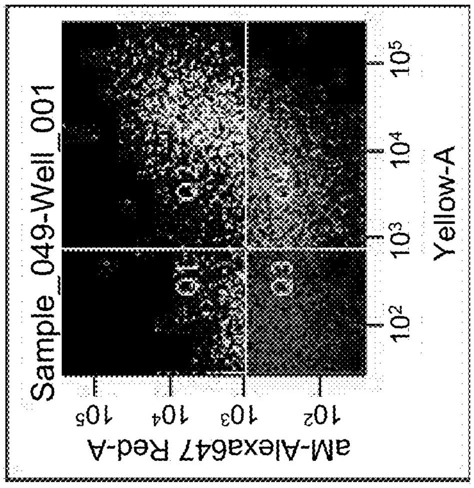
FIG. 4A and FIG. 4B show the binding of hybridoma supernatants 24H5 and 85A3 to HEK293 cells transiently transfected with human CLD18A2 and a fluorescent marker as determined by flow cytometry.
Figure 4A:
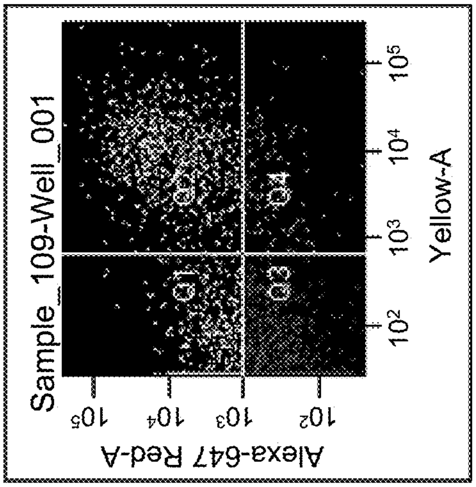
Figure 4C:
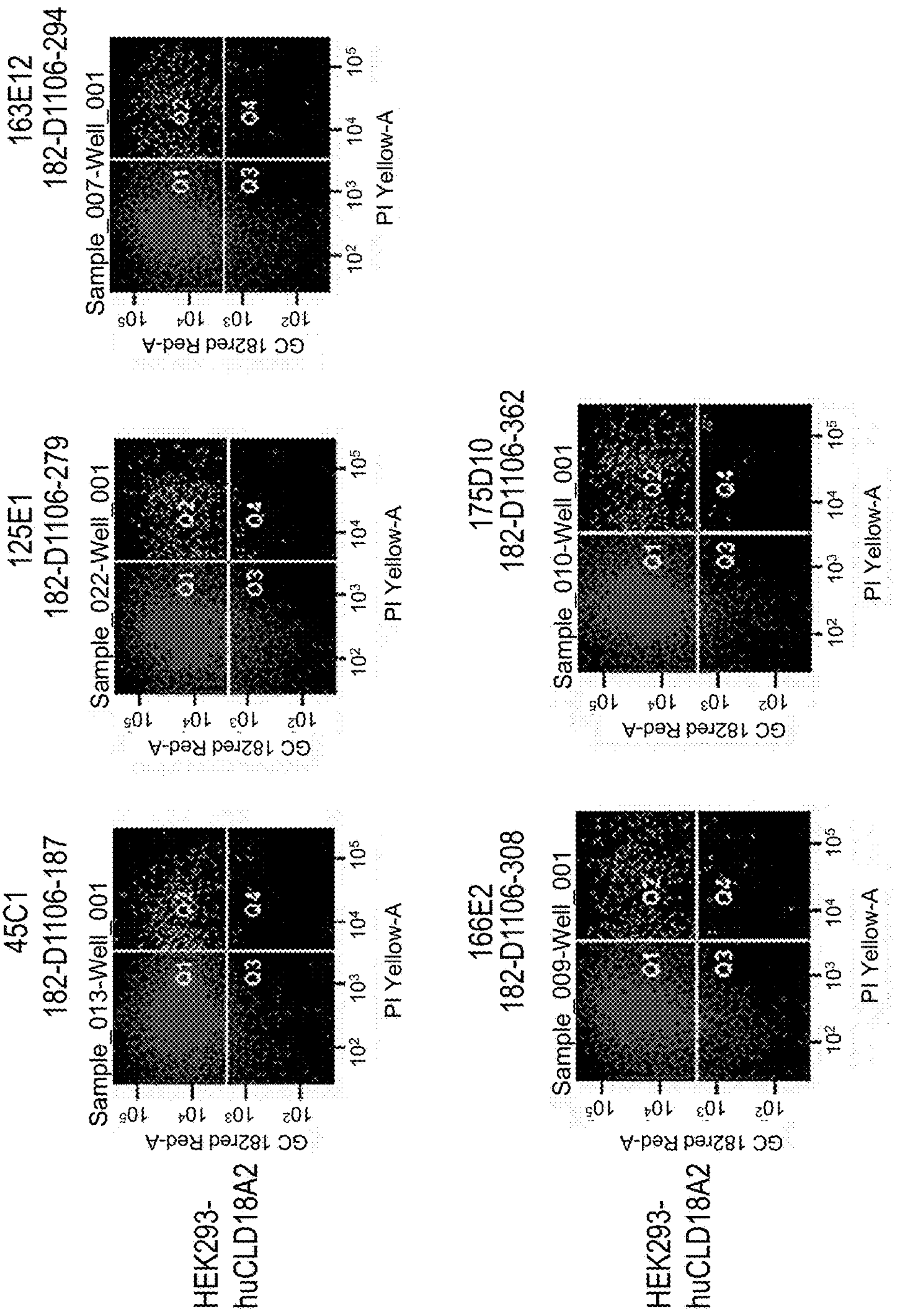
FIG. 4C shows the binding of hybridoma supernatants 45C1, 125E1, 163E12, 166E2 and 175D10 to HEK293 cells stably transfected with human CLD18A2 and counterstained with propidium iodide.
Figure 5A:
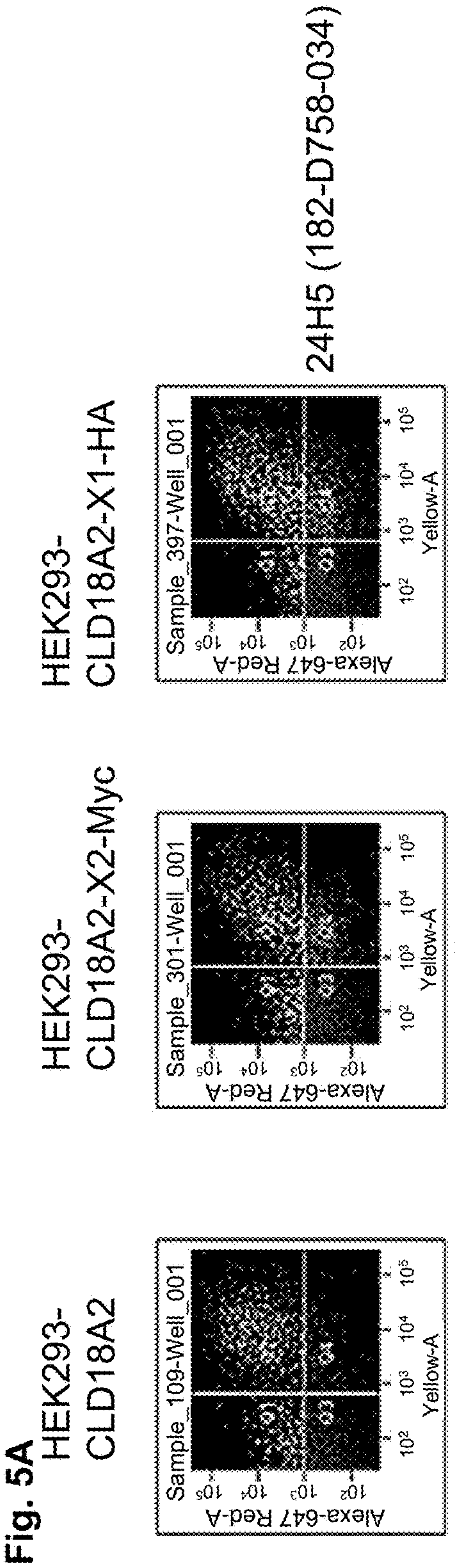
FIG. 5A, FIG. 5B, FIG. 5C, and FIG. 5D show binding of hybridoma supernatants 24H5 (FIG. 5A), 9E8 (FIG. 5B), 26B5 (FIG. 5C) and 19B9 (FIG. 5D), respectively, to HEK293 cells transiently transfected with a fluorescent marker and either human CLD18A2 or CLD18A2-Myc or CLD18A2-HA as analyzed by flow cytometry.
Figure 5B:
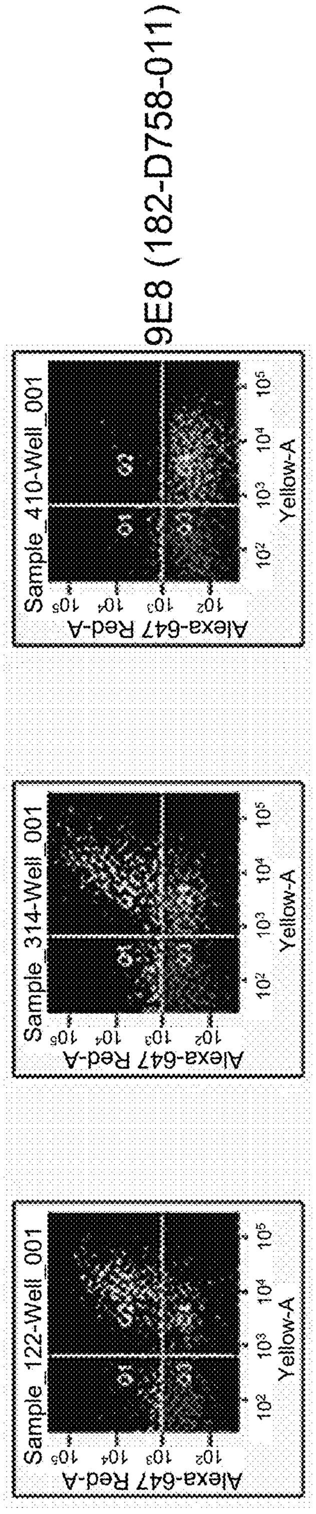
Figure 5C:
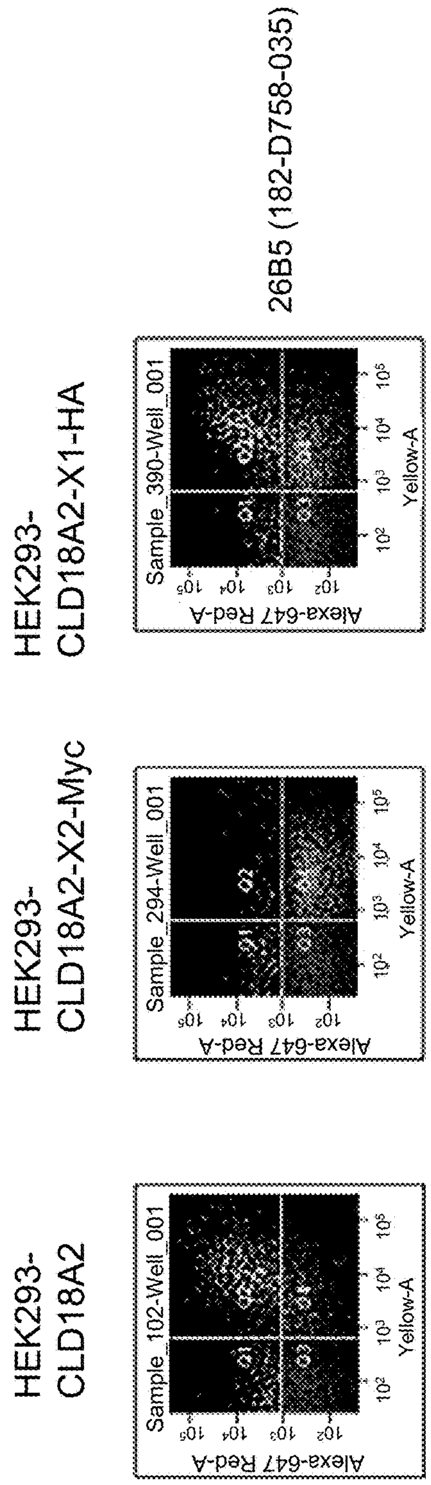
Figure 5D:
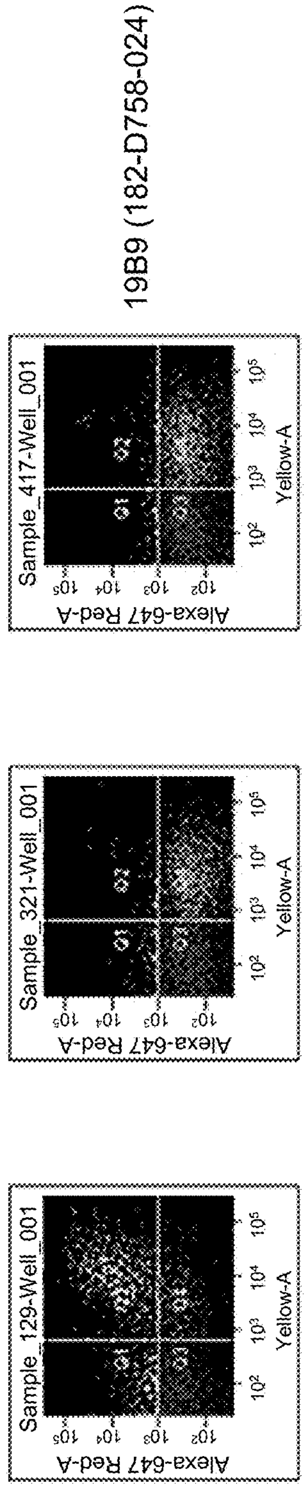
Figure 6A:
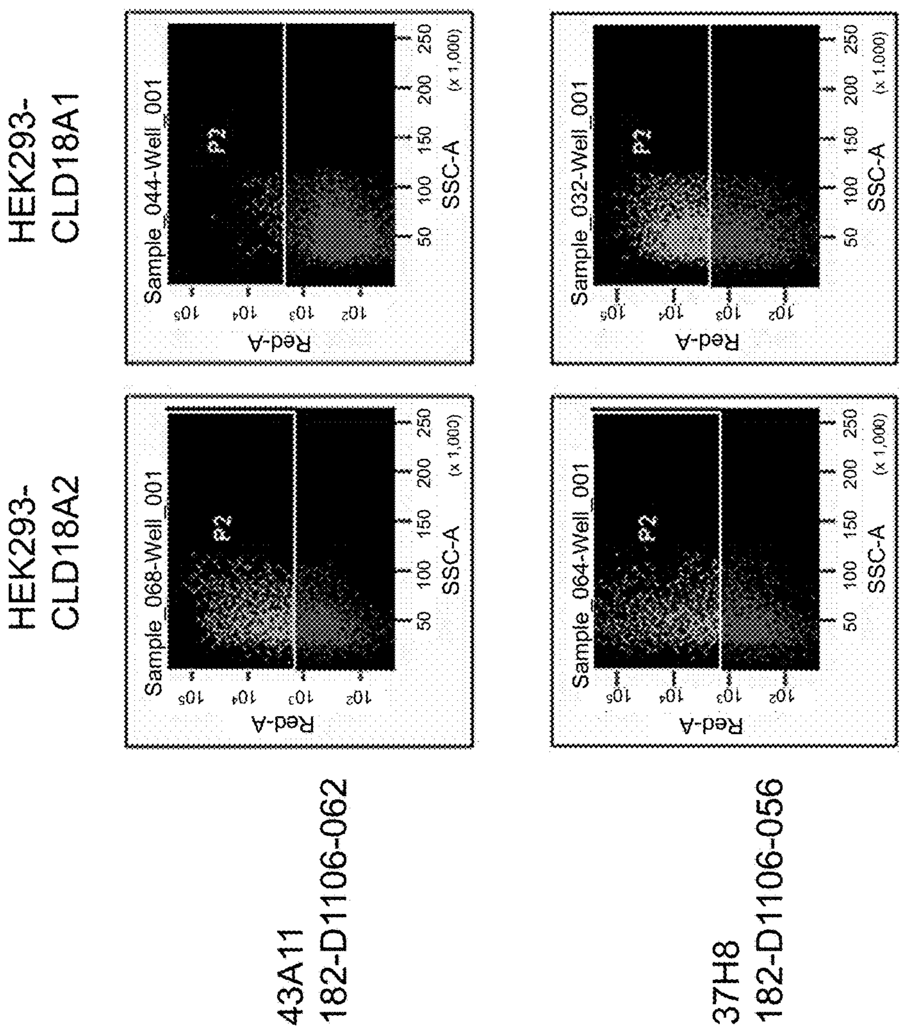
FIG. 6A and FIG. 6B show binding of hybridoma supernatants 37H8, 43A11, 45C1 and 163E12 to HEK293 cells stably transfected with either human CLD18A2 or CLD18A1 as determined by flow cytometry.
Figure 6B:
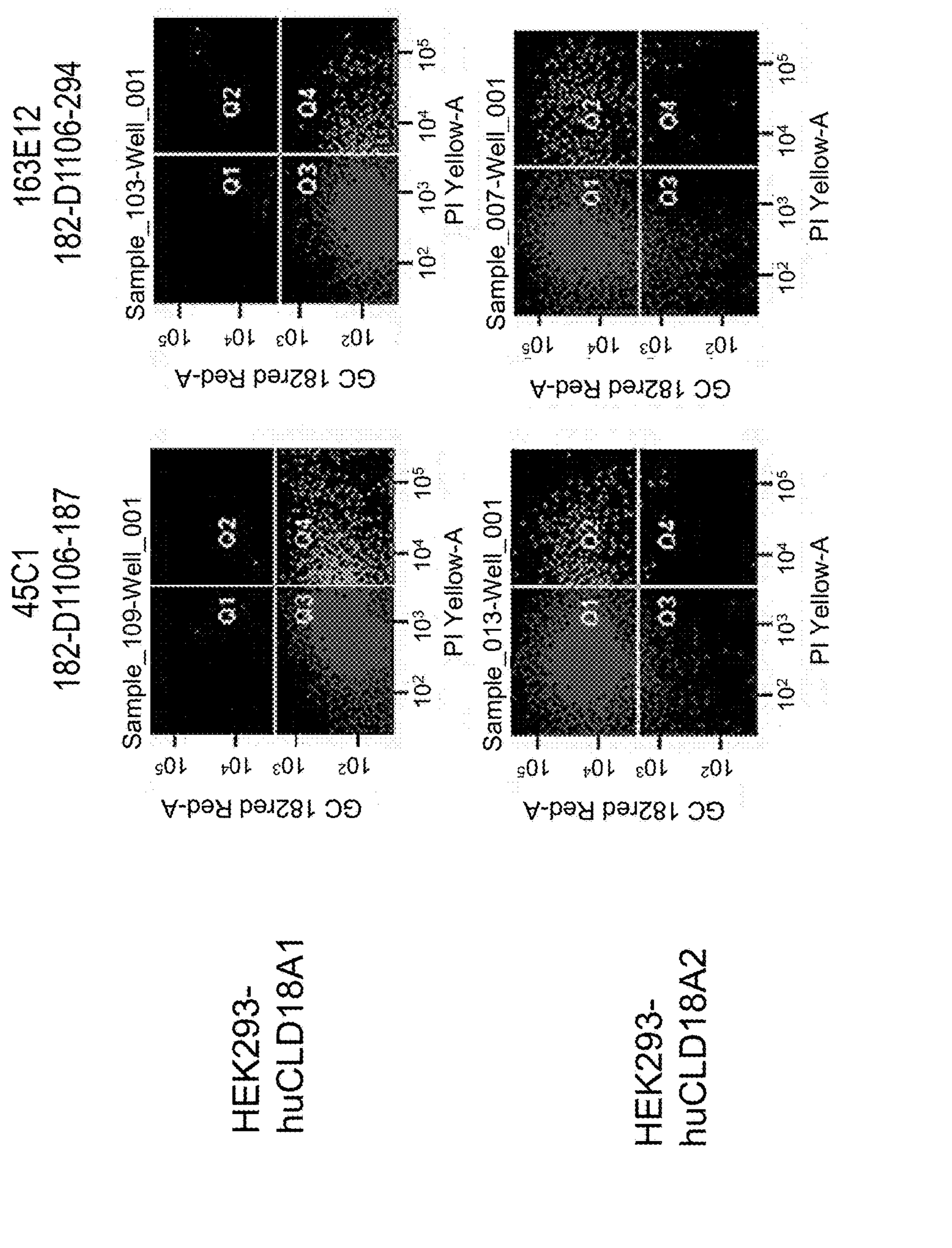
Figure 7A:
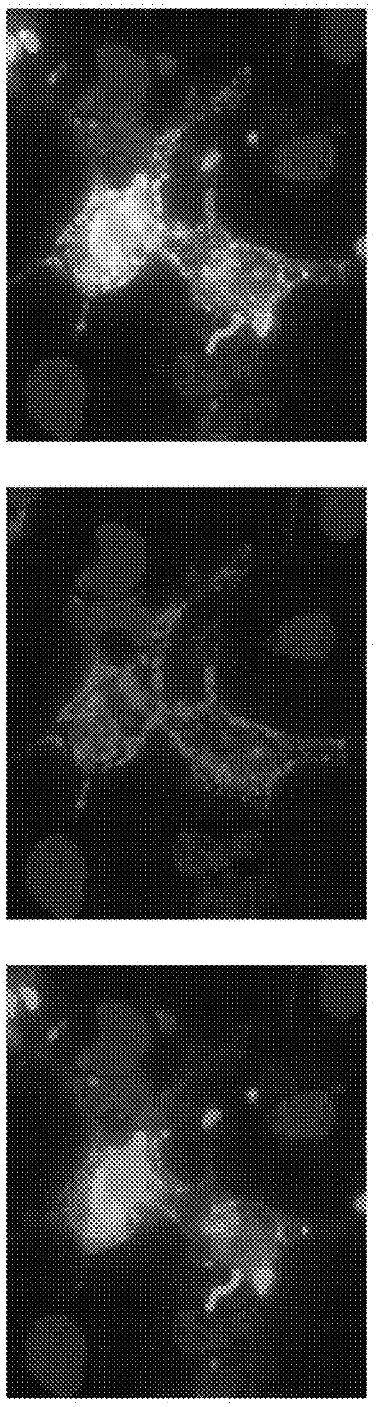
FIG. 7A, FIG. 7B, FIG. 7C, and FIG. 7D show immunofluorescence analysis of the CLD18A2 isoform specific monoclonal antibody 37G11 by staining HEK293 cells transfected with CLD18A2 (FIG. 7A, FIG. 7C) and CLD18A1 (FIG. 7B, FIG. 7D), respectively, under native (FIG. 7A, FIG. 7B) and paraformaldehyde fixation (FIG. 7C, FIG. 7D) conditions.
Figure 7B:
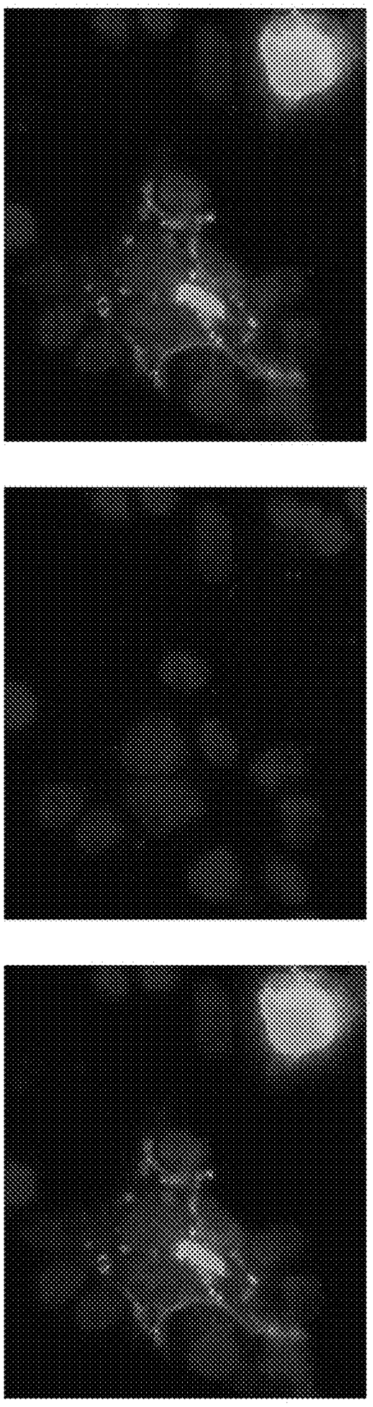

These heterologously CLD18 expressing cells were used for the following assays to test the specificity of antibody binding.

b. Selection of Monoclonal Antibodies Binding to CLD18/Primary Screens by Flow Cytometry:

HEK293 cells were co-transfected with expression vectors encoding human CLD18A2 (SEQ ID NOs: 1, 2) and a fluorescing reporter protein 40 h prior to the assay or alternatively HEK293 cells stably expressing human CLD18A2 (HEK293-CLD18A2) were used and counter-stained with propidium iodide (PI). After cell detachment using 2 mM EDTA/PBS cells were washed with complete growth medium and plated at approximately $1\text{-}5\times10^5$ cells/well in U-bottom microtiter plates. Cells were incubated for 30 min. at 4° C. with hybridoma supernatant followed by two washing steps with 1% heatinactivated FBS/PBS and finally incubation with APC or Alexa647-conjugated anti-mouse IgG specific secondary antibody. After two washing steps, co-transfected cells were fixed with CellFIX (BD Biosciences). Binding was assessed by flow cytometry using a BD FACSArray. Fluorescence marker expression is plotted on the horizontal axis against antibody binding on the vertical axis. All mouse antibodies 24H5, 26B5, 26D12, 28D10, 37G11, 37H8, 38G5, 38H3, 39F11, 41C6, 42E12, 43A11, 44E10, 47D12, 61C2, 75B8, 85A3, 9E8, 19B9, 45C1, 125E1, 163E12, 166E2, and 175D10 were detected to bind specifically to the surface of fluorescence marker expressing cells (FIG. 4A and FIG. 4B, cells in Q2) as exemplified for hybridoma supernatants containing monoclonal antibodies 24H5 (FIG. 4A, cells in Q2), 85A3 (FIG. 4B), 175D10, 125E1, 163E12, 166E2 and 45C1 (FIG. 4C, cells in Q1).

c. Comparison of Antibody Binding to Myc- or HA-tagged CLD18A2:

The binding characteristics of the identified CLD18-specific monoclonal antibodies were further specified. Therefore, monoclonal antibody binding was analyzed to CLD18A2 mutants, created by insertion of epitope tags. CLD8A2-HA (SEQ ID NO: 6) contains a HA-epitope tag in CLD18A2-loop1, whereas CLD18A2-Myc (SEQ ID NO: 4) contains a Myc-epitope tag inserted into CLD18A2-loop2. As insertion of these tags causes destruction of epitopes, the identified monoclonal antibodies, can be grouped according to the loss of binding to any of the mutants. HEK293 cells transiently co-transfected with a fluorescence marker and human CLD18A2, or with a fluorescence marker and CLD8A2-HA, or with a fluorescence marker and CLD18A2-Myc were incubated with hybridoma supernatants containing CLD18-specific monoclonal antibodies for 30 min. at 4° C., followed by incubation with Alexa647-conjugated anti-mouse IgG secondary antibody. Before analysis on a BD FACSArray, cells were fixed using CellFIX. As exemplified for 24H5, 9E8, 26B5 and 19B9 in FIG. 5, monoclonal antibodies could be separated based on their binding characteristics into four different groups: (i) antibodies that bind to unmodified CLD18A2 as well as to CLD18A2-HA and CLD18A2-Myc, e.g. 24H5, (FIG. 5A), or (ii) antibodies that do not bind to CLD18A2-HA, e.g. 9E8, (FIG. 5B), or (iii) antibodies that do not bind to CLD18A2-Myc, e.g. 26B5, (FIG. 5C), or (iv) antibodies that do not bind to CLD18A2-HA nor to CLD18A2-Myc, e.g. 19B9, (FIG. 5D).

d. Comparison of Antibody Binding to Human CLD18A Versus CLD18A2 Transfectants by Flow Cytometry:

Binding specificity of the identified monoclonal antibodies to CLD8A2 isoforms was analyzed by flow cytometry. HEK293 cells stably expressing human CLD18A2 (HEK293-CLD18A2) and HEK293 cells stably expressing human CLD18A1 (SEQ ID NOs: 7, 8) (HEK293-CLD18A1) were incubated for 30 min. at 4° C. with hybridoma supernatants containing monoclonal antibodies, followed by incubation with Alexa647-conjugated anti-mouse IgG secondary antibody and fixation of cells or alternatively without fixation but with PI counterstaining. Binding was assessed by flow cytometry using a BD FACSArray. FIG. 6A and FIG. 6B show examples for the two groups of monoclonal antibodies that were identified in the panel comprised of 24H5, 26B5, 26D12, 28D10, 37G11, 37H8, 38G5, 38H3, 39F11, 41C6, 42E12, 43A11, 44E10, 47D12, 61C2, 75B8, 85A3, 9E8, 19B9, 45C1, 125E1, 163E12, 166E2, 175D10: (i) monoclonal antibodies 43A11, 45C1, and 163E12 bind specifically to human CLD18A2 but not to human CLD18A1 (FIG. 6A, FIG. 6B), and (ii) monoclonal antibody 37H8 binds to both human isoforms (FIG. 6A).

e. Comparison of Antibody Binding to Human CLD18A1 Versus CLD18A2 Transfectants by Immunofluorescence Microscopy:

HEK293 cells were transiently transfected with an expression vector encoding a fusion protein of CLD18A1 (SEQ ID NO: 8) or CLD18A2 (SEQ ID NO: 2) with a fluorescence reporter and grown on chamber slides. Cells were either stained unfixed or after paraformaldehyde fixation with monoclonal antibody containing tissue culture supernatant for 30 min. at 37° C. After washing, cells were stained with an Alexa555-labelled anti-mouse Ig antibody (Molecular Probes). Binding of antibodies was evaluated by fluorescence microscopy. As shown in FIG. 7A, FIG. 7B, FIG. 7C, and FIG. 7D, antibody 37G11 specifically reacted with CLD18A2 (FIG. 7A) but not with CLD18A1 (FIG. 7B). In contrast, antibody 26B5 was reactive with both, CLD18A2 and CLD18A1 (FIG. 8A, FIG. 8B, FIG. 8C, and FIG. 8D).

Figure 7C:
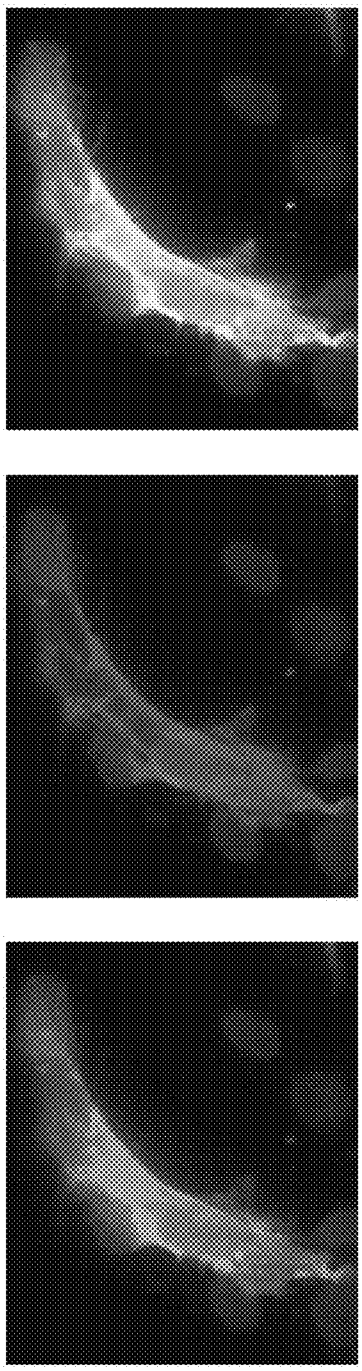
Figure 7D:
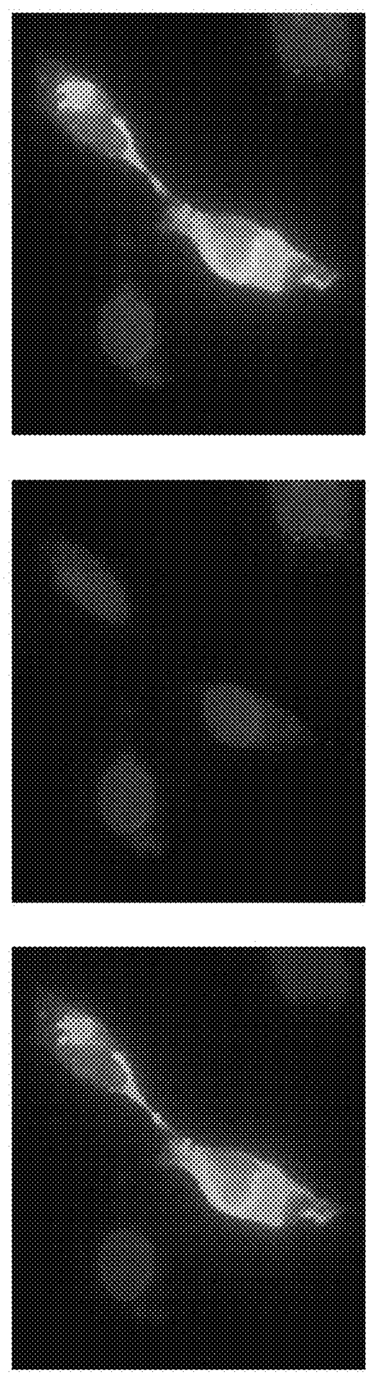
Figure 8A:
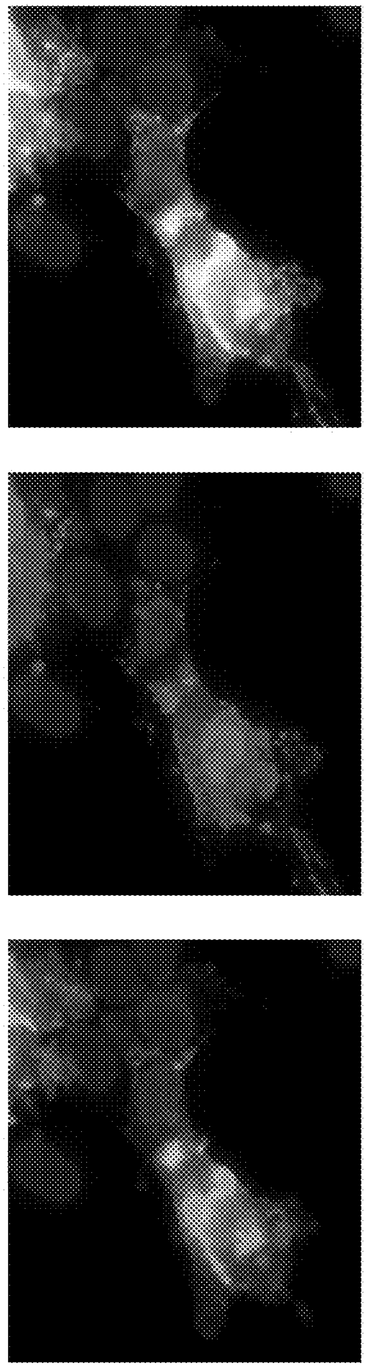
FIG. 8A, FIG. 8B, FIG. 8C, and FIG. 8D show an immunofluorescence analysis of the CLD18 monoclonal antibody 26B5 by staining HEK293 cells transfected with CLD18A2 (FIG. 8A, FIG. 8C) and CLD18A1 (FIG. 8B, FIG. 8D), respectively, under native (FIG. 8A, FIG. 8B) and paraformaldehyde fixation (FIG. 8C, FIG. 8D) conditions.
Figure 8B:
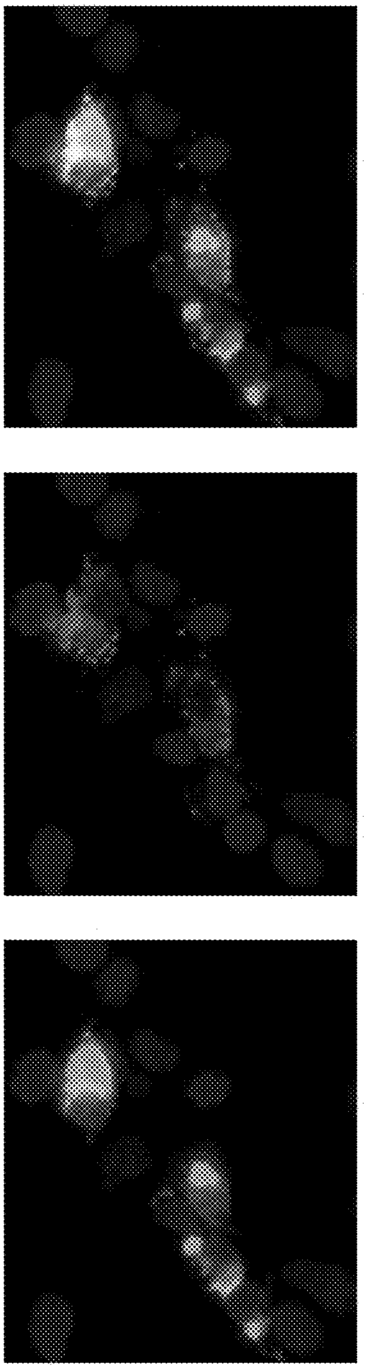
Figure 8C:
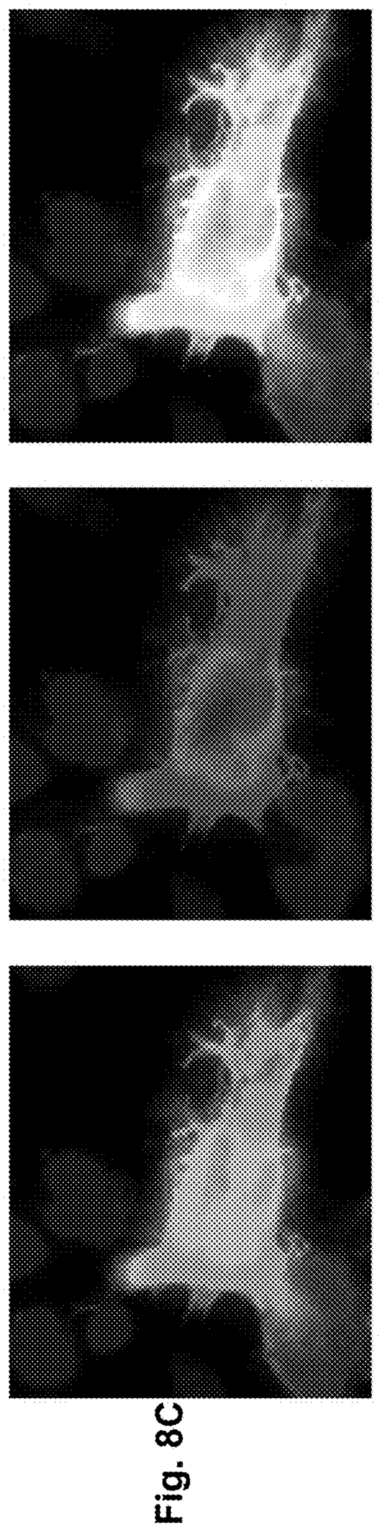
Figure 8D:
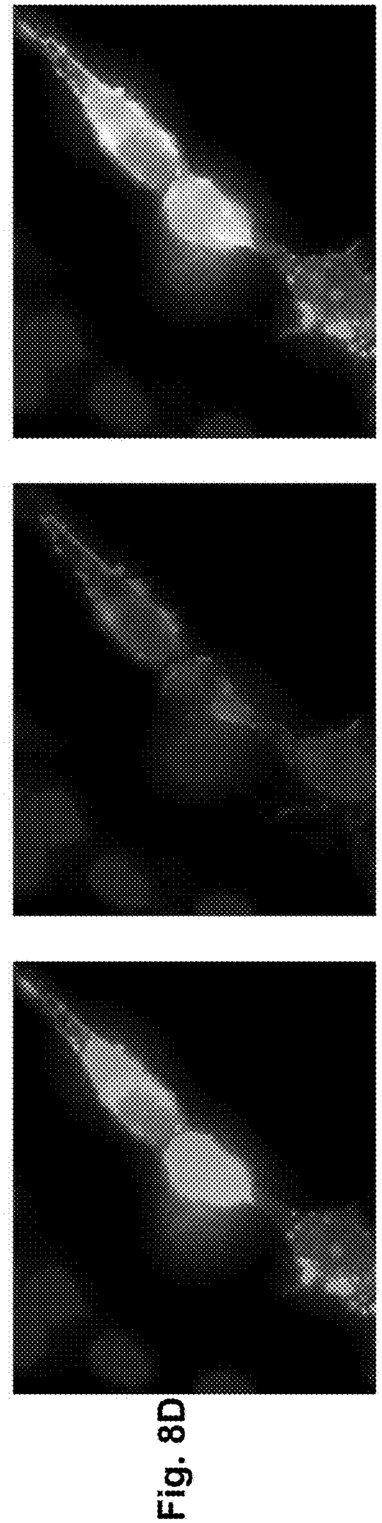
Figure 9:
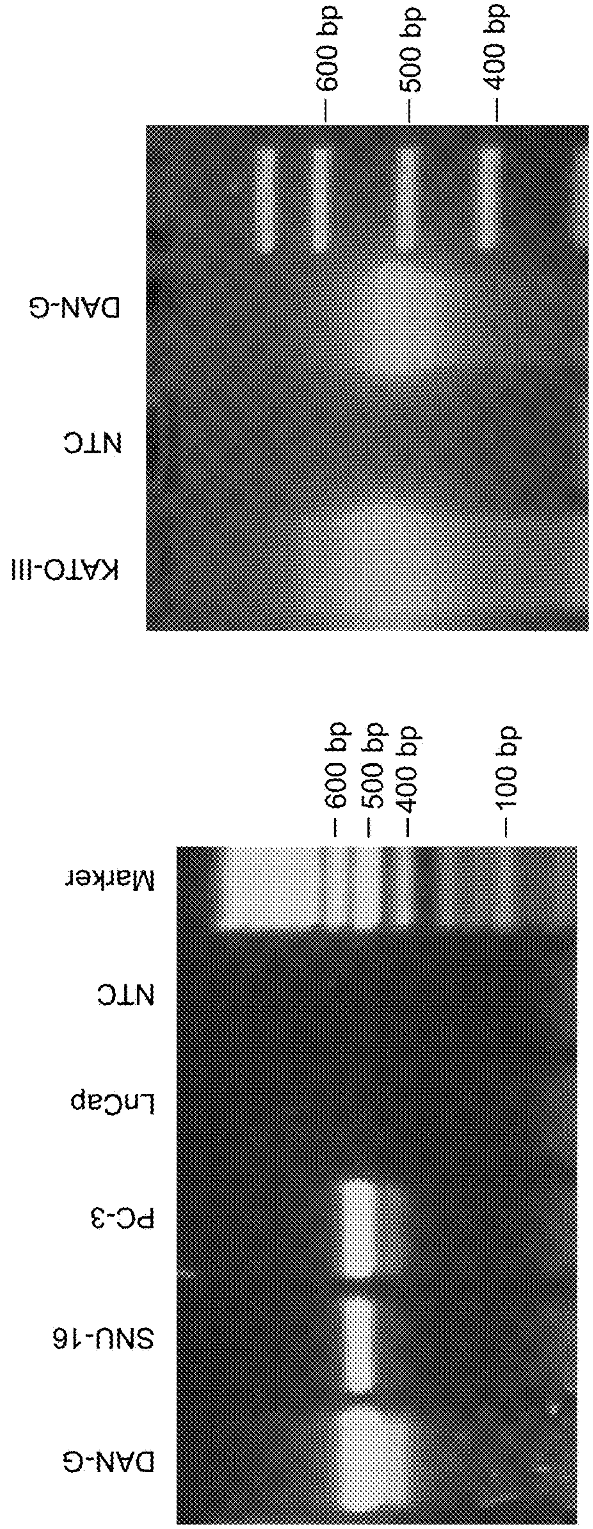
FIG. 9 shows results of cell line RT-PCR. RT-PCR analysis with CLD18A2-specific primers showed clear expression in 4/5 tested cell lines.
Figure 10:
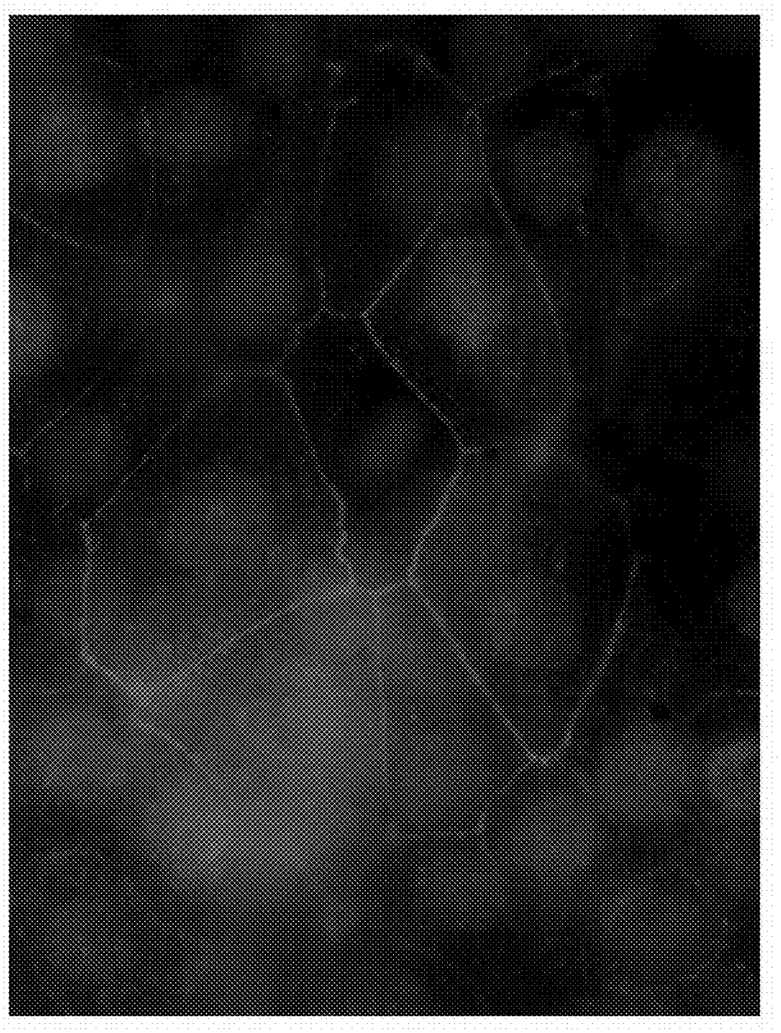
FIG. 10 shows an immunofluorescence analysis of DAN-G cells (subclone F2) and a polyclonal rabbit-anti-CLD18 antibody (Zymed, CRL 38-8000).
Figure 11:
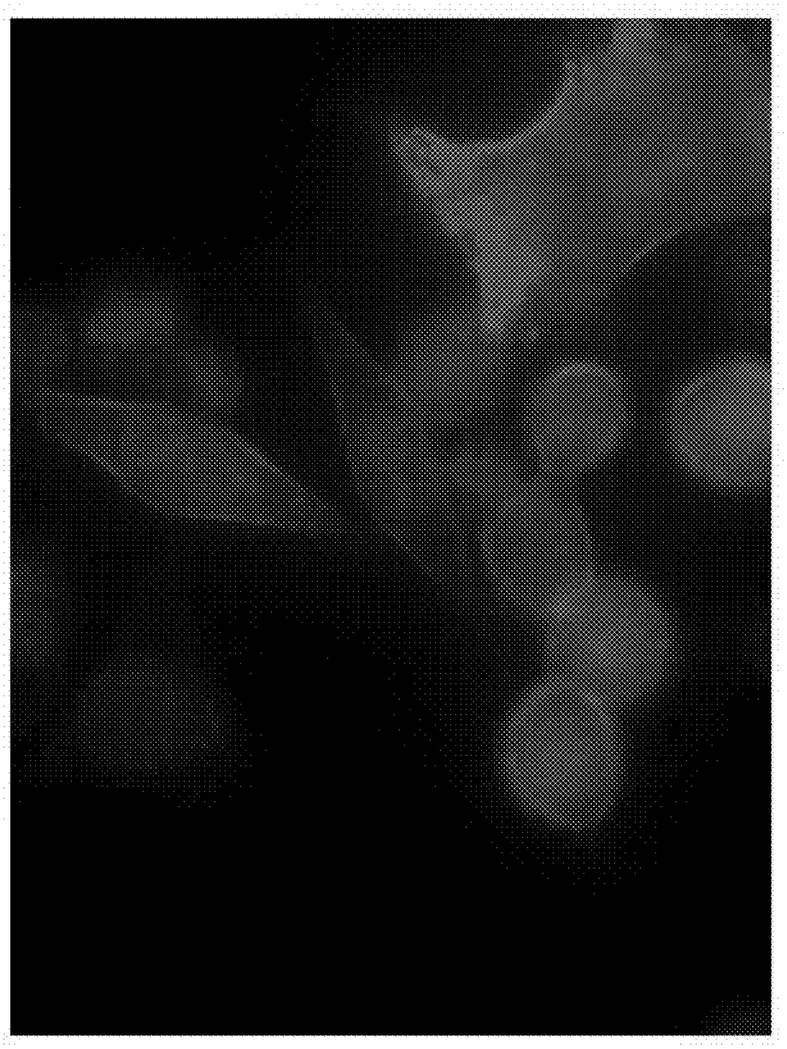
FIG. 11 shows an immunofluorescence analysis of KATO-III cells (subclone 3B9 4D5) and a polyclonal rabbit-anti-CLD18 antibody (Zymed, CRL 38-8000).
Figure 12A:
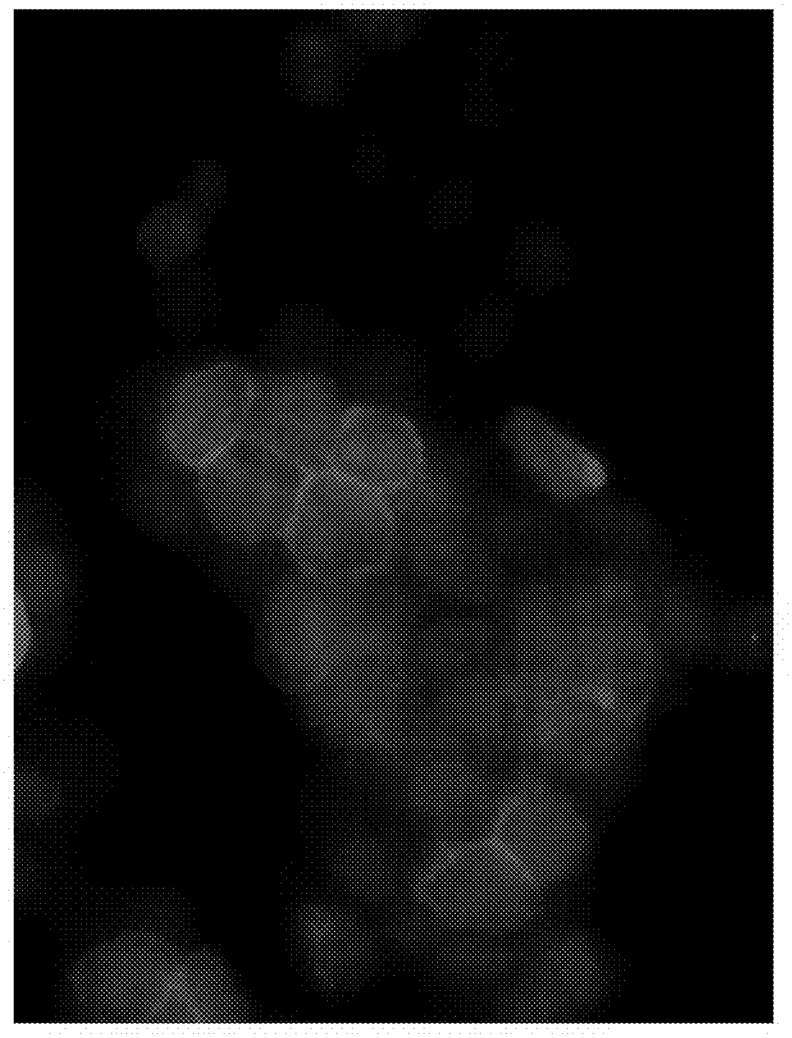
FIG. 12A shows an immunofluorescence analysis of SNU-16 cells (subclone G5) with a polyclonal rabbit-anti-CLD18 antibody (Zymed, CRL 38-8000).
Figure 12B:
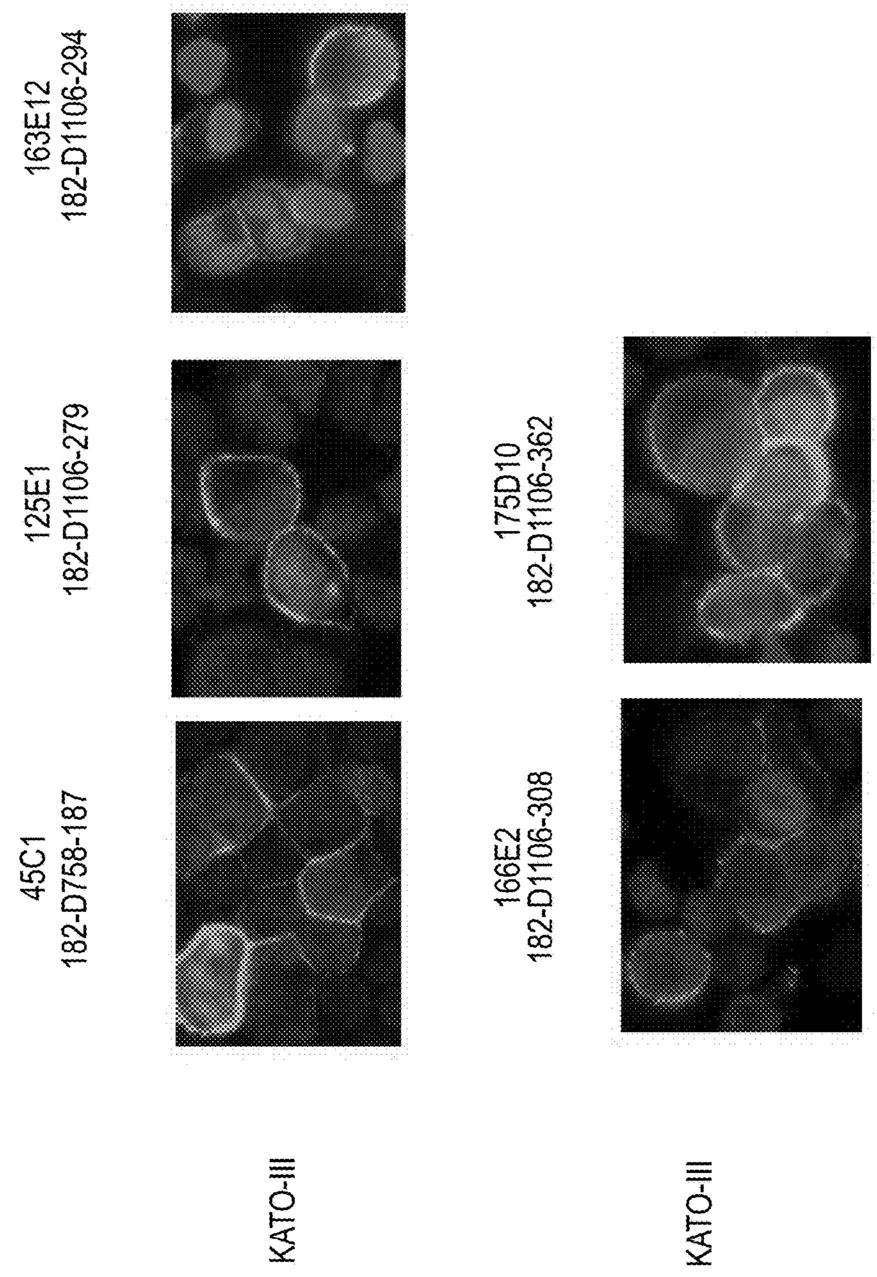
FIG. 12B shows an immunofluorescence analysis of KATO-III cells with monoclonal antibodies of the invention.
Figure 13:
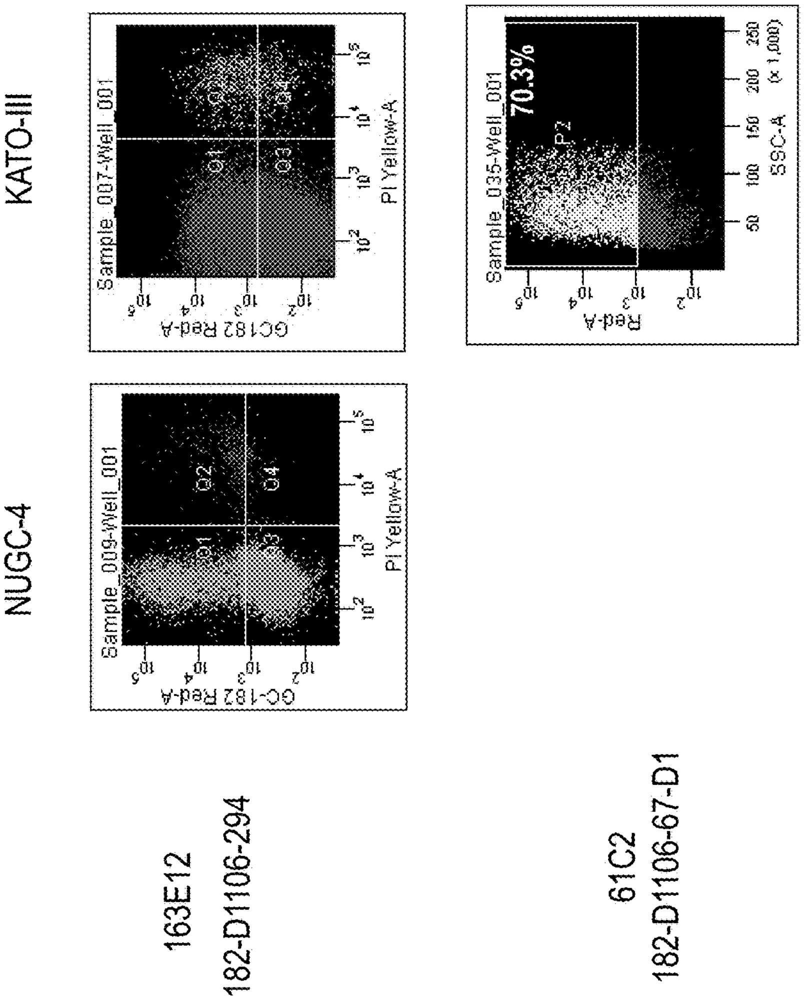
FIG. 13 shows surface expression of CLD18 on KATO-III and NUGC-4 cells as analyzed by staining of cells with monoclonal antibodies 61C2 and 163E12 followed by flow cytometrical analysis.
Figure 14:
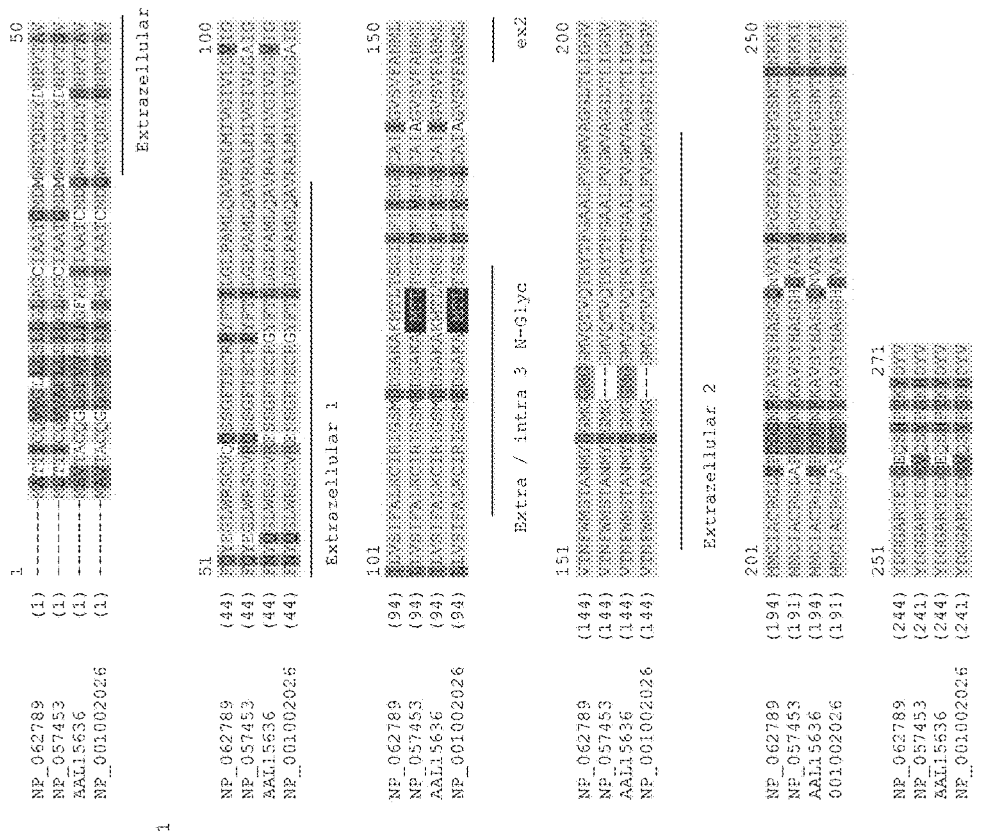
FIG. 14 shows protein-alignment of human CLD18A (NP_057453), human CLD8A2 (NP_001002026), mouse CLD18A1 (NP_062789) and mouse CLD18A2 (AAL15636).
Figure 15A:
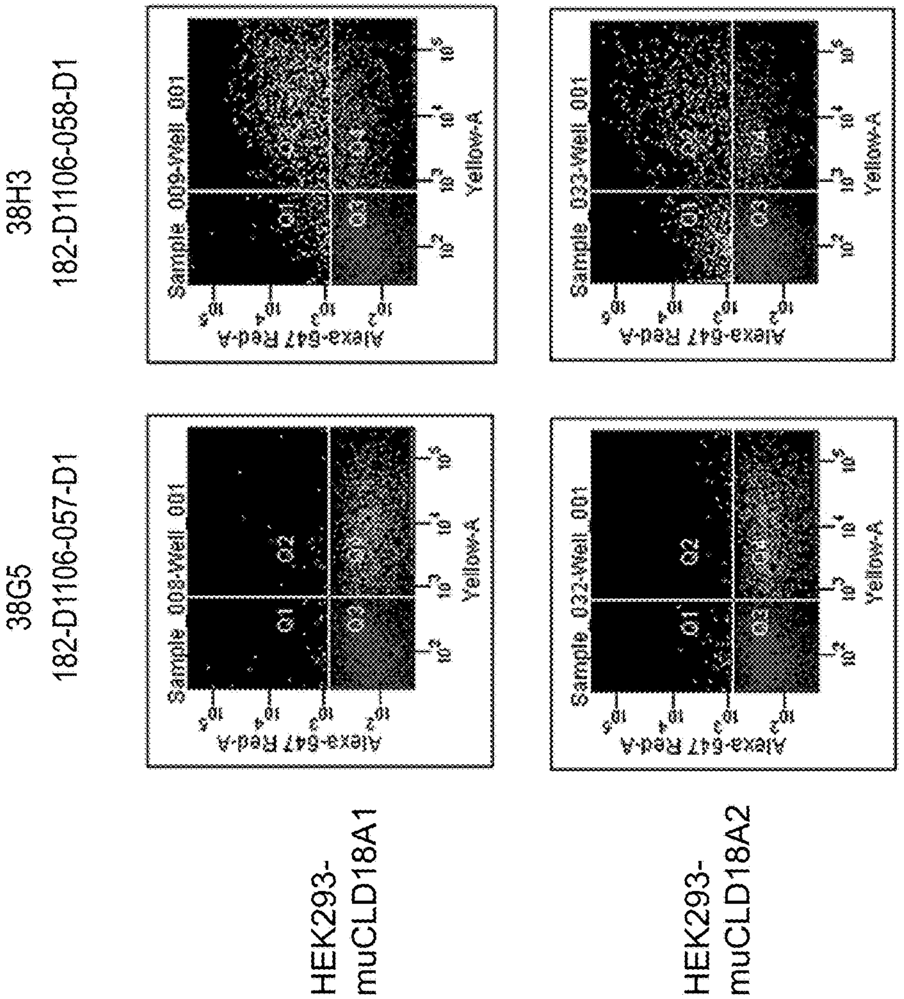
FIG. 15A and FIG. 15B show binding of hybridoma supernatants 38G5, 38H3, 37G11, 45C1, and 163E12, respectively, to HEK293 cells transiently transfected with a fluorescent marker and either murine CLD18A1 or murine CLD18A2 as analyzed by flow cytometry.
Figure 15B:
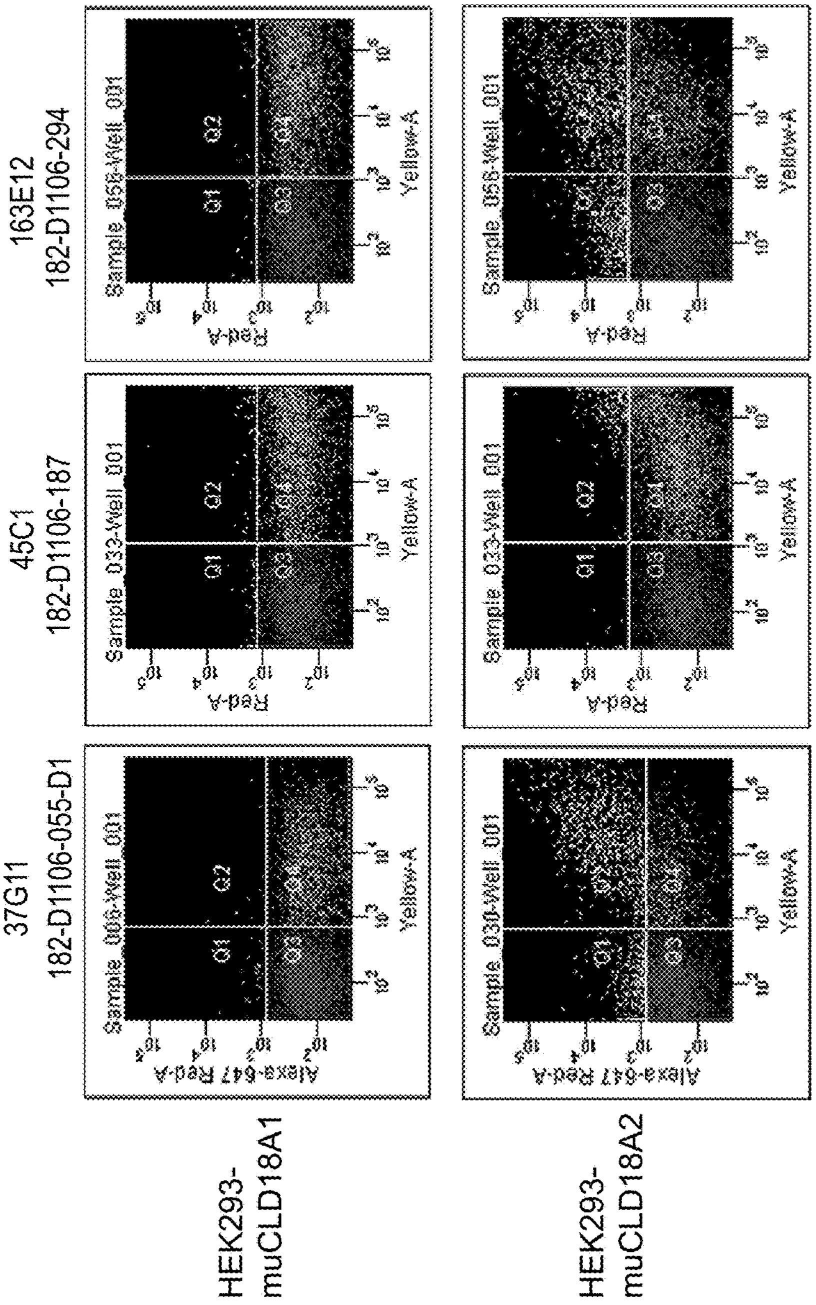

For antibodies 24H5, 26B5, 26D12, 28D10, 37G11, 37H8, 38G5, 38H3, 39F11, 41C6, 42E12, 43A11, 44E10, 47D12, 61C2, 75B8, 85A3, 9E8, 19B9, a clear difference between staining of living cells and paraformaldehyde fixed cells was observed. The antibodies formed an uniform membrane staining when cells were fixed (FIG. 7C, FIG. 8C, FIG. 8D). In contrast, incubation of living cells with these antibodies leads to the generation of protein clusters, visible as a speckle like staining pattern (FIG. 7A, FIG. 8A, FIG. 8B). This shows that all antibodies bind to native epitopes as found on the surface of living cells.

f. Determination of Endogenously Expressing Cell Lines:

A CLD18A2 gene-specific primer pair (SEQ ID NO: 11, 12) was used in RT-PCR analyses to screen cell lines for expression of CLD18A2. Human gastric carcinoma cell lines NCI-SNU-16 (ATCC CRL-5974), NUGC-4 (JCRB0834) and KATO-III (ATCC HTB-103) and human pancreas adenocarcinoma cell line DAN-G (DSMZ ACC249) were found to display robust endogenous expression of CLD18 (FIG. 9). Expression was confirmed on protein level by staining with a rabbit polyclonal serum against CLD18.

g. Staining of Endogenously Expressing Cell Lines with CLD18 Specific Antibodies and Immunofluorescence Analysis:

DAN-G, SNU-16, NUGC-4 and KATO-III cells were grown on chamber slides under standard conditions. Cells were unfixed or alternatively fixed with methanol and stained with the respective antibodies. For antibodies 24H5, 26B5, 26D12, 28D10, 37G11, 37H8, 38G5, 38H3, 39F11, 41C6, 42E12, 43A11, 44E10, 47D12, 61C2, 75B8, 85A3, 9E8, 19B9 staining of the cell surface was observed as exemplified in FIG. 10, FIG. 11 and FIG. 12A. For antibodies 45C1, 125E1, 163E12, 166E2, and 175D10 native epitope recognition was assayed and cell surface staining was observed on unfixed cells as shown in FIG. 12B. Subgroups of antibodies showed homogenous staining of the cell membrane either preponderantly at cell-cell interfaces or at free parts of the membrane not adjacent to other cells. Other antibodies stained discrete foci and aggregates on the cell membrane altogether demonstrating that the respective antibodies bind to different epitopes including epitopes which are masked by homotypic or heterotypic association of CLD18 as well as CLD18 epitopes accessible in preformed tight junctions.

h. Staining of Endogenously Expressing Cell Lines by Flow Cytometry:

Surface expression of constitutively expressed CLD18A2 on KATO-III and NUGC-4 living cells was analyzed by flow cytometry. This is exemplified by KATO-III and NUGC-4 cells stained with monoclonal antibody 61C2 or 163E12, followed by incubation with Alexa647-conjugated anti-mouse IgG secondary antibody and fixation of cells or alternatively without fixation. Binding was assessed by flow cytometry using a BD FACSArray. FIG. 13 shows a strong binding of 61C2 to at least 70.3% of KATO-III cells and of 163E12 to CLD18A2 on KATO-III and NUGC-4 cells.

i. Sequence Alignment of Mouse and Human CLD18A1 and CLD18A2:

Human CLD18A2 (NP_001002026) and human CLD18A1 (NP_057453) in a sequence comparison differ in the N-terminus and mouse CLD18 variants (NP_062789 and AAL15636) demonstrate high homology and sequence variation sites between the molecules (see FIG. 14).

j. Reactivity of Antibodies with Murine CLD18A1 and Murine CLD18A2 Analyzed by Flow Cytometry:

Binding of the identified monoclonal antibodies to murine CLD18A2 and CLD18A was analyzed by flow cytometry. HEK293 cells transiently co-transfected with a fluorescence marker and murine CLD18A2 (SEQ ID NOs: 33, 35) or with a fluorescence marker and murine CLD18A1 (SEQ ID NOs: 36, 37) were incubated with hybridoma supernatants containing the human CLD18-specific monoclonal antibodies 38G5, 38H3, 37G11, 45C1 and 163E12, respectively, for 30 min. at 4° C., followed by incubation with Alexa647-conjugated anti-mouse IgG secondary antibody and fixation of cells. Binding was assessed by flow cytometry using a BD FACSArray. FIG. 15A and FIG. 15B show three different binding profiles: 38G5, and 45C1 do not bind to any of the murine CLD18 isoforms, 37G11, and 163E12 bind to murine CLD18A2 but not to murine CLD18A1, and 38H3 binds to murine CLD18A1 and CLD18A2. These antibodies are valuable tools to determine a potential toxicity of CLD18 monoclonal antibodies in preclinical studies.

Altogether these data show, that monoclonal antibodies of the invention 24H5, 26B5, 26D12, 28D10, 37G11, 37H8, 38G05, 38H3, 39F11, 41C6, 42E12, 43A11, 44E10, 47D12, 61C2, 75B8, 85A3, 9E8, 19B9, 45C1, 125E1, 163E12, 166E2, and 175D10 generated against CLD18 represents a diversity of binding characteristics to different epitopes and topologies of human CLD18.

A combination of different properties described in examples 3b, c, d, e, g, h, and j can be used to categorize monoclonal antibodies into such different classes.

4. Immunohistochemistry (IHC)

Figure 16A:
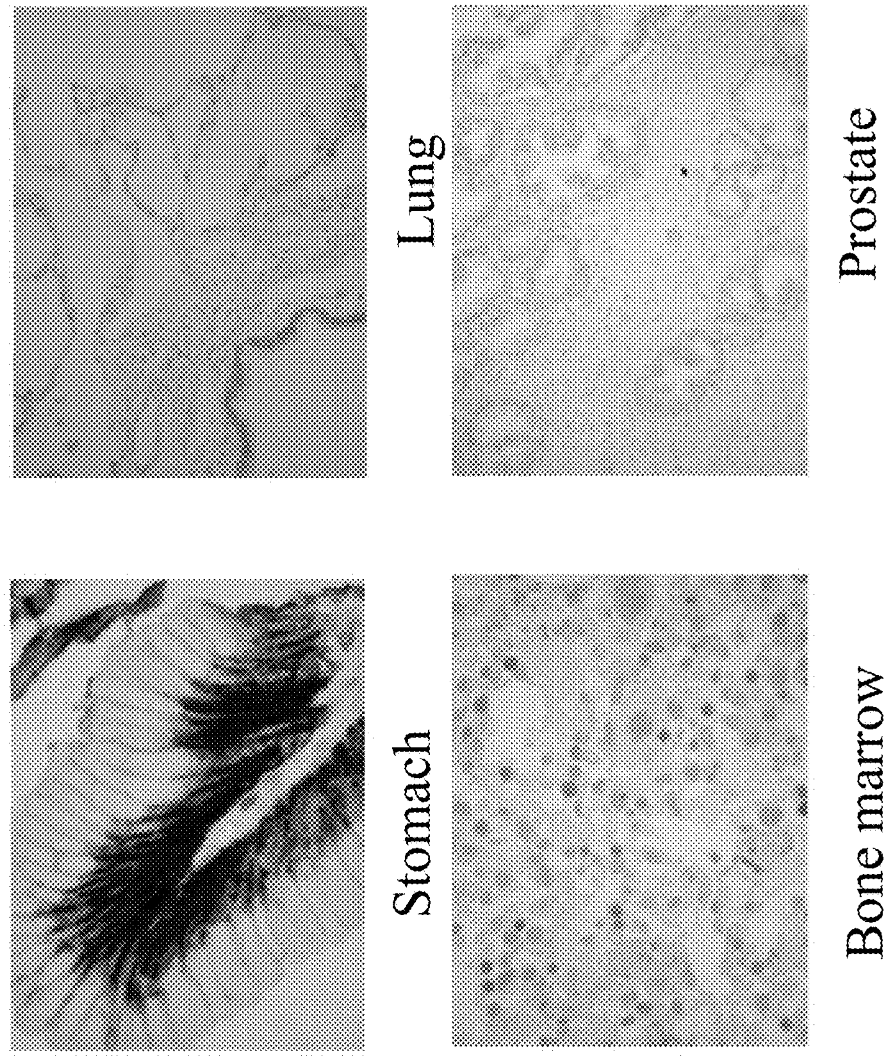
FIG. 16A, FIG. 16B, and FIG. 16C show immunohistochemical analyses with polyclonal AB p105. Immunohistochemical stainings on a subset of normal tissues (stomach, lung, bone marrow and prostate) confirm gastric tissue specificity (FIG. 16A). Expression was also detected in stomach carcinomas (upper row) and lung carcinomas (FIG. 16B). Only differentiated cells but not stem cells do express CLD18A2 (FIG. 16C).
Figure 16B:
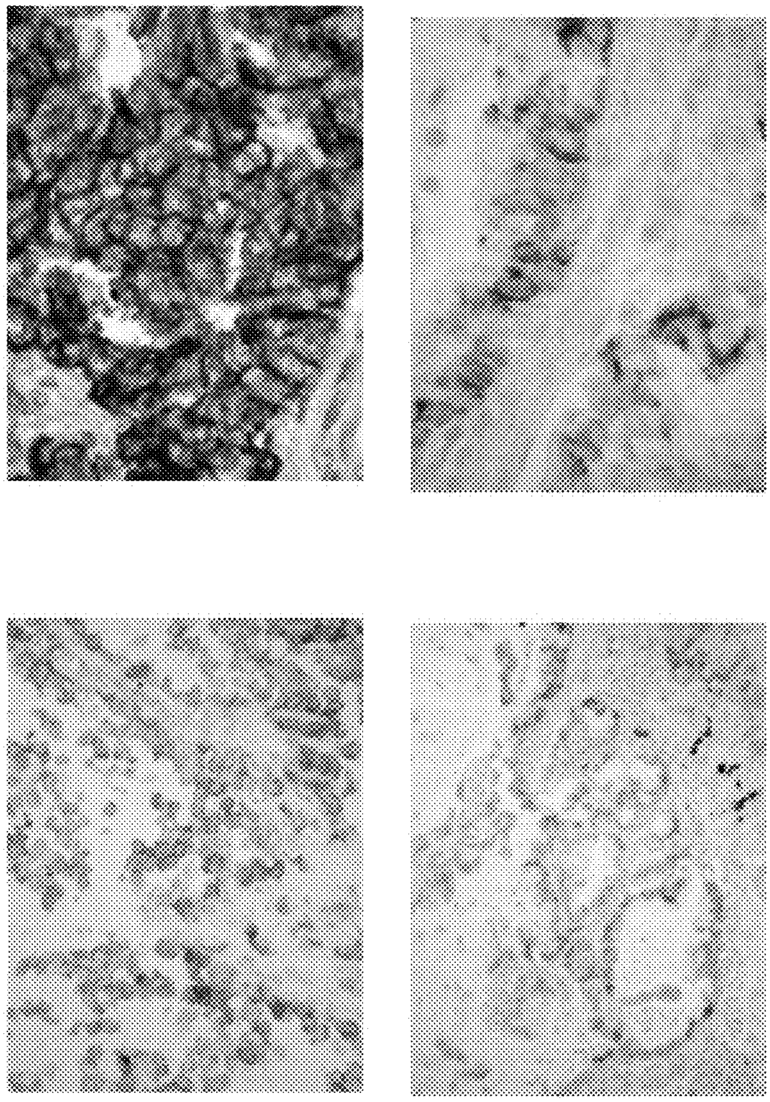

A CLD18A2 epitope specific antibody generated by immunization with the peptide of SEQ ID NO: 21 was used for immunohistochemical characterisation of CLD18A2 expression. Paraffin embedded tissue sections derived from a comprehensive panel of normal and tumor tissues were used for protein expression and localisation analyses. No significant expression was detected in any other normal organ tissue except stomach (see Tab. 2, FIG. 16A). In contrast, CLD18A2 expression was verified by immunohistochemistry in different cancers including stomach cancer and lung cancer (FIG. 16B).

Figure 16C:
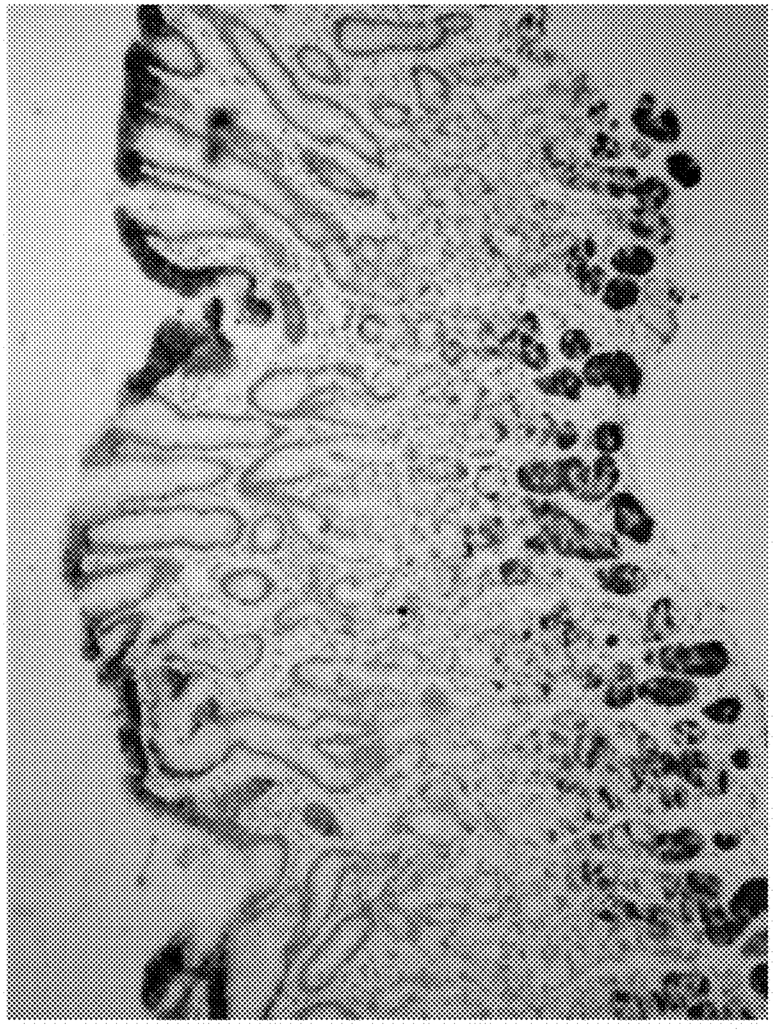

Interestingly, expression of CLD18A2 protein in gastric mucosa was restricted to terminally differentiated cells of the gastric epithelium in the base and pit regions. In contrast, cells in the neck region of gastric mucosa, in particular gastric stem cells in the isthmus part, which replenish the entire mucosa, do not express CLD8A2 (FIG. 16C).

TABLE 2

CLD18A2 expression in normal and tumor tissues as analysed by IHC

| Tissue type | Result |
|---|---|
| Adrenal | – |
| Bladder | – |
| Blood cells | – |
| Bone Marrow | – |
| Breast | – |
| Colon | – |
| Endothelium | – |
| Esophagus | – |
| Fallopian tube | – |
| Heart | – |
| Kidney (glomerulus, tubule) | – |
| Liver | – |
| Lung | – |
| Lymph node | – |
| Ovary | – |
| Pancreas | – |
| Parathyroid | – |
| Pituitary | – |
| Placenta | – |
| Prostate | – |
| Skin | – |
| Spleen | – |
| Stomach | + |
| Striated muscle | – |
| Testis | – |
| Thymus | – |
| Thyroid | – |
| Ureter | – |
| Uterus (cervix, endometrium) | – |

Figure 17A:
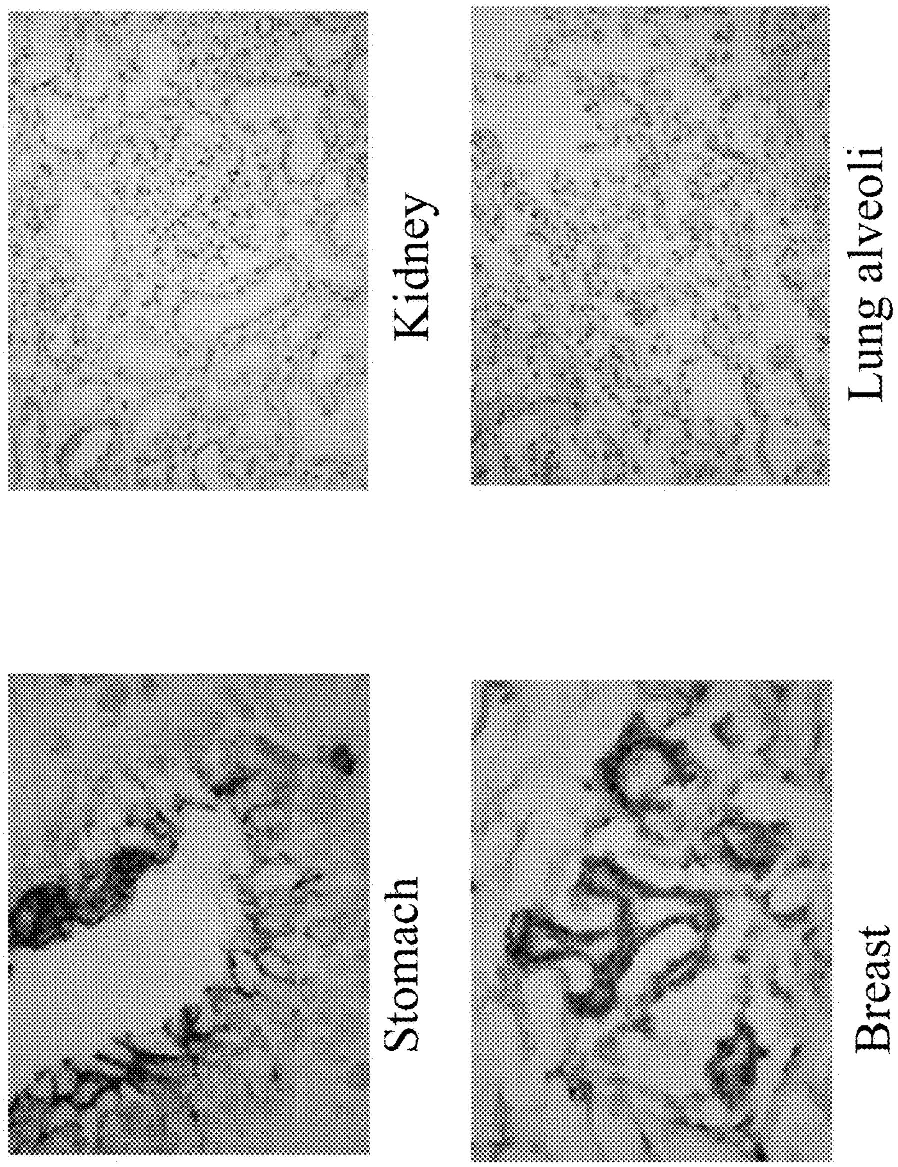
FIG. 17A and FIG. 17B show immunohistochemical analyses with monoclonal AB 39F1 D7.
Figure 17B:
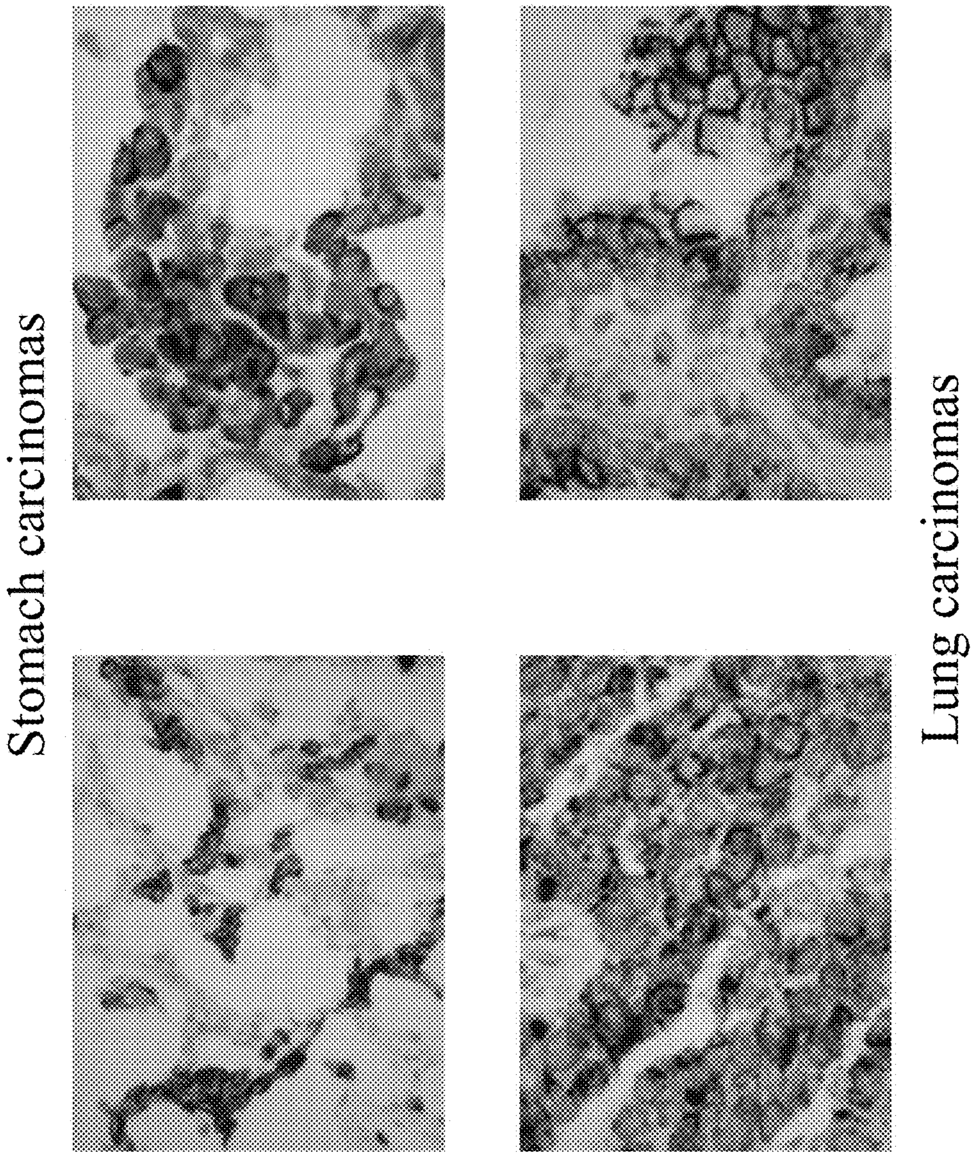

The monoclonal antibody 39F11 was used for immunohistochemical CLD18A2 specific studies. As shown in FIG. 17A, no significant reactivity was detectable on all tested normal tissues except stomach (FIG. 17A), whereas stomach carcinomas and lung carcinomas remain strongly positive (FIG. 17B).

Figure 18A:
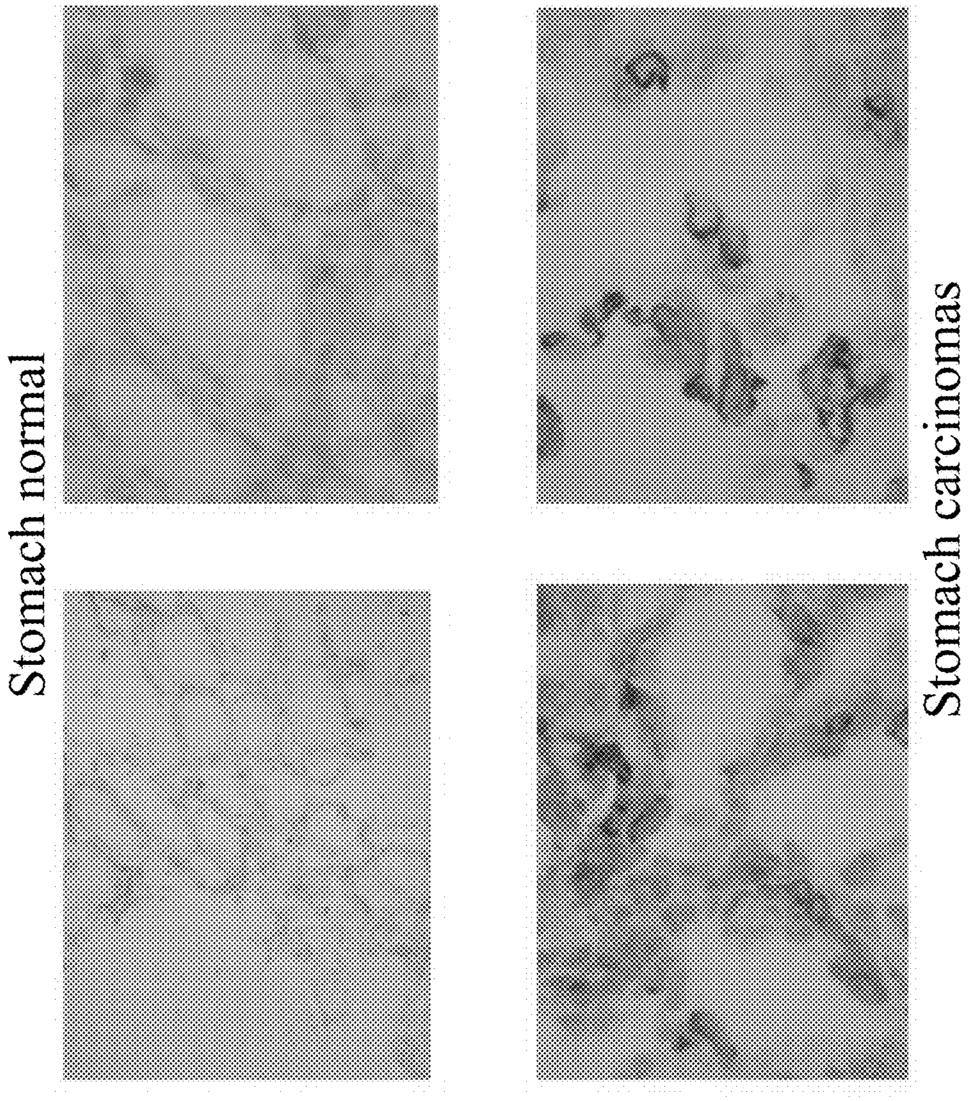
FIG. 18A, FIG. 18B, FIG. 18C, FIG. 18D, and FIG. 18E show immunohistochemical analyses with monoclonal AB 26B5 (FIG. 18A), 175D10 (FIG. 18B), 43A11 (FIG. 18C), 163E12 (FIG. 18D), and 45C1 (FIG. 18E). All antibodies show strong staining of HEK293-CLD18A2 xenograft tumors and gastric cancer specimens, but not HEK293-Mock control-transfected tumors.

Another group of antibodies of the invention shows a specific cancer staining pattern with binding to stomach cancer but no reactivity with normal stomach tissue. Such a staining pattern is shown in FIG. 18A with monoclonal antibody 26B5.

Figure 18B:
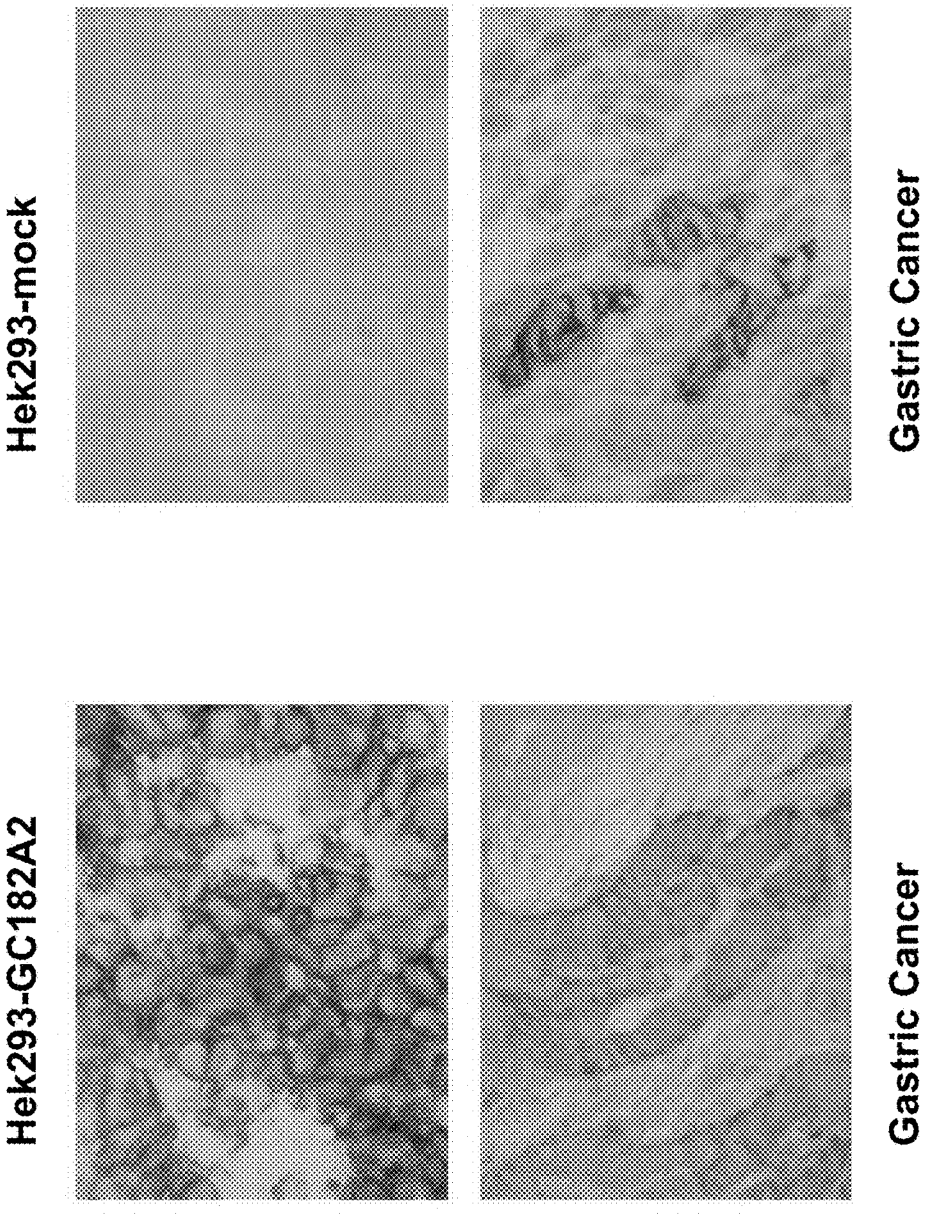
Figure 18C:
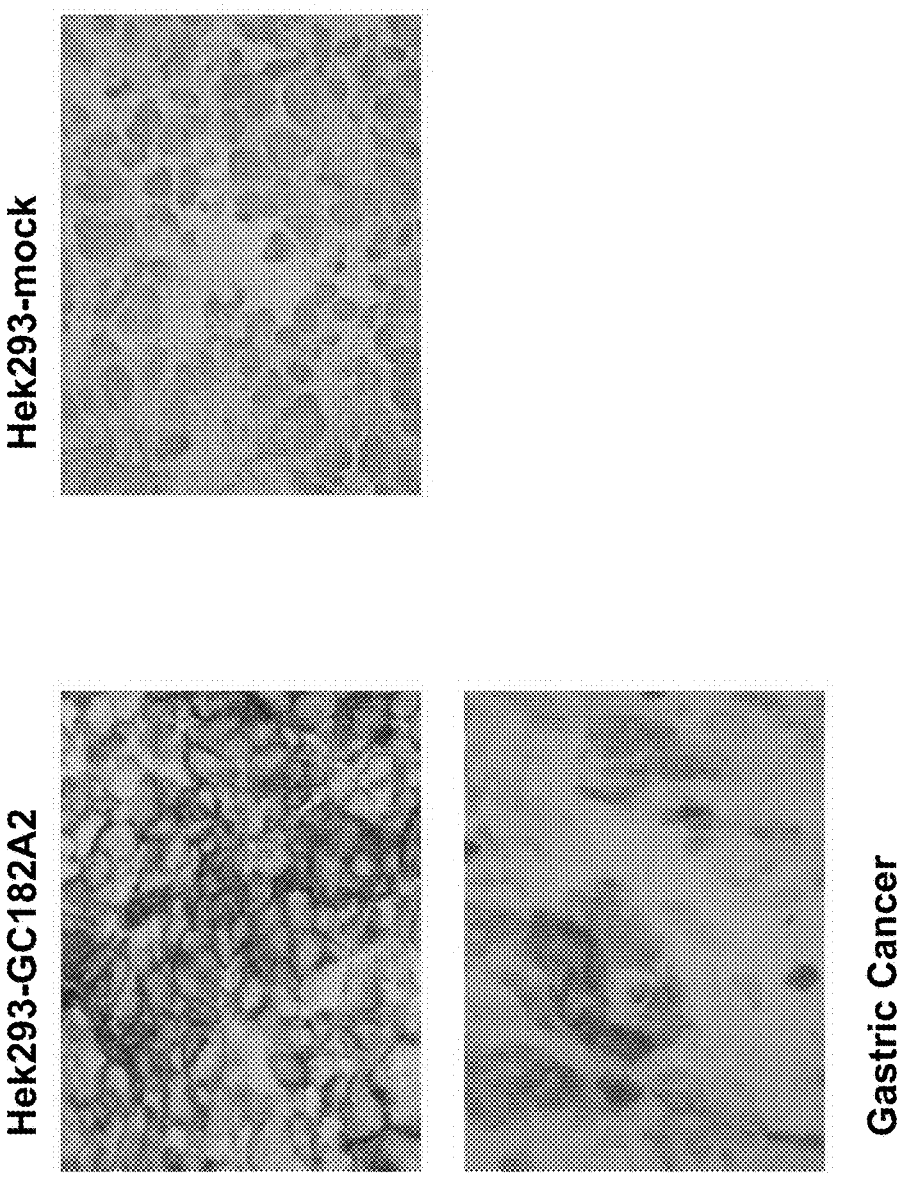
Figure 18D:
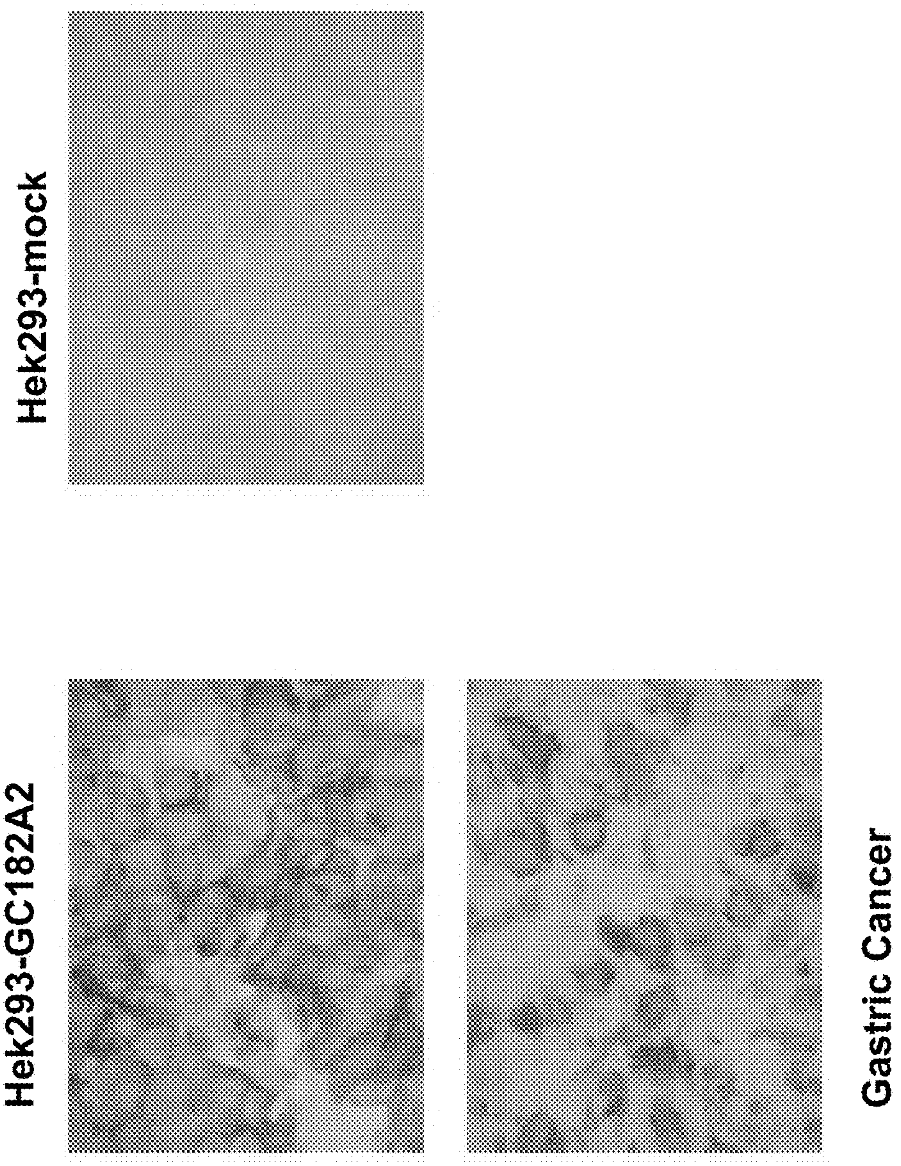
Figure 18E:
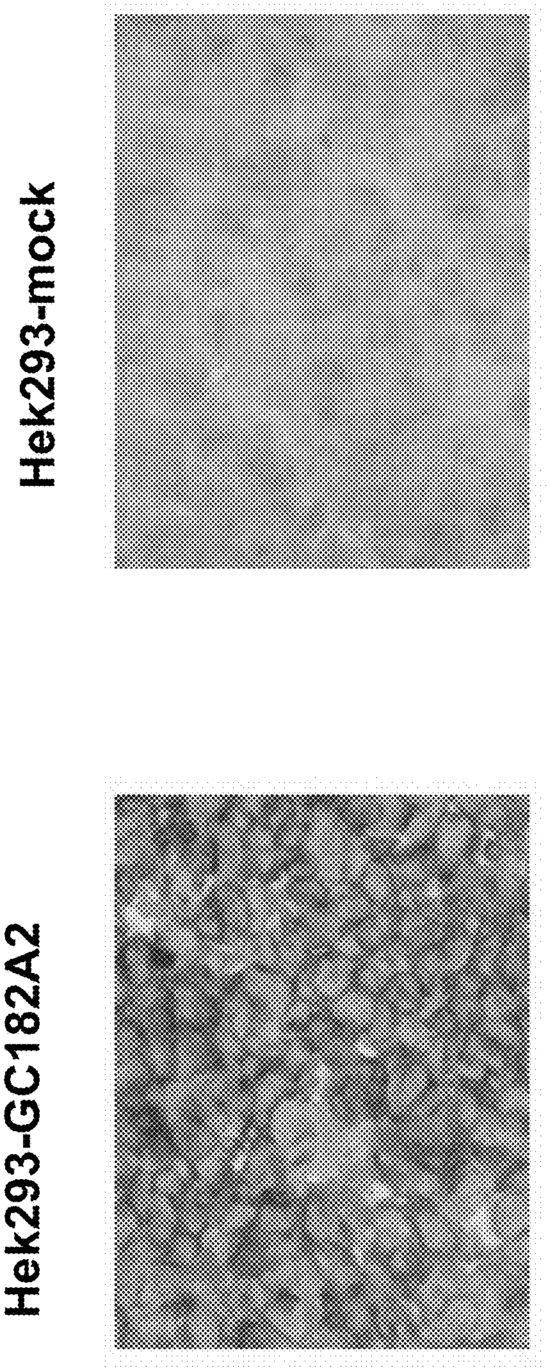

Immunohistochemistry was used for specificity analysis of 175D10 (FIG. 18B), 43A11 (FIG. 18C), 163E12 (FIG. 18D) and 45C1 (FIG. 18E) on sections derived from HEK293 tumor cell lines: HEK293 tumor cell lines stably expressing human CLD18A2 (HEK293-CLD18A2) or CLD18A1 (HEK293-CLD18A1) or being transfected with an expression control plasmid containing only the antibiotic resistance gene for selection (HEK293-mock) were xenografted into mice to form solid tumors. No expression was detectable in mock-transfected HEK293 xenograft tumors. In contrast, strong and homogeneous membrane-staining was observed in HEK293-CLD18A2 xenograft tumors and in stomach carcinoma specimens.

5. Complement Dependent Cytotoxicity (CDC)

a. CDC of Monoclonal Antibodies of Set1 as Measured by Flow Cytometry:

Plasma for complement lysis was prepared by drawing blood from healthy volunteers into S-Monovette-EDTA vacutainer tubes (Sarstedt, Nürmbrecht, Germany) which were then centrifuged at 600 g for 20 min. Plasma was harvested and stored at −20° C.

Figure 19:
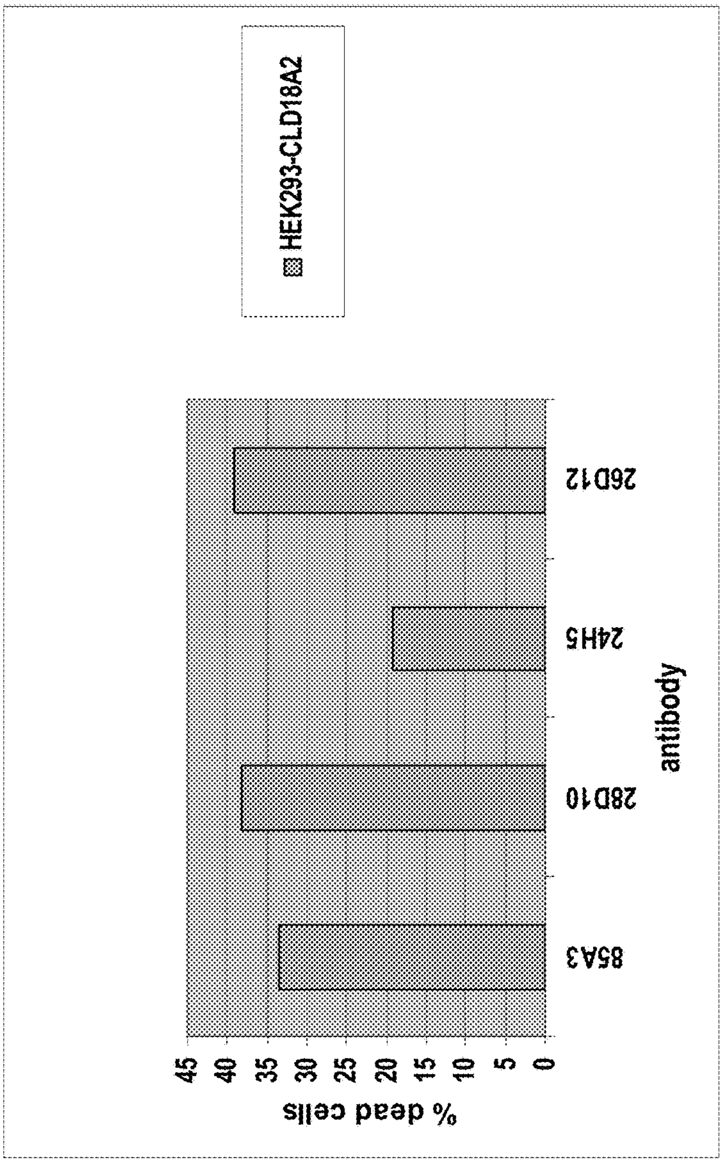
FIG. 19 is a graph comparing the percentage of dead cells after induction of CDC by 85A3, 28D10, 24H5, or 26D12 against HEK293 cells stably transfected with human CLD18A2 using flow cytometry.
Figure 20:
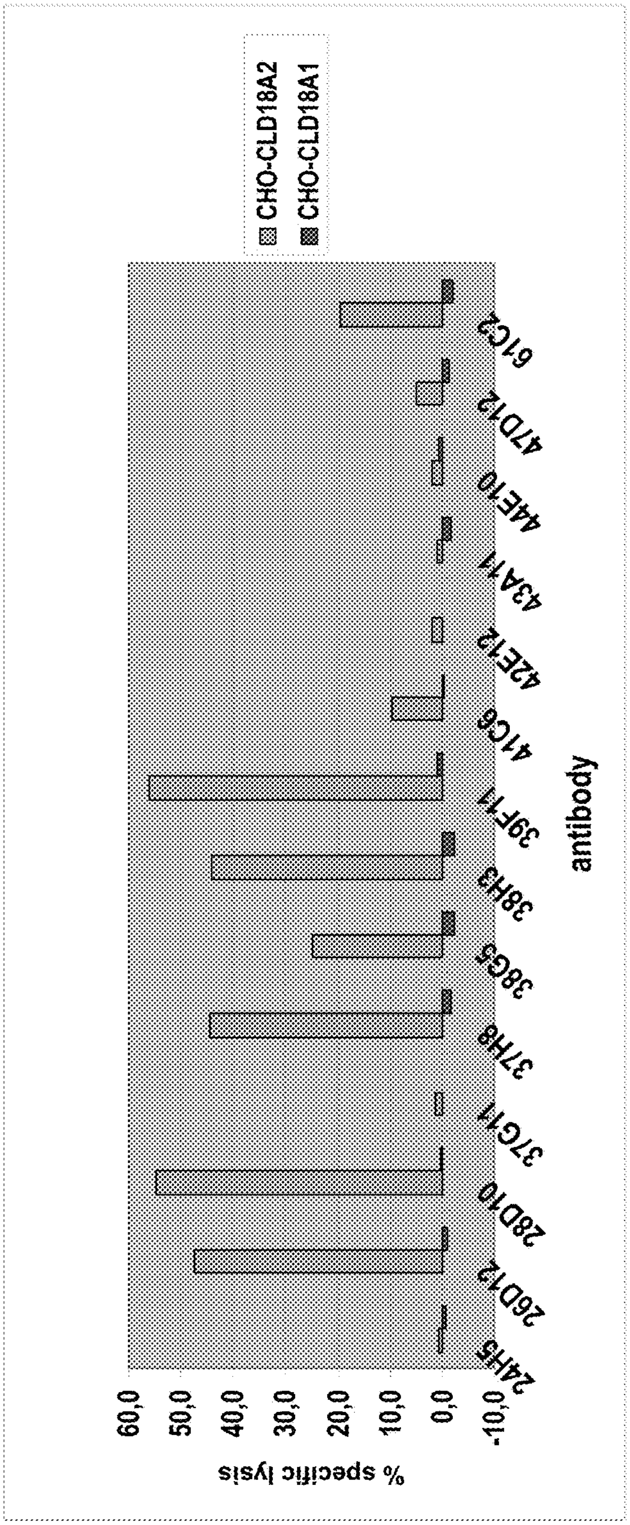
FIG. 20 is a graph comparing the percentage of specific cell lysis after induction of CDC by 24H5, 26D12, 28D10, 37G11, 37H8, 38G5, 38H3, 39F11, 41C6, 42E12, 43A11, 44E10, 47D12, or 61C2 against adherent CHO cells stably transfected with either human CLD18A2 or human CLD18A1 as determined by fluorescence measurement.
Figure 21A:
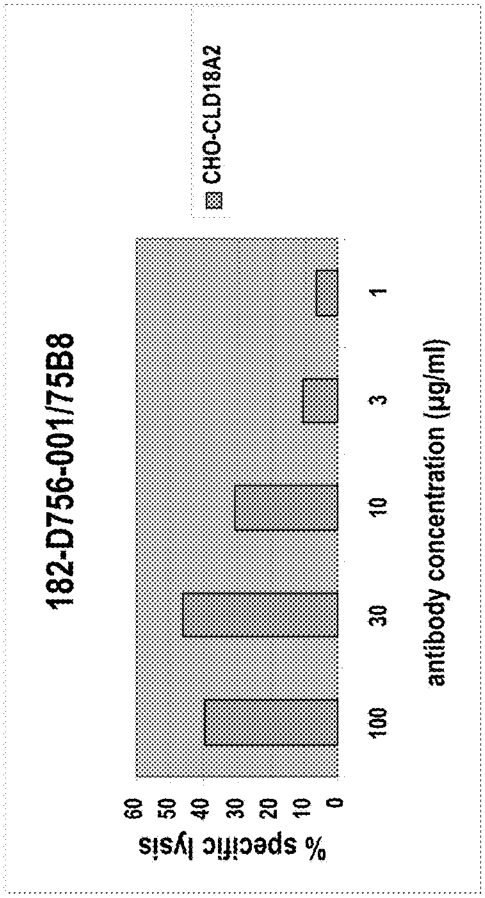
FIG. 21A, FIG. 21B, and FIG. 21C show concentration-dependent induction of CDC against CHO cells stably transfected with human CLD18A2 by 75B8 (FIG. 21A), 28D10 (FIG. 21B), or 37H8 (FIG. 21C) as determined by fluorescence measurement.
Figure 21B:
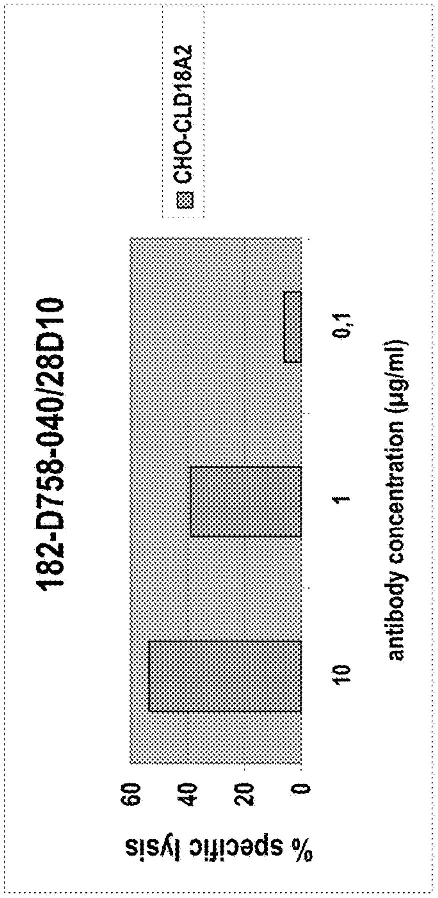
Figure 21C:
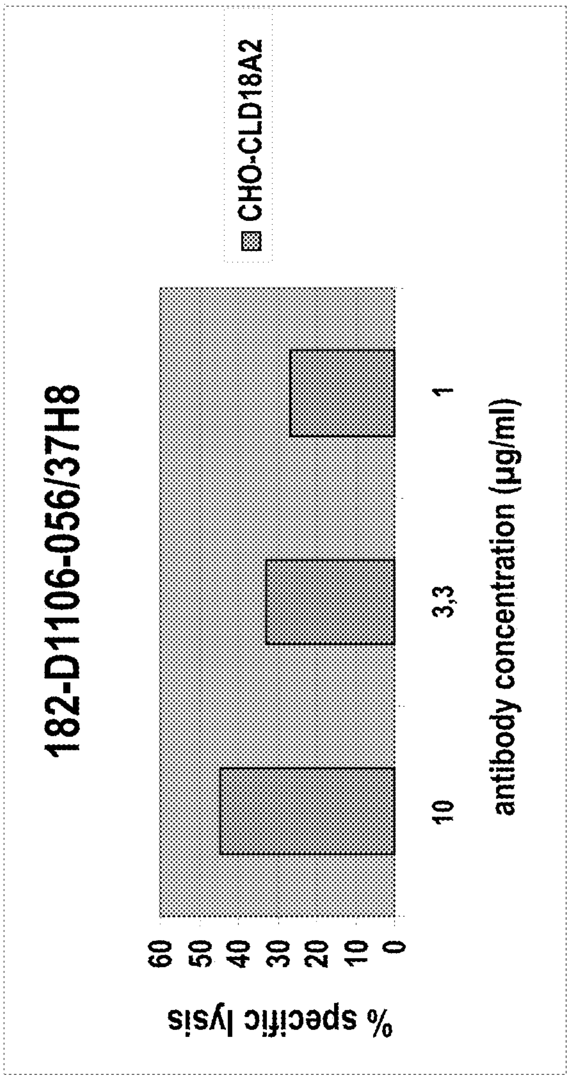

In a first set of experiments hybridoma supernatants were analyzed for their capability to induce complement dependent cytotoxicity (CDC) against HEK293 cells stably expressing human CLD18A2 (HEK293-CLD18A2). Cells were incubated with hybridoma supernatants containing monoclonal antibodies 85A3, 28D10, 24H5 or 26D12, respectively for 20 min. at room temperature. Following centrifugation (5 min. at 450 g) the supernatant was removed and 20% human plasma in DMEM (prewarmed to 37° C.) was added to the cells and incubated for another 20 min. at 37° C. Thereafter, cell lysis was determined on FACS by using the propidium iodide (PI) staining method. PI was added to a final concentration of 2.5 μg/ml. For flow cytometry, a BD FACSArray flow cytometer was used (BD Biosciences, Mountain View, Calif.). At least 10000 events were collected for analysis with cell debris excluded by adjustment of the forward sideward scatter (FCS) threshold. The percentage of lysed cells (PI-positive cells) is shown in FIG. 19. Monoclonal antibodies 85A3, 28D10 and 26D12 induced lysis of 33.5%, 38.2% and 39.2%, respectively of HEK293-CLD18A2 cells, whereas CDC mediated by 24H5 was only 19.3%.

b. CDC of Monoclonal Antibodies of Set1:

In a second set of experiments the specificity of monoclonal antibodies to induce CDC on CLD18A2 expressing cells was analyzed. Therefore, a set of antibodies binding either specific to human CLD18A2 or also binding to human CLD18A1 was tested for CDC-induction against CHO cells stably transfected with human CLD18A2 (CHO-CLD18A2) or human CLD18A1 (CHO-CLD18A1). CHO-CLD18A2 and CHO-CLD18A1 cells were seeded 24 h before the assay with a density of $3\times10^4$/well in tissue-culture flat-bottom microtiter plates. The next day growth medium was removed and the cells were incubated in triplicates with hybridoma supernatants adjusted to a concentration of 10 μg/ml containing monoclonal antibodies 24H5, 26D12, 28D10, 37G11, 37H8, 38G5, 38H3, 39F11, 41C6, 42E12, 43A11, 44E10, 47D12, and 61C2, respectively. Control cells were incubated with growth medium or growth medium containing 0.2% saponin for the determination of background lysis and maximal lysis, respectively. After incubation for 20 min. at room temperature supernatant was removed and 20% human plasma in DMEM (prewarmed to 37° C.) was added to the cells and incubated for another 20 min. at 37° C. Then, supernatants were replaced by PBS containing 2.5 μg/ml ethidium bromide and fluorescence emission after excitation at 520 nm was measured using a Tecan Safire. The percentage specific lysis was calculated as follows: % specific lysis=(fluorescence sample−fluorescence background)/(fluorescence maximal lysis−fluorescence background)×100. FIG. 20 shows that monoclonal antibodies 26D12, 28D10, 37H8, 38H3 and 39F11 mediate high, monoclonal antibody 38G5 mediates medium, monoclonal antibodies 41C6 and 61C2 mediate low, and monoclonal antibodies 24H5, 37G11, 42E12, 43A11, 44E10 and 47D12 mediate no CDC against CHO-CLD18A2 cells. In contrast, none of the antibodies is capable of inducing CDC against CHO-CLDA1 cells, although 26D12, 28D10, 37H8, 38H3, 39F11, 41C6, 47D12 and 61C2 also bind to CLD18A1 as determined by flow cytometry and immunofluorescence.

c. Monoclonal Antibody Titration and CDC Using Monoclonal Antibodies of Set1:

To measure the ability of the anti-CLD18 antibodies to induce CDC at low concentrations, an experiment was performed where three different antibodies were titrated. CHO-CLD18A2 cells growing in microtiter plates were incubated with a concentration range of 75B8 (100, 30, 10, 3 and 1 μg/ml), 37H8 (10, 3.3 and 1 μg/ml) and 28D10 (10, 1 and 0.1 μg/ml), respectively, for 20 min. at room temperature. Supernatant was removed and 20% human plasma in DMEM (prewarmed to 37° C.) was added to the cells and incubated for another 20 min. at 37° C. Before analysis using a Tecan Safire, supernatants were replaced by PBS containing 2.5 μg/ml ethidium bromide. FIG. 21A, FIG. 21B, and FIG. 21C show the percentage of specific lysis as a function of antibody concentration. Monoclonal antibody 75B8 induces lysis of 31.0% CHO-CLD18A2 cells at 10 μg/ml, and drops to 6.2% at 1 μg/ml (FIG. 21A), whereas monoclonal antibodies 28D10 and 37H8 still induce 39% and 26.5% specific lysis at 1 μg/ml (FIG. 21B, FIG. 21C), respectively.

d. CDC of Monoclonal Antibodies of Set2 as Measured by Flow Cytometry:

Serum for complement lysis was prepared by drawing blood from healthy volunteers into Serum-Monovette vacutainer tubes (Sarstedt, Nürmbrecht, Germany) which were then centrifuged at 600 g for 20 min. Serum was harvested and stored at −20° C. Control serum was heat inactivated at 56° C. for 30 min before storage.

Hybridoma supernatants were analyzed for their capability to induce complement dependent cytotoxicity (CDC) against KATO-III cells endogenously expressing human CLD18A2. Cells were incubated with crude or purified hybridoma supernatants containing monoclonal antibodies 45C1, 125E1, 163E12, 166E2, and 175D10, respectively for 30 min. at 37° C. 20% human serum in RPMI was added to the cells and incubated for another 30 min. at 37° C. Thereafter, cell lysis was determined on FACS by using the propidium iodide (P1) staining method. PI was added to a final concentration of 2.5 μg/ml. For flow cytometry a BD FACSArray flow cytometer was used (BD Biosciences, Mountain View, Calif.). At least 10000 events were collected for analysis with cell debris excluded by adjustment of the forward sideward scatter (FSC/SSC) threshold. Specific lysis was calculated by the following formula: specific lysis=(% PI-positive cells in sample−% PI-positive cells in sample with heat inactivated serum). Robust CDC mediated lysis was observed in particular for 163E12.

6. Antibody-Dependent Cellular Cytotoxicity (ADCC)

Figure 22:
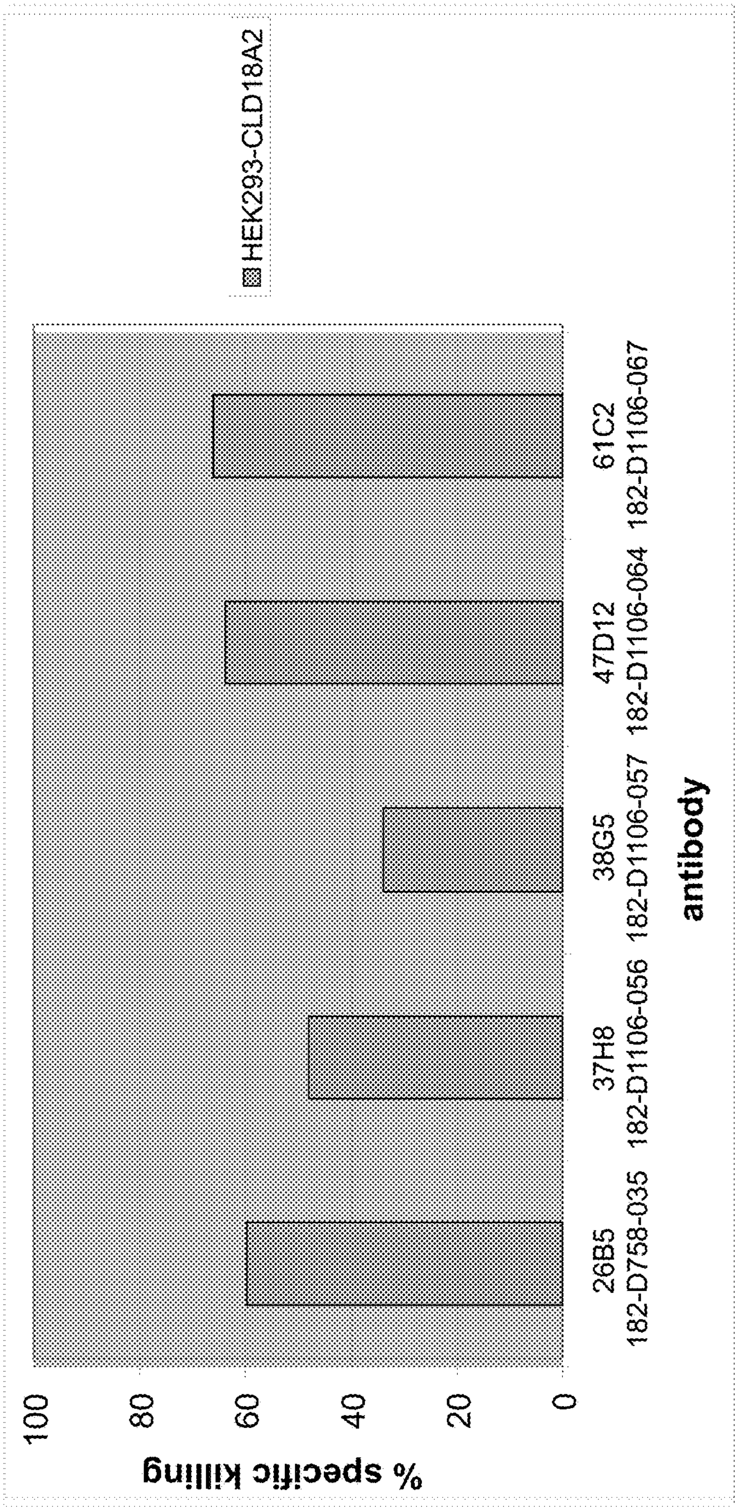
FIG. 22 shows lysis of HEK293-CLD18A2 cells by 26B5, 37H8, 38G5, 47D12, and 61C2, respectively, in the presence of MNCs.
Figure 23:
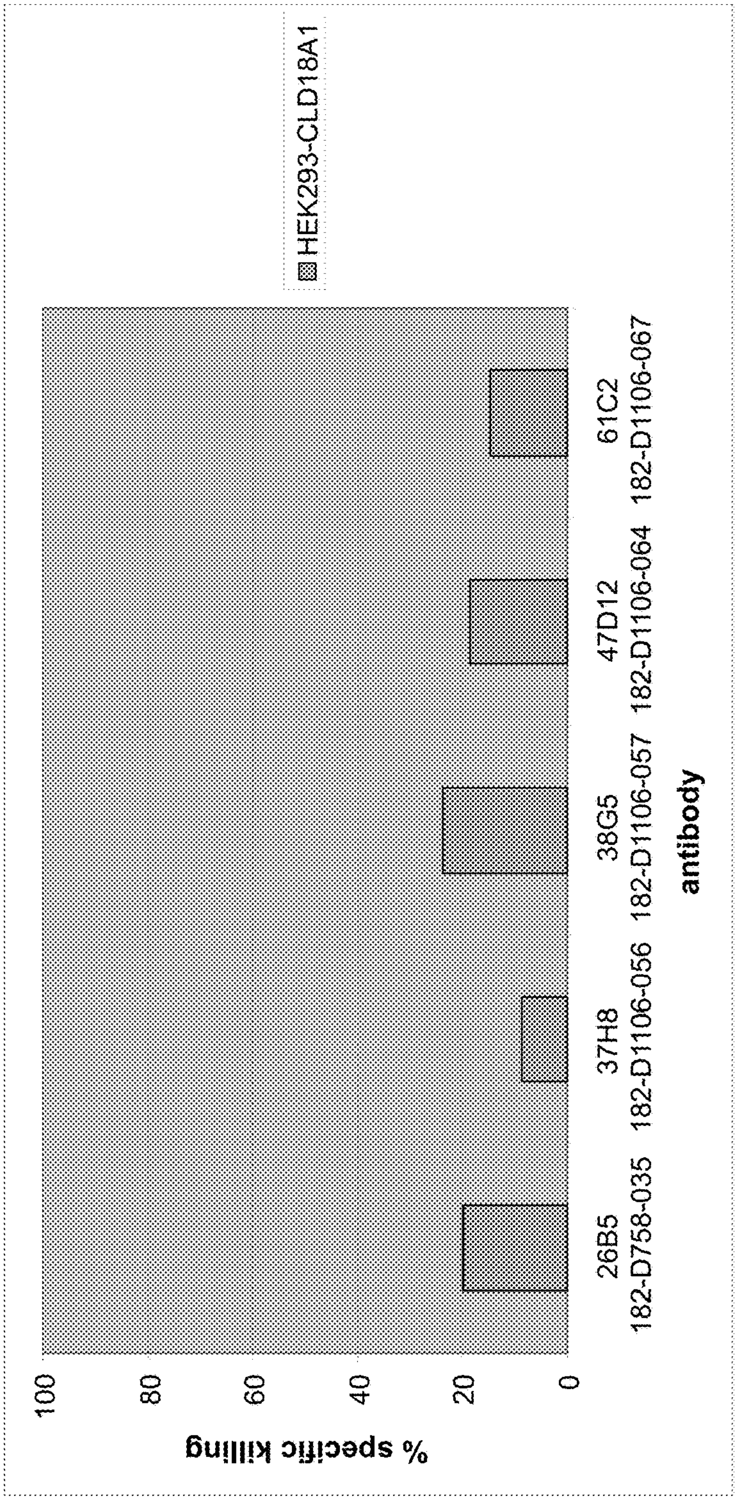
FIG. 23 shows lysis of HEK293-CLD18A1 cells by 26B5, 37H8, 38G5, 47D12, and 61C2, respectively, in the presence of MNCs.

Hybridoma supernatants were analyzed for their capability to induce antibody-dependent cellular cytotoxicity (ADCC) against HEK293 cells stably expressing human CLD18A2 (HEK293-CLD18A2) or human CLD18A1 (HEK293-CLD18A1).

a. Enrichment of human peripheral blood mononuclear cells: Human blood from healthy donors was diluted twice in phosphate buffer (PBS) and blood cells were layered on Ficoll (Lymphocyte Separation Medium 1077 g/ml, PAA Laboratories, cat. no. J15-004). Peripheral blood mononuclear cells (MNCs) were collected from the interphase, washed and resuspended in RPMI 1640 culture medium supplemented with 10% heat-inactivated fetal calf serum, 2 mM L-glutamine.

b. ADCC set up: Target cells were labeled with a fluorescence enhancing ligand (BADTA, Perkin Elmer cytotoxicity assay kit DELFIA EuTDA Cytotoxicity Reagents, cat. no. AD0116) for 30 minutes. After extensive washing in RPMI-10 supplemented with 10 mM probenecid (Sigma, cat. no. P8761), 10-20 mM HEPES, and 10% heat-inactivated fetal calf serum, the cells were adjusted to $1\times10^5$ cells/ml. Labeled target cells, effector cells (MNCs), and supernatants containing monoclonal antibodies adjusted to a concentration of 10 μg/ml were added to round-bottom microtiter plates. For isolated effector cells, an effector to target (E:T) ratio of 100:1 (data not shown for 50:1 and 25:1) was used. After incubation (2 hours, 37° C.), assays were stopped by centrifugation, and fluorescence ligand release from duplicates was measured in europium counts in a time-resolved fluorometer. Percentage of cellular cytotoxicity was calculated using the following formula: % specific lysis=(experimental release counts−spontaneous release counts)/(maximal release counts−spontaneous release counts)×100, with maximal fluorescence ligand release determined by adding Triton X-100 (0.25% final concentration) to target cells, and spontaneous release measured in the absence of antibodies and effector cells. FIG. 22 shows that monoclonal antibodies 26B5, 37H8, 38G5, 47D12, and 61C2 mediate ADCC against HEK293-CLD18A2 cells. In contrast, these antibodies induce no significant or only low level cytotoxicity on CLD18A1 targets demonstrating a CLD18A2 specific ADCC (FIG. 23).

7. Proliferation Inhibition

Purified murine monoclonal antibodies were analyzed for their capability to inhibit cell growth of KATO-III cells endogenously expressing human CLD18A2.

$1\times10^4$ target cells endogenously expressing CLD18A2 (KATO-III) were cultured in the presence of approximately 10 μg monoclonal antibodies.

DELFIA Cell Proliferation Kit (Perkin-Elmer, Cat. No. AD0200) is a non-isotopic immunoassay based on the measurement of 5-bromo-2'-deoxyuridine (BrdU) incorporation during DNA synthesis of proliferating cells in microplates. Incorporated BrdU is detected using europium labelled monoclonal antibody. To allow antibody detection cells are fixed and DNA denatured using Fix solution. Unbound antibody is washed away and DELFIA inducer is added to dissociate europium ions from the labelled antibody into solution, where they form highly fluorescent chelates with components of the DELFIA Inducer. The fluorescence measured—utilizing time-resolved fluorometry in the detection—is proportional to the DNA synthesis in the cell of each well.

Strong inhibition of proliferation was observed with antibodies 125E1, 163E12, 45C1, 37G11, 37H8, 28D10 and 166E2, respectively. Moderate inhibition of proliferation was observed with murine antibodies 43A11, 175D10, 42E12, 26D12, 61C2 and 38H3, respectively.

8. Performance in Therapeutic Mouse Xenograft Models

Therapeutic potential of the identified monoclonal antibodies binding specifically to CLD18A2 was studied in therapeutic xenograft models.

a. Early Treatment of Highly CLD18A2 Expressing Tumors in Mice

Figure 24:
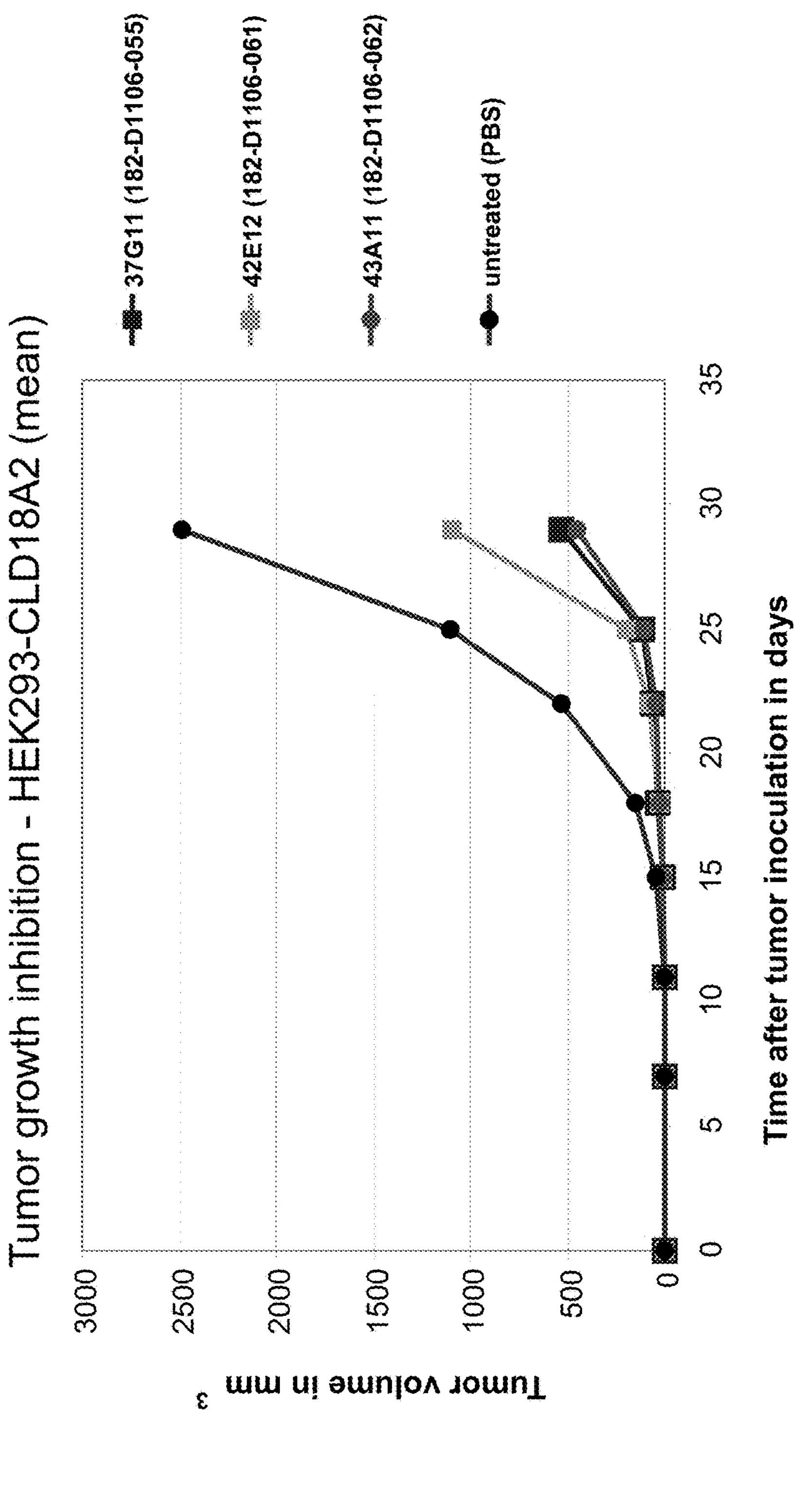
FIG. 24 shows tumor growth inhibition by antibodies of the invention in an early treatment xenograft model with HEK293-CLD18A2 cells.
Figure 25A:
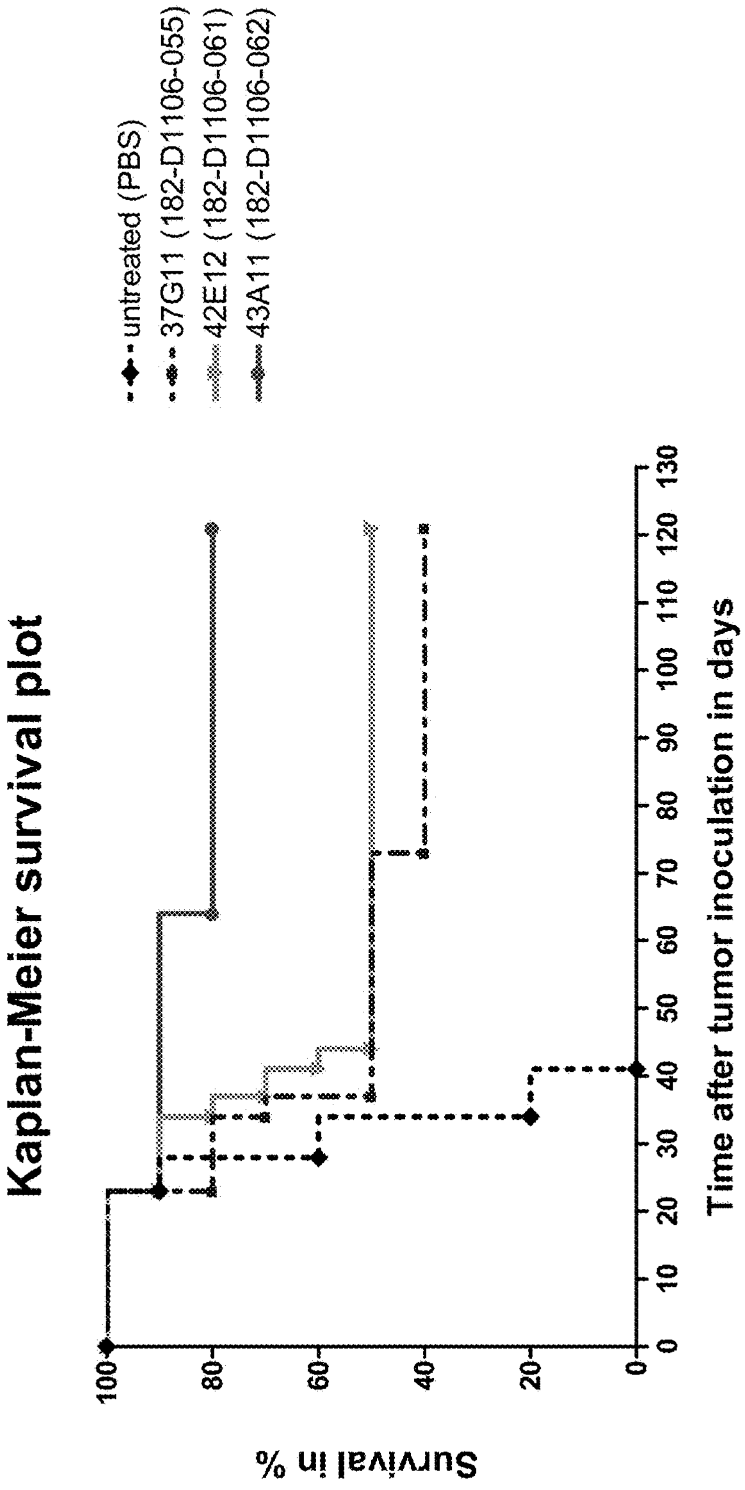
FIG. 25A and FIG. 25B show prolonged survival by treatment with antibodies of the invention in two early treatment xenograft models with HEK293-CLD18A2 cells.
Figure 25B:
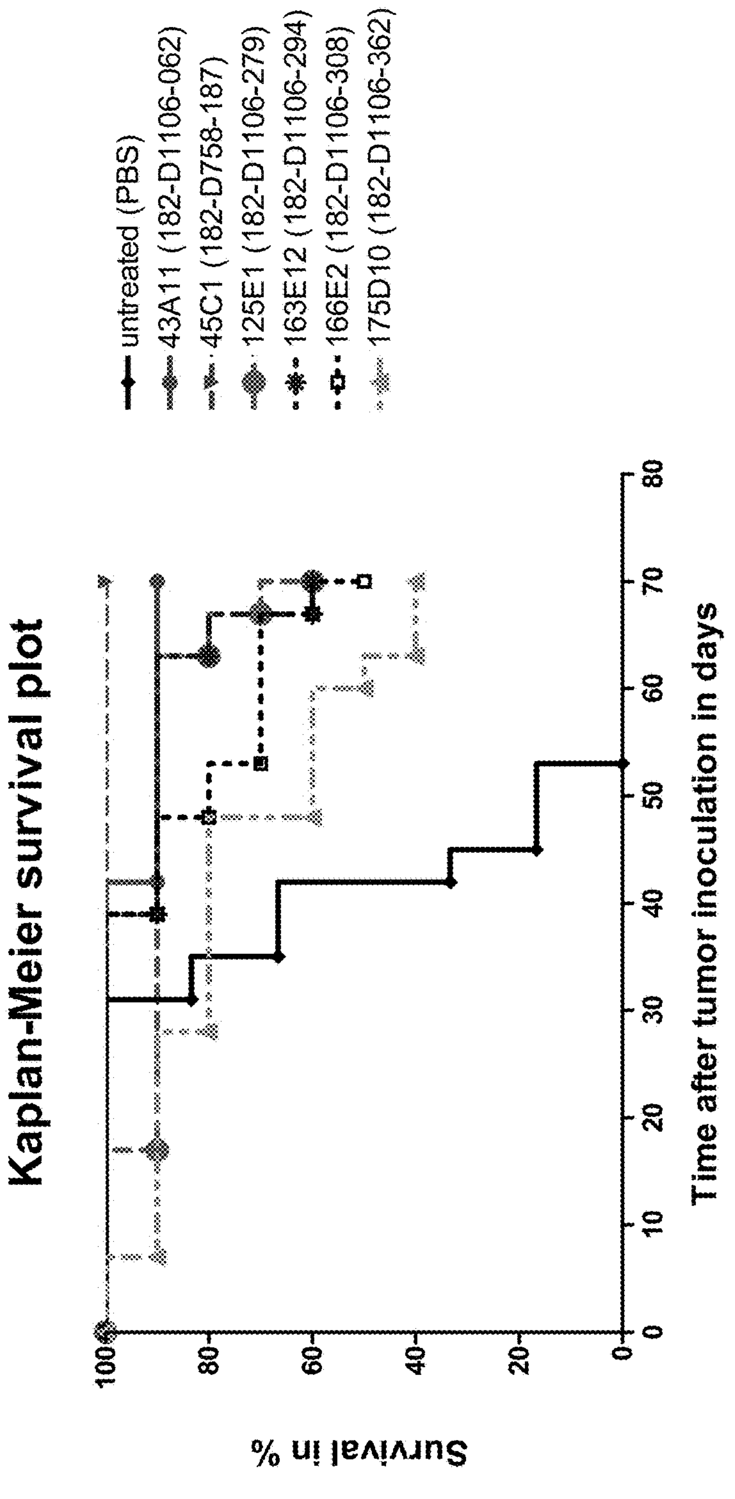

SCID mice were subcutaneously inoculated with $1\times10^7$ HEK293 cells stably expressing high levels of human CLD18A2 (HEK293-CLD18A2). Expression levels of human CLD18A2 in HEK293-CLD18A2 cells were comparable with expression levels in primary gastric cancers from patients. Each experimental treatment group comprised 10 mice (number of mice per group n=10). Therapy of mice started 3 days after tumor inoculation. 200 μg of purified hybridoma supernatants representing murine monoclonal antibodies 26B5, 26D12, 28D10, 37G11, 37H8, 38G5, 39F11, 42E12, 43A11, 38H3, or 61C2 were injected once per week for 4 weeks intravenously. Alternatively 200 μg of purified hybridoma supernatants containing murine monoclonal antibodies 45C1, 125E1, 163E12, 166E2, or 175D10 were administered twice per week for 6 weeks by alternating intravenous and intraperitoneal injection. Tumor growth of treated mice was monitored twice per week (Tumor Volume=Length×Width×Width divided by 2 in $mm^3$). The mice were killed if the tumor reached a volume of 500 $mm^3$ or in case of severe morbidity. FIG. 24 exemplifies robust inhibition of HEK293-CLD18A2 tumor cell growth by antibodies of the invention. FIGS. 25A and 25B show prolongation of survival by treatment with antibodies of the invention in an early treatment xenograft model using HEK293-CLD18A2 cells.

b. Late Onset Treatment of Advanced Highly CLD18A2 Expressing Tumors in Mice

Figure 26:
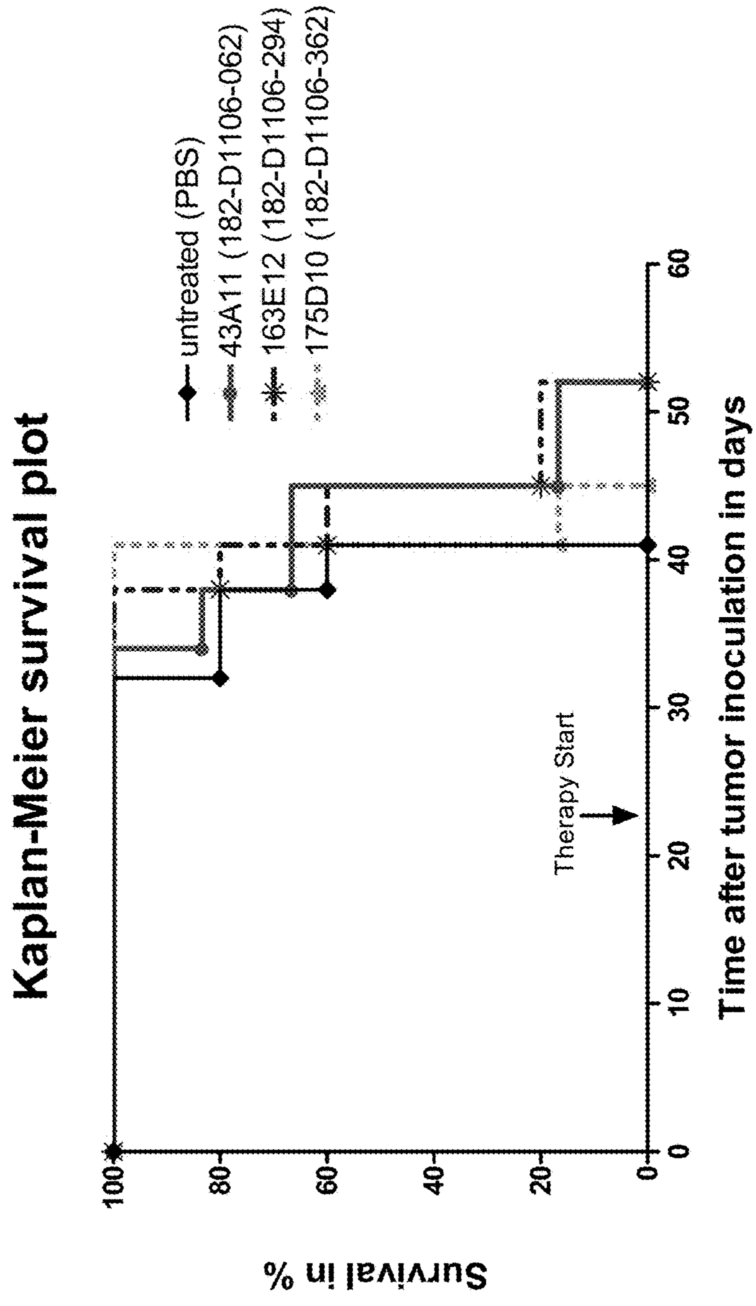
FIG. 26 shows prolongation of survival by antibodies of the invention in an advanced treatment xenograft model with HEK293-CLD18A2 cells.

The same tumor xenograft model based on HEK293-CLD18A2 cells was designed as a late therapy onset protocol as opposed to the early treatment described above. On day 27 after tumor cell inoculation mice were randomized in test groups each comprising 5-6 mice and therapy was initiated with 200 μg of purified hybridoma supernatants containing murine monoclonal antibodies 43A11, 163E12, and 175D10, respectively. Antibodies were administered twice per week for 6 weeks by alternating intravenous and intraperitoneal injection. Also in this model antibodies of the invention were shown to inhibit tumor growth. For several antibodies this resulted in prolongation of survival (FIG. 26).

c. Early Treatment of Tumors Expressing Low Levels of CLD18A2

Figure 27A:
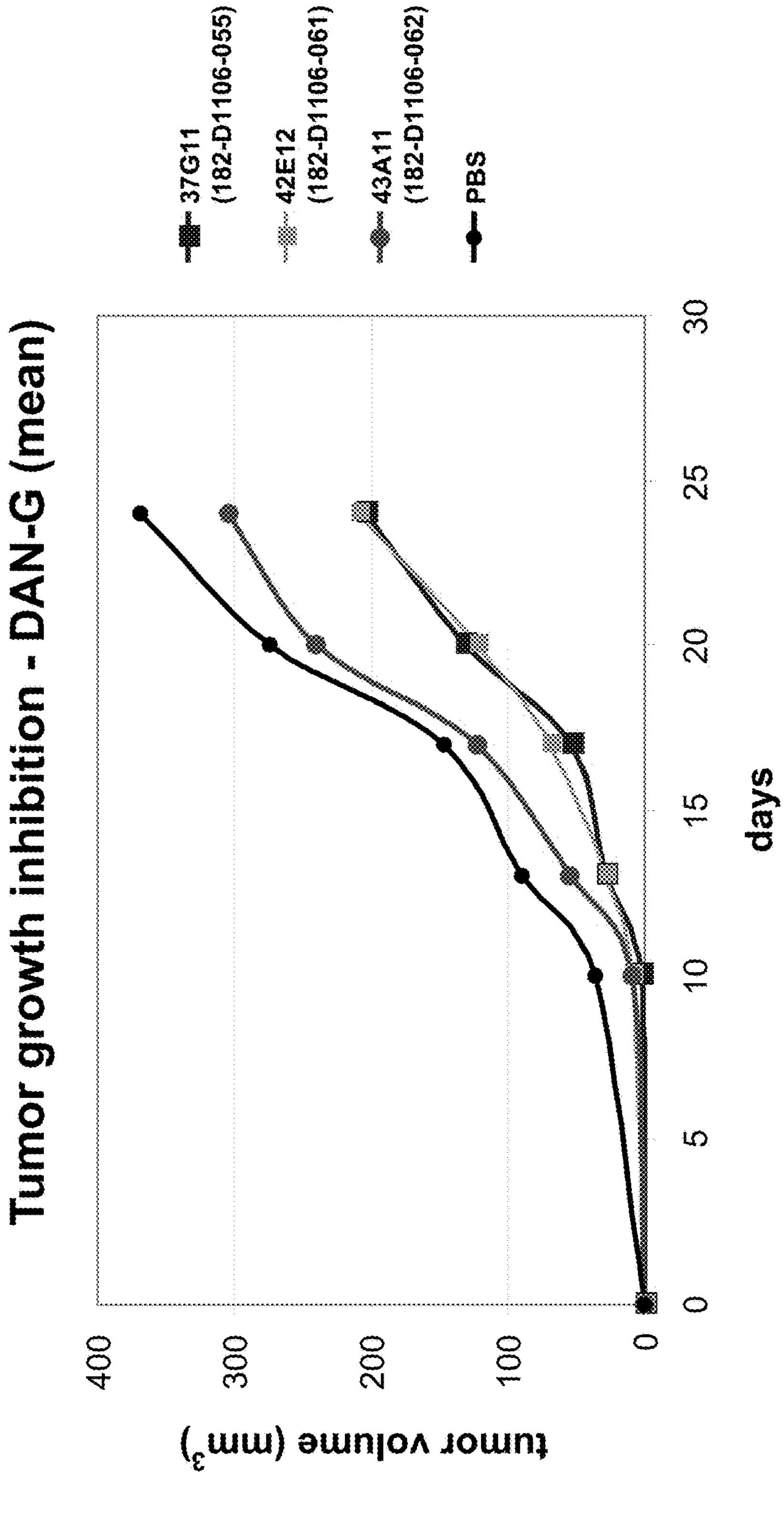
FIG. 27A shows tumor growth inhibition by antibodies of the invention in an early treatment xenograft model.
Figure 27B:
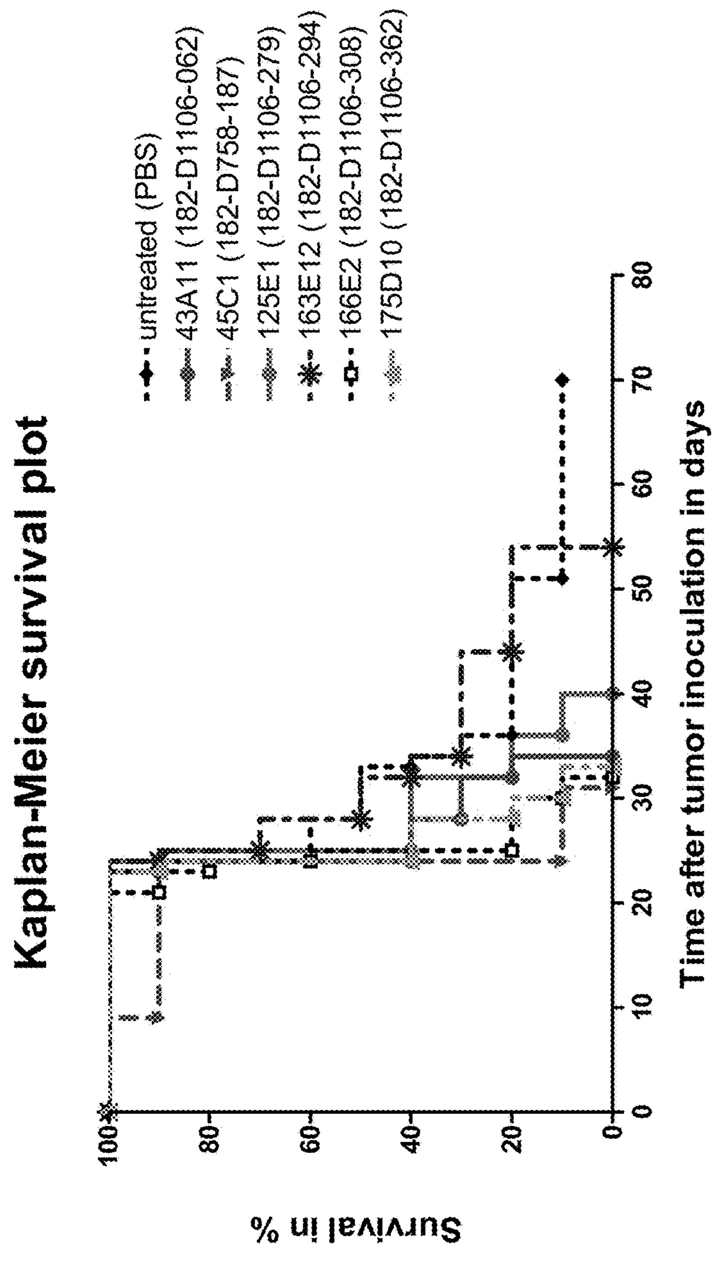
FIG. 27B shows prolongation of survival by antibodies of the invention in an early treatment xenograft model. Endogenously CLD18A2 expressing DAN-G cells were used.

SCID mice were subcutaneously inoculated with $2\times10^5$ cells of the DAN-G tumor cell line, an infiltrating human pancreatic adenocarcinoma cell line that constitutively expresses CLD18A2 protein at low level. Treatment of mice (10 per group) was initiated 3 days after tumor grafting: 200 μg of purified hybridoma supernatants containing murine monoclonal antibodies 45C1, 125E1, 163E12, 166E2, or 175D10 were administered twice per week for 6 weeks by alternating intravenous and intraperitoneal injection. Owing to the aggressive and fast tumor growth of the pancreatic DAN-G tumor cell line in vivo mice developed tumor cachexia and died within a few days. Even though, as a consequence, the window for measuring therapeutic effects was narrow, tumor growth inhibition and prolonged survival mediated by antibodies of the invention was also observed in this model (FIGS. 27A and 27B).

d. Antibodies of the Invention do not Elicit Side Effects in Mice

A murine CLD18A2-specific primer pair (s: CTA CCA AGG GCT ATG GCG TTC, as: GCA CCG AAG GTG TAC CTG GTC) was used in RT-PCR analyses to amplify cDNA derived from a comprehensive panel of normal mouse tissues (see FIG. 28).

Figure 28:
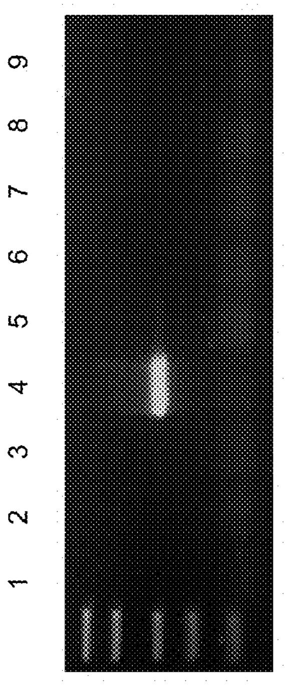
FIG. 28 shows CLD18A2 mRNA expression in mouse tissues. RT-PCR investigations with CLD18A2-specific primers showed no significant expression within all tested normal tissues except stomach. The following normal tissues were analysed: 1: small intestine, 2: spleen, 3: skin, 4: stomach, 5: lung, 6: pancreas, 7: lymph node, 8: thymus, 9: negative control
Figures 29A, 29B, 29C:
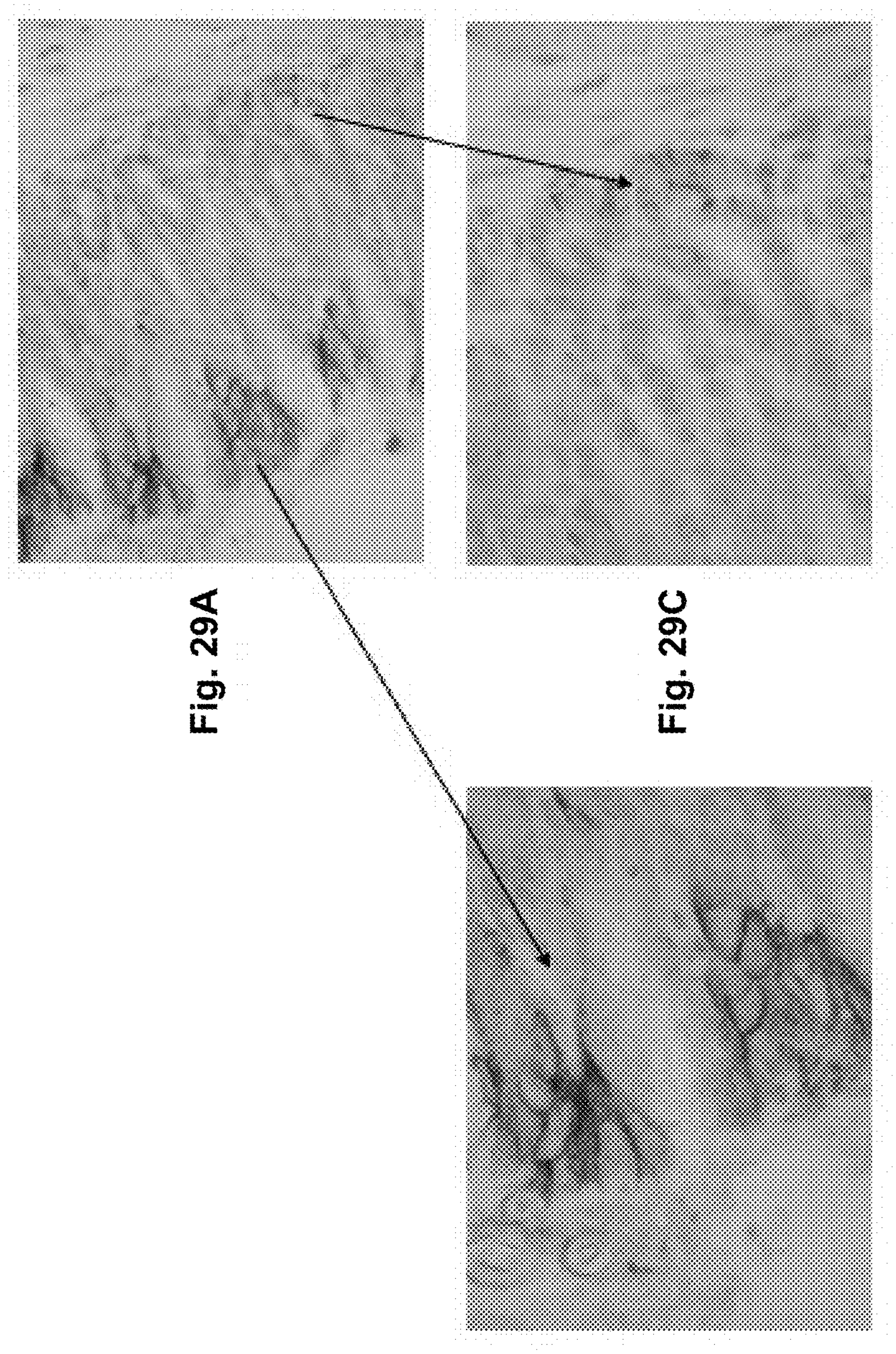
FIG. 29A, FIG. 29B, and FIG. 29C show CLD18 expression in normal stomach. Immunohistochemical analysis with CLD18 specific antibody of mouse stomach reveals conserved expression pattern. While the surface epithelia and deeper crypts express CLD18 in their cell surface, the central neck region is CLD18 negative.
Figure 30A:
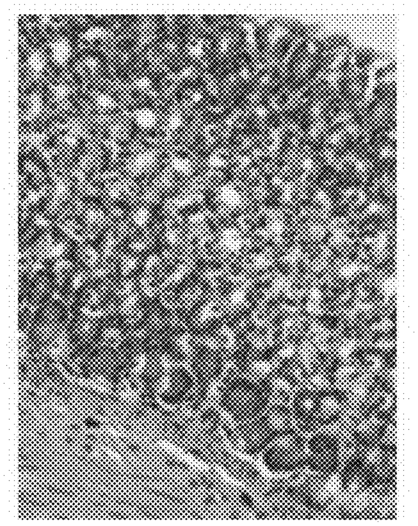
FIG. 30A, FIG. 30B.
Figure 30B:
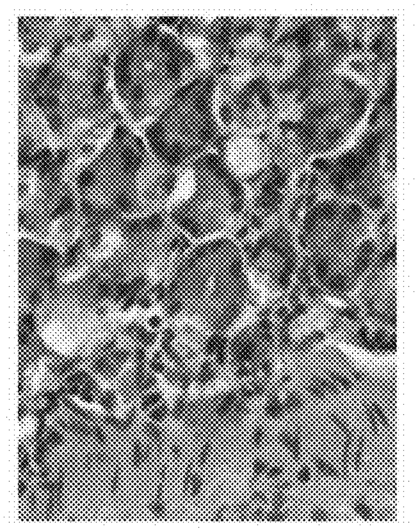
Figure 30C:
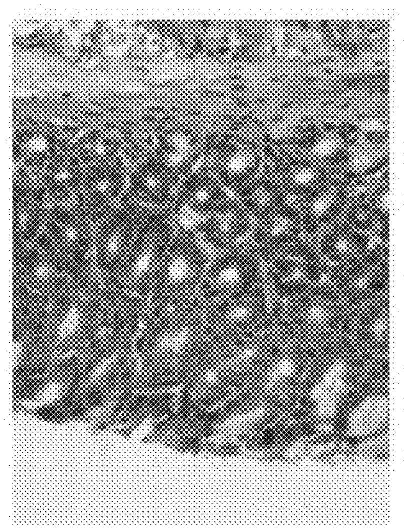
FIG. 30C, and FIG. 30D show haematoxylin and eosin staining of mice stomach tissues. Shown is an overview (FIG. 30A) and in detail (FIG. 30B) of the stomach of a 37G11-treated mouse in comparison to a control mouse (FIG. 30C and FIG. 30D), which was treated with PBS only.
Figure 30D:
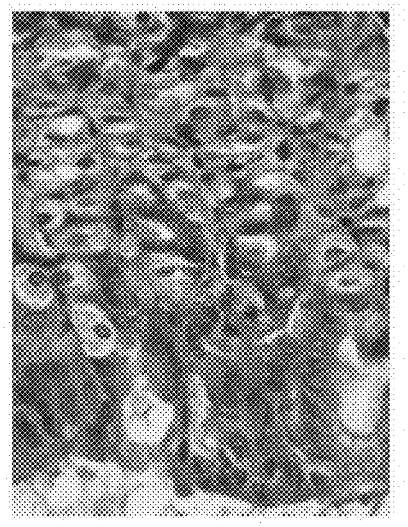

Expression of murine CLD18A2 was not detectable in any tested normal tissues, except stomach (see FIG. 28). Furthermore, an CLD18A2 specific antibody, which cross-reacts with human and mouse CLD18A2, was used for immunohistochemical analysis of CLD18A2 expression in a large panel of normal mouse tissues (see Tab. 3). Except for normal gastric tissue all tested normal tissues show no CLD18A2 expression. As we observed for the human CLD18A2, we also found for the mouse counterpart that while the surface epithelia- and deeper crypt cells express CLD18A2 at their cell surface, the central neck region is CLD18A2 negative (see FIG. 29A, FIG. 29B, and FIG. 29C). In summary, tissue distribution of CLD18A2 appears to be identical in men and mice.

TABLE 3

CLD18 expression within murine normal tissues as analysed by immunhistochemistry

| tissue | CLD18 expression |
|---|---|
| cerebellum | – |
| cerebrum | – |
| colon | – |
| esophagus | – |
| heart | – |
| kidney | – |
| liver | – |
| lung | – |
| lymph node | – |
| ovary | – |
| pancreas | – |
| skeletal muscle | – |
| spleen | – |
| stomach | + |
| thymus | – |
| bladder | – |

We further investigated potential side effects mediated by antibodies 125E1, 163E12, 166E2 and 175D10 in mice. All of these antibodies had been previously shown by FACS analysis to react with the murine CLD18A2 as well as with the human protein.

Neither were any visible side effects observed in mice during and after treatment with these antibodies, nor were any histomorphological correlates of toxicity observed in the gastric mucosa of antibody treated mice as compared to untreated (PBS-treated) mice (see FIG. 30A, FIG. 30B, FIG. 30C, and FIG. 30D).

9. Chimerization of Antibodies a. Generation of Mouse/Human Chimeric Monoclonal Antibodies Total RNA and subsequently single stranded cDNA was prepared from human peripheral blood mononuclear cells (PBMC) and from human spleen tissue by standard methods known to those skilled in the art, for example by using RNeasy Midi Kit (Qiagen) and Superscript II reverse transcriptase (Invitrogen).

The constant region of the human kappa light chain was amplified from PBMC cDNA by PCR. The sense oligomer (SEQ ID NO:38) added a BamHI restriction site at the 5' end of the constant region and changed the original nucleic acid sequence 5'-CGAACT-3' coding for the first two amino acids (Arg-Thr) of the constant region into 5'-CGTACG-3', generating a BsiWI restriction site without changing the amino acid sequence. The antisense oligomer (SEQ ID NO:39) included a stop codon and added a NotI restriction site at the 3' end of the amplified constant region. The PCR product as well as a standard expression vector (for example pcDNA3.1(+), Invitrogen) were sequentially incubated with BamHI and NotI restriction enzymes. The vector was additionally treated with calf intestinal alkaline phosphatase to prevent recirculation. The constant region was finally ligated into the vector, so that any forthcoming fusion of a variable region in front of the constant region is now possible via a HindIII restriction site (5'-AAGCTT-3') from the residual vector multiple cloning site and via the BsiWI restriction site (5'-CGTACG-3') generated with the PCR product. The sequence of the human kappa light chain constant region inserted into the vector is listed as SEQ ID NO:40, the amino acid sequence of the human kappa constant region is listed as SEQ ID NO:41.

The constant region of the human gamma-1 heavy chain was amplified from spleen cDNA by PCR. The 5' phosphorylated sense oligomer (SEQ ID NO:42) was placed over the naturally occurring ApaI restriction site, located 11 nucleotides downstream of the beginning of the constant region, and added a HindIII restriction site at the 5' end of the amplified part of the constant region. The 5' phosphorylated antisense oligomer (SEQ ID NO: 43) included a stop codon and added a NotI restriction site at the 3' end of the thus amplified constant region. The thus generated PCR product was blunt ended and 5' phosphorylated. The amplified gamma constant region was verified to be of the IgG1 subclass by PCR with a discriminating antisense oligomer (SEQ ID NO: 44) and by sequencing. A standard expression vector (for example pcDNA3.1(+)/Hygro, Invitrogen) with a different antibiotic resistance (for example hygromycin) than that of the vector used for expression of the light chain (for example neomycin) was incubated with PmeI restriction enzyme to completely remove the multiple cloning site leaving blunt ends. The vector was additionally treated with calf intestinal alkaline phosphatase to prevent recirculation. The constant region was finally ligated into the vector, so that any forthcoming fusion of a variable region in front of the constant region is now possible via the HindIII restriction site (5'-AAGCTT-3') and via the ApaI restriction site (5'-GGGCCC-3'), both generated with the PCR product. The correct orientation of the constant region in the vector, i.e. suitable for the preceding promoter of the vector, was verified by sequencing. Due to the position of the ApaI restriction site, any amplification of a variable region for this purpose has to include the first 11 nucleotides of the sequence of the human gamma-1 constant region in addition to the sequence of the ApaI site. The sequence of the thus amplified human gamma-1 heavy chain constant region inserted into the vector is listed as SEQ ID NO:45, the amino acid sequence of the thus expressed human gamma-1 constant region is listed as SEQ ID NO: 46.

Corresponding to their murine counterparts the chimeric monoclonal antibodies were named adding the prefix "ch-" e.g. ch-43A11, ch-163E12, ch-125E1, ch-166E2, ch-175D10, ch-45C1.

Amplification of the murine variable regions of light and heavy chains was carried out according to the "step-out PCR" method described in Matz et al. (Nucleic Acids Research, 1999, Vol. 27, No. 6). For this, total RNA was prepared from monoclonal hybridoma cell lines (see Tab. 4) by standard methods known to those skilled in the art, for example with the use of RNeasy Mini Kit (Qiagen). Single stranded cDNA was prepared according to the "template-switch" method also described in Matz et al. (Nucleic Acids Research, 1999, Vol. 27, No. 6, 1558). In addition to an (dT)30 oligomer (SEQ ID NO: 47), it included a DNA/RNA hybrid oligomer (SEQ ID NO: 48) serving as an 5' adaptor for template switching during polymerization of the cDNA strand. In this adaptor oligomer the last three nucleotides were ribo-instead of deoxyribonucleotides. The subsequent "step-out PCR" used an antisense oligomer targeted to the constant region of the mouse kappa chain or to the constant region of the subclasses 1, 2a or 3 of the gamma chains (SEQ ID NO: 49 to 52, respectively). The IgG subclass of the murine monoclonal antibody produced by the hybridoma cell lines was afore immunologically analyzed with IsoStrip (see Example 1), and the appropriate antisense oligomer was chosen accordingly (see Tab. 4). A primer mix served as the sense oligomer in the "step-out PCR", comprising the two oligomers listed in SEQ ID NO: 53 and 54. Some hybridoma cell lines expressed more than one heavy or light chain (in addition to the chains expressed by the myeloma cell line used for the generation of hybridomas). Table 4 summarizes the SEQ ID NOs of the cloned and sequenced variable regions of the murine antibody chains (SEQ ID NO: 55 to 69 and SEQ ID NO: 132 to 146) and of the cloned and sequenced full-length chimieric antibody chains (SEQ ID NO: 100 to 129).

The identified murine variable regions were then amplified by PCR omitting the 5' UTR and the 3' mouse constant region, adding restriction sites to the ends which allowed subcloning into the prepared expression vectors carrying the human constant regions. In addition, the sense oligomers provided a consensus Kozak sequence (5'-GCCGCCACC-3' or 5'-AGCCACC-3') and the antisense oligomers for heavy chain variable regions included the first 11 nucleotides of the human gamma-1 constant region in addition to the ApaI restriction site (see Tab. 4, SEQ ID NO: 70 to 99). Kappa light chain variable regions were cloned using HindIII and BsiWI restriction enzymes, gamma heavy chain variable regions demanded HindIII and ApaI restriction enzymes. The heavy gamma chain variable region of monoclonal antibody 45C1 contained an internal HindIII restriction site—here, the compatible BsaI enzyme was used instead (see SEQ ID NO: 80). SEQ ID NO: 100 to 114 show the nucleic acid sequences of the resulting chimerized antibodies (see Tab. 4). SEQ ID NO: 115 to 129 show the amino acid sequences of the accordingly expressed chimerized antibodies (see Tab. 4).

TABLE 4 mouse hybridoma cell lines used for antibody cloning

| | clone | mAb | Isotype | variable region | oligomer pair in PCR | chimerized antibody |
|---|---|---|---|---|---|---|
| heavy chain | 43A11 | 182-D1106-062 | IgG2a | SEQ ID NO: 55, 132 | SEQ ID NO: 70, 71 | SEQ ID NO: 100, 115 |
| | 163E12 | 182-D1106-294 | IgG3 | SEQ ID NO: 56, 133 | SEQ ID NO: 72, 73 | SEQ ID NO: 101, 116 |
| | 125E1 | 182-D1106-279 | IgG2a | SEQ ID NO: 57, 134 | SEQ ID NO: 74, 75 | SEQ ID NO: 102, 117 |
| | 166E2 | 182-D1106-308 | IgG3 | SEQ ID NO: 59, 136 | SEQ ID NO: 78, 79 | SEQ ID NO: 104, 119 |
| | 175D10 | 182-D1106-362 | IgG1 | SEQ ID NO: 58, 135 | SEQ ID NO: 76, 77 | SEQ ID NO: 103, 118 |
| | 45C1 | 182-D758-187 | IgG2a | SEQ ID NO: 60, 137 | SEQ ID NO: 80, 81 | SEQ ID NO: 105, 120 |
| light chain | 43A11 | 182-D1106-062 | IgK | SEQ ID NO: 62, 139 | SEQ ID NO: 84, 85 | SEQ ID NO: 107, 122 |
| | 163E12 | 182-D1106-294 | IgK | SEQ ID NO: 61, 138 | SEQ ID NO: 82, 83 | SEQ ID NO: 106, 121 |
| | 125E1 | 182-D1106-279 | IgK | SEQ ID NO: 63, 140 | SEQ ID NO: 86, 87 | SEQ ID NO: 108, 123 |
| | 166E2 | 182-D1106-308 | IgK | SEQ ID NO: 66, 143 | SEQ ID NO: 92, 93 | SEQ ID NO: 111, 126 |
| | 175D10 | 182-D1106-362 | IgK | SEQ ID NO: 65, 142 | SEQ ID NO: 90, 91 | SEQ ID NO: 110, 125 |
| | 45C1 | 182-D758-187 | IgK | SEQ ID NO: 64, 141 | SEQ ID NO: 88, 89 | SEQ ID NO: 109, 124 |
| | 45C1 | 182-D758-187 | IgK | SEQ ID NO: 67, 144 | SEQ ID NO: 94, 95 | SEQ ID NO: 112, 127 |
| | 45C1 | 182-D758-187 | IgK | SEQ ID NO: 68, 145 | SEQ ID NO: 96, 97 | SEQ ID NO: 113, 128 |
| | 45C1 | 182-D758-187 | IgK | SEQ ID NO: 69, 146 | SEQ ID NO: 98, 99 | SEQ ID NO: 114, 129 |

b. Generation and Production of Chimeric Antibodies Against CLD18

Mammalian cell lines producing chimeric antibodies with CLD18 specificity were generated. The cell lines derived from HEK293T cells (ATCC CRL-11268). One day before transfection, $2.5\times10^7$ cells were plated in a 14.5 cm tissue culture dish and cultured in 20 ml of complete medium, or alternatively $1\times10^7$ cells were plated in a 10 cm tissue culture dish and cultured in 10 ml of complete medium, or alternatively $0.6\times10^6$ cells were plated in a well of a 12-well tissue plate and cultured in 2-3 ml of complete medium (complete medium: DMEM:F12 medium supplemented with 10% FBS without antibiotics). The recommended cell density at the time of transfection should be 90% confluence. Immediately before transfection, medium was replaced by fresh medium. HEK293T cells were transfected with transfection reagents, e.g. Lipofectamine 2000 (Invitrogen, 11668-019) or alternatively Polyethylenimine (Sigma-Aldrich, 408727). Exemplified for transfection of HEK293T cells a total DNA amount of 110 μg or 296 g was used for a 14.5 cm tissue dish, and the ratio of transfection agent to DNA was 1:2.5 and 1:12 for Lipofectamine 2000 and PEI, respectively. 24 h after transfection medium was replaced with a GMP suitable medium, e.g. X-Vivo 15 (Cambrex) or a chemical defined medium like Pro293a (Cambrex) without serum. Transfected HEK293T cells producing chimeric monoclonal antibodies against CLD18 were cultured for further 96 h. Crude supernatants were harvested, sterile filtered and purified by protein A-sepharose. Antibody concentration was determined by BCA Assay and purity checked by sodium dodecylsulphate gel electrophoresis and coomassie staining.

c. Binding Characteristics of Chimeric Monoclonal Antibodies

Binding specificity of the cloned and generated chimeric monoclonal antibodies to CLD18A2 was analyzed by flow cytometry as described in Example 3. HEK293 living cells stably expressing human CLD18A2 (HEK293-CLD18A2) and HEK293 cells stably expressing human CLD18A1 (SEQ ID NOs: 7, 8) (HEK293-CLD18A1) were incubated for 30 min. at 4° C. with purified HEK293T cell culture supernatants containing chimeric monoclonal antibodies, followed by incubation with APC-conjugated $F(ab')_2$ fragment goat anti-human IgG Fcγ secondary antibody and counterstained with PI. Binding was assessed by flow cytometry using a BD FACSArray.

Similarly, endogenously CLD18A2 expressing human tumor cell lines, for example KATO-III and NUGC-4 cells, were analyzed by flow cytometry.

Figure 31A:
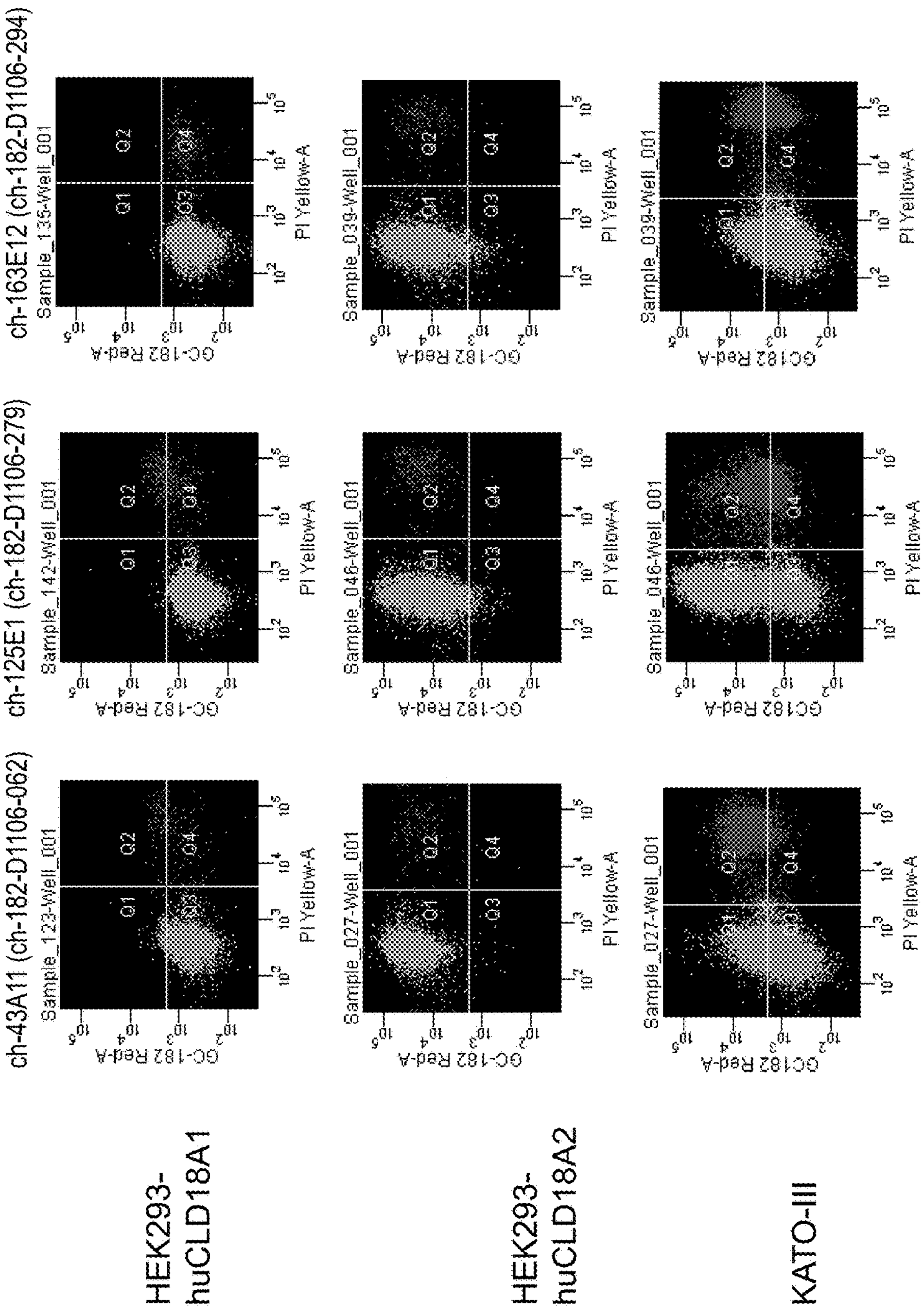
FIG. 31A and FIG. 31B show flowcytometric staining of HEK293 cells stably transfected with human CLD18A1 and A2, respectively, as well as endogenously expressing KATO-III cells with antibodies of the invention (43A11, 125E1, 163E12, 166E2, and 175D10).
Figure 31B:
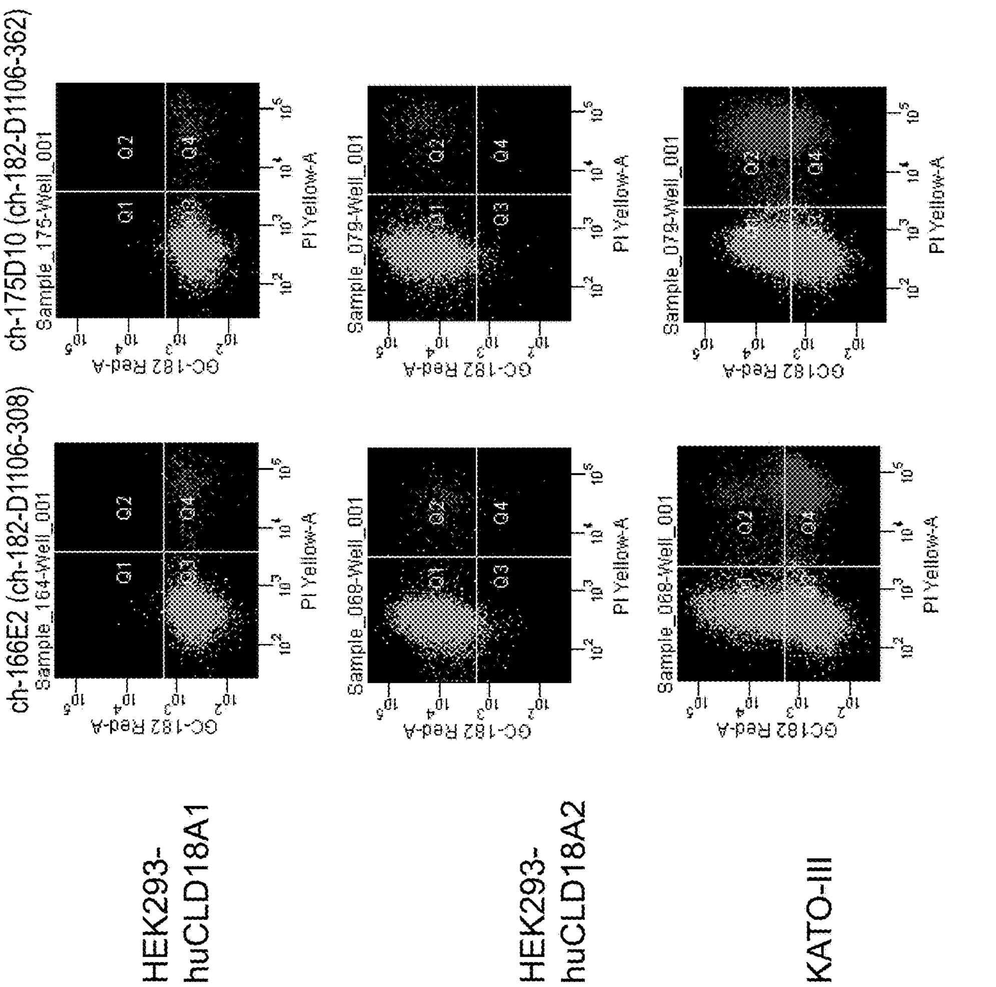

FIG. 31A and FIG. 31B show flowcytometric analyses of chimeric antibodies ch-43A11, ch-125E1, ch-163E12, ch-166E2, and ch-175D10. All of them show native epitope recognition and exhibit specific and strong binding to CLD18A2 but not CLD18A1 expressing cells.

d. Complement Dependent Cytotoxicity (CDC)

Serum for complement lysis was prepared by drawing blood from healthy volunteers into Serum-Monovette vacutainer tubes (Sarstedt, Nürmbrecht, Germany) which were then centrifuged at 600 g for 20 min. Serum was harvested and stored at −20° C. Control serum was heat inactivated at 56° C. for 30 min before storage.

Figure 32:
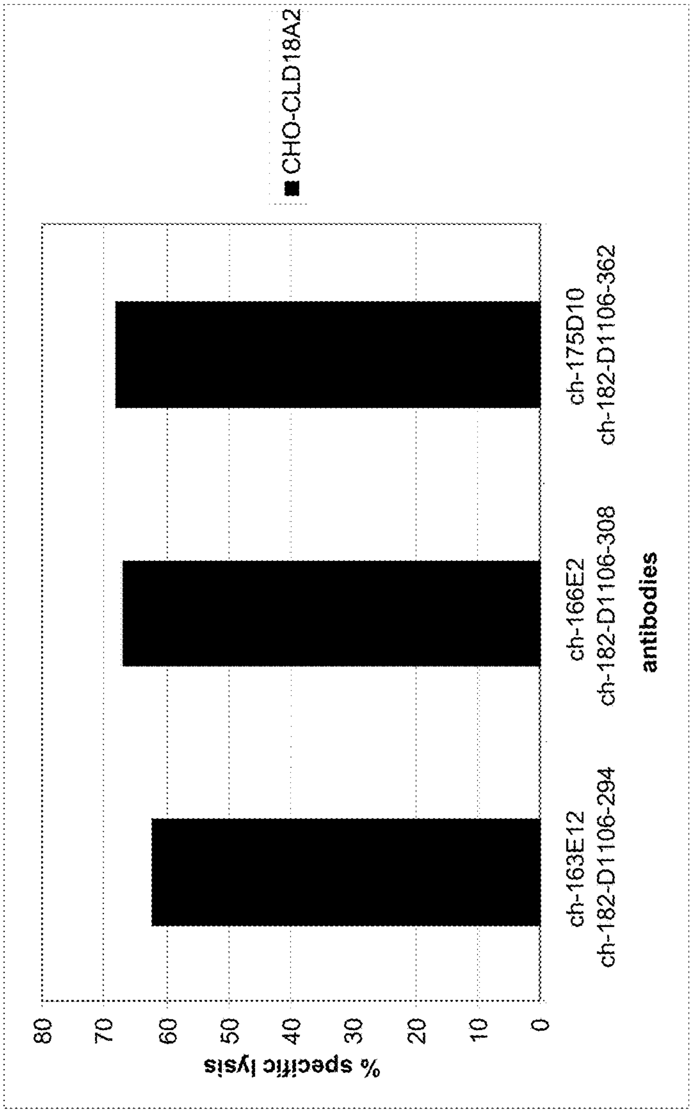
FIG. 32 shows CDC on CLD18A2 expressing cells mediated by chimeric antibodies of the invention.

Protein A-sepharose-purified chimeric antibodies of this invention were analyzed for their capability to induce complement dependent cytotoxicity (CDC) against KATO-III cells endogenously expressing human CLD18A2, as well as stably transfected CHO-CLD18A2 cells. Cells were incubated with monoclonal antibodies ch-163E12, ch-166E2, and ch-175D10, respectively, in a final concentration of 2.5 μg/ml to 35 μg/ml for 30 min. at 37° C. 20% human serum in RPMI was added to the cells and incubated for another 30 min. at 37° C. Thereafter, dead and living cells were discriminated by PI staining in a final concentration of 2.5 μg/ml and percentage of antibody-mediated cell lysis was determined by flow cytometry. For flow cytometric analysis a BD FACSArray flow cytometer was used (BD Biosciences, Mountain View, Calif.). At least 10000 events were collected for analysis with cell debris excluded by adjustment of the forward sideward scatter (FSC/SSC) threshold. Specific lysis was calculated by the following formula: specific lysis=(% PI-positive cells in sample−% PI-positive cells in sample with heat inactivated serum). Specific lysis mediated by CDC was shown for several antibodies. All three antibodies mediated robust CDC on CHO-CLD18A2 cells (FIG. 32). On KATO-III cells antibodies ch-163E12 and ch-175D10 were inducers of robust CDC.

e. Antibody-Dependent Cellular Cytotoxicity (ADCC)

FPLC-purified, chimeric antibodies of the invention were analyzed for their capability to induce antibody-dependent cellular cytotoxicity (ADCC) against KATO-III cells endogenously expressing human CLD18A2.

Human blood from healthy donors was diluted twice in phosphate buffer (PBS) and blood cells were layered on Ficoll (1077 g/ml, Pharmacia). After centrifugation, peripheral blood mononuclear cells (PBMC) were collected from the interphase, washed and resuspended in X-Vivo-15 culture medium supplemented with 5% heat-inactivated human serum. 15 h before the assay, KATO-ITT cells were transfected with luciferase and plated at $5\times10^4$ cells/well in a white microplate.

For the assay, effector cells (PBMC, prepared as described above) at an effector to target (E:T) ratio of 20:1 and FPLC-purified chimeric antibodies were added and incubated for 2-3 h at 37° C., 5% $CO_2$. Final concentration of the antibody in the well was 50 μg/ml. After 2-3 h of pre-incubation, lucifer yellow (BD Biosciences, San Jose USA) was added at 1 mg/ml. Luminescence resulting from the oxidation of lucifer yellow by the luciferase of viable cells was measured continually for up to 6 h using a microplate-reader (Infinite200, Tecan, Switzerland). Percentage of cellular cytotoxicity was calculated using the following formula: % specific lysis=100−((sample luminescence counts−spontaneous luminescence counts)/(maximal luminescence counts−spontaneous luminescence counts)×100), with the spontaneous luminescence determined by adding Triton X-100 (0.2% final concentration), and the maximal signal measured in the absence of antibodies.

Figure 33:
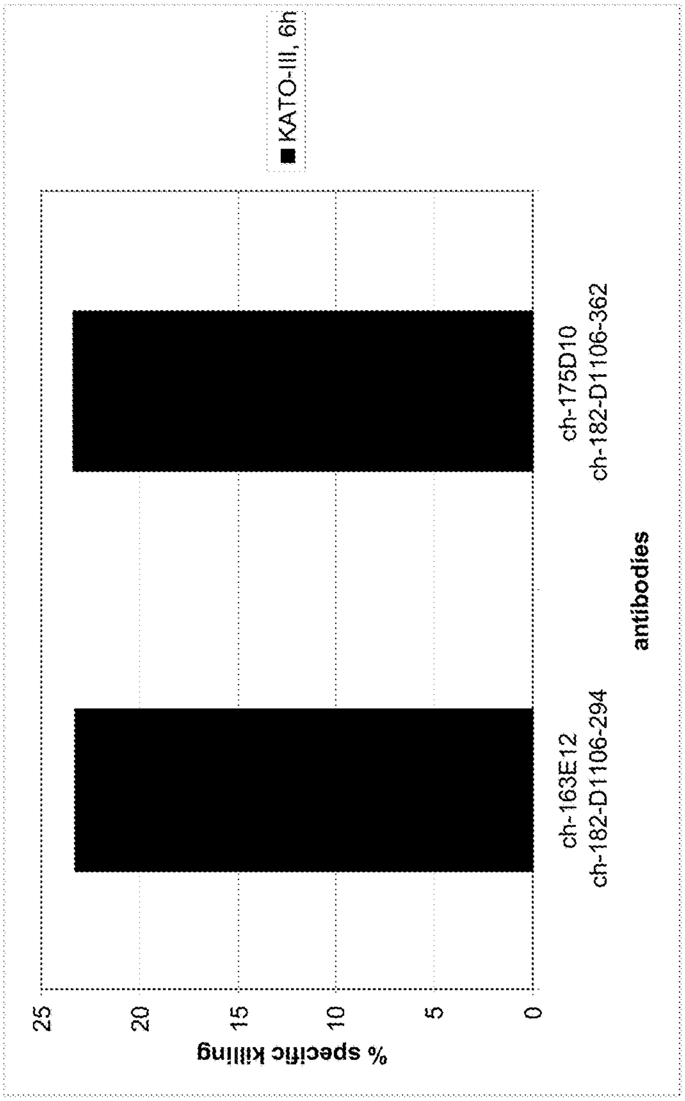
FIG. 33 shows ADCC on KATO-III cells mediated by chimeric antibodies of the invention.

Using this assay it was shown that monoclonal antibodies ch-163E12 and ch-175D10 mediate strong ADCC on KATO-III cells (FIG. 33).

f. Proliferation Inhibition

FPLC-purified chimeric antibodies of the invention were analyzed for their capability to inhibit cell growth of KATO-III cells endogenously expressing human CLD18A2.

Target cells (KATO-III) were cultured in the presence of chimeric respective antibodies (see proliferation inhibition of murine antibodies, Example 7). FPLC purified chimeric antibodies ch-163E12 and ch-166E2 were shown to inhibit cell proliferation.

10. Selection of Antibodies as Clinical Lead Candidates

Ideal clinical leads may cover a wide range of therapeutic and diagnostic applications (see also section IV—Uses and Methods of the Invention). According to the invention antibodies directed to CLD18-A2 are provided. It is shown that the antibodies provided according to the invention offer a broad spectrum of properties regarding specificity, ability to induce CDC and ADCC and inhibit proliferation of cells expressing CLD18, in particular tumor cells. Furthermore, it has been demonstrated that chimerisation of antibodies may lead to the acquisition of additional Fc-dependent effector functions not present in the parental murine molecule. For example, it is shown herein that antibody 175D10 with murine IgG does not induce complement dependent cytotoxicity (see Example 5), while ch-175D10 with human IgG1 induces specific lysis of constitutively CLD18 expressing tumor cells (see Tab. 5 and Tab. 6).

Antibodies provided according to the present invention may be categorized into distinct classes according to their binding properties and their ability to mediate effector functions on cells expressing CLD18. From the antibodies provided according to the present invention, clinical lead candidates may be selected based on their functional characteristics. An overview of properties for selected murine and chimeric antibodies of the invention is given in Tab. 5 and Tab. 6, respectively.

Clinical lead candidates of the invention may have one or more of the following properties:

a) binding to human CLD18A2 but not to human CLD18A1 (e.g. 43A11, 45C1, 125E1, 163E12, 166E2 and 175D10, and ch-43A11, ch-45C1, ch-125E1, ch-163E12, ch-166E2 and ch-175D10). For examples, see FIGS. 6A and 6B.

b) binding to mouse CLD18A2 but not to mouse CLD18A1 (e.g. 125E1, 163E12, 166E2 and 175D10). For examples, see FIGS. 15A and 15B.

c) binding to CLD18 naturally expressed by tumor cells (e.g. 45C1, 43A11, 125E1, 163E12, 166E2 and 175D10, and ch-45C1, ch-43A11, ch-125E1, ch-163E12, ch-166E2 and ch-175D10). For examples, see FIG. 13 d) binding to CLD18 in intercellular contact zones (e.g. 45C1, 43A11, 125E1, 163E12, 166E2 and 175D10). For examples, see FIGS. 12A and 12B.

e) mediating CDC induced killing of cells, which express CLD18 (e.g. 45C1, 125E1, 163E12, 166E2 and 175D10, and ch-163E12 and ch-175D10). For examples, see FIG. 32.

f) mediate ADCC induced killing of cells expressing CLD18 (e.g. ch-163E12 and ch-175D10). For examples, see FIG. 33.

g) inhibiting proliferation of cells expressing CLD18 (e.g. 45C1, 125E1, 163E12, 166E2 and 175D10, and ch-163E12 and ch-166E2).

h) inhibiting tumor growth in xenograft models with cells expressing CLD18 (e.g. 43A11, 125E1, 163E12, 166E2, and 175D10). For examples, see FIG. 24.

i) prolonging survival in xenograft models with cells expressing CLD18 (e.g. 43A11, 125E1, 163E12, 166E2 and 175D10). For examples, see FIG. 25B.

Exemplary Overview of Properties for Lead Candidate Selection

TABLE 5

| murine antibodies | | | | | | | | |
|---|---|---|---|---|---|---|---|---|
| antibody | binding of human CLD18A2 but not A1 | binding of mouse CLD18A2 but not A1 | binding of CLD18 on naturally expressing tumor cells | binding to CLD18 in contact zones | mediating CDC on CLD18 expressing cells | inhibiting proliferation of cells expressing CLD18 | inhibiting tumor growth in xenograft expressing CLD18 | prolonging survival in xenograft expressing CLD18 |
| 45C1 | + | − | + | + | (+) | + | (+) | (+) |
| 125E1 | + | + | + | + | (+) | + | + | + |
| 163E12 | + | + | + | + | + | + | + | + |
| 175D10 | + | + | + | + | (+) | (+) | + | + |

legend:
+ excellent performance,
(+) performance in different setups

TABLE 6

| chimeric antibodies | | | | | |
|---|---|---|---|---|---|
| antibody | binding of human CLD18A2 but not A1 | binding of CLD18 on naturally expressing tumor cells | mediating CDC on CLD18 expressing cells | mediating ADCC on CLD18 expressing cells | inhibiting pro-liferation of cells expressing CLD18 |
| ch-45C1 | + | + | n.d. | n.d. | n.d. |
| ch-125E1 | + | + | n.d. | n.d. | n.d. |
| ch-163E12 | + | + | + | + | + |
| ch-175D10 | + | + | + | + | n.d. |

legend:
+ excellent performance,
(+) performance in different setups,
n.d. not done.

The invention claimed is:

1. An anti-CLD18A2 antibody that binds to CLD18A2 but not to CLD18A1 and mediates killing of cells expressing CLD18A2, wherein the antibody binds to an epitope comprising amino acid residues within SEQ ID NO: 16, wherein the anti-CLD18A2 antibody comprises a combination of a heavy chain variable region ($V_H$) and a light chain variable region ($V_L$), wherein the $V_H$ comprises an amino acid sequence represented by SEQ ID NO: 135 and the $V_L$ comprises an amino acid sequence represented by SEQ ID NO: 142.

2. An anti-CLD18A2 antibody that binds to CLD18A2 but not to CLD18A1 and mediates killing of cells expressing CLD18A2, wherein the antibody binds to an epitope comprising amino acid residues within SEQ ID NO: 16, wherein the anti-CLD18A2 antibody comprises a combination of a heavy chain variable region ($V_H$) and a light chain variable region ($V_L$), wherein the anti-CLD18A2 antibody is a chimerized antibody comprising a $V_H$ having an amino acid sequence represented by SEQ ID NO: 135 and a $V_L$ having an amino acid sequence represented by SEQ ID NO: 142.

3. The anti-CLD18A2 antibody of claim 1, wherein the anti-CLD18A2 antibody is selected from the group consisting of an IgG1, an IgG2, an IgG3, an IgG4, an IgM, an IgA1, an IgA2, a secretory IgA, an IgD, and an IgE antibody.

4. The anti-CLD18A2 antibody of claim 1, wherein the anti-CLD18A2 antibody comprises a human IgG1 constant region.

5. A pharmaceutical composition comprising the anti-CLD18A2 antibody of claim 1 and a pharmaceutically acceptable carrier.

6. A method of treating a CLD18-related disease selected from the group consisting of gastric cancer, esophageal cancer, pancreatic cancer, lung cancer, ovarian cancer, colon cancer, hepatic cancer, head-neck cancer, and cancer of the gallbladder, comprising:

administering to a subject the anti-CLD18A2 antibody of claim 1.

7. The method of claim 6, wherein the CLD18-related disease is gastric cancer.

8. The method of claim 6, wherein the CLD18-related disease is pancreatic cancer.

9. The method of claim 6, further comprising administering to the subject a chemotherapeutic agent.

10. The method of claim 6, wherein the anti-CLD18A2 antibody is a chimerized antibody.

11. The anti-CLD18A2 antibody of claim 2, wherein the anti-CLD18A2 antibody comprises a human kappa light chain constant region.

12. The anti-CLD18A2 antibody of claim 2, wherein the anti-CLD18A2 antibody comprises a light chain constant region having an amino acid sequence represented by SEQ ID NO: 41.

13. The anti-CLD18A2 antibody of claim 2, wherein the anti-CLD18A2 antibody comprises a human IgG1 heavy chain constant region.

14. The anti-CLD18A2 antibody of claim 2, wherein the anti-CLD18A2 antibody comprises a heavy chain constant region having an amino acid sequence represented by SEQ ID NO: 46.

15. The anti-CLD18A2 antibody of claim 2, wherein the anti-CLD18A2 antibody comprises a heavy chain constant region having an amino acid sequence represented by SEQ ID NO: 150.

16. The anti-CLD18A2 antibody of claim 2, wherein the anti-CLD18A2 antibody comprises a human IgG1 heavy chain constant region and a human kappa light chain constant region.

17. The anti-CLD18A2 antibody of claim 2, wherein the anti-CLD18A2 antibody comprises a heavy chain constant region having an amino acid sequence represented by SEQ ID NO: 150 and a light chain constant region having an amino acid sequence represented by SEQ ID NO: 41.

18. A pharmaceutical composition comprising the anti-CLD18A2 antibody of claim 2 and a pharmaceutically acceptable carrier.

19. The anti-CLD18A2 antibody of claim 1, wherein the anti-CLD18A2 antibody comprises a heavy chain constant region having an amino acid sequence represented by SEQ ID NO: 46.

20. The anti-CLD18A2 antibody of claim 1, wherein the anti-CLD18A2 antibody comprises a heavy chain constant region having an amino acid sequence represented by SEQ ID NO: 150.

21. The anti-CLD18A2 antibody of claim 1, wherein the anti-CLD18A2 antibody comprises a human IgG1 heavy chain constant region and a human kappa light chain constant region.

22. The anti-CLD18A2 antibody of claim 1, wherein the anti-CLD18A2 antibody comprises a heavy chain constant region having an amino acid sequence represented by SEQ ID NO: 150 and a light chain constant region having an amino acid sequence represented by SEQ ID NO: 41.

23. The method of claim 10, wherein the chimerized antibody comprises a human IgG1 heavy chain constant region and a human kappa light chain constant region.

24. The method of claim 10, wherein the chimerized antibody comprises a heavy chain constant region having an amino acid sequence represented by SEQ ID NO: 150 and a light chain constant region having an amino acid sequence represented by SEQ ID NO: 41.

* * * * *

SEQUENCE LISTING

<160> NUMBER OF SEQ ID NOS: 150

<210> SEQ ID NO 1
<211> LENGTH: 786
<212> TYPE: DNA
<213> ORGANISM: Homo sapiens

<400> SEQUENCE: 1
atggccgtga ctgcctgtca gggcttgggg ttcgtggttt cactgattgg gattgcgggc 60
atcattgctg ccacctgcat ggaccagtgg agcacccaag acttgtacaa caaccccgta 120
acagctgttt tcaactacca ggggctgtgg cgctcctgtg tccgagagag ctctggcttc 180
accgagtgcc ggggctactt caccctgctg gggctgccag ccatgctgca ggcagtgcga 240
gccctgatga tcgtaggcat cgtcctgggt gccattggcc tcctggtatc catctttgcc 300
ctgaaatgca tccgcattgg cagcatggag gactctgcca aagccaacat gacactgacc 360
tccgggatca tgttcattgt ctcaggtctt tgtgcaattg ctggagtgtc tgtgtttgcc 420
aacatgctgg tgactaactt ctggatgtcc acagctaaca tgtacaccgg catgggtggg 480
atggtgcaga ctgttcagac caggtacaca tttggtgcgg ctctgttcgt gggctgggtc 540
gctggaggcc tcacactaat tgggggtgtg atgatgtgca tcgcctgccg gggcctggca 600
ccagaagaaa ccaactacaa agccgtttct tatcatgcct cgggccacag tgttgcctac 660
aagcctggag gcttcaaggc cagcactggc tttgggtcca acaccaaaaa caagaagata 720
tacgatggag gtgcccgcac agaggacgag gtacaatctt atccttccaa gcacgactat 780
gtgtaa 786

<210> SEQ ID NO 2
<211> LENGTH: 261
<212> TYPE: PRT
<213> ORGANISM: Homo sapiens

<400> SEQUENCE: 2

Met Ala Val Thr Ala Cys Gln Gly Leu Gly Phe Val Val Ser Leu Ile
1 5 10 15

Gly Ile Ala Gly Ile Ile Ala Ala Thr Cys Met Asp Gln Trp Ser Thr
20 25 30

Gln Asp Leu Tyr Asn Asn Pro Val Thr Ala Val Phe Asn Tyr Gln Gly
35 40 45

Leu Trp Arg Ser Cys Val Arg Glu Ser Ser Gly Phe Thr Glu Cys Arg
50 55 60

Gly Tyr Phe Thr Leu Leu Gly Leu Pro Ala Met Leu Gln Ala Val Arg
65 70 75 80

Ala Leu Met Ile Val Gly Ile Val Leu Gly Ala Ile Gly Leu Leu Val
85 90 95

Ser Ile Phe Ala Leu Lys Cys Ile Arg Ile Gly Ser Met Glu Asp Ser
100 105 110

Ala Lys Ala Asn Met Thr Leu Thr Ser Gly Ile Met Phe Ile Val Ser
115 120 125

Gly Leu Cys Ala Ile Ala Gly Val Ser Val Phe Ala Asn Met Leu Val
130 135 140

Thr Asn Phe Trp Met Ser Thr Ala Asn Met Tyr Thr Gly Met Gly Gly
145 150 155 160

Met Val Gln Thr Val Gln Thr Arg Tyr Thr Phe Gly Ala Ala Leu Phe
165 170 175

-continued

```
Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260


<210> SEQ ID NO 3
<211> LENGTH: 816
<212> TYPE: DNA
<213> ORGANISM: Homo sapiens

<400> SEQUENCE: 3

atggccgtga ctgcctgtca gggcttgggg ttcgtggttt cactgattgg gattgcgggc      60

atcattgctg ccacctgcat ggaccagtgg agcacccaag acttgtacaa caaccccgta     120

acagctgttt tcaactacca ggggctgtgg cgctcctgtg tccgagagag ctctggcttc     180

accgagtgcc ggggctactt caccctgctg gggctgccag ccatgctgca ggcagtgcga     240

gccctgatga tcgtaggcat cgtcctgggt gccattggcc tcctggtatc catctttgcc     300

ctgaaatgca tccgcattgg cagcatggag gactctgcca aagccaacat gacactgacc     360

tccgggatca tgttcattgt ctcaggtctt tgtgcaattg ctggagtgtc tgtgtttgcc     420

aacatgctgg tgactaactt ctggatgtcc acagctaaca tgtacaccgg catgggtgaa     480

caaaaactca tctcagaaga ggatctgggg atggtgcaga ctgttcagac caggtacaca     540

tttggtgcgg ctctgttcgt gggctgggtc gctggaggcc tcacactaat tgggggtgtg     600

atgatgtgca tcgcctgccg gggcctggca ccagaagaaa ccaactacaa agccgtttct     660

tatcatgcct cgggccacag tgttgcctac aagcctggag gcttcaaggc cagcactggc     720

tttgggtcca acaccaaaaa caagaagata tacgatggag gtgcccgcac agaggacgag     780

gtacaatctt atccttccaa gcacgactat gtgtaa                               816


<210> SEQ ID NO 4
<211> LENGTH: 271
<212> TYPE: PRT
<213> ORGANISM: Homo sapiens

<400> SEQUENCE: 4

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95
```

```
Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Glu
145                 150                 155                 160

Gln Lys Leu Ile Ser Glu Glu Asp Leu Gly Met Val Gln Thr Val Gln
                165                 170                 175

Thr Arg Tyr Thr Phe Gly Ala Ala Leu Phe Val Gly Trp Val Ala Gly
            180                 185                 190

Gly Leu Thr Leu Ile Gly Gly Val Met Met Cys Ile Ala Cys Arg Gly
        195                 200                 205

Leu Ala Pro Glu Glu Thr Asn Tyr Lys Ala Val Ser Tyr His Ala Ser
    210                 215                 220

Gly His Ser Val Ala Tyr Lys Pro Gly Gly Phe Lys Ala Ser Thr Gly
225                 230                 235                 240

Phe Gly Ser Asn Thr Lys Asn Lys Lys Ile Tyr Asp Gly Gly Ala Arg
                245                 250                 255

Thr Glu Asp Glu Val Gln Ser Tyr Pro Ser Lys His Asp Tyr Val
            260                 265                 270


<210> SEQ ID NO 5
<211> LENGTH: 813
<212> TYPE: DNA
<213> ORGANISM: Homo sapiens

<400> SEQUENCE: 5

atggccgtga ctgcctgtca gggcttgggg ttcgtggttt cactgattgg gattgcgggc      60

atcattgctg ccacctgcat ggaccagtgg agcacccaag acttgtacaa caaccccgta     120

acagctgttt tcaactacca ggggctgtgg cgctcctgtg tccgagagag ctctggcttc     180

accgagtgcc ggggctactt caccctgtac ccatacgacg tgccagacta cgcactgggg     240

ctgccagcca tgctgcaggc agtgcgagcc ctgatgatcg taggcatcgt cctgggtgcc     300

attggcctcc tggtatccat ctttgccctg aaatgcatcc gcattggcag catggaggac     360

tctgccaaag ccaacatgac actgacctcc gggatcatgt tcattgtctc aggtctttgt     420

gcaattgctg gagtgtctgt gtttgccaac atgctggtga ctaacttctg gatgtccaca     480

gctaacatgt acaccggcat gggtgggatg gtgcagactg ttcagaccag gtacacattt     540

ggtgcggctc tgttcgtggg ctgggtcgct ggaggcctca cactaattgg gggtgtgatg     600

atgtgcatcg cctgccgggg cctggcacca gaagaaacca actacaaagc cgtttcttat     660

catgcctcgg gccacagtgt tgcctacaag cctggaggct tcaaggccag cactggcttt     720

gggtccaaca ccaaaaacaa gaagatatac gatggaggtg cccgcacaga ggacgaggta     780

caatcttatc cttccaagca cgactatgtg taa                                  813


<210> SEQ ID NO 6
<211> LENGTH: 270
<212> TYPE: PRT
<213> ORGANISM: Homo sapiens

<400> SEQUENCE: 6

Met Ala Val Thr Ala Cys Gln Gly Leu Gly Phe Val Val Ser Leu Ile
```

```
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Tyr Pro Tyr Asp Val Pro Asp Tyr Ala Leu Gly
65                  70                  75                  80

Leu Pro Ala Met Leu Gln Ala Val Arg Ala Leu Met Ile Val Gly Ile
                85                  90                  95

Val Leu Gly Ala Ile Gly Leu Leu Val Ser Ile Phe Ala Leu Lys Cys
            100                 105                 110

Ile Arg Ile Gly Ser Met Glu Asp Ser Ala Lys Ala Asn Met Thr Leu
        115                 120                 125

Thr Ser Gly Ile Met Phe Ile Val Ser Gly Leu Cys Ala Ile Ala Gly
    130                 135                 140

Val Ser Val Phe Ala Asn Met Leu Val Thr Asn Phe Trp Met Ser Thr
145                 150                 155                 160

Ala Asn Met Tyr Thr Gly Met Gly Gly Met Val Gln Thr Val Gln Thr
                165                 170                 175

Arg Tyr Thr Phe Gly Ala Ala Leu Phe Val Gly Trp Val Ala Gly Gly
            180                 185                 190

Leu Thr Leu Ile Gly Gly Val Met Met Cys Ile Ala Cys Arg Gly Leu
        195                 200                 205

Ala Pro Glu Glu Thr Asn Tyr Lys Ala Val Ser Tyr His Ala Ser Gly
    210                 215                 220

His Ser Val Ala Tyr Lys Pro Gly Gly Phe Lys Ala Ser Thr Gly Phe
225                 230                 235                 240

Gly Ser Asn Thr Lys Asn Lys Lys Ile Tyr Asp Gly Gly Ala Arg Thr
                245                 250                 255

Glu Asp Glu Val Gln Ser Tyr Pro Ser Lys His Asp Tyr Val
            260                 265                 270
```

<210> SEQ ID NO 7
<211> LENGTH: 786
<212> TYPE: DNA
<213> ORGANISM: Homo sapiens

<400> SEQUENCE: 7

```
atgtccacca ccacatgcca agtggtggcg ttcctcctgt ccatcctggg gctggccggc     60

tgcatcgcgg ccaccgggat ggacatgtgg agcacccagg acctgtacga caaccccgtc    120

acctccgtgt tccagtacga agggctctgg aggagctgcg tgaggcagag ttcaggcttc    180

accgaatgca ggccctattt caccatcctg ggacttccag ccatgctgca ggcagtgcga    240

gccctgatga tcgtaggcat cgtcctgggt gccattggcc tcctggtatc catctttgcc    300

ctgaaatgca tccgcattgg cagcatggag gactctgcca aagccaacat gacactgacc    360

tccgggatca tgttcattgt ctcaggtctt tgtgcaattg ctggagtgtc tgtgtttgcc    420

aacatgctgg tgactaactt ctggatgtcc acagctaaca tgtacaccgg catgggtggg    480

atggtgcaga ctgttcagac caggtacaca tttggtgcgg ctctgttcgt gggctgggtc    540

gctggaggcc tcacactaat tgggggtgtg atgatgtgca tcgcctgccg gggcctggca    600

ccagaagaaa ccaactacaa agccgtttct tatcatgcct caggccacag tgttgcctac    660
```

aagcctggag gcttcaaggc cagcactggc tttgggtcca acaccaaaaa caagaagata 720
tacgatggag gtgcccgcac agaggacgag gtacaatctt atccttccaa gcacgactat 780
gtgtaa 786

<210> SEQ ID NO 8
<211> LENGTH: 261
<212> TYPE: PRT
<213> ORGANISM: Homo sapiens

<400> SEQUENCE: 8

Met Ser Thr Thr Thr Cys Gln Val Val Ala Phe Leu Leu Ser Ile Leu
1 5 10 15

Gly Leu Ala Gly Cys Ile Ala Ala Thr Gly Met Asp Met Trp Ser Thr
20 25 30

Gln Asp Leu Tyr Asp Asn Pro Val Thr Ser Val Phe Gln Tyr Glu Gly
35 40 45

Leu Trp Arg Ser Cys Val Arg Gln Ser Ser Gly Phe Thr Glu Cys Arg
50 55 60

Pro Tyr Phe Thr Ile Leu Gly Leu Pro Ala Met Leu Gln Ala Val Arg
65 70 75 80

Ala Leu Met Ile Val Gly Ile Val Leu Gly Ala Ile Gly Leu Leu Val
85 90 95

Ser Ile Phe Ala Leu Lys Cys Ile Arg Ile Gly Ser Met Glu Asp Ser
100 105 110

Ala Lys Ala Asn Met Thr Leu Thr Ser Gly Ile Met Phe Ile Val Ser
115 120 125

Gly Leu Cys Ala Ile Ala Gly Val Ser Val Phe Ala Asn Met Leu Val
130 135 140

Thr Asn Phe Trp Met Ser Thr Ala Asn Met Tyr Thr Gly Met Gly Gly
145 150 155 160

Met Val Gln Thr Val Gln Thr Arg Tyr Thr Phe Gly Ala Ala Leu Phe
165 170 175

Val Gly Trp Val Ala Gly Gly Leu Thr Leu Ile Gly Gly Val Met Met
180 185 190

Cys Ile Ala Cys Arg Gly Leu Ala Pro Glu Glu Thr Asn Tyr Lys Ala
195 200 205

Val Ser Tyr His Ala Ser Gly His Ser Val Ala Tyr Lys Pro Gly Gly
210 215 220

Phe Lys Ala Ser Thr Gly Phe Gly Ser Asn Thr Lys Asn Lys Lys Ile
225 230 235 240

Tyr Asp Gly Gly Ala Arg Thr Glu Asp Glu Val Gln Ser Tyr Pro Ser
245 250 255

Lys His Asp Tyr Val
260

<210> SEQ ID NO 9
<211> LENGTH: 795
<212> TYPE: DNA
<213> ORGANISM: Mus musculus

<400> SEQUENCE: 9
atggccacca ccacgtgcca ggtggtaggg cttctcctgt ccctcctggg tctggccggc 60
tgcatagccg ccactgggat ggacatgtgg agcactcaag acctgtatga caacccagtc 120
accgccgtgt tccagtatga agggctctgg aggagttgcg tgcaacagag ctcggggttc 180
accgagtgcc ggccatactt caccatcctg ggccttccag ccatgctgca agctgtacga 240
gccctgatga tcgtgggcat tgttctgggg gtcatcggta tcctcgtgtc catcttcgcc 300
ctgaagtgca ttcgcattgg tagcatggat gactctgcca aggccaagat gactctgact 360
tctgggatct tgttcatcat ctccggcatc tgtgcaatca ttggtgtgtc tgtgtttgcc 420
aacatgctgg tgaccaactt ctggatgtcc acagctaaca tgtacagcgg catgggcggc 480
atgggtggca tggtgcagac cgttcagacc aggtacacct ttggtgcagc tctgttcgtg 540
ggctgggttg ctggaggcct caccctgatt gggggagtga tgatgtgcat cgcctgccgt 600
ggcctgacac cagatgacag caacttcaaa gctgtgtctt accatgcctc tggccaaaat 660
gttgcctaca ggcctggagg ctttaaggcc agcactggct ttgggtccaa caccagaaac 720
aagaagatct acgatggggg tgcccgcaca gaagacgatg aacagtctca tcctaccaag 780
tatgactatg tgtag 795

<210> SEQ ID NO 10
<211> LENGTH: 795
<212> TYPE: DNA
<213> ORGANISM: Mus musculus

<400> SEQUENCE: 10
atgtcggtga ccgcctgcca gggcttgggg tttgtggtgt cactgatcgg gtttgcgggc 60
atcattgcag ccacttgtat ggaccagtgg agcacccagg atttatacaa caacccggtg 120
accgctgtat tcaactacca agggctatgg cgttcatgcg tccgagagag ctctggcttc 180
accgagtgcc gaggctactt caccctgttg ggttgccag ccatgctgca agctgtacga 240
gccctgatga tcgtgggcat tgttctgggg gtcatcggta tcctcgtgtc catcttcgcc 300
ctgaagtgca ttcgcattgg tagcatggat gactctgcca aggccaagat gactctgact 360
tctgggatct tgttcatcat ctccggcatc tgtgcaatca ttggtgtgtc tgtgtttgcc 420
aacatgctgg tgaccaactt ctggatgtcc acagctaaca tgtacagcgg catgggcggc 480
atgggtggca tggtgcagac cgttcagacc aggtacacct ttggtgcagc tctgttcgtg 540
ggctgggttg ctggaggcct caccctgatt gggggagtga tgatgtgcat cgcctgccgt 600
ggcctgacac cagatgacag caacttcaaa gctgtgtctt accatgcctc tggccaaaat 660
gttgcctaca ggcctggagg ctttaaggcc agcactggct ttgggtccaa caccagaaac 720
aagaagatct acgatggggg tgcccgcaca gaagacgatg aacagtctca tcctaccaag 780
tatgactatg tgtag 795

<210> SEQ ID NO 11
<211> LENGTH: 21
<212> TYPE: DNA
<213> ORGANISM: Artificial
<220> FEATURE:
<223> OTHER INFORMATION: Description of artificial sequence:
Oligonucleotide

<400> SEQUENCE: 11
tggctctgtg tcgacactgt g 21

<210> SEQ ID NO 12
<211> LENGTH: 21
<212> TYPE: DNA
<213> ORGANISM: Artificial
<220> FEATURE:
<223> OTHER INFORMATION: Description of artificial sequence:

Oligonucleotide

<400> SEQUENCE: 12
gtgtacatgt tagctgtgga c 21

<210> SEQ ID NO 13
<211> LENGTH: 55
<212> TYPE: PRT
<213> ORGANISM: Homo sapiens

<400> SEQUENCE: 13

```
Met Asp Met Trp Ser Thr Gln Asp Leu Tyr Asp Asn Pro Val Thr Ser
1               5                   10                  15

Val Phe Gln Tyr Glu Gly Leu Trp Arg Ser Cys Val Arg Gln Ser Ser
            20                  25                  30

Gly Phe Thr Glu Cys Arg Pro Tyr Phe Thr Ile Leu Gly Leu Pro Ala
        35                  40                  45

Met Leu Gln Ala Val Arg Ala
    50                  55
```

<210> SEQ ID NO 14
<211> LENGTH: 153
<212> TYPE: PRT
<213> ORGANISM: Homo sapiens

<400> SEQUENCE: 14

```
Met Asp Met Trp Ser Thr Gln Asp Leu Tyr Asp Asn Pro Val Thr Ser
1               5                   10                  15

Val Phe Gln Tyr Glu Gly Leu Trp Arg Ser Cys Val Arg Gln Ser Ser
            20                  25                  30

Gly Phe Thr Glu Cys Arg Pro Tyr Phe Thr Ile Leu Gly Leu Pro Ala
        35                  40                  45

Met Leu Gln Ala Val Arg Ala Leu Met Ile Val Gly Ile Val Leu Gly
    50                  55                  60

Ala Ile Gly Leu Leu Val Ser Ile Phe Ala Leu Lys Cys Ile Arg Ile
65                  70                  75                  80

Gly Ser Met Glu Asp Ser Ala Lys Ala Asn Met Thr Leu Thr Ser Gly
                85                  90                  95

Ile Met Phe Ile Val Ser Gly Leu Cys Ala Ile Ala Gly Val Ser Val
            100                 105                 110

Phe Ala Asn Met Leu Val Thr Asn Phe Trp Met Ser Thr Ala Asn Met
        115                 120                 125

Tyr Thr Gly Met Gly Gly Met Val Gln Thr Val Gln Thr Arg Tyr Thr
    130                 135                 140

Phe Gly Ala Ala Leu Phe Val Gly Trp
145                 150
```

<210> SEQ ID NO 15
<211> LENGTH: 390
<212> TYPE: DNA
<213> ORGANISM: Homo sapiens

<400> SEQUENCE: 15

```
atggagacag acacactcct gctatgggta ctgctgctct gggttccagg ttccactggt     60

gacgcggccc agccggccag gcgcgcgcgc cgtacgaagc ttggtaccga gctcggatcc    120

actccagtgt ggtggaattc tgcagatggc cgcatggacc agtggagcac ccaagacttg    180

tacaacaacc ccgtaacagc tgttttcaac taccaggggc tgtggcgctc ctgtgtccga    240
```

gagagctctg gcttcaccga gtgccggggc tacttcaccc tgctggggct gccagccatg 300
ctgcaggcag tgcgagcggc catccagcac agtggcggcc gctcgaggag ggcccgaaca 360
aaaactcatc tcagaagagg atctgaatag 390

<210> SEQ ID NO 16
<211> LENGTH: 129
<212> TYPE: PRT
<213> ORGANISM: Homo sapiens

<400> SEQUENCE: 16

Met Glu Thr Asp Thr Leu Leu Leu Trp Val Leu Leu Leu Trp Val Pro
1 5 10 15

Gly Ser Thr Gly Asp Ala Ala Gln Pro Ala Arg Arg Ala Arg Arg Thr
20 25 30

Lys Leu Gly Thr Glu Leu Gly Ser Thr Pro Val Trp Trp Asn Ser Ala
35 40 45

Asp Gly Arg Met Asp Gln Trp Ser Thr Gln Asp Leu Tyr Asn Asn Pro
50 55 60

Val Thr Ala Val Phe Asn Tyr Gln Gly Leu Trp Arg Ser Cys Val Arg
65 70 75 80

Glu Ser Ser Gly Phe Thr Glu Cys Arg Gly Tyr Phe Thr Leu Leu Gly
85 90 95

Leu Pro Ala Met Leu Gln Ala Val Arg Ala Ala Ile Gln His Ser Gly
100 105 110

Gly Arg Ser Arg Arg Ala Arg Thr Lys Thr His Leu Arg Arg Gly Ser
115 120 125

Glu

<210> SEQ ID NO 17
<211> LENGTH: 411
<212> TYPE: DNA
<213> ORGANISM: Homo sapiens

<400> SEQUENCE: 17
atggagacag acacactcct gctatgggta ctgctgctct gggttccagg ttccactggt 60
gacgcggccc agccggccag gcgcgcgcgc cgtacgaagc ttggtaccga gctcggatcc 120
actccagtgt ggtggaattc tgcagatggc cgcgccctga tgatcgtagg catcgtcctg 180
ggtgccattg gcctcctggt atccatcttt gccctgaaat gcatccgcat tggcagcatg 240
gaggactctg ccaaagccaa catgacactg acatccggga tcatgttcat tgtctcaggt 300
ctttgtgcaa ttgctggagt gtctgtgttt gccaacgcgg ccatccagca cagtggcggc 360
cgctcgagga gggcccgaac aaaaactcat ctcagaagag gatctgaata g 411

<210> SEQ ID NO 18
<211> LENGTH: 136
<212> TYPE: PRT
<213> ORGANISM: Homo sapiens

<400> SEQUENCE: 18

Met Glu Thr Asp Thr Leu Leu Leu Trp Val Leu Leu Leu Trp Val Pro
1 5 10 15

Gly Ser Thr Gly Asp Ala Ala Gln Pro Ala Arg Arg Ala Arg Arg Thr
20 25 30

Lys Leu Gly Thr Glu Leu Gly Ser Thr Pro Val Trp Trp Asn Ser Ala
35 40 45

```
Asp Gly Arg Ala Leu Met Ile Val Gly Ile Val Leu Gly Ala Ile Gly
    50                  55                  60

Leu Leu Val Ser Ile Phe Ala Leu Lys Cys Ile Arg Ile Gly Ser Met
65                  70                  75                  80

Glu Asp Ser Ala Lys Ala Asn Met Thr Leu Thr Ser Gly Ile Met Phe
                85                  90                  95

Ile Val Ser Gly Leu Cys Ala Ile Ala Gly Val Ser Val Phe Ala Asn
            100                 105                 110

Ala Ala Ile Gln His Ser Gly Gly Arg Ser Arg Arg Ala Arg Thr Lys
        115                 120                 125

Thr His Leu Arg Arg Gly Ser Glu
    130                 135


<210> SEQ ID NO 19
<211> LENGTH: 531
<212> TYPE: DNA
<213> ORGANISM: Homo sapiens

<400> SEQUENCE: 19

atggagacag acacactcct gctatgggta ctgctgctct gggttccagg ttccactggt      60

gacgcggccc agccggccag gcgcgccatg gaccagtgga gcacccaaga cttgtacaac     120

aaccccgtaa cagctgtttt caactaccag gggctgtggc gctcctgtgt ccgagagagc     180

tctggcttca ccgagtgccg gggctacttc accctgctgg ggctgccagc catgctgcag     240

gcagtgcgag ccctgatgat cgtaggcatc gtcctgggtg ccattggcct cctggtatcc     300

atctttgccc tgaaatgcat ccgcattggc agcatggagg actctgccaa agccaacatg     360

acactgacct ccgggatcat gttcattgtc tcaggtcttt gtgcaattgc tggagtgtct     420

gtgtttgcca acatgctggt gactaacttc tggatgtcca cagctaacat gtacaccggc     480

atgggtggga tggtgcagac tgttcagacc aggtacacat ttggtgcgta g              531


<210> SEQ ID NO 20
<211> LENGTH: 176
<212> TYPE: PRT
<213> ORGANISM: Homo sapiens

<400> SEQUENCE: 20

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Met Asp Gln
            20                  25                  30

Trp Ser Thr Gln Asp Leu Tyr Asn Asn Pro Val Thr Ala Val Phe Asn
        35                  40                  45

Tyr Gln Gly Leu Trp Arg Ser Cys Val Arg Glu Ser Ser Gly Phe Thr
    50                  55                  60

Glu Cys Arg Gly Tyr Phe Thr Leu Leu Gly Leu Pro Ala Met Leu Gln
65                  70                  75                  80

Ala Val Arg Ala Leu Met Ile Val Gly Ile Val Leu Gly Ala Ile Gly
                85                  90                  95

Leu Leu Val Ser Ile Phe Ala Leu Lys Cys Ile Arg Ile Gly Ser Met
            100                 105                 110

Glu Asp Ser Ala Lys Ala Asn Met Thr Leu Thr Ser Gly Ile Met Phe
        115                 120                 125

Ile Val Ser Gly Leu Cys Ala Ile Ala Gly Val Ser Val Phe Ala Asn
    130                 135                 140
```

```
Met Leu Val Thr Asn Phe Trp Met Ser Thr Ala Asn Met Tyr Thr Gly
145                 150                 155                 160

Met Gly Gly Met Val Gln Thr Val Gln Thr Arg Tyr Thr Phe Gly Ala
                165                 170                 175


<210> SEQ ID NO 21
<211> LENGTH: 10
<212> TYPE: PRT
<213> ORGANISM: Homo sapiens

<400> SEQUENCE: 21

Asp Gln Trp Ser Thr Gln Asp Leu Tyr Asn
1               5                   10


<210> SEQ ID NO 22
<211> LENGTH: 11
<212> TYPE: PRT
<213> ORGANISM: Homo sapiens

<400> SEQUENCE: 22

Asn Asn Pro Val Thr Ala Val Phe Asn Tyr Gln
1               5                   10


<210> SEQ ID NO 23
<211> LENGTH: 14
<212> TYPE: PRT
<213> ORGANISM: Homo sapiens

<400> SEQUENCE: 23

Ser Thr Gln Asp Leu Tyr Asn Asn Pro Val Thr Ala Val Phe
1               5                   10


<210> SEQ ID NO 24
<211> LENGTH: 12
<212> TYPE: PRT
<213> ORGANISM: Homo sapiens

<400> SEQUENCE: 24

Asp Met Trp Ser Thr Gln Asp Leu Tyr Asp Asn Pro
1               5                   10


<210> SEQ ID NO 25
<211> LENGTH: 12
<212> TYPE: PRT
<213> ORGANISM: Homo sapiens

<400> SEQUENCE: 25

Cys Arg Pro Tyr Phe Thr Ile Leu Gly Leu Pro Ala
1               5                   10


<210> SEQ ID NO 26
<211> LENGTH: 13
<212> TYPE: PRT
<213> ORGANISM: Homo sapiens

<400> SEQUENCE: 26

Thr Asn Phe Trp Met Ser Thr Ala Asn Met Tyr Thr Gly
1               5                   10


<210> SEQ ID NO 27
<211> LENGTH: 13
<212> TYPE: PRT
<213> ORGANISM: Homo sapiens
```

<400> SEQUENCE: 27

Asp Ser Ala Lys Ala Asn Met Thr Leu Thr Ser Gly Ile
1 5 10

<210> SEQ ID NO 28
<211> LENGTH: 55
<212> TYPE: PRT
<213> ORGANISM: Homo sapiens

<400> SEQUENCE: 28

Met Asp Gln Trp Ser Thr Gln Asp Leu Tyr Asn Asn Pro Val Thr Ala
1 5 10 15

Val Phe Asn Tyr Gln Gly Leu Trp Arg Ser Cys Val Arg Glu Ser Ser
20 25 30

Gly Phe Thr Glu Cys Arg Gly Tyr Phe Thr Leu Leu Gly Leu Pro Ala
35 40 45

Met Leu Gln Ala Val Arg Ala
50 55

<210> SEQ ID NO 29
<211> LENGTH: 24
<212> TYPE: PRT
<213> ORGANISM: Homo sapiens

<400> SEQUENCE: 29

Phe Ala Leu Lys Cys Ile Arg Ile Gly Ser Met Glu Asp Ser Ala Lys
1 5 10 15

Ala Asn Met Thr Leu Thr Ser Gly
20

<210> SEQ ID NO 30
<211> LENGTH: 40
<212> TYPE: PRT
<213> ORGANISM: Homo sapiens

<400> SEQUENCE: 30

Ala Asn Met Leu Val Thr Asn Phe Trp Met Ser Thr Ala Asn Met Tyr
1 5 10 15

Thr Gly Met Gly Gly Met Val Gln Thr Val Gln Thr Arg Tyr Thr Phe
20 25 30

Gly Ala Ala Leu Phe Val Gly Trp
35 40

<210> SEQ ID NO 31
<211> LENGTH: 153
<212> TYPE: PRT
<213> ORGANISM: Homo sapiens

<400> SEQUENCE: 31

Met Asp Gln Trp Ser Thr Gln Asp Leu Tyr Asn Asn Pro Val Thr Ala
1 5 10 15

Val Phe Asn Tyr Gln Gly Leu Trp Arg Ser Cys Val Arg Glu Ser Ser
20 25 30

Gly Phe Thr Glu Cys Arg Gly Tyr Phe Thr Leu Leu Gly Leu Pro Ala
35 40 45

Met Leu Gln Ala Val Arg Ala Leu Met Ile Val Gly Ile Val Leu Gly
50 55 60

Ala Ile Gly Leu Leu Val Ser Ile Phe Ala Leu Lys Cys Ile Arg Ile
65 70 75 80

-continued

```
Gly Ser Met Glu Asp Ser Ala Lys Ala Asn Met Thr Leu Thr Ser Gly
                85                  90                  95

Ile Met Phe Ile Val Ser Gly Leu Cys Ala Ile Ala Gly Val Ser Val
            100                 105                 110

Phe Ala Asn Met Leu Val Thr Asn Phe Trp Met Ser Thr Ala Asn Met
        115                 120                 125

Tyr Thr Gly Met Gly Gly Met Val Gln Thr Val Gln Thr Arg Tyr Thr
    130                 135                 140

Phe Gly Ala Ala Leu Phe Val Gly Trp
145                 150


<210> SEQ ID NO 32
<211> LENGTH: 3359
<212> TYPE: DNA
<213> ORGANISM: Homo sapiens

<400> SEQUENCE: 32

cacaccttcg gcagcaggag ggcggcagct tctcgcaggc ggcagggcgg gcggccagga     60

tcatgtccac caccacatgc caagtggtgg cgttcctcct gtccatcctg ggctggccg     120

gctgcatcgc ggccaccggg atggacatgt ggagcaccca ggacctgtac gacaaccccg    180

tcacctccgt gttccagtac gaagggctct ggaggagctg cgtgaggcag agttcaggct    240

tcaccgaatg caggccctat ttcaccatcc tgggacttcc agccatgctg caggcagtgc    300

gagccctgat gatcgtaggc atcgtcctgg gtgccattgg cctcctggta tccatctttg    360

ccctgaaatg catccgcatt ggcagcatgg aggactctgc caaagccaac atgacactga    420

cctccgggat catgttcatt gtctcaggtc tttgtgcaat tgctggagtg tctgtgtttg    480

ccaacatgct ggtgactaac ttctggatgt ccacagctaa catgtacacc ggcatgggtg    540

ggatggtgca gactgttcag accaggtaca catttggtgc ggctctgttc gtgggctggg    600

tcgctggagg cctcacacta attgggggtg tgatgatgtg catcgcctgc cggggcctgg    660

caccagaaga aaccaactac aaagccgttt cttatcatgc ctcaggccac agtgttgcct    720

acaagcctgg aggcttcaag gccagcactg gctttgggtc caacaccaaa aacaagaaga    780

tatacgatgg aggtgcccgc acagaggacg aggtacaatc ttatccttcc aagcacgact    840

atgtgtaatg ctctaagacc tctcagcacg ggcggaagaa actcccggag agctcaccca    900

aaaaacaagg agatcccatc tagatttctt cttgcttttg actcacagct ggaagttaga    960

aaagcctcga tttcatcttt ggagaggcca aatggtctta gcctcagtct ctgtctctaa   1020

atattccacc ataaaacagc tgagttattt atgaattaga ggctatagct cacattttca   1080

atcctctatt tcttttttta aatataactt tctactctga tgagagaatg tggttttaat   1140

ctctctctca cattttgatg atttagacag actccccctc ttcctcctag tcaataaacc   1200

cattgatgat ctatttccca gcttatcccc aagaaaactt ttgaaaggaa agagtagacc   1260

caaagatgtt attttctgct gtttgaattt tgtctcccca cccccaactt ggctagtaat   1320

aaacacttac tgaagaagaa gcaataagag aaagatattt gtaatctctc cagcccatga   1380

tctcggtttt cttacactgt gatcttaaaa gttaccaaac caaagtcatt ttcagtttga   1440

ggcaaccaaa cctttctact gctgttgaca tcttcttatt acagcaacac cattctagga   1500

gtttcctgag ctctccactg gagtcctctt tctgtcgcgg gtcagaaatt gtccctagat   1560

gaatgagaaa attatttttt ttaatttaag tcctaaatat agttaaaata aataatgttt   1620

tagtaaaatg atacactatc tctgtgaaat agcctcaccc ctacatgtgg atagaaggaa   1680
```

-continued

```
atgaaaaaat aattgctttg acattgtcta tatggtactt tgtaaagtca tgcttaagta   1740

caaattccat gaaaagctca ctgatcctaa ttctttccct ttgaggtctc tatggctctg   1800

attgtacatg atagtaagtg taagccatgt aaaaagtaaa taatgtctgg gcacagtggc   1860

tcacgcctgt aatcctagca ctttgggagg ctgaggagga aggatcactt gagcccagaa   1920

gttcgagact agcctgggca acatggagaa gccctgtctc tacaaaatac agagagaaaa   1980

aatcagccag tcatggtggc ctacacctgt agtcccagca ttccgggagg ctgaggtggg   2040

aggatcactt gagcccaggg aggttggggc tgcagtgagc catgatcaca ccactgcact   2100

ccagccaggt gacatagcga gatcctgtct aaaaaaataa aaaataaata atggaacaca   2160

gcaagtccta ggaagtaggt taaaactaat tctttaaaaa aaaaaaaaag ttgagcctga   2220

attaaatgta atgtttccaa gtgacaggta tccacatttg catggttaca agccactgcc   2280

agttagcagt agcactttcc tggcactgtg gtcggttttg ttttgttttg ctttgtttag   2340

agacggggtc tcactttcca ggctggcctc aaactcctgc actcaagcaa ttcttctacc   2400

ctggcctccc aagtagctgg aattacaggt gtgcgccatc acaactagct ggtggtcagt   2460

tttgttactc tgagagctgt tcacttctct gaattcacct agagtggttg gaccatcaga   2520

tgtttgggca aaactgaaag ctctttgcaa ccacacacct tccctgagct tacatcactg   2580

cccttttgag cagaaagtct aaattccttc caagacagta gaattccatc ccagtaccaa   2640

agccagatag gccccctagg aaactgaggt aagagcagtc tctaaaaact acccacagca   2700

gcattggtgc aggggaactt ggccattagg ttattatttg agaggaaagt cctcacatca   2760

atagtacata tgaaagtgac ctccaagggg attggtgaat actcataagg atcttcaggc   2820

tgaacagact atgtctgggg aaagaacgga ttatgcccca ttaaataaca agttgtgttc   2880

aagagtcaga gcagtgagct cagaggccct tctcactgag acagcaacat ttaaaccaaa   2940

ccagaggaag tatttgtgga actcactgcc tcagtttggg taaaggatga gcagacaagt   3000

caactaaaga aaaaagaaaa gcaaggagga gggttgagca atctagagca tggagtttgt   3060

taagtgctct ctggatttga gttgaagagc atccatttga gttgaaggcc acagggcaca   3120

atgagctctc ccttctacca ccagaaagtc cctggtcagg tctcaggtag tgcggtgtgg   3180

ctcagctggg tttttaatta gcgcattctc tatccaacat ttaattgttt gaaagcctcc   3240

atatagttag attgtgcttt gtaattttgt tgttgttgct ctatcttatt gtatatgcat   3300

tgagtattaa cctgaatgtt ttgttactta aatattaaaa acactgttat cctacagtt    3359
```

<210> SEQ ID NO 33
<211> LENGTH: 849
<212> TYPE: DNA
<213> ORGANISM: Mus musculus

<400> SEQUENCE: 33

```
gagaacctgc ctgtctcttg tcctctccat ttgtgtggac tctgtgctcc atcatgtcgg     60

tgaccgcctg ccagggcttg gggtttgtgg tgtcactgat cgggtttgcg ggcatcattg    120

cagccacttg tatggaccag tggagcaccc aggatttata caacaacccg gtgaccgctg    180

tattcaacta ccaagggcta tggcgttcat gcgtccgaga gagctctggc ttcaccgagt    240

gccgaggcta cttcaccctg ttggggttgc cagccatgct gcaagctgta cgagccctga    300

tgatcgtggg cattgttctg ggggtcatcg gtatcctcgt gtccatcttc gccctgaagt    360

gcattcgcat tggtagcatg gatgactctg ccaaggccaa gatgactctg acttctggga    420

tcttgttcat catctccggc atctgtgcaa tcattggtgt gtctgtgttt gccaacatgc    480
```

```
tggtgaccaa cttctggatg tccacagcta acatgtacag cggcatgggc ggcatgggtg    540

gcatggtgca gaccgttcag accaggtaca ccttcggtgc agctctgttc gtgggctggg    600

ttgctggagg cctcaccctg attgggggag tgatgatgtg catcgcctgc cgtggcctga    660

caccagatga cagcaacttc aaagctgtgt cttaccatgc ctctggccaa aatgttgcct    720

acaggcctgg aggctttaag gccagcactg gctttgggtc caacaccaga aacaagaaga    780

tctacgatgg gggtgcccgc acagaagacg atgaacagtc tcatcctacc aagtatgact    840

atgtgtagt                                                            849
```

<210> SEQ ID NO 34
<211> LENGTH: 3350
<212> TYPE: DNA
<213> ORGANISM: Homo sapiens

<400> SEQUENCE: 34

```
agaattgcgc tgtccacttg tcgtgtggct ctgtgtcgac actgtgcgcc accatggccg     60

tgactgcctg tcagggcttg gggttcgtgg tttcactgat tgggattgcg ggcatcattg    120

ctgccacctg catggaccag tggagcaccc aagacttgta caacaacccc gtaacagctg    180

ttttcaacta ccaggggctg tggcgctcct gtgtccgaga gagctctggc ttcaccgagt    240

gccggggcta cttcaccctg ctggggctgc cagccatgct gcaggcagtg cgagccctga    300

tgatcgtagg catcgtcctg ggtgccattg gcctcctggt atccatcttt gccctgaaat    360

gcatccgcat tggcagcatg gaggactctg ccaaagccaa catgacactg acctccggga    420

tcatgttcat tgtctcaggt ctttgtgcaa ttgctggagt gtctgtgttt gccaacatgc    480

tggtgactaa cttctggatg tccacagcta acatgtacac cggcatgggt gggatggtgc    540

agactgttca gaccaggtac acatttggtg cggctctgtt cgtgggctgg gtcgctggag    600

gcctcacact aattgggggt gtgatgatgt gcatcgcctg ccggggcctg gcaccagaag    660

aaaccaacta caaagccgtt tcttatcatg cctcaggcca cagtgttgcc tacaagcctg    720

gaggcttcaa ggccagcact ggctttgggt ccaacaccaa aaacaagaag atatacgatg    780

gaggtgcccg cacagaggac gaggtacaat cttatccttc caagcacgac tatgtgtaat    840

gctctaagac ctctcagcac gggcggaaga aactcccgga gagctcaccc aaaaaacaag    900

gagatcccat ctagatttct tcttgctttt gactcacagc tggaagttag aaaagcctcg    960

atttcatctt tggagaggcc aaatggtctt agcctcagtc tctgtctcta aatattccac   1020

cataaaacag ctgagttatt tatgaattag aggctatagc tcacattttc aatcctctat   1080

ttcttttttt aaatataact ttctactctg atgagagaat gtggttttaa tctctctctc   1140

acattttgat gatttagaca gactcccccct cttcctccta gtcaataaac ccattgatga   1200

tctatttccc agcttatccc caagaaaact tttgaaagga aagagtagac ccaaagatgt   1260

tattttctgc tgtttgaatt ttgtctcccc acccccaact tggctagtaa taaacactta   1320

ctgaagaaga agcaataaga gaaagatatt tgtaatctct ccagcccatg atctcggttt   1380

tcttacactg tgatcttaaa agttaccaaa ccaaagtcat tttcagtttg aggcaaccaa   1440

acctttctac tgctgttgac atcttcttat tacagcaaca ccattctagg agtttcctga   1500

gctctccact ggagtcctct ttctgtcgcg ggtcagaaat tgtccctaga tgaatgagaa   1560

aattattttt tttaatttaa gtcctaaata tagttaaaat aaataatgtt ttagtaaaat   1620

gatacactat ctctgtgaaa tagcctcacc cctacatgtg gatagaagga aatgaaaaaa   1680
```

-continued

```
taattgcttt gacattgtct atatggtact ttgtaaagtc atgcttaagt acaaattcca   1740

tgaaaagctc actgatccta attctttccc tttgaggtct ctatggctct gattgtacat   1800

gatagtaagt gtaagccatg taaaaagtaa ataatgtctg ggcacagtgg ctcacgcctg   1860

taatcctagc actttgggag gctgaggagg aaggatcact tgagcccaga agttcgagac   1920

tagcctgggc aacatggaga agccctgtct ctacaaaata cagagagaaa aaatcagcca   1980

gtcatggtgg cctacacctg tagtcccagc attccgggag gctgaggtgg gaggatcact   2040

tgagcccagg gaggttgggg ctgcagtgag ccatgatcac accactgcac tccagccagg   2100

tgacatagcg agatcctgtc taaaaaaata aaaaataaat aatggaacac agcaagtcct   2160

aggaagtagg ttaaaactaa ttctttaaaa aaaaaaaaaa gttgagcctg aattaaatgt   2220

aatgtttcca agtgacaggt atccacattt gcatggttac aagccactgc cagttagcag   2280

tagcactttc ctggcactgt ggtcggtttt gttttgtttt gctttgttta gagacggggt   2340

ctcactttcc aggctggcct caaactcctg cactcaagca attcttctac cctggcctcc   2400

caagtagctg gaattacagg tgtgcgccat cacaactagc tggtggtcag ttttgttact   2460

ctgagagctg ttcacttctc tgaattcacc tagagtggtt ggaccatcag atgtttgggc   2520

aaaactgaaa gctctttgca accacacacc ttccctgagc ttacatcact gccctttga   2580

gcagaaagtc taaattcctt ccaagacagt agaattccat cccagtacca aagccagata   2640

ggccccctag gaaactgagg taagagcagt ctctaaaaac tacccacagc agcattggtg   2700

caggggaact tggccattag gttattattt gagaggaaag tcctcacatc aatagtacat   2760

atgaaagtga cctccaaggg gattggtgaa tactcataag gatcttcagg ctgaacagac   2820

tatgtctggg gaaagaacgg attatgcccc attaaataac aagttgtgtt caagagtcag   2880

agcagtgagc tcagaggccc ttctcactga gacagcaaca tttaaaccaa accagaggaa   2940

gtatttgtgg aactcactgc ctcagtttgg gtaaaggatg agcagacaag tcaactaaag   3000

aaaaaagaaa agcaaggagg agggttgagc aatctagagc atggagtttg ttaagtgctc   3060

tctggatttg agttgaagag catccatttg agttgaaggc cacagggcac aatgagctct   3120

cccttctacc accagaaagt ccctggtcag gtctcaggta gtgcggtgtg gctcagctgg   3180

gtttttaatt agcgcattct ctatccaaca tttaattgtt tgaaagcctc catatagtta   3240

gattgtgctt tgtaattttg ttgttgttgc tctatcttat tgtatatgca ttgagtatta   3300

acctgaatgt tttgttactt aaatattaaa aacactgtta tcctacagtt              3350
```

<210> SEQ ID NO 35
<211> LENGTH: 264
<212> TYPE: PRT
<213> ORGANISM: Mus musculus

<400> SEQUENCE: 35

```
Met Ser Val Thr Ala Cys Gln Gly Leu Gly Phe Val Val Ser Leu Ile
1               5                   10                  15

Gly Phe Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80
```

-continued

```
Ala Leu Met Ile Val Gly Ile Val Leu Gly Val Ile Gly Ile Leu Val
                85                  90                  95

Ser Ile Phe Ala Leu Lys Cys Ile Arg Ile Gly Ser Met Asp Asp Ser
            100                 105                 110

Ala Lys Ala Lys Met Thr Leu Thr Ser Gly Ile Leu Phe Ile Ile Ser
        115                 120                 125

Gly Ile Cys Ala Ile Ile Gly Val Ser Val Phe Ala Asn Met Leu Val
    130                 135                 140

Thr Asn Phe Trp Met Ser Thr Ala Asn Met Tyr Ser Gly Met Gly Gly
145                 150                 155                 160

Met Gly Gly Met Val Gln Thr Val Gln Thr Arg Tyr Thr Phe Gly Ala
                165                 170                 175

Ala Leu Phe Val Gly Trp Val Ala Gly Gly Leu Thr Leu Ile Gly Gly
            180                 185                 190

Val Met Met Cys Ile Ala Cys Arg Gly Leu Thr Pro Asp Asp Ser Asn
        195                 200                 205

Phe Lys Ala Val Ser Tyr His Ala Ser Gly Gln Asn Val Ala Tyr Arg
    210                 215                 220

Pro Gly Gly Phe Lys Ala Ser Thr Gly Phe Gly Ser Asn Thr Arg Asn
225                 230                 235                 240

Lys Lys Ile Tyr Asp Gly Gly Ala Arg Thr Glu Asp Asp Glu Gln Ser
                245                 250                 255

His Pro Thr Lys Tyr Asp Tyr Val
            260
```

<210> SEQ ID NO 36
<211> LENGTH: 2786
<212> TYPE: DNA
<213> ORGANISM: Mus musculus

<400> SEQUENCE: 36

```
ggccgggaac cttcccagca agagggtggt ggttgctcct ggaagcctgc gcccagcagc     60

tgaagccatg gccaccacca cgtgccaggt ggtagggctt ctcctgtccc tcctgggtct    120

ggccggctgc atagccgcca ctgggatgga catgtggagc actcaagacc tgtatgacaa    180

cccagtcacc gccgtgttcc agtatgaagg gctctggagg agttgcgtgc aacagagctc    240

ggggttcacc gagtgccggc catacttcac catcctgggc cttccagcca tgctgcaagc    300

tgtacgagcc ctgatgatcg tgggcattgt tctgggggtc atcggtatcc tcgtgtccat    360

cttcgccctg aagtgcattc gcattggtag catggatgac tctgccaagg ccaagatgac    420

tctgacttct gggatcttgt tcatcatctc cggcatctgt gcaatcattg gtgtgtctgt    480

gtttgccaac atgctggtga ccaacttctg gatgtccaca gctaacatgt acagcggcat    540

gggcggcatg ggtggcatgg tgcagaccgt tcagaccagg tacaccttcg gtgcagctct    600

gttcgtgggc tgggttgctg gaggcctcac cctgattggg ggagtgatga tgtgcatcgc    660

ctgccgtggc ctgacaccag atgacagcaa cttcaaagct gtgtcttacc atgcctctgg    720

ccaaaatgtt gcctacaggc ctggaggctt taaggccagc actggctttg ggtccaacac    780

cagaaacaag aagatctacg atgggggtgc ccgcacagaa gacgatgaac agtctcatcc    840

taccaagtat gactatgtgt agtgctctaa gacccgccaa cctgtgtgca ggaggaaccc    900

ttccccaaga agagctcacc ccaaagcaac gggagtctac cttgttccct tgttgatttc    960

aactgacatc tgaaagttgg taaagcctga ttttcatcca tagggaggct agacagtctt   1020

ggccacatgt gtctgcctct aaatatccca tcacaaaaca gctgagttat cgtttatgag   1080
```

ttagaggcca taacactcac tttagcccaa ccctctgctt tttaccgtag actttctttt 1140
catctggtga tggaatggaa tttgactcac agactaatac tttaatggtt tagagaaact 1200
ttccttcctc gtacttaata agcctgctga tggtcgattt tccagcttga ccaccaaggg 1260
aaattttaaa aggaaaaaaa aatacattaa aaggcattat ttcctactca attgtgcctt 1320
acccaccccc aacttgactg ataataataa tgaacaccac ttaaagaaag aatgccagag 1380
gaaagatagt tgtgtttccc cccagccagt catctgagtc cccctatgtg gtgatctaga 1440
acattactcg ccacagtgat tttcaaagaa ggcaagcgag cctgttcgct ctgctcagca 1500
tctgctgatt ccagcaaggc ccttccagag ctttccacta gaagtcctcc ttctctcgga 1560
agtcagaaat tccccctaga agagtaagaa atagattctt ttgggtaacc tgagtcctag 1620
gtatagttat aataaatagt atattagcaa aacggtttgg tatctcagtg aattagtttc 1680
agccttacat atagaaaaag ctggggaaaa aaaaagcatc ccttgacatt gtctatagcg 1740
taagatccta tataaatcca agcttcaaca aaagctcact gagtctaata gttttctttt 1800
gaggtctcca cggccttagt actcatagat gcagcccctg tttaaaagta aaaaaattaa 1860
agtagcttaa aacgggttct tttttttttt tttttttca aaaaatccaa tagagacctg 1920
tgtgtctggc atagctacag ttactgccaa tcgacagggc cacttctttg gtcctgtagg 1980
cagttttgca gttctgacag ctgcgccggg catcaatatg cagaccacac ccttctctgt 2040
gcttgtagga cgacccgttc aaggagaaag catgaactcc atctccatgt gagcctgaat 2100
gctcccagga aatggagata gggtgctctc caaaacccac ctgaacctga aacagctgta 2160
gcgctatgct gtaagagcct ggccatcaag ttcctatgga gaaaaagggc agtccttgca 2220
ttaatagtgc atatataagt ggcctctggg gggcagggat gaatattcag tggtggctcc 2280
gagtatgtac agaccgtcta aggagctgtg ttgaccaaga gccaggttaa tacgcagagt 2340
ttttcccact gggactacag tgattttaga ctatactgaa gaaggccctc tggaaaatca 2400
ttatctgaaa tggcataaag aatgaacaga ccaaacaatt taaggggagg gggcaggtgg 2460
aaggaggggg aaggaggtag aaataagaat ctagggcatg aagattgtta aggttcttgg 2520
ggtccaaatg gaaggtcacc cctttgaggc catggacaca atgcacccca cccctacccc 2580
cacctgccca cccaccagaa agtccctggt cggactggag gcagtgagaa tcagctgttt 2640
tcagttagtg ggtctcggtg tagcacctgg ctgtttcaaa gcttcccctt gctttgccgt 2700
tttttccgcc attgctgtct tgttttctgt gttattaacc tccatgtttt gtacgttaaa 2760
tattaaaaca ctgttaacat ccattc 2786

<210> SEQ ID NO 37
<211> LENGTH: 264
<212> TYPE: PRT
<213> ORGANISM: Mus musculus

<400> SEQUENCE: 37

Met Ala Thr Thr Thr Cys Gln Val Val Gly Leu Leu Leu Ser Leu Leu
1 5 10 15

Gly Leu Ala Gly Cys Ile Ala Ala Thr Gly Met Asp Met Trp Ser Thr
20 25 30

Gln Asp Leu Tyr Asp Asn Pro Val Thr Ala Val Phe Gln Tyr Glu Gly
35 40 45

Leu Trp Arg Ser Cys Val Gln Gln Ser Ser Gly Phe Thr Glu Cys Arg
50 55 60

-continued

```
Pro Tyr Phe Thr Ile Leu Gly Leu Pro Ala Met Leu Gln Ala Val Arg
65                  70                  75                  80

Ala Leu Met Ile Val Gly Ile Val Leu Gly Val Ile Gly Ile Leu Val
                85                  90                  95

Ser Ile Phe Ala Leu Lys Cys Ile Arg Ile Gly Ser Met Asp Asp Ser
            100                 105                 110

Ala Lys Ala Lys Met Thr Leu Thr Ser Gly Ile Leu Phe Ile Ile Ser
        115                 120                 125

Gly Ile Cys Ala Ile Ile Gly Val Ser Val Phe Ala Asn Met Leu Val
    130                 135                 140

Thr Asn Phe Trp Met Ser Thr Ala Asn Met Tyr Ser Gly Met Gly Gly
145                 150                 155                 160

Met Gly Gly Met Val Gln Thr Val Gln Thr Arg Tyr Thr Phe Gly Ala
                165                 170                 175

Ala Leu Phe Val Gly Trp Val Ala Gly Gly Leu Thr Leu Ile Gly Gly
            180                 185                 190

Val Met Met Cys Ile Ala Cys Arg Gly Leu Thr Pro Asp Asp Ser Asn
        195                 200                 205

Phe Lys Ala Val Ser Tyr His Ala Ser Gly Gln Asn Val Ala Tyr Arg
    210                 215                 220

Pro Gly Gly Phe Lys Ala Ser Thr Gly Phe Gly Ser Asn Thr Arg Asn
225                 230                 235                 240

Lys Lys Ile Tyr Asp Gly Gly Ala Arg Thr Glu Asp Asp Glu Gln Ser
                245                 250                 255

His Pro Thr Lys Tyr Asp Tyr Val
            260


<210> SEQ ID NO 38
<211> LENGTH: 40
<212> TYPE: DNA
<213> ORGANISM: Artificial
<220> FEATURE:
<223> OTHER INFORMATION: Description of artificial sequence:
      Oligonucleotide

<400> SEQUENCE: 38

gagaggatcc cgtacggtgg ctgcaccatc tgtcttcatc                           40


<210> SEQ ID NO 39
<211> LENGTH: 37
<212> TYPE: DNA
<213> ORGANISM: Artificial
<220> FEATURE:
<223> OTHER INFORMATION: Description of artificial sequence:
      Oligonucleotide

<400> SEQUENCE: 39

gagagcggcc gcctaacact ctcccctgtt gaagctc                              37


<210> SEQ ID NO 40
<211> LENGTH: 324
<212> TYPE: DNA
<213> ORGANISM: Artificial
<220> FEATURE:
<223> OTHER INFORMATION: Description of artificial sequence: PCR product

<400> SEQUENCE: 40

cgtacggtgg ctgcaccatc tgtcttcatc ttcccgccat ctgatgagca gttgaaatct     60

ggaactgcct ctgttgtgtg cctgctgaat aacttctatc ccagagaggc caaagtacag    120
```

-continued tggaaggtgg ataacgccct ccaatcgggt aactcccagg agagtgtcac agagcaggac 180
agcaaggaca gcacctacag cctcagcagc accctgacgc tgagcaaagc agactacgag 240
aaacacaaag tctacgcctg cgaagtcacc catcagggcc tgagctcgcc cgtcacaaag 300
agcttcaaca ggggagagtg ttag 324

<210> SEQ ID NO 41
<211> LENGTH: 107
<212> TYPE: PRT
<213> ORGANISM: Artificial
<220> FEATURE:
<223> OTHER INFORMATION: Description of artificial sequence: Translation of PCR product

<400> SEQUENCE: 41

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 42
<211> LENGTH: 34
<212> TYPE: DNA
<213> ORGANISM: Artificial
<220> FEATURE:
<223> OTHER INFORMATION: Description of artificial sequence: Oligonucleotide

<400> SEQUENCE: 42
gagaaagctt tccaccaagg gcccatcggt cttc 34

<210> SEQ ID NO 43
<211> LENGTH: 36
<212> TYPE: DNA
<213> ORGANISM: Artificial
<220> FEATURE:
<223> OTHER INFORMATION: Description of artificial sequence: Oligonucleotide

<400> SEQUENCE: 43
gagagcggcc gctcatttac ccggagacag ggagag 36

<210> SEQ ID NO 44
<211> LENGTH: 21
<212> TYPE: DNA
<213> ORGANISM: Artificial
<220> FEATURE:
<223> OTHER INFORMATION: Description of artificial sequence: Oligonucleotide

<400> SEQUENCE: 44
taccagttga acttgacctc a 21

<210> SEQ ID NO 45
<211> LENGTH: 981
<212> TYPE: DNA
<213> ORGANISM: Artificial
<220> FEATURE:
<223> OTHER INFORMATION: Description of artificial sequence: PCR product

<400> SEQUENCE: 45
ggcccatcgg tcttcccct ggcaccctcc tccaagagca cctctggggg cacagcggcc 60
ctgggctgcc tggtcaagga ctacttcccc gaaccggtga cggtgtcgtg gaactcaggc 120
gccctgacca gcggcgtgca caccttcccg gctgtcctac agtcctcagg actctactcc 180
ctcagcagcg tggtgaccgt gccctccagc agcttgggca cccagaccta catctgcaac 240
gtgaatcaca agcccagcaa caccaaggtg gacaagaaag ttgagcccaa atcttgtgac 300
aaaactcaca catgcccacc gtgcccagca cctgaactcc tggggggacc gtcagtcttc 360
ctcttccccc caaaacccaa ggacaccctc atgatctccc ggacccctga ggtcacatgc 420
gtggtggtgg acgtgagcca cgaagaccct gaggtcaagt tcaactggta cgtggacggc 480
gtggaggtgc ataatgccaa gacaaagccg cgggaggagc agtacaacag cacgtaccgt 540
gtggtcagcg tcctcaccgt cctgcaccag gactggctga atggcaagga gtacaagtgc 600
aaggtctcca acaaagccct cccagccccc atcgagaaaa ccatctccaa agccaaaggg 660
cagccccgag aaccacaggt gtacaccctg cccccatccc gggatgagct gaccaagaac 720
caggtcagcc tgacctgcct ggtcaaaggc ttctatccca gcgacatcgc cgtggagtgg 780
gagagcaatg ggcagccgga gaacaactac aagaccacgc ctcccgtgct ggactccgac 840
ggctccttct tcctctatag caagctcacc gtggacaaga gcaggtggca gcaggggaac 900
gtcttctcat gctccgtgat gcatgaggct ctgcacaacc actacacgca gaagagcctc 960
tccctgtctc cgggtaaatg a 981

<210> SEQ ID NO 46
<211> LENGTH: 326
<212> TYPE: PRT
<213> ORGANISM: Artificial
<220> FEATURE:
<223> OTHER INFORMATION: Description of artificial sequence: Translation of PCR product

<400> SEQUENCE: 46

Gly Pro Ser Val Phe Pro Leu Ala Pro Ser Ser Lys Ser Thr Ser Gly
1 5 10 15

Gly Thr Ala Ala Leu Gly Cys Leu Val Lys Asp Tyr Phe Pro Glu Pro
20 25 30

Val Thr Val Ser Trp Asn Ser Gly Ala Leu Thr Ser Gly Val His Thr
35 40 45

Phe Pro Ala Val Leu Gln Ser Ser Gly Leu Tyr Ser Leu Ser Ser Val
50 55 60

Val Thr Val Pro Ser Ser Ser Leu Gly Thr Gln Thr Tyr Ile Cys Asn
65 70 75 80

Val Asn His Lys Pro Ser Asn Thr Lys Val Asp Lys Lys Val Glu Pro
85 90 95

Lys Ser Cys Asp Lys Thr His Thr Cys Pro Pro Cys Pro Ala Pro Glu
100 105 110

Leu Leu Gly Gly Pro Ser Val Phe Leu Phe Pro Pro Lys Pro Lys Asp
115 120 125

-continued

```
Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 47
<211> LENGTH: 32
<212> TYPE: DNA
<213> ORGANISM: Artificial
<220> FEATURE:
<223> OTHER INFORMATION: Description of artificial sequence:
      Oligonucleotide
<220> FEATURE:
<221> NAME/KEY: misc_feature
<222> LOCATION: (31)..(32)
<223> OTHER INFORMATION: n is a, c, g, or t

<400> SEQUENCE: 47

tttttttttt tttttttttt tttttttttt nn                                   32


<210> SEQ ID NO 48
<211> LENGTH: 30
<212> TYPE: DNA
<213> ORGANISM: Artificial
<220> FEATURE:
<223> OTHER INFORMATION: Description of artificial sequence:
      Oligonucleotide

<400> SEQUENCE: 48

aagcagtggt atcaacgcag agtacgcggg                                      30


<210> SEQ ID NO 49
<211> LENGTH: 26
<212> TYPE: DNA
<213> ORGANISM: Artificial
<220> FEATURE:
<223> OTHER INFORMATION: Description of artificial sequence:
      Oligonucleotide

<400> SEQUENCE: 49
```

ctgctcactg gatggtggga agatgg 26

<210> SEQ ID NO 50
<211> LENGTH: 25
<212> TYPE: DNA
<213> ORGANISM: Artificial
<220> FEATURE:
<223> OTHER INFORMATION: Description of artificial sequence:
Oligonucleotide

<400> SEQUENCE: 50
gggacagtca ctgagctgct cagag 25

<210> SEQ ID NO 51
<211> LENGTH: 25
<212> TYPE: DNA
<213> ORGANISM: Artificial
<220> FEATURE:
<223> OTHER INFORMATION: Description of artificial sequence:
Oligonucleotide

<400> SEQUENCE: 51
acaggggcca gtggatagac cgatg 25

<210> SEQ ID NO 52
<211> LENGTH: 27
<212> TYPE: DNA
<213> ORGANISM: Artificial
<220> FEATURE:
<223> OTHER INFORMATION: Description of artificial sequence:
Oligonucleotide

<400> SEQUENCE: 52
agccagggac caagggatag acagatg 27

<210> SEQ ID NO 53
<211> LENGTH: 45
<212> TYPE: DNA
<213> ORGANISM: Artificial
<220> FEATURE:
<223> OTHER INFORMATION: Description of artificial sequence:
Oligonucleotide

<400> SEQUENCE: 53
gtaatacgac tcactatagg gcaagcagtg gtatcaacgc agagt 45

<210> SEQ ID NO 54
<211> LENGTH: 22
<212> TYPE: DNA
<213> ORGANISM: Artificial
<220> FEATURE:
<223> OTHER INFORMATION: Description of artificial sequence:
Oligonucleotide

<400> SEQUENCE: 54
gtaatacgac tcactatagg gc 22

<210> SEQ ID NO 55
<211> LENGTH: 351
<212> TYPE: DNA
<213> ORGANISM: Artificial
<220> FEATURE:
<223> OTHER INFORMATION: Description of artificial sequence: PCR product

<400> SEQUENCE: 55
caggttcagc tgcagcagtc tggagctgag ctgatgaagc ctggggcctc agtgaagata 60
tcctgcaagg ctactggcta cacattcagt agctactgga tagagtgggt aaagcagagg 120
cctggacatg gccttgagtg gattggagag attttacctg gaagtggtag tactaactac 180
aatgagaagt tcaagggcaa ggccacattc actgcagata catcctccaa cacagcctac 240
atgcaactca gcagcctgac atctgaggac tctgccgtct attactgtgc aagatatgat 300 taccccctggt ttgcttactg gggccaaggg actctggtca ctgtctctgc a 351

<210> SEQ ID NO 56
<211> LENGTH: 354
<212> TYPE: DNA
<213> ORGANISM: Artificial
<220> FEATURE:
<223> OTHER INFORMATION: Description of artificial sequence: PCR product

<400> SEQUENCE: 56
cagatccagt tggtgcagtc tggacctgag ctgaagaagc ctggagagac agtcaagatc 60
tcctgcaagg cttctgggta taccttcaca aactatggaa tgaactgggt gaagcaggct 120
ccaggaaagg gtttaaagtg gatgggctgg ataaacacca acactggaga gccaacatat 180
gctgaagagt tcaagggacg gtttgccttc tctttggaaa cctctgccag cactgcctat 240
ttgcagatca acaacctcaa aaatgaggac acggctacat atttctgtgc aagactgggt 300
tttggtaatg ctatggacta ctggggtcaa ggaacctcag tcaccgtctc ctca 354

<210> SEQ ID NO 57
<211> LENGTH: 348
<212> TYPE: DNA
<213> ORGANISM: Artificial
<220> FEATURE:
<223> OTHER INFORMATION: Description of artificial sequence: PCR product

<400> SEQUENCE: 57
caggttcagc tgcagcagtc tggagctgag ctggcgaggc ccggggcttc agtgaagctg 60
tcctgcaagg cttctggcta caccttcact gactactata taaactgggt gaagcagagg 120
actggacagg gccttgagtg gattggagag atttatcctg gaagtggtaa tacttactac 180
aatgagaagt tcaagggcaa ggccacactg actgcagaca aatcctccag cacagcctac 240
atgcagctca gcagcctgac atctgaggac tctgcagtct atttctgtgc aagatcgtat 300
ggtgcctttg actactgggg ccaaggcacc actctcacag tctcctca 348

<210> SEQ ID NO 58
<211> LENGTH: 354
<212> TYPE: DNA
<213> ORGANISM: Artificial
<220> FEATURE:
<223> OTHER INFORMATION: Description of artificial sequence: PCR product

<400> SEQUENCE: 58
caggtccaac tgcagcagcc tggggctgag ctggtgaggc ctggggcttc agtgaagctg 60
tcctgcaagg cttctggcta caccttcacc agctactgga taaactgggt gaagcagagg 120
cctggacaag gccttgagtg gatcggaaat atttatcctt ctgatagtta tactaactac 180
aatcaaaagt tcaaggacaa ggccacattg actgtagaca aatcctccag cacagcctac 240
atgcagctca gcagcccgac atctgaggac tctgcggtct attactgtac aagatcgtgg 300
aggggtaact cctttgacta ctggggccaa ggcaccactc tcacagtctc ctca 354

<210> SEQ ID NO 59

<211> LENGTH: 354
<212> TYPE: DNA
<213> ORGANISM: Artificial
<220> FEATURE:
<223> OTHER INFORMATION: Description of artificial sequence: PCR product

<400> SEQUENCE: 59
caggttcagc tgcagcagtc tggacctgag ctggtgaagc ctggggcttc agtgaagatg 60
tcctgcaagg cttctggata cacattcact gactatgtta taagctgggt gaagcagaga 120
actggacagg gccttgagtg gattggagag atttatcctg gaagtggtag tacttactac 180
aatgagaagt tcaagggcaa ggccacactg actgcagaca aatcctccaa cacagcctac 240
atgcagctca gcagcctgac atctgaggac tctgcggtct atttctgtgc aagaggggta 300
ttactacggg ctatggacta ctggggtcaa ggaacctcag tcaccgtctc ctca 354

<210> SEQ ID NO 60
<211> LENGTH: 360
<212> TYPE: DNA
<213> ORGANISM: Artificial
<220> FEATURE:
<223> OTHER INFORMATION: Description of artificial sequence: PCR product

<400> SEQUENCE: 60
caggttcacc tacaacagtc tggttctgaa ctgaggagtc ctgggtcttc agtaaagctt 60
tcatgcaagg attttgattc agaagtcttc ccttttgctt atatgagttg gattaggcag 120
aagcctgggc atggatttga atggattgga gacatactcc caagtattgg tagaacaatc 180
tatggagaga agtttgagga caaagccaca ctggatgcag acacagtgtc caacacagcc 240
tacttggagc tcaacagtct gacatctgag gactctgcta tctactactg tgcaaggggg 300
gagggctacg gtgcctggtt tgcttactgg ggccaaggga ctctggtcac tgtctctgca 360

<210> SEQ ID NO 61
<211> LENGTH: 339
<212> TYPE: DNA
<213> ORGANISM: Artificial
<220> FEATURE:
<223> OTHER INFORMATION: Description of artificial sequence: PCR product

<400> SEQUENCE: 61
gacattgtga tgacacagtc tccatcctcc ctgactgtga cagcaggaga gaaggtcact 60
atgagctgca agtccagtca gagtctgtta aacagtggaa atcaaaagaa ctacttgacc 120
tggtaccagc agaaaccagg gcagcctcct aaactgttga tctactgggc atccactagg 180
gaatctgggg tccctgatcg cttcacaggc agtggatctg gaacagattt cactctcacc 240
atcagcagtg tgcaggctga agacctggca gtttattact gtcagaatga ttatagttat 300
ccgctcacgt tcggtgctgg gaccaagctg gagctgaaa 339

<210> SEQ ID NO 62
<211> LENGTH: 318
<212> TYPE: DNA
<213> ORGANISM: Artificial
<220> FEATURE:
<223> OTHER INFORMATION: Description of artificial sequence: PCR product

<400> SEQUENCE: 62
caaattgttc tcacccagtc tccagcaatc atgtctgcat ctccagggga gaaggtcacc 60
ataacctgca gtgccagctc aagtgtaagt tacatgcact ggttccagca gaagccaggc 120
acttctccca aactctggat ttatagcaca tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cacccacgtt cggagggggg 300
accaagctgg aaataaaa 318

<210> SEQ ID NO 63
<211> LENGTH: 321
<212> TYPE: DNA
<213> ORGANISM: Artificial
<220> FEATURE:
<223> OTHER INFORMATION: Description of artificial sequence: PCR product

<400> SEQUENCE: 63
gacattgtga tgacccagtc tcaaaaattc atgtccacat cagtaggaga cagggtcagc 60
atcacctgca aggccagtca gaatgttcgt actgctgtag cctggtatca acagaaacca 120
gggcagtctc ctaaagcact gatttacttg gcatccaacc ggcacactgg agtccctgat 180
cgcttcacag gcagtggatc tgggacagat ttcactctca ccattagcaa tgtgcaatct 240
gaagacctgg cagattattt ctgtctgcaa cattggaatt atcctctgac gttcggtgga 300
ggcaccaagc tggaaatcaa a 321

<210> SEQ ID NO 64
<211> LENGTH: 339
<212> TYPE: DNA
<213> ORGANISM: Artificial
<220> FEATURE:
<223> OTHER INFORMATION: Description of artificial sequence: PCR product

<400> SEQUENCE: 64
gacattgtga tgtcacagtc tccatcctcc ctagctgtgt cagttggaga gaaggttact 60
atgagctgca agtccagtca gagcctttta tatagtagca atcaaaagaa ctacttggcc 120
tggtaccagc agaaaccagg gcagtctcct aaactgctga tttactgggc atccactagg 180
gaatctgggg tccctgatcg cttcacaggc agtggatctg ggacagattt cactctcacc 240
atcagcagtg tgaaggctga agacctggca gtttattact gtcagcaata ttatagctat 300
ccgctcacgt tcggtgctgg gaccaagctg gagctgaaa 339

<210> SEQ ID NO 65
<211> LENGTH: 339
<212> TYPE: DNA
<213> ORGANISM: Artificial
<220> FEATURE:
<223> OTHER INFORMATION: Description of artificial sequence: PCR product

<400> SEQUENCE: 65
gacattgtga tgacacagtc tccatcctcc ctgactgtga cagcaggaga gaaggtcact 60
atgagctgca agtccagtca gagtctgtta aacagtggaa atcaaaagaa ctacttgacc 120
tggtaccagc agaaaccagg gcagcctcct aaactgttga tctactgggc atccactagg 180
gaatctgggg tccctgatcg cttcacaggc agtggatctg gaacagattt cactctcacc 240
atcagcagtg tgcaggctga agacctggca gtttattact gtcagaatga ttatagttat 300
ccattcacgt tcggctcggg gacaaagttg gaaataaaa 339

<210> SEQ ID NO 66
<211> LENGTH: 336
<212> TYPE: DNA
<213> ORGANISM: Artificial
<220> FEATURE:

<223> OTHER INFORMATION: Description of artificial sequence: PCR product

<400> SEQUENCE: 66
gacattgtga tgtcacagtc tccatcctcc ctggctgtgt cagcaggaga gaaggtcact 60
atgagctgca aatccagtca gagtctgctc aacagtagaa cccgaaagaa ctacttggct 120
tggtaccagc agaaaccagg gcagtctcct aaactgctga tctactgggc atccactagg 180
gaatctgggg tccctgatcg cttcacaggc agtggatctg ggacagattt cactctcacc 240
atcagcagtg tgcaggctga agacctggca gtttattact gcaagcaatc ttataatctg 300
tacacgttcg gaggggggac caagctggaa ataaaa 336

<210> SEQ ID NO 67
<211> LENGTH: 339
<212> TYPE: DNA
<213> ORGANISM: Artificial
<220> FEATURE:
<223> OTHER INFORMATION: Description of artificial sequence: PCR product

<400> SEQUENCE: 67
gacatcgtga tgtcacagtc tccatcctcc ctagctgtgt cagttggaga gaaggttact 60
atgagctgca agtccagtca gagcctttta tatagtagca atcaaaagaa ctacttggcc 120
tggtaccagc agaaaccagg gcagtctcct aaactgctga tttactgggc atccactagg 180
gaatctgggg tccctgatcg cttcacaggc agtggatctg caacagattt cactctgacc 240
atcagcagtg tgcaggctga agaccttgca gattatcact gtggacaggg ttacagctat 300
ccgtacacgt tcggaggggg gaccaagctg gaaataaaa 339

<210> SEQ ID NO 68
<211> LENGTH: 339
<212> TYPE: DNA
<213> ORGANISM: Artificial
<220> FEATURE:
<223> OTHER INFORMATION: Description of artificial sequence: PCR product

<400> SEQUENCE: 68
gacattgtga tgtcacagtc tccatcctcc ctagctgtgt cagttggaga gaaggttact 60
atgagctgca agtccagtca gagcctttta tatagtagca atcaaaagaa ctacttggcc 120
tggtaccagc agaaaccagg gcagtctcct aaactgctga tttactgggc atccactagg 180
gaatctgggg tccctgatcg cttcacaggc agtggatctg ggacagattt cactctcacc 240
atcagcagtg tgaaggctga agacctggca gtttattact gtcagcaata ttatagctat 300
ccgctcacgt tcggtgctgg gaccaagctg gagctgaaa 339

<210> SEQ ID NO 69
<211> LENGTH: 321
<212> TYPE: DNA
<213> ORGANISM: Artificial
<220> FEATURE:
<223> OTHER INFORMATION: Description of artificial sequence: PCR product

<400> SEQUENCE: 69
aacattgtaa tgacccaatc tcccaaatcc atgtccatgt cagtaggaga gagggtcacc 60
ttgacctgca aggccagtga gaatgtggtt acttatgttt cctggtatca acagaaacca 120
gagcagtctc ctaaactgct gatatacggg gcatccaacc ggtacactgg ggtccccgat 180
cgcttcacag gcagtggatc tgcaacagat ttcactctca ccatcagcag tgtgaaggct 240
gaagacctgg cagtttatta ctgtcagcaa tattatagct atccgctcac gttcggtgct 300
gggaccaagc tggagctgaa a 321

<210> SEQ ID NO 70
<211> LENGTH: 43
<212> TYPE: DNA
<213> ORGANISM: Artificial
<220> FEATURE:
<223> OTHER INFORMATION: Description of artificial sequence:
Oligonucleotide

<400> SEQUENCE: 70
gagaaagctt gccgccacca tggaatggac ctgggtcttt ctc 43

<210> SEQ ID NO 71
<211> LENGTH: 43
<212> TYPE: DNA
<213> ORGANISM: Artificial
<220> FEATURE:
<223> OTHER INFORMATION: Description of artificial sequence:
Oligonucleotide

<400> SEQUENCE: 71
gagagggccc ttggtggagg ctgcagagac agtgaccaga gtc 43

<210> SEQ ID NO 72
<211> LENGTH: 47
<212> TYPE: DNA
<213> ORGANISM: Artificial
<220> FEATURE:
<223> OTHER INFORMATION: Description of artificial sequence:
Oligonucleotide

<400> SEQUENCE: 72
gagaaagctt gccgccacca tggattggct gtggaacttg ctattcc 47

<210> SEQ ID NO 73
<211> LENGTH: 44
<212> TYPE: DNA
<213> ORGANISM: Artificial
<220> FEATURE:
<223> OTHER INFORMATION: Description of artificial sequence:
Oligonucleotide

<400> SEQUENCE: 73
gagagggccc ttggtggagg ctgaggagac ggtgactgag gttc 44

<210> SEQ ID NO 74
<211> LENGTH: 46
<212> TYPE: DNA
<213> ORGANISM: Artificial
<220> FEATURE:
<223> OTHER INFORMATION: Description of artificial sequence:
Oligonucleotide

<400> SEQUENCE: 74
gagaaagctt gccgccacca tggaatggat ctggatcttt ctcttc 46

<210> SEQ ID NO 75
<211> LENGTH: 44
<212> TYPE: DNA
<213> ORGANISM: Artificial
<220> FEATURE:
<223> OTHER INFORMATION: Description of artificial sequence:
Oligonucleotide

<400> SEQUENCE: 75
gagagggccc ttggtggagg ctgaggagac tgtgagagtg gtgc 44

<210> SEQ ID NO 76
<211> LENGTH: 46
<212> TYPE: DNA
<213> ORGANISM: Artificial
<220> FEATURE:
<223> OTHER INFORMATION: Description of artificial sequence:
Oligonucleotide

<400> SEQUENCE: 76
gagaaagctt gccgccacca tgggatggag ctgtatcatc ctcttc 46

<210> SEQ ID NO 77
<211> LENGTH: 43
<212> TYPE: DNA
<213> ORGANISM: Artificial
<220> FEATURE:
<223> OTHER INFORMATION: Description of artificial sequence:
Oligonucleotide

<400> SEQUENCE: 77
gagagggccc ttggtggagg ctgaggagac tgtgagagtg gtg 43

<210> SEQ ID NO 78
<211> LENGTH: 47
<212> TYPE: DNA
<213> ORGANISM: Artificial
<220> FEATURE:
<223> OTHER INFORMATION: Description of artificial sequence:
Oligonucleotide

<400> SEQUENCE: 78
gagaaagctt gccgccacca tggaatggag gatctttctc ttcatcc 47

<210> SEQ ID NO 79
<211> LENGTH: 44
<212> TYPE: DNA
<213> ORGANISM: Artificial
<220> FEATURE:
<223> OTHER INFORMATION: Description of artificial sequence:
Oligonucleotide

<400> SEQUENCE: 79
gagagggccc ttggtggagg ctgaggagac ggtgactgag gttc 44

<210> SEQ ID NO 80
<211> LENGTH: 51
<212> TYPE: DNA
<213> ORGANISM: Artificial
<220> FEATURE:
<223> OTHER INFORMATION: Description of artificial sequence:
Oligonucleotide

<400> SEQUENCE: 80
gagaggtctc aagcttagcc accatggact ggatttggat catgctccat c 51

<210> SEQ ID NO 81
<211> LENGTH: 44
<212> TYPE: DNA
<213> ORGANISM: Artificial
<220> FEATURE:
<223> OTHER INFORMATION: Description of artificial sequence:
Oligonucleotide

<400> SEQUENCE: 81
gagagggccc ttggtggagg ctgcagagac agtgaccaga gtcc 44

<210> SEQ ID NO 82
<211> LENGTH: 43
<212> TYPE: DNA
<213> ORGANISM: Artificial
<220> FEATURE:
<223> OTHER INFORMATION: Description of artificial sequence:
Oligonucleotide

<400> SEQUENCE: 82
gagaaagctt gccgccacca tggaatcaca gactcaggtc ctc 43

<210> SEQ ID NO 83
<211> LENGTH: 34
<212> TYPE: DNA
<213> ORGANISM: Artificial
<220> FEATURE:
<223> OTHER INFORMATION: Description of artificial sequence:
Oligonucleotide

<400> SEQUENCE: 83
cacacgtacg tttcagctcc agcttggtcc cagc 34

<210> SEQ ID NO 84
<211> LENGTH: 46
<212> TYPE: DNA
<213> ORGANISM: Artificial
<220> FEATURE:
<223> OTHER INFORMATION: Description of artificial sequence:
Oligonucleotide

<400> SEQUENCE: 84
gagaaagctt gccgccacca tgcattttca agtgcagatt ttcagc 46

<210> SEQ ID NO 85
<211> LENGTH: 30
<212> TYPE: DNA
<213> ORGANISM: Artificial
<220> FEATURE:
<223> OTHER INFORMATION: Description of artificial sequence:
Oligonucleotide

<400> SEQUENCE: 85
cacacgtacg ttttatttcc agcttggtcc 30

<210> SEQ ID NO 86
<211> LENGTH: 44
<212> TYPE: DNA
<213> ORGANISM: Artificial
<220> FEATURE:
<223> OTHER INFORMATION: Description of artificial sequence:
Oligonucleotide

<400> SEQUENCE: 86
gagaaagctt gccgccacca tggagtttca gacccaggtc tttg 44

<210> SEQ ID NO 87
<211> LENGTH: 33
<212> TYPE: DNA
<213> ORGANISM: Artificial
<220> FEATURE:
<223> OTHER INFORMATION: Description of artificial sequence:
Oligonucleotide

<400> SEQUENCE: 87
cacacgtacg tttgatttcc agcttggtgc ctc 33

<210> SEQ ID NO 88
<211> LENGTH: 46
<212> TYPE: DNA
<213> ORGANISM: Artificial
<220> FEATURE:
<223> OTHER INFORMATION: Description of artificial sequence: Oligonucleotide

<400> SEQUENCE: 88
gagaaagctt gccgccacca tggattcaca ggcccaggtt cttatg 46

<210> SEQ ID NO 89
<211> LENGTH: 30
<212> TYPE: DNA
<213> ORGANISM: Artificial
<220> FEATURE:
<223> OTHER INFORMATION: Description of artificial sequence: Oligonucleotide

<400> SEQUENCE: 89
cacacgtacg tttcagctcc agcttggtcc 30

<210> SEQ ID NO 90
<211> LENGTH: 46
<212> TYPE: DNA
<213> ORGANISM: Artificial
<220> FEATURE:
<223> OTHER INFORMATION: Description of artificial sequence: Oligonucleotide

<400> SEQUENCE: 90
gagaaagctt gccgccacca tggaatcaca gactcaggtc ctcatg 46

<210> SEQ ID NO 91
<211> LENGTH: 30
<212> TYPE: DNA
<213> ORGANISM: Artificial
<220> FEATURE:
<223> OTHER INFORMATION: Description of artificial sequence: Oligonucleotide

<400> SEQUENCE: 91
cacacgtacg ttttatttcc aactttgtcc 30

<210> SEQ ID NO 92
<211> LENGTH: 49
<212> TYPE: DNA
<213> ORGANISM: Artificial
<220> FEATURE:
<223> OTHER INFORMATION: Description of artificial sequence: Oligonucleotide

<400> SEQUENCE: 92
gagaaagctt gccgccacca tggattcaca ggcccaggtt cttatattg 49

<210> SEQ ID NO 93
<211> LENGTH: 30
<212> TYPE: DNA
<213> ORGANISM: Artificial
<220> FEATURE:
<223> OTHER INFORMATION: Description of artificial sequence: Oligonucleotide

<400> SEQUENCE: 93
cacacgtacg ttttatttcc agcttggtcc 30

-continued

<210> SEQ ID NO 94
<211> LENGTH: 46
<212> TYPE: DNA
<213> ORGANISM: Artificial
<220> FEATURE:
<223> OTHER INFORMATION: Description of artificial sequence:
Oligonucleotide

<400> SEQUENCE: 94
gagaaagctt gccgccacca tggattcaca ggcccaggtt cttatg 46

<210> SEQ ID NO 95
<211> LENGTH: 30
<212> TYPE: DNA
<213> ORGANISM: Artificial
<220> FEATURE:
<223> OTHER INFORMATION: Description of artificial sequence:
Oligonucleotide

<400> SEQUENCE: 95
cacacgtacg ttttatttcc agcttggtcc 30

<210> SEQ ID NO 96
<211> LENGTH: 46
<212> TYPE: DNA
<213> ORGANISM: Artificial
<220> FEATURE:
<223> OTHER INFORMATION: Description of artificial sequence:
Oligonucleotide

<400> SEQUENCE: 96
gagaaagctt gccgccacca tggattcaca ggctcaggtt cttatg 46

<210> SEQ ID NO 97
<211> LENGTH: 33
<212> TYPE: DNA
<213> ORGANISM: Artificial
<220> FEATURE:
<223> OTHER INFORMATION: Description of artificial sequence:
Oligonucleotide

<400> SEQUENCE: 97
cacacgtacg tttcagctcc agcttggtcc cag 33

<210> SEQ ID NO 98
<211> LENGTH: 41
<212> TYPE: DNA
<213> ORGANISM: Artificial
<220> FEATURE:
<223> OTHER INFORMATION: Description of artificial sequence:
Oligonucleotide

<400> SEQUENCE: 98
gagaaagctt agccaccatg gaatcacaga ctctggtctt c 41

<210> SEQ ID NO 99
<211> LENGTH: 30
<212> TYPE: DNA
<213> ORGANISM: Artificial
<220> FEATURE:
<223> OTHER INFORMATION: Description of artificial sequence:
Oligonucleotide

<400> SEQUENCE: 99
cacacgtacg tttcagctcc agcttggtcc 30

<210> SEQ ID NO 100

<211> LENGTH: 1401
<212> TYPE: DNA
<213> ORGANISM: Artificial
<220> FEATURE:
<223> OTHER INFORMATION: Description of artificial sequence: chimeric monoclonal antibody

<400> SEQUENCE: 100

```
atggaatgga cctgggtctt tctcttcctc ctgtcagtaa ctgcaggtgt ccactcccag      60

gttcagctgc agcagtctgg agctgagctg atgaagcctg gggcctcagt gaagatatcc     120

tgcaaggcta ctggctacac attcagtagc tactggatag agtgggtaaa gcagaggcct     180

ggacatggcc ttgagtggat tggagagatt ttacctggaa gtggtagtac taactacaat     240

gagaagttca agggcaaggc cacattcact gcagatacat cctccaacac agcctacatg     300

caactcagca gcctgacatc tgaggactct gccgtctatt actgtgcaag atatgattac     360

ccctggtttg cttactgggg ccaagggact ctggtcactg tctctgcagc ctccaccaag     420

ggcccatcgg tcttcccct ggcaccctcc tccaagagca cctctggggg cacagcggcc      480

ctgggctgcc tggtcaagga ctacttcccc gaaccggtga cggtgtcgtg gaactcaggc     540

gccctgacca gcggcgtgca caccttcccg gctgtcctac agtcctcagg actctactcc     600

ctcagcagcg tggtgaccgt gccctccagc agcttgggca cccagaccta catctgcaac     660

gtgaatcaca agcccagcaa caccaaggtg gacaagaaag ttgagcccaa atcttgtgac     720

aaaactcaca catgcccacc gtgcccagca cctgaactcc tggggggacc gtcagtcttc     780

ctcttccccc caaaacccaa ggacaccctc atgatctccc ggacccctga ggtcacatgc     840

gtggtggtgg acgtgagcca cgaagaccct gaggtcaagt tcaactggta cgtggacggc     900

gtggaggtgc ataatgccaa gacaaagccg cgggaggagc agtacaacag cacgtaccgt     960

gtggtcagcg tcctcaccgt cctgcaccag gactggctga atggcaagga gtacaagtgc    1020

aaggtctcca acaaagccct cccagccccc atcgagaaaa ccatctccaa agccaaaggg    1080

cagccccgag aaccacaggt gtacaccctg cccccatccc gggatgagct gaccaagaac    1140

caggtcagcc tgacctgcct ggtcaaaggc ttctatccca gcgacatcgc cgtggagtgg    1200

gagagcaatg ggcagccgga gaacaactac aagaccacgc ctcccgtgct ggactccgac    1260

ggctccttct tcctctatag caagctcacc gtggacaaga gcaggtggca gcaggggaac    1320

gtcttctcat gctccgtgat gcatgaggct ctgcacaacc actacacgca gaagagcctc    1380

tccctgtctc cgggtaaatg a                                              1401
```

<210> SEQ ID NO 101
<211> LENGTH: 1404
<212> TYPE: DNA
<213> ORGANISM: Artificial
<220> FEATURE:
<223> OTHER INFORMATION: Description of artificial sequence: chimeric monoclonal antibody

<400> SEQUENCE: 101

```
atggattggc tgtggaactt gctattcctg atggcagctg cccaaagtat ccaagcacag      60

atccagttgg tgcagtctgg acctgagctg aagaagcctg gagagacagt caagatctcc     120

tgcaaggctt ctgggtatac cttcacaaac tatggaatga actgggtgaa gcaggctcca     180

ggaaagggtt taaagtggat gggctggata aacaccaaca ctggagagcc aacatatgct     240

gaagagttca agggacggtt tgccttctct ttggaaacct ctgccagcac tgcctatttg     300

cagatcaaca acctcaaaaa tgaggacacg gctacatatt tctgtgcaag actgggtttt     360
```

```
ggtaatgcta tggactactg gggtcaagga acctcagtca ccgtctcctc agcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga aagttgagcc caaatcttgt    720
gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                          1404
```

<210> SEQ ID NO 102
<211> LENGTH: 1398
<212> TYPE: DNA
<213> ORGANISM: Artificial
<220> FEATURE:
<223> OTHER INFORMATION: Description of artificial sequence: chimeric monoclonal antibody

<400> SEQUENCE: 102

```
atggaatgga tctggatctt tctcttcatc ctctcaggaa ctgcaggtgt ccactcccag     60
gttcagctgc agcagtctgg agctgagctg gcgaggcccg gggcttcagt gaagctgtcc    120
tgcaaggctt ctggctacac cttcactgac tactatataa actgggtgaa gcagaggact    180
ggacagggcc ttgagtggat tggagagatt tatcctggaa gtggtaatac ttactacaat    240
gagaagttca agggcaaggc cacactgact gcagacaaat cctccagcac agcctacatg    300
cagctcagca gcctgacatc tgaggactct gcagtctatt tctgtgcaag atcgtatggt    360
gcctttgact actggggcca aggcaccact ctcacagtct cctcagcctc caccaagggc    420
ccatcggtct tccccctggc accctcctcc aagagcacct ctgggggcac agcggccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcaccc agacctacat ctgcaacgtg    660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa aacccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
```

```
gtcagcgtcc tcaccgtcct gcaccaggac tggctgaatg gcaaggagta caagtgcaag   1020

gtctccaaca aagccctccc agcccccatc gagaaaacca tctccaaagc caaagggcag   1080

ccccgagaac cacaggtgta caccctgccc ccatcccggg atgagctgac caagaaccag   1140

gtcagcctga cctgcctggt caaaggcttc tatcccagcg acatcgccgt ggagtgggag   1200

agcaatgggc agccggagaa caactacaag accacgcctc ccgtgctgga ctccgacggc   1260

tccttcttcc tctatagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaatga                                                 1398
```

<210> SEQ ID NO 103
<211> LENGTH: 1404
<212> TYPE: DNA
<213> ORGANISM: Artificial
<220> FEATURE:
<223> OTHER INFORMATION: Description of artificial sequence: chimeric monoclonal antibody

<400> SEQUENCE: 103

```
atgggatgga gctgtatcat cctcttcttg gtagcaacag ctacaggtgt ccactcccag     60

gtccaactgc agcagcctgg ggctgagctg gtgaggcctg gggcttcagt gaagctgtcc    120

tgcaaggctt ctggctacac cttcaccagc tactggataa actgggtgaa gcagaggcct    180

ggacaaggcc ttgagtggat cggaaatatt tatccttctg atagttatac taactacaat    240

caaaagttca aggacaaggc cacattgact gtagacaaat cctccagcac agcctacatg    300

cagctcagca gcccgacatc tgaggactct gcggtctatt actgtacaag atcgtggagg    360

ggtaactcct ttgactactg gggccaaggc accactctca cagtctcctc agcctccacc    420

aagggcccat cggtcttccc cctggcaccc tcctccaaga gcacctctgg gggcacagcg    480

gccctgggct gcctggtcaa ggactacttc cccgaaccgg tgacggtgtc gtggaactca    540

ggcgccctga ccagcggcgt gcacaccttc ccggctgtcc tacagtcctc aggactctac    600

tccctcagca gcgtggtgac cgtgccctcc agcagcttgg gcacccagac ctacatctgc    660

aacgtgaatc acaagcccag caacaccaag gtggacaaga aagttgagcc caaatcttgt    720

gacaaaactc acacatgccc accgtgccca gcacctgaac tcctgggggg accgtcagtc    780

ttcctcttcc ccccaaaacc caaggacacc ctcatgatct cccggacccc tgaggtcaca    840

tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggatga gctgaccaag   1140

aaccaggtca gcctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcta tagcaagctc accgtggaca agagcaggtg gcagcagggg   1320

aacgtcttct catgctccgt gatgcatgag gctctgcaca accactacac gcagaagagc   1380

ctctccctgt ctccgggtaa atga                                          1404
```

<210> SEQ ID NO 104
<211> LENGTH: 1401

<212> TYPE: DNA
<213> ORGANISM: Artificial
<220> FEATURE:
<223> OTHER INFORMATION: Description of artificial sequence: chimeric
monoclonal antibody

<400> SEQUENCE: 104
atggaatgga ggatctttct cttcatcctg tcaggaactg caggtgtcca ctcccaggtt 60
cagctgcagc agtctggacc tgagctggtg aagcctgggg cttcagtgaa gatgtcctgc 120
aaggcttctg gatacacatt cactgactat gttataagct gggtgaagca gagaactgga 180
cagggccttg agtggattgg agagatttat cctggaagtg gtagtactta ctacaatgag 240
aagttcaagg gcaaggccac actgactgca gacaaatcct ccaacacagc ctacatgcag 300
ctcagcagcc tgacatctga ggactctgcg gtctatttct gtgcaagagg ggtattacta 360
cgggctatgg actactgggg tcaaggaacc tcagtcaccg tctcctcagc ctccaccaag 420
ggcccatcgg tcttcccct ggcaccctcc tccaagagca cctctggggg cacagcggcc 480
ctgggctgcc tggtcaagga ctacttcccc gaaccggtga cggtgtcgtg gaactcaggc 540
gccctgacca gcggcgtgca caccttcccg gctgtcctac agtcctcagg actctactcc 600
ctcagcagcg tggtgaccgt gccctccagc agcttgggca cccagaccta catctgcaac 660
gtgaatcaca agcccagcaa caccaaggtg gacaagaaag ttgagcccaa atcttgtgac 720
aaaactcaca catgcccacc gtgcccagca cctgaactcc tggggggacc gtcagtcttc 780
ctcttccccc caaaacccaa ggacaccctc atgatctccc ggacccctga ggtcacatgc 840
gtggtggtgg acgtgagcca cgaagaccct gaggtcaagt tcaactggta cgtggacggc 900
gtggaggtgc ataatgccaa gacaaagccg cgggaggagc agtacaacag cacgtaccgt 960
gtggtcagcg tcctcaccgt cctgcaccag gactggctga atggcaagga gtacaagtgc 1020
aaggtctcca acaaagccct cccagccccc atcgagaaaa ccatctccaa agccaaaggg 1080
cagccccgag aaccacaggt gtacaccctg cccccatccc gggatgagct gaccaagaac 1140
caggtcagcc tgacctgcct ggtcaaaggc ttctatccca gcgacatcgc cgtggagtgg 1200
gagagcaatg ggcagccgga gaacaactac aagaccacgc ctcccgtgct ggactccgac 1260
ggctccttct tcctctatag caagctcacc gtggacaaga gcaggtggca gcaggggaac 1320
gtcttctcat gctccgtgat gcatgaggct ctgcacaacc actacacgca gaagagcctc 1380
tccctgtctc cgggtaaatg a 1401

<210> SEQ ID NO 105
<211> LENGTH: 1410
<212> TYPE: DNA
<213> ORGANISM: Artificial
<220> FEATURE:
<223> OTHER INFORMATION: Description of artificial sequence: chimeric
monoclonal antibody

<400> SEQUENCE: 105
atggactgga tttggatcat gctccatctg ctggcagcag ctacaggtat ccaatcccag 60
gttcacctac aacagtctgg ttctgaactg aggagtcctg ggtcttcagt aaagctttca 120
tgcaaggatt ttgattcaga agtcttccct tttgcttata tgagttggat taggcagaag 180
cctgggcatg gatttgaatg gattggagac atactcccaa gtattggtag aacaatctat 240
ggagagaagt ttgaggacaa agccacactg gatgcagaca cagtgtccaa cacagcctac 300
ttggagctca acagtctgac atctgaggac tctgctatct actactgtgc aagggggggag 360

-continued

```
ggctacggtg cctggtttgc ttactggggc caagggactc tggtcactgt ctctgcagcc    420

tccaccaagg gcccatcggt cttccccctg gcaccctcct ccaagagcac ctctgggggc    480

acagcggccc tgggctgcct ggtcaaggac tacttccccg aaccggtgac ggtgtcgtgg    540

aactcaggcg ccctgaccag cggcgtgcac accttcccgg ctgtcctaca gtcctcagga    600

ctctactccc tcagcagcgt ggtgaccgtg ccctccagca gcttgggcac ccagacctac    660

atctgcaacg tgaatcacaa gcccagcaac accaaggtgg acaagaaagt tgagcccaaa    720

tcttgtgaca aaactcacac atgcccaccg tgcccagcac ctgaactcct ggggggaccg    780

tcagtcttcc tcttcccccc aaaacccaag gacaccctca tgatctcccg gacccctgag    840

gtcacatgcg tggtggtgga cgtgagccac gaagaccctg aggtcaagtt caactggtac    900

gtggacggcg tggaggtgca taatgccaag acaaagccgc gggaggagca gtacaacagc    960

acgtaccgtg tggtcagcgt cctcaccgtc ctgcaccagg actggctgaa tggcaaggag   1020

tacaagtgca aggtctccaa caaagccctc ccagccccca tcgagaaaac catctccaaa   1080

gccaaagggc agccccgaga accacaggtg tacaccctgc ccccatcccg ggatgagctg   1140

accaagaacc aggtcagcct gacctgcctg gtcaaaggct tctatcccag cgacatcgcc   1200

gtggagtggg agagcaatgg gcagccggag aacaactaca agaccacgcc tcccgtgctg   1260

gactccgacg gctccttctt cctctatagc aagctcaccg tggacaagag caggtggcag   1320

caggggaacg tcttctcatg ctccgtgatg catgaggctc tgcacaacca ctacacgcag   1380

aagagcctct ccctgtctcc gggtaaatga                                     1410
```

```
<210> SEQ ID NO 106
<211> LENGTH: 723
<212> TYPE: DNA
<213> ORGANISM: Artificial
<220> FEATURE:
<223> OTHER INFORMATION: Description of artificial sequence: chimeric
      monoclonal antibody

<400> SEQUENCE: 106

atggaatcac agactcaggt cctcatgtcc ctgctgttct gggtatctgg tacctgtggg     60

gacattgtga tgacacagtc tccatcctcc ctgactgtga cagcaggaga gaaggtcact    120

atgagctgca agtccagtca gagtctgtta aacagtggaa atcaaaagaa ctacttgacc    180

tggtaccagc agaaaccagg gcagcctcct aaactgttga tctactgggc atccactagg    240

gaatctgggg tccctgatcg cttcacaggc agtggatctg gaacagattt cactctcacc    300

atcagcagtg tgcaggctga agacctggca gtttattact gtcagaatga ttatagttat    360

ccgctcacgt tcggtgctgg gaccaagctg gagctgaaac gtacggtggc tgcaccatct    420

gtcttcatct tcccgccatc tgatgagcag ttgaaatctg gaactgcctc tgttgtgtgc    480

ctgctgaata acttctatcc cagagaggcc aaagtacagt ggaaggtgga taacgccctc    540

caatcgggta actcccagga gagtgtcaca gagcaggaca gcaaggacag cacctacagc    600

ctcagcagca ccctgacgct gagcaaagca gactacgaga aacacaaagt ctacgcctgc    660

gaagtcaccc atcagggcct gagctcgccc gtcacaaaga gcttcaacag gggagagtgt    720

tag                                                                  723
```

```
<210> SEQ ID NO 107
<211> LENGTH: 708
<212> TYPE: DNA
<213> ORGANISM: Artificial
<220> FEATURE:
```

<223> OTHER INFORMATION: Description of artificial sequence: chimeric
monoclonal antibody

<400> SEQUENCE: 107
atgcattttc aagtgcagat tttcagcttc ctgctaatca gtgcctcagt cataatgtcc 60
agaggacaaa ttgttctcac ccagtctcca gcaatcatgt ctgcatctcc aggggagaag 120
gtcaccataa cctgcagtgc cagctcaagt gtaagttaca tgcactggtt ccagcagaag 180
ccaggcactt ctcccaaact ctggatttat agcacatcca acctggcttc tggagtccct 240
gctcgcttca gtggcagtgg atctgggacc tcttactctc tcacaatcag ccgaatggag 300
gctgaagatg ctgccactta ttactgccag caaaggagta gttacccacc cacgttcgga 360
ggggggacca agctggaaat aaaacgtacg gtggctgcac catctgtctt catcttcccg 420
ccatctgatg agcagttgaa atctggaact gcctctgttg tgtgcctgct gaataacttc 480
tatcccagag aggccaaagt acagtggaag gtggataacg ccctccaatc gggtaactcc 540
caggagagtg tcacagagca ggacagcaag gacagcacct acagcctcag cagcaccctg 600
acgctgagca aagcagacta cgagaaacac aaagtctacg cctgcgaagt cacccatcag 660
ggcctgagct cgcccgtcac aaagagcttc aacaggggag agtgttag 708

<210> SEQ ID NO 108
<211> LENGTH: 705
<212> TYPE: DNA
<213> ORGANISM: Artificial
<220> FEATURE:
<223> OTHER INFORMATION: Description of artificial sequence: chimeric
monoclonal antibody

<400> SEQUENCE: 108
atggagtttc agacccaggt ctttgtattc gtgttgctct ggttgtctgg tgttgatgga 60
gacattgtga tgacccagtc tcaaaaattc atgtccacat cagtaggaga cagggtcagc 120
atcacctgca aggccagtca gaatgttcgt actgctgtag cctggtatca acagaaacca 180
gggcagtctc ctaaagcact gatttacttg gcatccaacc ggcacactgg agtccctgat 240
cgcttcacag gcagtggatc tgggacagat ttcactctca ccattagcaa tgtgcaatct 300
gaagacctgg cagattattt ctgtctgcaa cattggaatt atcctctgac gttcggtgga 360
ggcaccaagc tggaaatcaa acgtacggtg gctgcaccat ctgtcttcat cttcccgcca 420
tctgatgagc agttgaaatc tggaactgcc tctgttgtgt gcctgctgaa taacttctat 480
cccagagagg ccaaagtaca gtggaaggtg gataacgccc tccaatcggg taactcccag 540
gagagtgtca cagagcagga cagcaaggac agcacctaca gcctcagcag caccctgacg 600
ctgagcaaag cagactacga gaaacacaaa gtctacgcct gcgaagtcac ccatcagggc 660
ctgagctcgc ccgtcacaaa gagcttcaac aggggagagt gttag 705

<210> SEQ ID NO 109
<211> LENGTH: 723
<212> TYPE: DNA
<213> ORGANISM: Artificial
<220> FEATURE:
<223> OTHER INFORMATION: Description of artificial sequence: chimeric
monoclonal antibody

<400> SEQUENCE: 109
atggattcac aggcccaggt tcttatgtta ctgctgctat gggtatctgg tacctgtggg 60
gacattgtga tgtcacagtc tccatcctcc ctagctgtgt cagttggaga gaaggttact 120
atgagctgca agtccagtca gagcctttta tatagtagca atcaaaagaa ctacttggcc 180
tggtaccagc agaaaccagg gcagtctcct aaactgctga tttactgggc atccactagg 240
gaatctgggg tccctgatcg cttcacaggc agtggatctg ggacagattt cactctcacc 300
atcagcagtg tgaaggctga agacctggca gtttattact gtcagcaata ttatagctat 360
ccgctcacgt tcggtgctgg gaccaagctg gagctgaaac gtacggtggc tgcaccatct 420
gtcttcatct tcccgccatc tgatgagcag ttgaaatctg gaactgcctc tgttgtgtgc 480
ctgctgaata acttctatcc cagagaggcc aaagtacagt ggaaggtgga taacgccctc 540
caatcgggta actcccagga gagtgtcaca gagcaggaca gcaaggacag cacctacagc 600
ctcagcagca ccctgacgct gagcaaagca gactacgaga aacacaaagt ctacgcctgc 660
gaagtcaccc atcagggcct gagctcgccc gtcacaaaga gcttcaacag gggagagtgt 720
tag 723

<210> SEQ ID NO 110
<211> LENGTH: 723
<212> TYPE: DNA
<213> ORGANISM: Artificial
<220> FEATURE:
<223> OTHER INFORMATION: Description of artificial sequence: chimeric monoclonal antibody

<400> SEQUENCE: 110
atggaatcac agactcaggt cctcatgtcc ctgctgttct gggtatctgg tacctgtggg 60
gacattgtga tgacacagtc tccatcctcc ctgactgtga cagcaggaga gaaggtcact 120
atgagctgca agtccagtca gagtctgtta aacagtggaa atcaaaagaa ctacttgacc 180
tggtaccagc agaaaccagg gcagcctcct aaactgttga tctactgggc atccactagg 240
gaatctgggg tccctgatcg cttcacaggc agtggatctg gaacagattt cactctcacc 300
atcagcagtg tgcaggctga agacctggca gtttattact gtcagaatga ttatagttat 360
ccattcacgt tcggctcggg gacaaagttg gaaataaaac gtacggtggc tgcaccatct 420
gtcttcatct tcccgccatc tgatgagcag ttgaaatctg gaactgcctc tgttgtgtgc 480
ctgctgaata acttctatcc cagagaggcc aaagtacagt ggaaggtgga taacgccctc 540
caatcgggta actcccagga gagtgtcaca gagcaggaca gcaaggacag cacctacagc 600
ctcagcagca ccctgacgct gagcaaagca gactacgaga aacacaaagt ctacgcctgc 660
gaagtcaccc atcagggcct gagctcgccc gtcacaaaga gcttcaacag gggagagtgt 720
tag 723

<210> SEQ ID NO 111
<211> LENGTH: 720
<212> TYPE: DNA
<213> ORGANISM: Artificial
<220> FEATURE:
<223> OTHER INFORMATION: Description of artificial sequence: chimeric monoclonal antibody

<400> SEQUENCE: 111
atggattcac aggcccaggt tcttatattg ctgctgctat gggtatctgg tacctgtggg 60
gacattgtga tgtcacagtc tccatcctcc ctggctgtgt cagcaggaga gaaggtcact 120
atgagctgca aatccagtca gagtctgctc aacagtagaa cccgaaagaa ctacttggct 180
tggtaccagc agaaaccagg gcagtctcct aaactgctga tctactgggc atccactagg 240
gaatctgggg tccctgatcg cttcacaggc agtggatctg ggacagattt cactctcacc 300

```
atcagcagtg tgcaggctga agacctggca gtttattact gcaagcaatc ttataatctg    360

tacacgttcg gaggggggac caagctggaa ataaaacgta cggtggctgc accatctgtc    420

ttcatcttcc cgccatctga tgagcagttg aaatctggaa ctgcctctgt tgtgtgcctg    480

ctgaataact tctatcccag agaggccaaa gtacagtgga aggtggataa cgccctccaa    540

tcgggtaact cccaggagag tgtcacagag caggacagca aggacagcac ctacagcctc    600

agcagcaccc tgacgctgag caaagcagac tacgagaaac acaaagtcta cgcctgcgaa    660

gtcacccatc agggcctgag ctcgcccgtc acaaagagct tcaacagggg agagtgttag    720
```

```
<210> SEQ ID NO 112
<211> LENGTH: 723
<212> TYPE: DNA
<213> ORGANISM: Artificial
<220> FEATURE:
<223> OTHER INFORMATION: Description of artificial sequence: chimeric
      monoclonal antibody

<400> SEQUENCE: 112

atggattcac aggcccaggt tcttatgtta ctgctgctat gggtatctgg tacctgtggg     60

gacatcgtga tgtcacagtc tccatcctcc ctagctgtgt cagttggaga gaaggttact    120

atgagctgca agtccagtca gagcctttta tatagtagca atcaaaagaa ctacttggcc    180

tggtaccagc agaaaccagg gcagtctcct aaactgctga tttactgggc atccactagg    240

gaatctgggg tccctgatcg cttcacaggc agtggatctg caacagattt cactctgacc    300

atcagcagtg tgcaggctga agaccttgca gattatcact gtggacaggg ttacagctat    360

ccgtacacgt tcggaggggg gaccaagctg gaaataaaac gtacggtggc tgcaccatct    420

gtcttcatct tcccgccatc tgatgagcag ttgaaatctg gaactgcctc tgttgtgtgc    480

ctgctgaata acttctatcc cagagaggcc aaagtacagt ggaaggtgga taacgccctc    540

caatcgggta actcccagga gagtgtcaca gagcaggaca gcaaggacag cacctacagc    600

ctcagcagca ccctgacgct gagcaaagca gactacgaga aacacaaagt ctacgcctgc    660

gaagtcaccc atcagggcct gagctcgccc gtcacaaaga gcttcaacag gggagagtgt    720

tag                                                                  723
```

```
<210> SEQ ID NO 113
<211> LENGTH: 723
<212> TYPE: DNA
<213> ORGANISM: Artificial
<220> FEATURE:
<223> OTHER INFORMATION: Description of artificial sequence: chimeric
      monoclonal antibody

<400> SEQUENCE: 113

atggattcac aggctcaggt tcttatgtta ctgctgctat gggtatctgg tacctgtggg     60

gacattgtga tgtcacagtc tccatcctcc ctagctgtgt cagttggaga gaaggttact    120

atgagctgca agtccagtca gagcctttta tatagtagca atcaaaagaa ctacttggcc    180

tggtaccagc agaaaccagg gcagtctcct aaactgctga tttactgggc atccactagg    240

gaatctgggg tccctgatcg cttcacaggc agtggatctg ggacagattt cactctcacc    300

atcagcagtg tgaaggctga agacctggca gtttattact gtcagcaata ttatagctat    360

ccgctcacgt tcggtgctgg gaccaagctg gagctgaaac gtacggtggc tgcaccatct    420

gtcttcatct tcccgccatc tgatgagcag ttgaaatctg gaactgcctc tgttgtgtgc    480
```

```
ctgctgaata acttctatcc cagagaggcc aaagtacagt ggaaggtgga taacgccctc    540

caatcgggta actcccagga gagtgtcaca gagcaggaca gcaaggacag cacctacagc    600

ctcagcagca ccctgacgct gagcaaagca gactacgaga aacacaaagt ctacgcctgc    660

gaagtcaccc atcagggcct gagctcgccc gtcacaaaga gcttcaacag gggagagtgt    720

tag                                                                   723


<210> SEQ ID NO 114
<211> LENGTH: 705
<212> TYPE: DNA
<213> ORGANISM: Artificial
<220> FEATURE:
<223> OTHER INFORMATION: Description of artificial sequence: chimeric
      monoclonal antibody

<400> SEQUENCE: 114

atggaatcac agactctggt cttcatatcc atactgctct ggttatatgg agctgatggg     60

aacattgtaa tgacccaatc tcccaaatcc atgtccatgt cagtaggaga gagggtcacc    120

ttgacctgca aggccagtga gaatgtggtt acttatgttt cctggtatca acagaaacca    180

gagcagtctc ctaaactgct gatatacggg gcatccaacc ggtacactgg ggtccccgat    240

cgcttcacag gcagtggatc tgcaacagat ttcactctca ccatcagcag tgtgaaggct    300

gaagacctgg cagtttatta ctgtcagcaa tattatagct atccgctcac gttcggtgct    360

gggaccaagc tggagctgaa acgtacggtg gctgcaccat ctgtcttcat cttcccgcca    420

tctgatgagc agttgaaatc tggaactgcc tctgttgtgt gcctgctgaa taacttctat    480

cccagagagg ccaaagtaca gtggaaggtg gataacgccc tccaatcggg taactcccag    540

gagagtgtca cagagcagga cagcaaggac agcacctaca gcctcagcag caccctgacg    600

ctgagcaaag cagactacga gaaacacaaa gtctacgcct gcgaagtcac ccatcagggc    660

ctgagctcgc ccgtcacaaa gagcttcaac aggggagagt gttag                    705


<210> SEQ ID NO 115
<211> LENGTH: 466
<212> TYPE: PRT
<213> ORGANISM: Artificial
<220> FEATURE:
<223> OTHER INFORMATION: Description of artificial sequence: chimeric
      monoclonal antibody

<400> SEQUENCE: 115

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Thr Gly Tyr Thr Phe
        35                  40                  45

Ser Ser Tyr Trp Ile Glu Trp Val Lys Gln Arg Pro Gly His Gly Leu
    50                  55                  60

Glu Trp Ile Gly Glu Ile Leu Pro Gly Ser Gly Ser Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Tyr Asp Tyr Pro Trp Phe Ala Tyr Trp Gly Gln
        115                 120                 125
```

```
Gly Thr Leu Val Thr Val Ser Ala Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 116
<211> LENGTH: 467
<212> TYPE: PRT
<213> ORGANISM: Artificial
<220> FEATURE:
<223> OTHER INFORMATION: Description of artificial sequence: chimeric
      monoclonal antibody

<400> SEQUENCE: 116

Met Asp Trp Leu Trp Asn Leu Leu Phe Leu Met Ala Ala Ala Gln Ser
```

-continued

```
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430
```

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 117
<211> LENGTH: 465
<212> TYPE: PRT
<213> ORGANISM: Artificial
<220> FEATURE:
<223> OTHER INFORMATION: Description of artificial sequence: chimeric
      monoclonal antibody

<400> SEQUENCE: 117

Met Glu Trp Ile Trp Ile Phe Leu Phe Ile Leu Ser Gly Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Asp Tyr Tyr Ile Asn Trp Val Lys Gln Arg Thr Gly Gln Gly Leu
    50                  55                  60

Glu Trp Ile Gly Glu Ile Tyr Pro Gly Ser Gly Asn Thr Tyr Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Ser Tyr Gly Ala Phe Asp Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val

-continued

```
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 118
<211> LENGTH: 467
<212> TYPE: PRT
<213> ORGANISM: Artificial
<220> FEATURE:
<223> OTHER INFORMATION: Description of artificial sequence: chimeric
      monoclonal antibody

<400> SEQUENCE: 118

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190
```

```
Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 119
<211> LENGTH: 466
<212> TYPE: PRT
<213> ORGANISM: Artificial
<220> FEATURE:
<223> OTHER INFORMATION: Description of artificial sequence: chimeric
      monoclonal antibody

<400> SEQUENCE: 119

Met Glu Trp Arg Ile Phe Leu Phe Ile Leu Ser Gly Thr Ala Gly Val
1               5                   10                  15

His Ser Gln Val Gln Leu Gln Gln Ser Gly Pro Glu Leu Val Lys Pro
            20                  25                  30

Gly Ala Ser Val Lys Met Ser Cys Lys Ala Ser Gly Tyr Thr Phe Thr
        35                  40                  45

Asp Tyr Val Ile Ser Trp Val Lys Gln Arg Thr Gly Gln Gly Leu Glu
    50                  55                  60

Trp Ile Gly Glu Ile Tyr Pro Gly Ser Gly Ser Thr Tyr Tyr Asn Glu
65                  70                  75                  80
```

```
Lys Phe Lys Gly Lys Ala Thr Leu Thr Ala Asp Lys Ser Ser Asn Thr
                85                  90                  95

Ala Tyr Met Gln Leu Ser Ser Leu Thr Ser Glu Asp Ser Ala Val Tyr
            100                 105                 110

Phe Cys Ala Arg Gly Val Leu Leu Arg Ala Met Asp Tyr Trp Gly Gln
        115                 120                 125

Gly Thr Ser Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 120
<211> LENGTH: 469

<212> TYPE: PRT
<213> ORGANISM: Artificial
<220> FEATURE:
<223> OTHER INFORMATION: Description of artificial sequence: chimeric monoclonal antibody

<400> SEQUENCE: 120

```
Met Asp Trp Ile Trp Ile Met Leu His Leu Leu Ala Ala Ala Thr Gly
1               5                   10                  15

Ile Gln Ser Gln Val His Leu Gln Gln Ser Gly Ser Glu Leu Arg Ser
            20                  25                  30

Pro Gly Ser Ser Val Lys Leu Ser Cys Lys Asp Phe Asp Ser Glu Val
        35                  40                  45

Phe Pro Phe Ala Tyr Met Ser Trp Ile Arg Gln Lys Pro Gly His Gly
    50                  55                  60

Phe Glu Trp Ile Gly Asp Ile Leu Pro Ser Ile Gly Arg Thr Ile Tyr
65                  70                  75                  80

Gly Glu Lys Phe Glu Asp Lys Ala Thr Leu Asp Ala Asp Thr Val Ser
                85                  90                  95

Asn Thr Ala Tyr Leu Glu Leu Asn Ser Leu Thr Ser Glu Asp Ser Ala
            100                 105                 110

Ile Tyr Tyr Cys Ala Arg Gly Glu Gly Tyr Gly Ala Trp Phe Ala Tyr
        115                 120                 125

Trp Gly Gln Gly Thr Leu Val Thr Val Ser Ala Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380
```

```
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465
```

<210> SEQ ID NO 121
<211> LENGTH: 240
<212> TYPE: PRT
<213> ORGANISM: Artificial
<220> FEATURE:
<223> OTHER INFORMATION: Description of artificial sequence: chimeric monoclonal antibody

<400> SEQUENCE: 121

```
Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Asn Ser Gly Asn Gln Lys Asn Tyr Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Leu Thr Phe Gly Ala Gly Thr
        115                 120                 125

Lys Leu Glu Leu Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 122
<211> LENGTH: 235
<212> TYPE: PRT

<213> ORGANISM: Artificial
<220> FEATURE:
<223> OTHER INFORMATION: Description of artificial sequence: chimeric monoclonal antibody

<400> SEQUENCE: 122

```
Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
        35                  40                  45

Ser Ser Val Ser Tyr Met His Trp Phe Gln Gln Lys Pro Gly Thr Ser
    50                  55                  60

Pro Lys Leu Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 123
<211> LENGTH: 234
<212> TYPE: PRT
<213> ORGANISM: Artificial
<220> FEATURE:
<223> OTHER INFORMATION: Description of artificial sequence: chimeric monoclonal antibody

<400> SEQUENCE: 123

```
Met Glu Phe Gln Thr Gln Val Phe Val Phe Val Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Ile Thr Cys Lys Ala Ser Gln Asn
        35                  40                  45

Val Arg Thr Ala Val Ala Trp Tyr Gln Gln Lys Pro Gly Gln Ser Pro
    50                  55                  60

Lys Ala Leu Ile Tyr Leu Ala Ser Asn Arg His Thr Gly Val Pro Asp
65                  70                  75                  80

Arg Phe Thr Gly Ser Gly Ser Gly Thr Asp Phe Thr Leu Thr Ile Ser
```

-continued

```
                85                  90                  95

Asn Val Gln Ser Glu Asp Leu Ala Asp Tyr Phe Cys Leu Gln His Trp
            100                 105                 110

Asn Tyr Pro Leu Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 124
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 124

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
        115                 120                 125

Lys Leu Glu Leu Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205
```

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 125
<211> LENGTH: 240
<212> TYPE: PRT
<213> ORGANISM: Artificial
<220> FEATURE:
<223> OTHER INFORMATION: Description of artificial sequence: chimeric monoclonal antibody

<400> SEQUENCE: 125

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Asn Ser Gly Asn Gln Lys Asn Tyr Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Phe Thr Phe Gly Ser Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 126
<211> LENGTH: 239
<212> TYPE: PRT
<213> ORGANISM: Artificial
<220> FEATURE:
<223> OTHER INFORMATION: Description of artificial sequence: chimeric monoclonal antibody

<400> SEQUENCE: 126

Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
            20                  25                  30

-continued

```
Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Tyr Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 127
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 127

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Ala Thr Asp
                85                  90                  95

Phe Thr Leu Thr Ile Ser Ser Val Gln Ala Glu Asp Leu Ala Asp Tyr
            100                 105                 110

His Cys Gly Gln Gly Tyr Ser Tyr Pro Tyr Thr Phe Gly Gly Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160
```

```
Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 128
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 128

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
        115                 120                 125

Lys Leu Glu Leu Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 129
<211> LENGTH: 234
<212> TYPE: PRT
<213> ORGANISM: Artificial
<220> FEATURE:
<223> OTHER INFORMATION: Description of artificial sequence: chimeric
```

monoclonal antibody

<400> SEQUENCE: 129

```
Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Lys Ala Glu Asp Leu Ala Val Tyr Tyr Cys Gln Gln Tyr Tyr
            100                 105                 110

Ser Tyr Pro Leu Thr Phe Gly Ala Gly Thr Lys Leu Glu Leu Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 130
<211> LENGTH: 18
<212> TYPE: DNA
<213> ORGANISM: Artificial
<220> FEATURE:
<223> OTHER INFORMATION: Description of artificial sequence: Oligonucleotide

<400> SEQUENCE: 130
ccaagggcta tggcgttc 18

<210> SEQ ID NO 131
<211> LENGTH: 18
<212> TYPE: DNA
<213> ORGANISM: Artificial
<220> FEATURE:
<223> OTHER INFORMATION: Description of artificial sequence: Oligonucleotide

<400> SEQUENCE: 131
ccgaaggtgt acctggtc 18

<210> SEQ ID NO 132
<211> LENGTH: 117
<212> TYPE: PRT

<213> ORGANISM: Artificial
<220> FEATURE:
<223> OTHER INFORMATION: Description of artificial sequence: Translation
of PCR product

<400> SEQUENCE: 132

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Pro Trp Phe Ala Tyr Trp Gly Gln Gly Thr Leu
            100                 105                 110

Val Thr Val Ser Ala
        115
```

<210> SEQ ID NO 133
<211> LENGTH: 118
<212> TYPE: PRT
<213> ORGANISM: Artificial
<220> FEATURE:
<223> OTHER INFORMATION: Description of artificial sequence: Translation
of PCR product

<400> SEQUENCE: 133

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Phe Gly Asn Ala Met Asp Tyr Trp Gly Gln Gly Thr
            100                 105                 110

Ser Val Thr Val Ser Ser
        115
```

<210> SEQ ID NO 134
<211> LENGTH: 116
<212> TYPE: PRT
<213> ORGANISM: Artificial
<220> FEATURE:
<223> OTHER INFORMATION: Description of artificial sequence: Translation
of PCR product

<400> SEQUENCE: 134

```
Gln Val Gln Leu Gln Gln Ser Gly Ala Glu Leu Ala Arg Pro Gly Ala
1               5                   10                  15
```

```
Ser Val Lys Leu Ser Cys Lys Ala Ser Gly Tyr Thr Phe Thr Asp Tyr
            20                  25                  30

Tyr Ile Asn Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Tyr Gly Ala Phe Asp Tyr Trp Gly Gln Gly Thr Thr Leu
            100                 105                 110

Thr Val Ser Ser
        115


<210> SEQ ID NO 135
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 135

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser
        115


<210> SEQ ID NO 136
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 136

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Thr Tyr Tyr Asn Glu Lys Phe
    50                  55                  60
```

```
Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Leu Leu Arg Ala Met Asp Tyr Trp Gly Gln Gly Thr
            100                 105                 110

Ser Val Thr Val Ser Ser
        115


<210> SEQ ID NO 137
<211> LENGTH: 120
<212> TYPE: PRT
<213> ORGANISM: Artificial
<220> FEATURE:
<223> OTHER INFORMATION: Description of artificial sequence: Translation
      of PCR product

<400> SEQUENCE: 137

Gln Val His Leu Gln Gln Ser Gly Ser Glu Leu Arg Ser Pro Gly Ser
1               5                   10                  15

Ser Val Lys Leu Ser Cys Lys Asp Phe Asp Ser Glu Val Phe Pro Phe
            20                  25                  30

Ala Tyr Met Ser Trp Ile Arg Gln Lys Pro Gly His Gly Phe Glu Trp
        35                  40                  45

Ile Gly Asp Ile Leu Pro Ser Ile Gly Arg Thr Ile Tyr Gly Glu Lys
    50                  55                  60

Phe Glu Asp Lys Ala Thr Leu Asp Ala Asp Thr Val Ser Asn Thr Ala
65                  70                  75                  80

Tyr Leu Glu Leu Asn Ser Leu Thr Ser Glu Asp Ser Ala Ile Tyr Tyr
                85                  90                  95

Cys Ala Arg Gly Glu Gly Tyr Gly Ala Trp Phe Ala Tyr Trp Gly Gln
            100                 105                 110

Gly Thr Leu Val Thr Val Ser Ala
        115                 120


<210> SEQ ID NO 138
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 138

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110
```

Lys

<210> SEQ ID NO 139
<211> LENGTH: 106
<212> TYPE: PRT
<213> ORGANISM: Artificial
<220> FEATURE:
<223> OTHER INFORMATION: Description of artificial sequence: Translation of PCR product

<400> SEQUENCE: 139

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Lys Leu Glu Ile Lys
            100                 105
```

<210> SEQ ID NO 140
<211> LENGTH: 107
<212> TYPE: PRT
<213> ORGANISM: Artificial
<220> FEATURE:
<223> OTHER INFORMATION: Description of artificial sequence: Translation of PCR product

<400> SEQUENCE: 140

```
Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Gly Gly Thr Lys Leu Glu Ile Lys
            100                 105
```

<210> SEQ ID NO 141
<211> LENGTH: 113
<212> TYPE: PRT
<213> ORGANISM: Artificial
<220> FEATURE:
<223> OTHER INFORMATION: Description of artificial sequence: Translation of PCR product

<400> SEQUENCE: 141

```
Asp Ile Val Met Ser Gln Ser Pro Ser Ser Leu Ala Val Ser Val Gly
```

```
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys


<210> SEQ ID NO 142
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 142

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys


<210> SEQ ID NO 143
<211> LENGTH: 112
<212> TYPE: PRT
<213> ORGANISM: Artificial
<220> FEATURE:
<223> OTHER INFORMATION: Description of artificial sequence: Translation
      of PCR product

<400> SEQUENCE: 143

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60
```

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Lys Gln
85 90 95

Ser Tyr Asn Leu Tyr Thr Phe Gly Gly Gly Thr Lys Leu Glu Ile Lys
100 105 110

<210> SEQ ID NO 144
<211> LENGTH: 113
<212> TYPE: PRT
<213> ORGANISM: Artificial
<220> FEATURE:
<223> OTHER INFORMATION: Description of artificial sequence: Translation of PCR product

<400> SEQUENCE: 144

Asp Ile Val Met Ser Gln Ser Pro Ser Ser Leu Ala Val Ser Val Gly
1 5 10 15

Glu Lys Val Thr Met Ser Cys Lys Ser Ser Gln Ser Leu Leu Tyr Ser
20 25 30

Ser Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Ala Thr Asp Phe Thr Leu Thr
65 70 75 80

Ile Ser Ser Val Gln Ala Glu Asp Leu Ala Asp Tyr His Cys Gly Gln
85 90 95

Gly Tyr Ser Tyr Pro Tyr Thr Phe Gly Gly Gly Thr Lys Leu Glu Ile
100 105 110

Lys

<210> SEQ ID NO 145
<211> LENGTH: 113
<212> TYPE: PRT
<213> ORGANISM: Artificial
<220> FEATURE:
<223> OTHER INFORMATION: Description of artificial sequence: Translation of PCR product

<400> SEQUENCE: 145

Asp Ile Val Met Ser Gln Ser Pro Ser Ser Leu Ala Val Ser Val Gly
1 5 10 15

Glu Lys Val Thr Met Ser Cys Lys Ser Ser Gln Ser Leu Leu Tyr Ser
20 25 30

Ser Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Tyr Ser Tyr Pro Leu Thr Phe Gly Ala Gly Thr Lys Leu Glu Leu
100 105 110

Lys

<210> SEQ ID NO 146

<211> LENGTH: 107
<212> TYPE: PRT
<213> ORGANISM: Artificial
<220> FEATURE:
<223> OTHER INFORMATION: Description of artificial sequence: Translation of PCR product

<400> SEQUENCE: 146

```
Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Lys Ala
65                  70                  75                  80

Glu Asp Leu Ala Val Tyr Tyr Cys Gln Gln Tyr Tyr Ser Tyr Pro Leu
                85                  90                  95

Thr Phe Gly Ala Gly Thr Lys Leu Glu Leu Lys
            100                 105
```

<210> SEQ ID NO 147
<211> LENGTH: 324
<212> TYPE: DNA
<213> ORGANISM: Artificial
<220> FEATURE:
<223> OTHER INFORMATION: Description of artificial sequence: codon optimized nucleic acid

<400> SEQUENCE: 147

```
cgtacggtgg ccgctcccag cgtgttcatc ttccccccca gcgacgagca gctgaagtcc     60

ggcaccgcca gcgtggtgtg cctgctgaac aacttctacc cccgggaggc caaggtgcag    120

tggaaggtgg acaacgccct gcagagcggc aacagccagg agagcgtcac cgagcaggac    180

agcaaggact ccacctacag cctgagcagc accctgaccc tgagcaaggc cgactacgag    240

aagcacaagg tgtacgcctg cgaggtgacc caccagggcc tgtccagccc cgtgaccaag    300

agcttcaaca ggggcgagtg ctag                                           324
```

<210> SEQ ID NO 148
<211> LENGTH: 107
<212> TYPE: PRT
<213> ORGANISM: Artificial
<220> FEATURE:
<223> OTHER INFORMATION: Description of artificial sequence: codon optimized protein

<400> SEQUENCE: 148

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 149
<211> LENGTH: 981
<212> TYPE: DNA
<213> ORGANISM: Artificial
<220> FEATURE:
<223> OTHER INFORMATION: Description of artificial sequence: codon optimized nucleic acid

<400> SEQUENCE: 149
ggcccaagcg tgttcccct ggcccccagc agcaagagca ccagcggcgg cacagccgcc 60
ctgggctgcc tggtgaagga ctacttcccc gagcccgtga ccgtgagctg gaacagcgga 120
gccctgacct ccggcgtgca caccttcccc gccgtgctgc agagcagcgg cctgtacagc 180
ctgagcagcg tggtgaccgt gcccagcagc agcctgggca cccagaccta catctgcaac 240
gtgaaccaca agcccagcaa caccaaggtg gacaagagag tggagcccaa gagctgcgac 300
aagacccaca cctgcccccc ctgcccagcc ccagagctgc tgggcggacc cagcgtgttc 360
ctgttccccc ccaagcccaa ggacaccctg atgatcagca ggacccccga ggtgacctgc 420
gtggtggtgg acgtgagcca cgaggaccca gaggtgaagt tcaactggta cgtggacggc 480
gtggaggtgc acaacgccaa gaccaagccc agagaggagc agtacaacag cacctacagg 540
gtggtgtccg tgctgaccgt gctgcaccag gactggctga acggcaagga atacaagtgc 600
aaggtctcca acaaggccct gccagccccc atcgaaaaga ccatcagcaa ggccaagggc 660
cagccacggg agccccaggt gtacaccctg ccccccagcc gggaggagat gaccaagaac 720
caggtgtccc tgacctgtct ggtgaagggc ttctacccca gcgacatcgc cgtggagtgg 780
gagagcaacg gccagcccga gaacaactac aagaccaccc ccccagtgct ggacagcgac 840
ggcagcttct tcctgtacag caagctgacc gtggacaagt ccaggtggca gcagggcaac 900
gtgttcagct gcagcgtgat gcacgaggcc ctgcacaacc actacaccca gaagtccctg 960
agcctgagcc ccggcaagta g 981

<210> SEQ ID NO 150
<211> LENGTH: 326
<212> TYPE: PRT
<213> ORGANISM: Artificial
<220> FEATURE:
<223> OTHER INFORMATION: Description of artificial sequence: codon optimized protein

<400> SEQUENCE: 150

Gly Pro Ser Val Phe Pro Leu Ala Pro Ser Ser Lys Ser Thr Ser Gly
1 5 10 15

Gly Thr Ala Ala Leu Gly Cys Leu Val Lys Asp Tyr Phe Pro Glu Pro
20 25 30

Val Thr Val Ser Trp Asn Ser Gly Ala Leu Thr Ser Gly Val His Thr
35 40 45

Phe Pro Ala Val Leu Gln Ser Ser Gly Leu Tyr Ser Leu Ser Ser Val
50 55 60

Val Thr Val Pro Ser Ser Ser Leu Gly Thr Gln Thr Tyr Ile Cys Asn
65 70 75 80

Val Asn His Lys Pro Ser Asn Thr Lys Val Asp Lys Arg Val Glu Pro
85 90 95

-continued

```
Lys Ser Cys Asp Lys Thr His Thr Cys Pro Pro Cys Pro Ala Pro Glu
            100                 105                 110

Leu Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```